US010766929B2

(12) United States Patent
Baker et al.

(10) Patent No.: US 10,766,929 B2
(45) Date of Patent: Sep. 8, 2020

(54) DE NOVO DESIGNED HEMAGGLUTININ BINDING PROTEINS

(71) Applicant: UNIVERSITY OF WASHINGTON, Seattle, WA (US)

(72) Inventors: David Baker, Seattle, WA (US); Aaron Arthur Chevalier, Seattle, WA (US); Gabriel Jacob Rocklin, Seattle, WA (US); Christopher David Bahl, Seattle, WA (US); Lance Joseph Stewart, Seattle, WA (US); Daniel Adriano Silva Manzano, Seattle, WA (US); Deborah L. Fuller, Seattle, WA (US); Merika Treants Koday, Seattle, WA (US); Jason Gilmore, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/483,865

(22) PCT Filed: Mar. 15, 2018

(86) PCT No.: PCT/US2018/022647
§ 371 (c)(1),
(2) Date: Aug. 6, 2019

(87) PCT Pub. No.: WO2018/170273
PCT Pub. Date: Sep. 20, 2018

(65) Prior Publication Data
US 2020/0017552 A1 Jan. 16, 2020

Related U.S. Application Data

(60) Provisional application No. 62/471,637, filed on Mar. 15, 2017.

(51) Int. Cl.
*A61K 38/00* (2006.01)
*C07K 14/00* (2006.01)
*A61P 31/16* (2006.01)
*C07K 16/00* (2006.01)
*G01N 33/569* (2006.01)

(52) U.S. Cl.
CPC ............ *C07K 14/001* (2013.01); *A61P 31/16* (2018.01); *C07K 16/00* (2013.01); *G01N 33/56983* (2013.01); *A61K 38/00* (2013.01); *G01N 2333/11* (2013.01); *G01N 2500/04* (2013.01); *G01N 2800/26* (2013.01)

(58) Field of Classification Search
None
See application file for complete search history.

(56) References Cited

U.S. PATENT DOCUMENTS

| 8,444,986 B2 | 5/2013 | Qian et al. |
| 8,900,590 B2 | 12/2014 | Olsen et al. |
| 2015/0071952 A1 | 3/2015 | Fnu et al. |
| 2015/0104459 A1 | 4/2015 | Grandea, III et al. |
| 2015/0259400 A1 | 9/2015 | Xu et al. |
| 2016/0024155 A1 | 1/2016 | Baker et al. |

FOREIGN PATENT DOCUMENTS

WO 2016/079250 5/2016

OTHER PUBLICATIONS

The International Search Report (ISR) with Written Opinion for PCT/US2018022647 dated Jul. 26, 2018, pp. 1-15.
Adams et al, "The Phenix software for automated determination of macromolecular structures," Methods. 55: 94-106 (2011).
Alberts, "The cell as a collection of protein machines: preparing the next generation of molecular biologists." Cell 92 (3):291-294 (1998).
Avouac et al, "Increased risk of osteoporosis and fracture in women with systemic sclerosis: a comparative study with rheumatoid arthritis," Arthritis Care Res (Hoboken) 64(12):1871-1878 (2012).
Bawono et al, "Praline: A Versatile Multiple Sequence Alignment Toolkit. Methods in Molecular Biology," pp. 245-262 (2013).
Benatuil et al, "An improved yeast transformation method for the generation of very large human antibody libraries," Protein Eng Des Sel. 23: 155-159 (2010).
Berendsen, H. J. C. Transport Properties Computed by Linear Response through Weak Coupling to a Bath. in Computer Simulation in Materials Science 139-155 (1991).
Berger et al, Computationally designed high specificity inhibitors delineate the roles of BCL2 family proteins in cancer. Elife. 5. doi:10.7554/eLife.20352 (2016).
Berman et al, The protein data bank, 1999—International Tables for Crystallography. John Wiley & Sons, Ltd, Hoboken, NJ, 675-684. (2006).
Berntsson et al, "Structure of Botulinum neurotoxin B binding domain in complex with both synaptotagmin II and GD1a," doi:10.2210/pdb4kbb/pdb (2013).
Bhardwaj et al, "Accurate de novo design of hyperstable constrained peptides," Nature. 538: 329-335 (2016).
Cleary et al, "Production of complex nucleic acid libraries using highly parallel in situ oligonucleotide synthesis," Nat Methods. 1: 241-248 (2004).
Corrao et al, "Mortality in patients with coeliac disease and their relatives: a cohort study," Lancet 358 (9279):356-361(2001).
Corti et al, "A neutralizing antibody selected from plasma cells that binds to group 1 and group 2 influenza A hemagglutinins," Science 333, 850-856 (2011).
Corti et al, "Broadly Neutralizing Antiviral Antibodies. Annual Review of Immunology," 31, 705-742 (2013).
De Wolf et al, "Ligand-binding proteins: their potential for application in systems for controlled delivery and uptake of ligands," Pharmacol Rev 52(2):207-236 (2000).

(Continued)

*Primary Examiner* — Jeanette M Lieb
(74) *Attorney, Agent, or Firm* — McDonnell Boehnen Hulbert & Berghoff LLP

(57) ABSTRACT

Polypeptides that bind to viral hemagglotinin are disclosed and methods for their use in treating or limiting influenza infection, and diagnosing influenza infection.

19 Claims, 1 Drawing Sheet
Specification includes a Sequence Listing.

(56) References Cited

OTHER PUBLICATIONS

Emsley et al, "Coot: model-building tools for molecular graphics," Acta Crystallogr D Biol Crystallogr. 60: 2126-2132 (2004).
Essmann et al, "A smooth particle mesh Ewald method. J Chem Phys," 103: 8577 (1995).
Farrell et al, "State-of-the-art vitamin D assays: a comparison of automated immunoassays with liquid chromatography-tandem mass spectrometry methods," Clin Chem 58(3):531-542 (2012).
Fasano et al, "Prevalence of celiac disease in at-risk and not-at-risk groups in the United States: a large multicenter study," Arch Intern Med 163(3):286-292 (2003).
Fleischman et al, "Community-wide assessment of protein-interface modeling suggests improvements to design methodology," J Mol Biol 414(2):289-302 (2011).
Fleishman et al, "Computational design of proteins targeting the conserved stem region of influenza hemagglutinin," Science 332, 816-821 (2011).
Jacobs et al, "SwiftLib: rapid degenerate-codon-library optimization through dynamic programming," Nucleic Acids Res. 43: e34 (2014).
Janin et al, "Protein-protein interaction and quaternary structure," Q Rev Biophys 41(2):133-180 (2008).
Jardine et al, "Rational HIV immunogen design to target specific germline B cell receptors," Science 340 (6133):711-716 (2013).
Jin et al, "Botulinum neurotoxin B recognizes its protein receptor with high affinity and specificity," Nature 444: 1092-1095 (2006).
Jorgensen et al, "Comparison of simple potential functions for simulating liquid water," J Chem Phys. 79: 926 (1983).
Kabsch et al, "XS" Acta Crystallogr D Biol Crystallogr. 66:125-32 (2010).
Kanekiyo et al, "Self-assembling influenza nanoparticle vaccines elicit broadly neutralizing H1N1 antibodies," Nature 499(7456):102-106 (2013).
King et al, "Removing T-cell epitopes with computational protein design," Proc. Natl. Acad. Sci. U. S. A. 111, 8577-8582 (2014).
King et al, Computational design of self-assembling protein nanomaterials with atomic level accuracy, Science 336 (6085):1171-1174 (2012).
Kintzing et al, "Engineered knottin peptides as diagnostics, therapeutics, and drug delivery vehicles," Curr Opin Chem Biol. 34: 143-150 (2016).
Koday et al, "A Computationally Designed Hemagglutinin Stem-Binding Protein Provides In Vivo Protection from Influenza Independent of a Host Immune Response," PLoS Pathog. 12: e1005409 (2016).
Koga et al, "Principles for designing ideal protein structures," Nature. 491: 222-227 (2012).
Leaver-Fay et al, "ROSETTA3: an object-oriented software suite for the simulation and design of macromolecules," Methods Enzymol 487:545-574 (2011).
Lin et al, "Control over overall shape and size in de novo designed proteins," Proc Natl Acad Sci U S A. 112: E5478-85 (2015).
Lindfors et al, "Future treatment strategies for celiac disease," Expert Opin Ther Targets 16(7):665-675 (2012).
Lindorff-Larsen et al, "Improved side-chain torsion potentials for the Amber ff99SB protein force field," Proteins. 78: 1950-1958 (2010).
Logan et al, "Mortality in celiac disease," (Translated from eng) Gastroenterology 97(2):265-271 (1989).
Mauskopf et al, "Cost-effectiveness analysis of the use of digoxin immune Fab (ovine) for treatment of digoxin toxicity," Am J Cardiol 68(17):1709-1714 (1991).
McCoy et al, Phaser crystallographic software. J. Appl. Crystallogr. 40, 658-674 (2007).
Midhagen et al, "High rate of gastrointestinal symptoms in celiac patients living on a gluten-free diet: controlled study," Am J Gastroenterol 98(9)2023-2026 (2003).
Millman et al, "Python for Scientists and Engineers," Comput Sci Eng 13, 9-12. (2011).
Moretti et al, "Community-wide evaluation of methods for predicting the effect of mutations on protein-protein interactions," Proteins (2013).
Mulcahy et al, "We have met the enemy and he is us," Ewing Marion Kauffman Foundation Reports: 1-51 (2012).
Naeem, "Vitamin d deficiency—an ignored epidemic," Int J Health Sci (Qassim) 4(1):V-VI (2010).
Nose et al, "Constant pressure molecular dynamics for molecular systems," Mol Phys. 50: 1055-1076 (1983).
Otwinowski et al, "[20] Processing of X-ray diffraction data collected in oscillation mode," Methods in Enzymology, pp. 307-326 (1997).
Paul et al, "How to improve R&D productivity: the pharmaceutical industry's grand challenge," Nat Rev Drug Discov 9(3):203-214 (2010).
Perez et al, "IPython: a system for interactive scientific computing," Comput Sci Eng 9, 21-29. (2007).
Pietzak, "Follow-up of patients with celiac disease: achieving compliance with treatment," Gastroenterology 128(4 Suppl 1):S135-141 (2005).
Procko et al, "A computationally designed inhibitor of an Epstein-Barr viral Bcl-2 protein induces apoptosis in infected cells," Cell. 2014;157: 1644-1656 (2014).
Rocklin et al, "Global analysis of protein folding using massively parallel design, synthesis, and testing," Science 357, 168-175 (2017).
Shriver et al, "Antibody-based strategies to prevent and treat influenza. Frontiers in Immunology," 6 (315) (2015).
Silva et al, "Motif-Driven Design of Protein-Protein Interfaces. Methods in Molecular Biology," pp. 285-304 (2016).
Silva et al., "Structures and disulfide cross-linking of de novo designed therapeutic mini-proteins" The FEBS Journal 285:1783-85 (2018).
Skalickova et al, "Perspective of use of antiviral peptides against influenza virus. Viruses," 7, 5428-5442 (2015).
Solaymani-Dodaran et al, "Long-term mortality in people with celiac disease diagnosed in childhood compared with adulthood: a population-based cohort study," Am J Gastroenterol 102(4):864-870 (2007).
Sui et al, "Structural and Functional Bases for Broad-spectrum neutralization of Avian and Human Influenza A viruses," Nature: Structural and Molecular Biology vol. 16 265-273 (2009).
Sun et al, "Protein engineering by highly parallel screening of computationally designed variants," Sci Adv 2, e1600692 (2016).
Tinberg et al, "Computational Design of Ligand Binding Proteins with High Affinity and Selectivity. Nature in Press," (2013).
Van Der Spoel et al, "GROMACS: fast, flexible, and free. J Comput Chem," 26: 1701-1718 (2005).
Vazquez-Lombardi et al, Challenges and opportunities for non-antibody scaffold drugs. Drug Discov Today. 20: 1271-1283 (2015).
Wallace et al, "Measurement of 25-hydroxyvitamin D in the clinical laboratory: current procedures, performance characteristics and limitations," Steroids 75(7):477-488 (2010).
Waskom et al, seaborn: v0.7.1 doi:10.5281/zenodo.54844 (2016).
Whitehead et al, "Optimization of affinity, specificity and function of designed influenza inhibitors using deep sequencing," Nat Biotechnol. 30: 543-548 (2012).
Zahnd et al, "Efficient tumor targeting with high-affinity designed ankyrin repeat proteins: effects of affinity and molecular size," Cancer Res. 70: 1595-1605 (2010).
Zhang et al, "PEAR: a fast and accurate Illumina Paired-End reAd mergeR," Bioinformatics. 30: 614-620 (2013).
Bischoff-Ferrari et al, "Estimation of optimal serum concentrations of 25-hydroxyvitamin D for multiple health outcomes," Am J Clin Nutr 84(1):18-28 (2006).
Blitzer, "Spasmodic dysphonia and botulinum toxin: experience from the largest treatment series," Eur J Neurol. 17:28-30 (2010).
Brünger, "Free R value: a novel statistical quantity for assessing the accuracy of crystal structures," Nature. 355:472-475 (1992).
Brun et al, "Semisynthetic fluorescent sensor proteins based on self-labeling protein tags," J Am Chem Soc 131(16):5873-5884 (2009).
Bussi et al, "Canonical sampling through velocity rescaling," J Chem Phys. 126: 014101 (2007).

(56) References Cited

OTHER PUBLICATIONS

Carter, "Estimation of optimal serum concentrations of 25-hydroxyvitamin D for multiple health outcomes," Am J Clin Nutr 84(1):18-28 (2009).

Cass et al, "L. M. R., Efthymiopoulos, C. & Bye, A. Pharmacokinetics of Zanamivir After Intravenous, Oral, Inhaled or Intranasal Administration to Healthy Volunteers," Clin. Pharmacokinet. 36, 1-11 (1999).

Catassi et al, "A prospective, double-blind, placebo-controlled trial to establish a safe gluten threshold for patients with celiac disease," Am J Clin Nutr 85(1):160-166 (2007).

Chao et al, "Isolating and engineering human antibodies using yeast surface display," Nat Protoc. 1: 755-768 (2006).

Chen et al, "MolProbity: all-atom structure validation for macromolecular crystallography," Acta Crystallogr D Biol Crystallogr. 66: 12-21 (2010).

Chevalier et al, "Massively parallel de novo protein design for targeted therapeutics," Nature 550, 74-79. (2017).

Fleishman et al, "RosettaScripts: a scripting language interface to the Rosetta macromolecular modeling suite," PLoS One 6, e20161 (2011).

Gamblin et al, "The structure and receptor binding properties of the 1918 influenza hemagglutinin," Science. 303:1838-1842 (2004).

Gebauer et al, "Engineered protein scaffolds as next-generation antibody therapeutics," Curr Opin Chem Biol. 13:245-255.

Goodsell et al, "Structural symmetry and protein function," Annu Rev Biophys Biomol Struct 29:105-153 (2000).

Gordon et al, "Computational design of an alpha-gliadin peptidase." J Am Chem Soc 134(50):20513-20520 (2012).

Hess et al, "Johannes G E. LINCS: A linear constraint solver for molecular simulations," J Comput Chem. 8: 1463-1472 (1997).

Hoover, DNAWorks: an automated method for designing oligonucleotides for PCR-based gene synthesis, Nucleic Acids Res. 30: 43e-43 (2002).

Hu et al, "Conservation of polar residues as hot spots at protein interfaces. Proteins 39, 331-342," (2000).

Huang et al, "RosettaRemodel: a generalized framework for flexible backbone protein design," PLoS One. 6: e24109 (2011).

Hurt et al, "Antiviral resistance during the 2009 influenza A H1N1 pandemic: public health, laboratory, and clinical perspectives," Lancet Infect Dis. 12: 240-248 (2012).

Insight&Intelligence "Top 20 Biopharma R&D Spenders: Which companies have the deepest pockets for research and development?," Genetic Engineering News (2013).

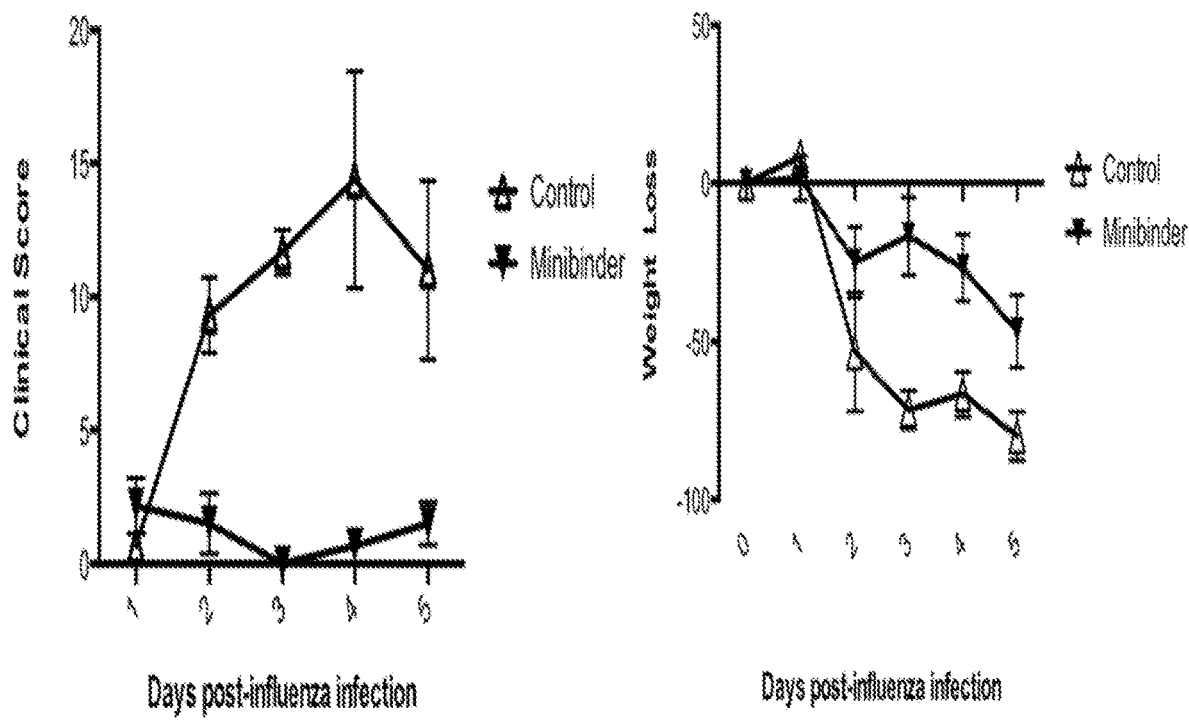

DE NOVO DESIGNED HEMAGGLUTININ BINDING PROTEINS

CROSS-REFERENCE

This application is a U.S. national phase of International Application No. PCT/US2018/022647, filed on Mar. 15, 2018, which claims priority to U.S. Provisional Application No. 62/471,637, filed Mar. 15, 2017, both of which are incorporated by reference herein in their entirety.

STATEMENT REGARDING FEDERALLY SPONSORED RESEARCH OR DEVEOPEMENT

This invention was made with government support under Grant no. AI119258 awarded by National Institutes of Health. The government has certain rights in the invention.

BACKGROUND

Influenza virus is a member of Orthomyxoviridae family. There are three subtypes of influenza viruses designated A, B, and C. The influenza virion contains a segmented negative-sense RNA genome, encoding, among other proteins, hemagglutinin (HA) and neuraminidase (NA). Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. So fair, chemical analogs of the receptor have not been successful as viral-entry blockers. Current treatment options include therapeutic antibodies, small-molecules drugs and vaccination. These therapies allow protection against circulating subtypes, but may not protect against newly emerging strains. Hence, general or quickly adaptable solutions for cheap treatment options represent a constant need. Additionally, in order to rapidly diagnose early whether a patient indeed suffers from influenza, sensitive diagnostics are desirable, as treatment at the onset of the infection have been shown to be more efficient. Influenza presents a serious public-health challenge and new therapies are needed to combat viruses that are resistant to existing antivirals or escape neutralization by the immune system.

Small (4-12 kDa) binding proteins have the potential to bridge the gap between monoclonal antibodies and small molecule drugs, with advantages of stability and chemical synthesis over monoclonal antibodies, and in selectivity and designability over small molecules. Directed evolution has been used starting from naturally occurring small protein scaffolds to generate new binding proteins. While powerful, such approaches have limitations: they cannot modify the overall shape of the starting scaffold protein(s), they can only sample a very small fraction of sequence space, and naturally occurring disulfide mini-proteins can be difficult to express. Computational protein design has the potential to overcome these limitations by efficiently sampling both shape and sequence space on a much larger scale, and generating readily producible proteins, as recently demonstrated by the design of stapled mini protein scaffolds with a wide range of shapes. Despite this potential, the high cost to synthesize genes for each designed protein has generally limited testing to small numbers (tens) of designs for an one application, which is too few to systematically explore the capability of this approach and to provide feedback to improve the computational model.

SUMMARY

In one aspect are provided isolated polypeptides comprising an amino acid sequence having at least 70% sequence identity over its length to the amino acid sequence of any one of SEQ ID NOS:1-462. In various embodiments, the polypeptide comprises an amino acid sequence having at least 70%, 75%, 80%, 85%, 90%, 91%, 92%, 93%, 94%, 95%, 96%, 97%, 98%, 99%, or 100% sequence identity over its length to the amino acid sequence of any one of SEQ ID NOS: 1-462. In various embodiments, the polypeptide is 75, 70, 65, 60, 55, or fewer amino acid residues in length. In other embodiments, the polypeptide comprises a tag.

In other aspects are provided isolated nucleic acids encoding the polypeptide of any embodiment of the disclosure, recombinant expression vectors comprising the nucleic acid of the disclosure operatively linked to a suitable control sequence, recombinant host cell comprising the recombinant expression vector of the disclosure, antibodies that selectively binds to a polypeptide of the disclosure, and pharmaceutical compositions, comprising one or more polypeptides of the disclosure and a pharmaceutically acceptable carrier.

In a further aspect, methods are provided for limiting and/or treating an influenza infection, comprising administering to a subject in need thereof an therapeutically effective amount of one or more polypeptides of the disclosure, salts thereof, conjugates thereof, or pharmaceutical compositions thereof, to treat and/or limit the influenza infection. In various embodiments, the polypeptides may be administered mucosally, such as by intranasal or inhaled administration, or orally. In other embodiments, the subject is immune-compromised and/or is 65 years of age or older.

In another aspect, methods are provided for diagnosing an influenza infection, or monitoring progression of an influenza infection, comprising (a) contacting a biological sample from a subject suspected of having an influenza infection with a diagnostically elective amount of one or more polypeptides of the disclosure, under conditions suitable for binding of the polypeptide to a viral hemagglutinin protein present in the sample; and (b) detecting polypeptide-viral hemagglutinin binding complexes, where the presence of such binding complexes indicates that the subject has an influenza infection, or provides a measure progression of an influenza infection.

In another aspect, methods are provided for identifying candidate influenza vaccines, comprising contacting test compounds with one or more polypeptides of the disclosure under conditions suitable for polypeptide binding;

removing unbound test compounds; and identifying those test compounds that bind to the polypeptide of the disclosure, wherein such test compounds are candidate influenza vaccines, In one aspect methods are provided for identifying candidate compounds for preventing, treating, limiting, and/or diagnosing influenza infection, comprising contacting an influenza hemagglutinin protein with (i) test compounds and (ii) polypeptide of the disclosure, under conditions suitable for binding of the hemagglutinin protein to the polypeptide of the present disclosure; and identifying those test compounds that outcompete the polypeptide for binding to the hemagglutinin protein, wherein such test compounds are candidate compounds for preventing, treating, limiting, and/or diagnosing influenza infection.

DESCRIPTION OF THE FIGURES

FIG. 1. Bioefficacy of A13 in a Ferret Model of Influenza Infection. Ferrets (N=6/group) weighing 610-710 grams were challenged by aerosol with pathogenic H1N1 (CA09) influenza virus. Twenty-four hours post-challenge, A13 treated animals received a total of 10 mg dose of A13 protein (resulting in a dose of 14-16 mg/kg, average 15 mg/kg) using an A13 formulation at ~19.5 mg/ml prepared a. Control animals received the same volume of buffer only (placebo controls). The 10 mg A13 dose was administered via two routes of delivery consisting of a combination of intranasal droplet (5 mg) and intratracheal droplets (5 mg) to achieve distribution of the A13 minibinder into both upper and lower respiratory tract. Ferrets were monitored twice daily for clinical signs of disease using a standardize scoring scale of 1-10 for various clinical signs including posture, activity level, ocular discharge, pulmonary function (sneezing, coughing, labored breathing) and changes in food and water consumption and elimination (Left Panel). In addition, weight loss (Right Panel) was measured twice daily. Both control and test animals showed no significant changes in temperature (measured twice daily) throughout the study (not shown). Technicians performing scoring evaluations were blinded to group assignment.

DETAILED DESCRIPTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutsheer, ed., (1990) Academic Press, Inc.); *PCR Protocols: A Guide to Methods and Applications* (Innis, et al, 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog Amnion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R); cysteine (Cys; C), glutamic acid (Glu; E), glutamine (Gln; Q); glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect are disclosed isolated polypeptides comprising an amino acid sequence having at least 70% sequence identity over its length: to the amino acid sequence of any one of SEQ NOS:1-462.

The polypeptides of all aspects/embodiments of the disclosure bind to hemagglutinin (HA); binding of the polypeptides to the HA protein can be determined using binding assays as detailed in the examples that follow. The polypeptides of the disclosure can thus be used, for example, to treat or detect/diagnose influenza infection. Exemplary polypeptides of the disclosure have been extensively tested and demonstrated in the examples that follow to strongly bind to the HA protein and inhibit viral entry into cells. Polypeptide binding to the stem-region of the HA protein is alone sufficient for highly effective in vivo protection against influenza, which is preferable to antibody-based therapeutics because it avoids immune activation and antibody-dependent enhancement of disease.

The polypeptides of the disclosure also provide a cheaper, more selective alternative to currently used hemagglutinin binding antibodies, which are costly to produce. The polypeptides of the disclosure can also be used for in vivo biosensing applications, whereas the antibodies cannot because of their structurally necessary disulfide bonds and difficulty to express robustly.

As disclosed in the examples that follow, exemplary HA-binding polypeptides of the disclosure have been identified and subjected to extensive mutational analysis against a variety of viral strains. These studies have identified residues where modifications are tolerated, and where they may lead to additional functionality. In vitro testing via deep mutational scanning shows that a number of these mutations lead to increased binding specificity against distinct subtypes of influenza, which could be highly useful in a diagnostic role or for therapeutic use against existing, new, or emerging strains of influenza. In various embodiments, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Len (L). Ile (I), Pro (P), Phe (F), Trp (W), Met (M); (2) uncharged polar: Gly (G), Ser (S), Thr (T), Cys (C) Tyr (Y), Asn (N), Gln (Q); (3) acidic: Asp (D) Glu (E): (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu, Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile co into Leu.

In various embodiments, the isolated polypeptides comprises an amino acid sequence having at least 75%, 80%, 85%, 90%, 91%, 92%, 93%, 94%, 95%, 96%, 97%, 98%, 99%, or 100% sequence identity over its length to the amino acid sequence of any one of SEQ ID NOS:1-462 (Table 1), which have been designed as disclosed in the examples that follow.

TABLE 1

| ID | Sequence |
|---|---|
| HB1G2.3396.4 | KKKITVESPFTAWMLAMWLWAFGIPVTCTTHGTKITCKEE (SEQ ID NO: 2) |
| HB1G2.4074.4 | TIEFNVYSPFSAKMAAMWCEVFGAPYTVHKHGTKITVKCE (SEQ ID NO: 3) |
| HB1G2.3802.4 | TETYHFTSFDLAMRAAWKAAFNNLEVHCENHNGTVQCHVK (SEQ ID NO: 4) |
| HB1G2.4669.4 | STTVTIECPFNAWMFAMWARAFGREVHCEKHGDKVTCTFE (SEQ ID NO: 5) |
| HB1G2.3136.4 | TIHIQETSRFNCAMRAMWAWAFGAPVEIQEHNGQCQVHIK (SEQ ID NO: 6) |
| HB1G2.4380.4 | TEKYTWHSPFACKMAAMWWRAFGRDVQVHQKNGTCTVEVH (SEQ ID NO: 7) |
| HB1G2.10123.4 | TEHSVARSIFSAWIAAKIAAEFGLDVTCTLKNGKCTCQVN (SEQ ID NO: 8) |
| HB1G2.10166.4 | TCHTTSNAPFACAIARDIAIEFNLEVHITQKNGKCTLEIR (SEQ ID NO: 9) |
| HB1G2.10325.4 | CYKSQAKMPFAAQIAAEIAREFNIPVKVQQHGDTLKVEHC (SEQ ID NO: 10) |
| HB1G2.9236.4 | CVTSQARQPFAAEIAAQIMKEFNIEVHCEKKGPTLKCTSC (SEQ ID NO: 11) |
| HB1G2.9388.4 | CYTTIAHTPFAAKIAAKIAAEFGYEVHVQQHGPTVKLQVC (SEQ ID NO: 12) |
| HB1G2.10778.4 | TYTKESNMPFAAAIAAKIWWEFGIPVTCSQHGNTVKCHVN (SEQ ID NO: 13) |
| HB1G2.1931.4 | TTTYTWDSFDAAMKAMWLLVFKGIPVQITAKNGKWQVKEH (SEQ ID NO: 14) |
| HB1G2.2065.4 | TEEYTFDTFDEAMRAAWEAVFKGLEVHVRSKNGKWTVHVK (SEQ ID NO: 15) |
| HB1G2.1039.4 | TINIEIHCFDAAMRAMWWAAFAGKQVIITQTNGQWHVQVQ (SEQ ID NO: 16) |
| HB1G2.1317.4 | TVDLENYSPFAAEMARMWAQAFNAPYTVEKHNGRFHVKVA (SEQ ID NO: 17) |
| HB1G2.0344.4 | TTTIQFDRFDNAMKAAWKLAFLGIPYKVTQVNGSWTVTQK (SEQ ID NO: 18) |
| HB1G2.2152.4 | TETCTCHSFDEAMRLMWYAVFHNLDVTFHKHGNKIKVEIN (SEQ ID NO: 19) |
| HB1G2.0807.4 | TRTITVVSPFAAWMAMMWAAAFGAPFTVETHGDTFKVTIH (SEQ ID NO: 20) |
| HB1G2.1352.4 | STQINVESPFAAWMAKMWALAFGAEVHVTQKNGTWHIQLK (SEQ ID NO: 21) |
| HB1G2.1234.4 | GKEIKVQNPFSAWMAAMWAKAFGTPVTLKQDGNTFHLHQH (SEQ ID NO: 22) |
| HB1G2.1924.4 | TITIKVDCFDQAMRAMWAAVFAGLELEQQTHNGTIHVHLK (SEQ ID NO: 23) |
| HB1G2.6991.4 | TQTFKYDSFSKAIAAAIKAEFKGLPFKVKMNGDWVEVEIT (SEQ ID NO: 24) |
| HB1G2.6042.4 | EITRTSSKEFAAWIAAEINREFGYDVQVRKKNGKYHVHVK (SEQ ID NO: 25) |
| HB1G2.5841.4 | KITREAKCPFAAEIAARILREFGKDATVTTLNGHVVVTFT (SEQ ID NO: 26) |
| HB1G2.4760.4 | TYETNAPSPFAAAIAAEIARQFGWEVTLKKKNGKLTVHVE (SEQ ID NO: 27) |
| HB1G2.6963.4 | TTTSDAKAPFAARIAAEIAREFGYDVQLTKHNGQLQITLK (SEQ ID NO: 28) |
| HB1G2.7574.4 | TYTSYAHSPFAAQIAAEIAREFGWDVTYTQHGDTLKVHVN (SEQ ID NO: 29) |
| HB1G2.6784.4 | TIKQTARSPFAAQIAADIAAEFGYTVKLSQKNGKWHLHVN (SEQ ID NO: 30) |
| HB1G2.4750.4 | TREINARSPFAAWIAAEIAKEFGYEVEVHKKNGKFTLHSQ (SEQ ID NO: 31) |
| HB1G2.6674.4 | TLEINARSPFAAAIAAEIARQFGYEVEVHKKNGKFTLHSQ (SEQ ID NO: 32) |

TABLE 1-continued

| ID | Sequence |
|---|---|
| HB1G2.5330.4 | KITIKVTMFAQAIAAVIKALFWGLPVTVQEHGNTIKIQVK (SEQ ID NO: 33) |
| HB1G2.7803.4 | KTTYHAPSKFAAQIAAEILREFGIPVTVTKAGDTYVLQEK (SEQ ID NO: 34) |
| HB1G2.5794.4 | TRHTTAPSEFAAEIARQIAASFRIPVTVTKKNGKLTVKVH (SEQ ID NO: 35) |
| HB1G2.8098.4 | TTHLTYRSPFAAQIAAEILREFGLPVNVWKNGPTLTVQVN (SEQ ID NO: 36) |
| HB1G2.6225.4 | TKTIKVPDFSKAIAEAIRAEFKGLDVKVHALNGVAVVTFS (SEQ ID NO: 37) |
| HB1G2.5334.4 | TSTSEASKNFAAAIAAKILAEFGIKFKLTQNGDTYKVTAH (SEQ ID NO: 38) |
| HB1G2.7913.4 | TWTSTAASEFAAAIAAEIAREFGYEVHVTKKNGQFQVTVK (SEQ ID NO: 39) |
| HB1G2.7225.4 | TYTSVAKSEFAAEIAARIAAEFGYEVHVTKKNGQFQVTVK (SEQ ID NO: 40) |
| HB1G2.6825.4 | TQTSQSSPFAAWIAAEILKEFGIPVTVQRHGDTVKVKQK (SEQ ID NO: 41) |
| HB1G2.6722.4 | TIQTTAWYPFAAWIYAKILKEFNIPLQVHVKNGKVTVHKE (SEQ ID NO: 42) |
| HB1G2.6169.4 | TWTSVASKEFAAQIAADIAAEFGWPVTVKKNGNYYTVHFD (SEQ ID NO: 43) |
| HB1G2.7385.4 | TYTSVARSPFAAQIAAEILKEFGYDVTVTQHGDQLKVTVE (SEQ ID NO: 44) |
| HB1G2.6083.4 | TQTTVAKSPFAAEIAARIWAEFGYDVTVTQHGDQLKVTVE (SEQ ID NO: 45) |
| HB1G2.4946.4 | TTTVTVEDFAKAIAAAILLEFNGKDVQVEHHGKYVTLQQH (SEQ ID NO: 46) |
| HB1G2.3168.3 | TVTIKVEDKFSCEMAIMWLKAFGQDCTFELHGNTCHIQCK (SEQ ID NO: 47) |
| HB1G2.9432.3 | TIHSTANAPFACRIAAEIAREFNIPVTLREHGDTCTIQNK (SEQ ID NO: 48) |
| HB1G2.9087.3 | TETSVAHAPFAAQIAAEIWREFGYKVTCTEKNGTVTCKVQ (SEQ ID NO: 49) |
| HB1G2.8766.3 | TYHSTARAPFACKIAAEIARQFNWEVHLHEKNGKCTLQIK (SEQ ID NO: 50) |
| HB1G2.10829.3 | CMTSHTYAPFAAAIAAKIAAEFGYDVQLHDGTKLTVHSC (SEQ ID NO: 51) |
| HB1G2.8722.3 | CMTSHTTAPFAAWIAAEIAKEFGYDVQLHDGTKLTVHSC (SEQ ID NO: 52) |
| HB1G2.9917.3 | CYHSTTASPFAAKIAAEILRQFNQEVTVTQHGDKLTVQWC (SEQ ID NO: 53) |
| HB1G2.9882.3 | CYHSTTRSPFAAKIAADILKEFNQEVTVTQHGDKLTVQWC (SEQ ID NO: 54) |
| HB1G2.10916.3 | CVTSHSNSTFAAEIAARIAAEFGLEVHVQKNGPRVEVTVC (SEQ ID NO: 55) |
| HB1G2.10895.3 | CYKSVSSAPFAAAISQEIARQFNWDVQCTQHGDTITCHMC (SEQ ID NO: 56) |
| HB1G2.10636.3 | TYTTWTAMPFSAEIVRQIAEEFGYEVHCTQHGRYVECKVK (SEQ ID NO: 57) |
| HB1G2.10167.3 | TWTSQARSEFAAQIAADIANSFGLPCTVKQNGPTYKVHCN (SEQ ID NO: 58) |
| HB1G2.9369.3 | TWTSVATAPFACKIAAEIAREFNWDVTVTQHGRTCKVHVE (SEQ ID NO: 59) |
| HB1G2.11018.3 | TCYIEAKAPFACAIVAEINRQFRLEVHVTKKNGTCHVEIK (SEQ ID NO: 60) |
| HB1G2.8580.3 | TWKSVSHSPFACQIAAEIWREFGYDVQVHQKNGTCTVEVH (SEQ ID NO: 61) |
| HB1G2.9913.3 | TWKTVAHSPFACWIAAKIWKEFGYDVQVHQKNGTCTVEVH (SEQ ID NO: 62) |
| HB1G2.9205.3 | TYKVVSHSPFACQIAAEIWREFNYDVQVHQKNGTCTVEVH (SEQ ID NO: 63) |
| HB1G2.9164.3 | TWKTVAHSPFACEIAARIWAEFGYDVQVHQKNGTCTVEVH (SEQ ID NO: 64) |
| HB1G2.9843.3 | TYKTYAHSPFACEIAARIWKEFGYDVQVHQKNGTCTVEVH (SEQ ID NO: 65) |
| HB1G2.10125.3 | CWISVSHSPFAAEIVREIVRQFGYEVHVQQHGDTVKVQVC (SEQ ID NO: 66) |
| HB1G2.8840.3 | TYTSVAWSDFACKIAADIAAEFGWEVGLENHNGKCKVTVK (SEQ ID NO: 67) |
| HB1G2.8759.3 | TYTSVAWSEFACKIAAEIAAEFGWEVHLENHNGKCKVTVK (SEQ ID NO: 68) |
| HB1G2.8456.3 | TIKYTARSPFAAEISARILWEFGAEVHCTQHGDRVECREK (SEQ ID NO: 69) |
| HB1G2.10980.3 | TVTLHVTNFAQAIAAIIKCEFLGLPVTVEDHGNTIKIQCT (SEQ ID NO: 70) |
| HB1G2.0906.3 | TTKLKFHSFDKAMEALWRLAFLGIPAQATQENGTWLVKKH (SEQ ID NO: 71) |

TABLE 1-continued

| ID | Sequence |
|---|---|
| HB1G2.2267.3 | RTKFTFDSFDKAMRAAWKAVFNNLTVHQTKKNGKYHVELQ (SEQ ID NO: 72) |
| HB1G2.0134.3 | TIHIQVTAFDEAMEAAWRAAFNGLPVEIQSHNGQYQVHIK (SEQ ID NO: 73) |
| HB1G2.1245.3 | KTTYTFDSFDEAMRAAWEAVFRGLPVQLHMKNGKWQVTVE (SEQ ID NO: 74) |
| HB1G2.2727.3 | TKTIKVDSFDAAMKTAWDLAFKGIPFKITQLNGTWVVQQG (SEQ ID NO: 75) |
| HB1G2.2039.3 | TKTIKVDSFDAAMETAWRLAFKGIPFKITQLNGTWVVQQG (SEQ ID NO: 76) |
| HB1G2.0645.3 | TETIKVQDFDNAMRAMWEAVFRNIPVEVEIHGPTLKVHIK (SEQ ID NO: 77) |
| HB1G2.0478.3 | TITIVVDSPFAAKMAAMWAKAFGSEVEVHRHGDLIKIQLH (SEQ ID NO: 78) |
| HB1G2.0620.3 | KQTIQFPSFDAAMEAVWRAAFKGLPVTMTKVNGTWKVKIK (SEQ ID NO: 79) |
| HB1G2.2424.3 | TTYQKVEAPFSAWMVAMWLAAFGIPFKVQKKNGTWHIQKQ (SEQ ID NO: 80) |
| HB1G2.1972.3 | STKYHVKSFDEAMKQAWKAAFKGLEVHLRSKNGTWTVEVR (SEQ ID NO: 81) |
| HB1G2.2066.3 | TTTYTLDSFDAAMKAMWKAVFNGIPVTCTQKNGKWQVTIQ (SEQ ID NO: 82) |
| HB1G2.6592.3 | KATSQSSSSFAAQIAAEIAKEFGIPVTVEDVGDTYKVHNE (SEQ ID NO: 83) |
| HB1G2.5081.3 | EITVTSDKSFAAAIAAEIWRQFGYDVQVRKKNGKYHVHVK (SEQ ID NO: 84) |
| HB1G2.5189.3 | EITRTSSKSFAAKIAADINKEFGYDVQVRKKNGKYHVHVK (SEQ ID NO: 85) |
| HB1G2.5223.3 | TYTSKACKPFAAQIAADIAKEFGYEVHVTQKGGTVVVTRK (SEQ ID NO: 86) |
| HB1G2.7256.3 | TPQSTARSPFAAEIAARILKEFNIPYDVQTHGDKVTVTAH (SEQ ID NO: 87) |
| HB1G2.7918.3 | TPQSTAYSPFAAWIAAKILEEFNIPYDVQTHGDKVTVTAH (SEQ ID NO: 88) |
| HB1G2.5924.3 | TQTIKAQSSFAAWIAAEILRQFNIPVTLQTHGSTYKVEQH (SEQ ID NO: 89) |
| HB1G2.6837.3 | TFHSVAYSPFAAEIARQILEEFGIPVEVHVKNGKVEVKSK (SEQ ID NO: 90) |
| HB1G2.8053.3 | TYTSISHSPFAAQIAADIAAEFGWDVTYTQHGDTLKVHVN (SEQ ID NO: 91) |
| HB1G2.7829.3 | TKTVTARSKFAADIAAEILREFGIDVQITTKNGKYQLQNK (SEQ ID NO: 92) |
| HB1G2.7214.3 | KITFHVTRFAEAIAAAIKAQFLGLPYTVEVHGTEIKIKVE (SEQ ID NO: 93) |
| HB1G2.7646.3 | TETYTAPSEFSAAIAAEIAREFGYDLQVTKLNGKWVVHQK (SEQ ID NO: 94) |
| HB1G2.6737.3 | TQTIQVDSFANAIAAAILALFKNLPVTCHRDGDTVKLHVK (SEQ ID NO: 95) |
| HB1G2.5061.3 | TWTTHTKGPFAAWIAAQILLEFNLDVQVEDHNGKFTLHSK (SEQ ID NO: 96) |
| HB1G2.5657.3 | TNKFDAPSPFAAKIAAEILKEFGYDVTVKQKNGQVWVEQK (SEQ ID NO: 97) |
| HB1G2.7258.3 | TYTIHASSPFAAWIAAEIAREFRIPVQVQQHGDTVQVHEH (SEQ ID NO: 98) |
| HB1G2.4767.3 | TQHTQAKSEFAAQIAAEILKEFGIDAQVVKVGPTYKVKET (SEQ ID NO: 99) |
| HB1G2.7360.3 | TYHTQTKSEFAAEIAARILKEFGIDAQVVKVGPTYKVKET (SEQ ID NO: 100) |
| HB1G2.5981.3 | TSTSQVRMPFAAAIAAEIMRQFGYDVQVEQHGDTLKITSK (SEQ ID NO: 101) |
| HB1G2.6453.3 | TIKSVTKSSFAAAIAAKIWAEFGYDVQVTQNGDQYTVHVK (SEQ ID NO: 102) |
| HB1G2.5982.3 | ETTFEAPSPFAAEIAARIAAEFGIKLTLKKVNGVLVVTKK (SEQ ID NO: 103) |
| HB1G2.8055.3 | TMKITSRSKFAALIAAEIWRQFGYEVHILTHGDTYQVEVN (SEQ ID NO: 104) |
| HB1G2.6165.3 | TMKITTESKFSADIAAKIWAEFGYEVHILTHGDTYQVEVN (SEQ ID NO: 105) |
| HB1G2.6637.3 | TTTYQYPNFALAIAAAIKAEFKGLEVHTTSDGDTYKITVH (SEQ ID NO: 106) |
| HB1G2.7812.3 | KRTLKANSNFAAQIAAKINKEFGYEVHVTQQNGTWQVTVK (SEQ ID NO: 107) |
| HB1G2.7494.3 | TFTSTAAKSFAAEIAARIMKEFGIEVKLQKKNGKVQVQAH (SEQ ID NO: 108) |
| HB1G2.5343.3 | TYTSVAASEFAAQIAAEIAREFGWEVHVTKKNGQFQVTVK (SEQ ID NO: 109) |
| HB1G2.5953.3 | TKTVKVDRFAEAIAEAIRALFKGLEVHITQINGTAHVQIK (SEQ ID NO: 110) |

TABLE 1-continued

| ID | Sequence |
|---|---|
| HB1G2.7585.3 | TQQSHAADSFAAWIAAEINREFGYEVHVTQVNGTFTVKTK (SEQ ID NO: 111) |
| HB1G2.8041.3 | RQKIQARAPFAAAIAVKIAAEFGWTLTVTKHGDTLTVHEE (SEQ ID NO: 112) |
| HB1G2.4885.3 | TMTTKSSSPFAAKIAYEIAREFGWDAHITQKNGTWHVTVK (SEQ ID NO: 113) |
| HB1G2.7228.3 | TKTFQARSEFAAAIAAQIAKEFGYEVHLHKSGNTLKVEVR (SEQ ID NO: 114) |
| HB1G2.6753.3 | TWTSVASKYFAAEIARQIAEEFGWPVTVKKNGNYYTVHFD (SEQ ID NO: 115) |
| HB1G2.8030.3 | TKTIKVDSFAEAIAAAIRAWFKGIEVHVTRVNGTASVKQH (SEQ ID NO: 116) |
| HB1G2.5911.3 | TYTSVARSPFAAQIAADILREFGYDVTVTQHGDQLKVTVE (SEQ ID NO: 117) |
| HB1G2.6158.3 | TYTSVARSPFAAQIAAEILREFGYDVTVTQHGDQLKVTVE (SEQ ID NO: 118) |
| HB1G2.7502.3 | TTQIQVKSFAEAIAEAIRAQFKGLPATVKSDGKTAHVEFE (SEQ ID NO: 119) |
| HB1G2.4966.3 | TYTSQSHSPFAANIAAEILKEFGIEFTQTKVGDTLKTISH (SEQ ID NO: 120) |
| HB1G2.5149.3 | TETVQVDSFAAAIAASIKIEFRGLEVKIQEVGDTVKVELH (SEQ ID NO: 121) |
| HB1G2.6732.3 | TWQSVSVKKFAAAIARDIALEFGWDVQLTQQNGKWTLHIN (SEQ ID NO: 122) |
| HB1G2.3271.2 | TETVNVTCPFWCWMAAMWWKAFGSEVHVHQDGNKCTIQIK (SEQ ID NO: 123) |
| HB1G2.4023.2 | TTETTFDSFDEAMQAMWDAAFKGLEVHCTQKNGTVTCKIH (SEQ ID NO: 124) |
| HB1G2.4394.2 | EIHIHETAPFDCWMRYMWLAAFGSNVTVTERGNKCTVTVT (SEQ ID NO: 125) |
| HB1G2.4070.2 | CKKVQVESPFSAWMEAMWAKAFNIPVKVQQHGDTLKVEHC (SEQ ID NO: 126) |
| HB1G2.3285.2 | TITIKRESPFACWMAIMWAKAFGATFELKQHGLTCKLHVK (SEQ ID NO: 127) |
| HB1G2.4086.2 | CTTLKVDSFDKAMRIAWELAFRGVRAYVRLCNGTAFVQKC (SEQ ID NO: 128) |
| HB1G2.3139.2 | TITFHVVCPFSAKMVAMWCAAFGSPFEVQTHNGTLTIHCD (SEQ ID NO: 129) |
| HB1G2.3167.2 | KEEYTYESPFECWMAAMWLRAFGLDVQVHTDGLTCTVKVK (SEQ ID NO: 130) |
| HB1G2.8964.2 | CSHITSNSEFAAWIAAEIAKEFGLEVHLHKKNGTYTVQVC (SEQ ID NO: 131) |
| HB1G2.10183.2 | TYHTVSRAPFACQIVAEIAREFNIEVKVETHNGTCEIQAK (SEQ ID NO: 132) |
| HB1G2.9980.2 | RYKSTNWTPFACEIAKRIIDEFNIPVEIHITNGKCTIHVS (SEQ ID NO: 133) |
| HB1G2.10266.2 | RFKSTNWNPFACEIARQIIEEFNIPVEIHITNGKCTIHTS (SEQ ID NO: 134) |
| HB1G2.9989.2 | RWKSTCWSPFACAIAAKIIKEFNIPVEIHITNGKCTIHVS (SEQ ID NO: 135) |
| HB1G2.10202.2 | TWTSVAVSDFACTIAAEIARQFGWEVHVEKHNGTCKVKIH (SEQ ID NO: 136) |
| HB1G2.9204.2 | CITIDVDRFANAIACKIEAEFRGLDVQLENHNGKLKLHLC (SEQ ID NO: 137) |
| HB1G2.10783.2 | TWTSHAKAPFACQIAADIAAEFGWTCTVEKHNGTCEINCQ (SEQ ID NO: 138) |
| HB1G2.10467.2 | TWTSHANAPFACEIARQIAEEFGWTCTVEKHNGTCEINCQ (SEQ ID NO: 139) |
| HB1G2.9996.2 | TWTSHANAPFACEIARRIAEEFGWTCTVEKHNGTCEINCQ (SEQ ID NO: 140) |
| HB1G2.10690.2 | TWTSHAKAPFACRIAAEIAREFGWTCTVEKHNGTCEINCQ (SEQ ID NO: 141) |
| HB1G2.8592.2 | EMHVHSMAPFACEIARQILEEFNQNVTVTERGNKCTVTVT (SEQ ID NO: 142) |
| HB1G2.9914.2 | EMHIHARAPFACQIAYEILREFGQNVTVTERGNKCTVTVT (SEQ ID NO: 143) |
| HB1G2.10587.2 | KKKIQVDRFAEAIAVAIKCEFNNLEVHQTFINGYIVLTCK (SEQ ID NO: 144) |
| HB1G2.9247.2 | CFTSVAHSKFACDIIAQILAEFNQEVHVETHGDECRVTSC (SEQ ID NO: 145) |
| HB1G2.9134.2 | CFTSVAHSEFACRIIVEILRQFGQEVHVETHGDECRVTSC (SEQ ID NO: 146) |
| HB1G2.10540.2 | TSHITSNAPFACQIAADIAAEFNWEVHLHEKNGKCTLQIK (SEQ ID NO: 147) |
| HB1G2.9054.2 | TYHSTANAPFACQIAAEIAKSFNWEVHLHEKNGKCTLQIK (SEQ ID NO: 148) |
| HB1G2.9297.2 | TSHSTAKAPFACAIAAEIAARFNWEVHLHEKNGKCTLQIK (SEQ ID NO: 149) |

TABLE 1-continued

| ID | Sequence |
|---|---|
| HB1G2.10938.2 | CMTSHTYAPFAAWIAAEIAKEFGYDVQLQHDGTKLTVHSC (SEQ ID NO: 150) |
| HB1G2.8540.2 | CMTSHTRSPFAAEIAARIAAEFGYDVQLQHDGTKLTVHSC (SEQ ID NO: 151) |
| HB1G2.9915.2 | TITFHCKAPFAAKISAEILKSFRLEVHCQQHGNQVTCKVS (SEQ ID NO: 152) |
| HB1G2.8348.2 | CNKSVCDAPFAAAIAAKIAAEFNWDVQFTQHGSTITLHCC (SEQ ID NO: 153) |
| HB1G2.8951.2 | CYKSVTKSPFAAEIARQIAEEFNWDVQCTQHGDTITCHMC (SEQ ID NO: 154) |
| HB1G2.8611.2 | CTTSVATSPFAAWIAAKILAEFNYEVHVHQHGTQVTVEMC (SEQ ID NO: 155) |
| HB1G2.10885.2 | TYTSIVSSPFAAEIVRQIAAEFGYEVHCTQHGNYVECKVK (SEQ ID NO: 156) |
| HB1G2.8646.2 | TYTTWVQSPFAAEIVRQIAEEFGYEVHCTQHGNYVECKVK (SEQ ID NO: 157) |
| HB1G2.9150.2 | KTQFKVDSFANAIAQAIKCEFNNLPFTVEIHGRTIKIKCK (SEQ ID NO: 158) |
| HB1G2.9572.2 | CVTSQAKTPFAAQIAAEIMREFNIEVHCEKKGPTLKCTSC (SEQ ID NO: 159) |
| HB1G2.10680.2 | TWTSVSAAPFACKIAAEIAREFNWDVTVTQHGRTCKVHVE (SEQ ID NO: 160) |
| HB1G2.8526.2 | TNQSQASSKFAALIAADICREFGLEVHLHKKNGTWTVECN (SEQ ID NO: 161) |
| HB1G2.9791.2 | CVTSQCHSPFACAIAAKIMKEFGWEVHVEEHNGTCHLQVC (SEQ ID NO: 162) |
| HB1G2.10552.2 | TYKSYAHSPFACQIAADIFAEFGYDVQVHQKNGTCTVEVH (SEQ ID NO: 163) |
| HB1G2.931401 | TWKSVSHSPFACEIAAKIFKEFGYDVQVHQKNGTCTVEVH (SEQ ID NO: 164) |
| HB1G2.8291.2 | TYKSYSHSPFACQIAAEIFREFGFDVQVHQKNGTCTVEVH (SEQ ID NO: 165) |
| HB1G2.10604.2 | TWKSVSHSPFACAIAAKIFKEFGYDVQVHQKNGTCTVEVH (SEQ ID NO: 166) |
| HB1G2.9682.2 | TWKSVSHSPFACAIAAEIFRQFGYDVQVHQKNGTCTVEVH (SEQ ID NO: 167) |
| HB1G2.8770.2 | TWKTVSHSPFACWIAAQIWLEFGYDVQVHQKNGTCTVEVH (SEQ ID NO: 168) |
| HB1G2.8257.2 | TWKSVSHSPFACQIAAEIFREFGYDVQVHQKNGTCTVEVH (SEQ ID NO: 169) |
| HB1G2.9627.2 | TWKSYAHSPFACQIAAEIFREFGYDVQVHQKNGTCTVEVH (SEQ ID NO: 170) |
| HB1G2.9197.2 | TFKSYSHSPFACAIAAKIAKEFGWDVQVHQKNGTCTVEVH (SEQ ID NO: 171) |
| HB1G2.10674.2 | CYKIVARAPFACEIAARIAAEFRWDVKIHQHGDHCTVEVC (SEQ ID NO: 172) |
| HB1G2.9172.2 | TRKVEVDDFSNAIAVQIKCEFKGLPYTVTIHGKRVTVHCK (SEQ ID NO: 173) |
| HB1G2.10546.2 | TNQSFARSTFACQIAAEICKEFGLDVQIQKHNGTCHVHCN (SEQ ID NO: 174) |
| HB1G2.1756.2 | ETTYTFDRFDEAMRFAWEAVFKGIPVQWTTKNGKFQVTQH (SEQ ID NO: 175) |
| HB1G2.2629.2 | TTTYTVYSPFDAWMRAMWLKVFGRTVTLHEKNGKVKLETK (SEQ ID NO: 176) |
| HB1G2.2298.2 | TTKYTYESFDEAMRAMWKLAFKGLDVRLTVVNGKWVLETH (SEQ ID NO: 177) |
| HB1G2.0355.2 | KTTYTFPRFDLAMEAMWRAVFNNIPVTVTWKNGKWQVTVK (SEQ ID NO: 178) |
| HB1G2.1783.2 | TPQITIKSPFSAWMAAMWLQAFNIPYDVQTHGDKVTVTQH (SEQ ID NO: 179) |
| HB1G2.2719.2 | TKLIKVDSFDAAMRVAWKLVFLGIPCKITQVNGTWVVQKG (SEQ ID NO: 180) |
| HB1G2.0984.2 | TETLTFTNFDEAMRAMWEYAFKGIPVTVTVKNGKWQVQIN (SEQ ID NO: 181) |
| HB1G2.0014.2 | KKTITVDCFDAAMRQAWKAAFNNIPVTATKKNGKFQVHQK (SEQ ID NO: 182) |
| HB1G2.2718.2 | TETVKVPSFDEAMRQAWAAVFKGIDVRITNLNGTWVLQKN (SEQ ID NO: 183) |
| HB1G2.0923.2 | TTTIVVLAPFSADMARMWAWVFGSPVEVQKHNGTFKIHIH (SEQ ID NO: 184) |
| HB1G2.2578.2 | TKTITVLSPFDAAMRAMWLKVFGIPVEVHTHGDKIKLQKK (SEQ ID NO: 185) |
| HB1G2.1822.2 | TTTIQFDMFDEAMRAAWELAFLGIPYKVTQVNGSWTVTQK (SEQ ID NO: 186) |
| HB1G2.0916.2 | GTKYTFDSFDEAMRFAWKLDFKGIPYTITKKNGKFQVEEK (SEQ ID NO: 187) |
| HB1G2.0718.2 | TQHIQVDSFDEAMRAMWAWVFQGVPVTFHMSGGEFHVEVN (SEQ ID NO: 188) |

TABLE 1-continued

| ID | Sequence |
|---|---|
| HB1G2.2448.2 | TPTTTVYAPFNAWMLAMWLQAFGIDAEIHTHGLTITIKFE (SEQ ID NO: 189) |
| HB1G2.0005.2 | KQTIQFPSFDEAMKAVWKAAFKGLPVTMTKVNGTWKVKIK (SEQ ID NO: 190) |
| HB1G2.1315.2 | TTEIKVDSFDKAMREAWREAFNGKVVHFHCKNGTVTLHIK (SEQ ID NO: 191) |
| HB1G2.2605.2 | ETKVKVDSFDLAMYLAWMYAFNGLPVEIQQHNGTFTLHVK (SEQ ID NO: 192) |
| HB1G2.0806.2 | KTTYTLTAPFDAWMFAMWAAAFGREVHLTKHGDHLKITVG (SEQ ID NO: 193) |
| HB1G2.0901.2 | GRKITVEAPFAAKMVKMWVLAFGSEVHVQEKNGKFTIESR (SEQ ID NO: 194) |
| HB1G2.0841.2 | TTTYTLDSFDAAMEAMWRAVFNGIPVTCTQKNGKWQVTIQ (SEQ ID NO: 195) |
| HB1G2.0157.2 | TKTFTWQNFDNAMKFAWWAAFHGIPVTVTWKNGTAQVTQH (SEQ ID NO: 196) |
| HB1G2.7916.2 | TYTSTSYSSFAAAIAAEILRQFGLEVHVTKKNGTYQVEEN (SEQ ID NO: 197) |
| HB1G2.5453.2 | TYTSTSYSSFAAAIAAEILREFGLEVHVTKKNGTYQVEEN (SEQ ID NO: 198) |
| HB1G2.6187.2 | KITSTCSSSFAAAIAVEILRQFNIPATVTQHGDKWQVTAE (SEQ ID NO: 199) |
| HB1G2.5355.2 | TKTLHVPSFALAIAAAIKAEFKGLEVHLTSRNGEAQVKIK (SEQ ID NO: 200) |
| HB1G2.6182.2 | TTTSDAKAPFAAQIAAEIAREFGYDVQLTKHNGQLQITLK (SEQ ID NO: 201) |
| HB1G2.5166.2 | TWHTTVLSPFAARIAADIAKEFGIPVTLREHGDTITIQMK (SEQ ID NO: 202) |
| HB1G2.7678.2 | TCVVTASSEFAARIAAEIARQFGYEVHVHKKNGTYQVEVR (SEQ ID NO: 203) |
| HB1G2.7380.2 | TYTSFAHSPFAAQIAAKIAAEFGWDVTYTQHGDTLKVHVN (SEQ ID NO: 204) |
| HB1G2.5536.2 | TTTSQAAAKFAADIAAEIARQFGYELHVTKVNGTYKVTQH (SEQ ID NO: 205) |
| HB1G2.5337.2 | TVHITVTRFAAAIAAQILAEFWNLPYTVEIHGTQITVQVQ (SEQ ID NO: 206) |
| HB1G2.4870.2 | ESHTTTRSEFAAWIAAEIWREFGKEVHVKKNGDQYTVTVK (SEQ ID NO: 207) |
| HB1G2.7932.2 | KTTYHMPSKFAAAIAAKILAEFGIPVTVTKAGDTYVLQEK (SEQ ID NO: 208) |
| HB1G2.5276.2 | TNTLYASSKFAALIAAEIARQFNWDVTVSQINGTWVVTVH (SEQ ID NO: 209) |
| HB1G2.4921.2 | TTHLTYRSPFAARIAAEILREFGLPVNVQKNGPTLTVQVN (SEQ ID NO: 210) |
| HB1G2.5417.2 | TTHLTYRSPFAAAIAAEILRQFGLPVNVQKNGPTLTVQVN (SEQ ID NO: 211) |
| HB1G2.8018.2 | TYTSTATSKFAAEIAAQIAAEFGIKVEVHQKNNRWQVTEK (SEQ ID NO: 212) |
| HB1G2.6777.2 | TWHSTSSKEFAADIARQIFEEFGYDVQVHEKNGQYEVQVH (SEQ ID NO: 213) |
| HB1G2.6834.2 | TWHSHAYSQFAAEIAARIAKEFNIPVQLHEKNGKVEVQMH (SEQ ID NO: 214) |
| HB1G2.6526.2 | TYTITSHSSFAAKIAADILKEFNIPFELHKKNGTVQVQNE (SEQ ID NO: 215) |
| HB1G2.5588.2 | EVTRNAASKFAADIAAKIAAEFGLKVTVTQKNGQFFVTEK (SEQ ID NO: 216) |
| HB1G2.7255.2 | TQTCTSKDSFAARIAAEILREFNIPVSFTQHGDTFQVTCH (SEQ ID NO: 217) |
| HB1G2.6621.2 | TLESTAESPFAAEIAARIMAEFGYKVTTHKKGDTLTVKIE (SEQ ID NO: 218) |
| HB1G2.6411.2 | TTTSTARNPFAAWIAAEIAKEFNWEVHLEDTNGTLTVHIH (SEQ ID NO: 219) |
| HB1G2.5045.2 | TQTITAEASFAARIAAEILREFGYEVHVEQHGSTYTVHEK (SEQ ID NO: 220) |
| HB1G2.7035.2 | TLKIQAHSPFAAQIAADIWKEFGYDVQVHQKNGTFTVEVH (SEQ ID NO: 221) |
| HB1G2.6337.2 | TVTSTANDKFAAEIARQILEEFGIPVKIHKKNGTWQVESH (SEQ ID NO: 222) |
| HB1G2.7598.2 | TTKSTAKSPFAAAIAAEIARQFGWEVHVTQHGDKVTVKIG (SEQ ID NO: 223) |
| HB1G2.4925.2 | TYQTQARSEFAARIAAEINREFGYEVHVTQVGPTYKVTVK (SEQ ID NO: 224) |
| HB1G2.3579.1 | TIEFDVESPFSAKMAQMWCAAFGAPYTVHKHGTKITVKCE (SEQ ID NO: 225) |
| HB1G2.3837.1 | TEKIQVESPFAAKMVAMWCLAFGAPFTVKQHGDTVTIHCS (SEQ ID NO: 226) |
| HB1G2.4063.1 | GVTYTYHSPFDAEMARMWCWAFGSPVEIQEHGDKIQVTCG (SEQ ID NO: 227) |

TABLE 1-continued

| ID | Sequence |
|---|---|
| HB1G2.4379.1 | TIHLHLTHFDIVMRAMWKCVFNGLKVQTKKKNGTITLECH (SEQ ID NO: 228) |
| HB1G2.3562.1 | KKKVQVESPFSAWMRAMWALVFGTPVTCEQHGDTVTCHIK (SEQ ID NO: 229) |
| HB1G2.3586.1 | ETTVKVDSFDAAMRAMWKAAFKGLEVHCEQHGDTVKCTIH (SEQ ID NO: 230) |
| HB1G2.4235.1 | ETTVKVDSFDAAMRAMWKAAFLGLEVHCEQHGDTVKCTIH (SEQ ID NO: 231) |
| HB1G2.4676.1 | ETTVKVDSFDNAMRAMWKAAFKGLEVHCEQHGDTVKCTIH (SEQ ID NO: 232) |
| HB1G2.3254.1 | KKTVTVHSPFEAWMRAMWAKAFGLEVHCTQHGDQITCHIE (SEQ ID NO: 233) |
| HB1G2.3011.1 | CTTYHVECPFNCWMRYMWAAAFGAEVHLHQHGDTCQVTVC (SEQ ID NO: 234) |
| HB1G2.4249.1 | REKIVVHSPFDAAMAKMWCEVFGVPVEIRKKNGTYTVHCG (SEQ ID NO: 235) |
| HB1G2.4103.1 | TETYEFDSPFDAWMRAMWWQAFGIPVTCSQHGNTVKCHVN (SEQ ID NO: 236) |
| HB1G2.8494.1 | EETSTSYAPFACEIARQIAEEFNWKVRCTQHGNQCTCHVH (SEQ ID NO: 237) |
| HB1G2.10864.1 | TIHSTAYAPFACRIAAKIAKEFNIPVTLREHGDTCTIQMK (SEQ ID NO: 238) |
| HB1G2.8472.1 | CQHITSNSEFAAEIAARIAAEFGLEVHLHKKNGTYTVQVC (SEQ ID NO: 239) |
| HB1G2.11001.1 | RYKSTAWSPFACEIARQIIEKFNIPVEIHITNGKCTIHVS (SEQ ID NO: 240) |
| HB1G2.8527.1 | RYKSTNWNPFACEIAKRIILEFNIPVEIHITNGKCTIHVS (SEQ ID NO: 241) |
| HB1G2.10787.1 | RFKSTNWSPFACEIARQIIEKFNIPVEIHITNGKCTIHVS (SEQ ID NO: 242) |
| HB1G2.9157.1 | RWKSTAWSPFACKIAEKIIREFNIPVEIHITNGKCTIHVS (SEQ ID NO: 243) |
| HB1G2.9597.1 | RYKSTNWTPFACEIARQIIEEFNIPVEIHITNGKCTIHVS (SEQ ID NO: 244) |
| HB1G2.8343.1 | TFTSVAYSSFACAIAAEIARQFGWEVHVEKHNGTCKVKIH (SEQ ID NO: 245) |
| HB1G2.10204.1 | TWTTVSNSPFAAWIAAEIARQFNLEVHCETHNGTVTCHTK (SEQ ID NO: 246) |
| HB1G2.8984.1 | TWTSHAKAPFACEIARQIAEEFGWTCTVEKHNGTCEINCQ (SEQ ID NO: 247) |
| HB1G2.9022.1 | TYTSHARAPFACEIARQIAEEFGWTCTVEKHNGTCEINCQ (SEQ ID NO: 248) |
| HB1G2.9467.1 | TYTSHAAAPFACEIAKQIAAEFGWTCTVEKHNGTCEINCQ (SEQ ID NO: 249) |
| HB1G2.10009.1 | TWTSHAKAPFACEIARRIAEEFGWTCTVEKHNGTCEINCQ (SEQ ID NO: 250) |
| HB1G2.10398.1 | EMHIHARAPFACQIAYDILKEFGQNVTVTERGNKCTVTVT (SEQ ID NO: 251) |
| HB1G2.9389.1 | TSKSTSMSEFAAEIAARICKEFGWPVRVRKNGDKYTVECE (SEQ ID NO: 252) |
| HB1G2.9327.1 | CFTSVAHSEFACRIIAKILWEFGQEVHVETHGDECRVTSC (SEQ ID NO: 253) |
| HB1G2.8453.1 | CFTSVAHSQFACEIIAEILRQFGQEVHVETHGDECRVTSC (SEQ ID NO: 254) |
| HB1G2.10392.1 | TSHITSNAPFACAIAAKIAAEFNWEVHLHEKNGKCTLQIK (SEQ ID NO: 255) |
| HB1G2.11004.1 | TYHSTSNAPFACQIAAEIAKEFRWEVHLHEKNGKCTLQIK (SEQ ID NO: 256) |
| HB1G2.9563.1 | TAHITARAPFACRIAAEIAREFNWEVHLHEKNGKCTLQIK (SEQ ID NO: 257) |
| HB1G2.9764.1 | TSHITSEAPFACQIAAEIAKEFNWEVHLHEKNGKCTLQIK (SEQ ID NO: 258) |
| HB1G2.8782.1 | TSHITSESPFACQIAAEIAKEFNWEVHLHEKNGKCTLQIK (SEQ ID NO: 259) |
| HB1G2.10339.1 | TDHSTSRAPFACQIAAEIAKEFNWEVHLHEKNGKCTLQIK (SEQ ID NO: 260) |
| HB1G2.10008.1 | CMTTHTRAPFAAQIAADIAAKFGYDVQLQHDGTKLTVHSC (SEQ ID NO: 261) |
| HB1G2.10426.1 | CMTIHTYAPFAAEIAARIAAEFGYDVQLQHDGTKLTVHSC (SEQ ID NO: 262) |
| HB1G2.10665.1 | CMTIHTRMPFAAEIAARIAKEFGYDVQLQHDGTKLTVHSC (SEQ ID NO: 263) |
| HB1G2.9538.1 | CTTIEVTRFAQAIAAAIKCEFKGKKITTHAHGDTIKLTCC (SEQ ID NO: 264) |
| HB1G2.10109.1 | TQTSISWCPFACQIAVDIAASFNWDVTVTQHGDKCTVHIN (SEQ ID NO: 265) |
| HB1G2.8399.1 | TQTSISWCPFACEIARQIAESFNWDVTVTQHGDKCTVHIN (SEQ ID NO: 266) |

TABLE 1-continued

| ID | Sequence |
|---|---|
| HB1G2.8678.1 | TETSISYCPFACRIAVEIARSFNWDVTVTQHGDKCTVHIN (SEQ ID NO: 267) |
| HB1G2.10037.1 | CRTSKCYSPFAAAIAAEIARQFNWKVTVHQHGDTIHVTIC (SEQ ID NO: 268) |
| HB1G2.10381.1 | CYKSVTKSPFAAEIARQIAEEFNWDVQCTQHGTTITCHMC (SEQ ID NO: 269) |
| HB1G2.8579.1 | TYTTWTSSPFSAEIVRQIAEEFGYEVHCTQHGNRVECKVK (SEQ ID NO: 270) |
| HB1G2.9655.1 | KTQFKVDSFANAIAQAILCEFNNLPFTVEIHGRTIKIKCK (SEQ ID NO: 271) |
| HB1G2.10353.1 | CITSQAKTPFAAQIAAEIMREFNIEVHCEKKGPTLKCTSC (SEQ ID NO: 272) |
| HB1G2.9828.1 | TCRAQSKSKFAALIAAEICRQFGLEVHLHKKNGTWTVECN (SEQ ID NO: 273) |
| HB1G2.9560.1 | TAVACSRSSFSAAIAAEICRQFRWEWHIETHGDVYKVTCK (SEQ ID NO: 274) |
| HB1G2.10898.1 | TYKLVSHSPFACAIAAEIFRQFNYDVQVHQKNGTCTVEVH (SEQ ID NO: 275) |
| HB1G2.10454.1 | TYKLVSHSPFACKIAAEIFKEFNYDVQVHQKNGTCTVEVH (SEQ ID NO: 276) |
| HB1G2.10646.1 | TWKSYSHSPFACQIAAEILREFGFDVQVHQKNGTCTVEVH (SEQ ID NO: 277) |
| HB1G2.9040.1 | TWKTYAHSPFACWIAAEIFKEFGFDVQVHQKNGTCTVEVH (SEQ ID NO: 278) |
| HB1G2.8417.1 | TWKSVSHSPFACKIAAEIFKEFGYDVQVHQKNGTCTVEVH (SEQ ID NO: 279) |
| HB1G2.8683.1 | TWKSYSHSPFACEIAARIFKEFGYDVQVHQKNGTCTVEVH (SEQ ID NO: 280) |
| HB1G2.8882.1 | TWKTVSHSPFACEIAARIWKEFGYDVQVHQKNGTCTVEVH (SEQ ID NO: 281) |
| HB1G2.10023.1 | TRTSQQESEFACRIAAEIARQFGLEVHLTKHGPQCKITVK (SEQ ID NO: 282) |
| HB1G2.8418.1 | TTTYKFQSFALAIAAAIKCEFNQVPYEVQNHGTTYKVKCT (SEQ ID NO: 283) |
| HB1G2.9437.1 | TYTSTASYDFACQIIAEICRQFGWPVDVETHGKTCHVKCH (SEQ ID NO: 284) |
| HB1G2.8607.1 | TSTSTASSSFACQIIADICANFGWPVDVETHGKTCHVKCH (SEQ ID NO: 285) |
| HB1G2.8740.1 | TYESRARSPFACWILAEILREFGGEVHCTEQNGTCTCKVQ (SEQ ID NO: 286) |
| HB1G2.1509.1 | TTTYTWDSFDAAMEAMWRLAFNGIPVQITMKNGKWQVKEH (SEQ ID NO: 287) |
| HB1G2.0419.1 | TETLHFQSFDEAMEAAWRAAFKGVPYEVQVHGKTYTVHIK (SEQ ID NO: 288) |
| HB1G2.0463.1 | TPQITIKSPFSAWMAAMWLEAFNIPYDVQTHGDKVTVTQH (SEQ ID NO: 289) |
| HB1G2.1134.1 | TKTVQVDSFDEAMRVAWKAAFNNIKVQIQKVGTTVKLHLH (SEQ ID NO: 290) |
| HB1G2.2540.1 | TETLTFTNFDEAMRAMWEWVFKGIPVTVTVKNGKWQVQIN (SEQ ID NO: 291) |
| HB1G2.1190.1 | TTTYTYLSPFNAWMRAMWKQAFGIPVTWKKHGDTLTVHEH (SEQ ID NO: 292) |
| HB1G2.2863.1 | TEKIQVYAPFNAWMRAMWALVFGVPVKVTQKNGTLTLHLN (SEQ ID NO: 293) |
| HB1G2.2883.1 | ETTYTYESPFEAAMAAMWWRAFGVPVTVHTHGTKIKVTTK (SEQ ID NO: 294) |
| HB1G2.1323.1 | KKEVVVYSPFSAKMVAMWAQVFGVPYEVHQHGTTITVKID (SEQ ID NO: 295) |
| HB1G2.0948.1 | TQKFTYDSFDEAMRAMWKLVFNGVPARVTILNGKWQVEKK (SEQ ID NO: 296) |
| HB1G2.2957.1 | TKQIKVDSFDAAMKAMWEAVFRNLDVQIQQENGTWTVKTK (SEQ ID NO: 297) |
| HB1G2.2430.1 | TEHITVDSFDKAMDTAWRYVFQGIPATVTWKNGQWTVKVH (SEQ ID NO: 298) |
| HB1G2.1361.1 | TTTYTYDSFDEAMRAMWEAVFKGLEVHIEIHGKQFQVTVH (SEQ ID NO: 299) |
| HB1G2.0540.1 | TQHITKEAKFAAKMAMMWAKVFGSEVRVTQHGTQLTIELH (SEQ ID NO: 300) |
| HB1G2.2286.1 | TKFIKYDSKFAAEMARMWYEVFGSEVHVSQINGTWVVKEN (SEQ ID NO: 301) |
| HB1G2.2495.1 | TTTYTLDSFDAAMRAMWKAVFKGIPVTCTQKNGKWQVTIQ (SEQ ID NO: 302) |
| HB1G2.2908.1 | TTTYTLDSFDAAMRMWKAVFKGIPVTCTMKNGKWQVTIQ (SEQ ID NO: 303) |
| HB1G2.2858.1 | TTTYTLDSFSAAMKAMWEAVFNGIPVTCTQKNGKWQVTIQ (SEQ ID NO: 304) |
| HB1G2.2732.1 | GTTYQFHSFTEAMRAAWKAVFLNLPYEITQVGDTFQVTIK (SEQ ID NO: 305) |

TABLE 1-continued

| ID | Sequence |
|---|---|
| HB1G2.7767.1 | TMHSWASDQFAAEIAARIAREFGYDVTFTEKNGHVEVEVN (SEQ ID NO: 306) |
| HB1G2.7118.1 | TIHSWASDQFAAKIAADIAREFGYDVTFTEKNGHVEVEVN (SEQ ID NO: 307) |
| HB1G2.6432.1 | TATVTTRSEFAAKIAAEIWREFGYEVHVHKKNGTYQVEVR (SEQ ID NO: 308) |
| HB1G2.7833.1 | TATNTTRSKFAALIAAKIWAEFGYEVHVHKKNGTYQVEVR (SEQ ID NO: 309) |
| HB1G2.5156.1 | TPQTTAYSPFAAEIAAKILREFNIPYDVQTHGDKVTVTAH (SEQ ID NO: 310) |
| HB1G2.7382.1 | TPQTTAYSPFAAWIAAKILEEFNIPYDVQTHGDKVTVTAH (SEQ ID NO: 311) |
| HB1G2.7896.1 | TQTCEARMPFAAEIAARIAAEFNWPVKLHHHGDTITVQVN (SEQ ID NO: 312) |
| HB1G2.6842.1 | KYTSTASDSFAAKIAALILKEFNIPFEVQTHNGTYKVTSK (SEQ ID NO: 313) |
| HB1G2.6582.1 | TIKSTARSPFAAAIAAKIAAEFGYTVKLSQKNGKWHLHVN (SEQ ID NO: 314) |
| HB1G2.7191.1 | TDTSHAKSKFAAEIAARILAEFGIPAKVSKLNGTWVVHEN (SEQ ID NO: 315) |
| HB1G2.7301.1 | TKTITARSEFAARIAAEILRQFGIDVQITTKNGKYQLQNK (SEQ ID NO: 316) |
| HB1G2.5676.1 | SYFSTANSPFAAQIAAEILASFNIPVTLRTLNGKVQVERH (SEQ ID NO: 317) |
| HB1G2.5858.1 | TAEVNARSPFAAKIAALIWKEFGYEVEVHKKNGKFTLHSQ (SEQ ID NO: 318) |
| HB1G2.5468.1 | QTTSTSNMPFAAEIAARIAWEFNIPVEFTQHGTKVKLTVK (SEQ ID NO: 319) |
| HB1G2.5062.1 | KTTYHMPSKFAARIAAEILREFGIPVTVTKAGDTYVLQEK (SEQ ID NO: 320) |
| HB1G2.6661.1 | TRTLYASSDFAAKIAAKIAASFNWDVTVSQINGTWVVTVH (SEQ ID NO: 321) |
| HB1G2.4910.1 | TYTAEASAKFAARIAAEIFREFGYEVHITQKNGKWQVTVK (SEQ ID NO: 322) |
| HB1G2.6181.1 | TYTIVVNSPFAAWIAAEIAREFNWEVQVEDHGNTFKLKVN (SEQ ID NO: 323) |
| HB1G2.5231.1 | TSTSQVRMPFAAWIAAEIMKEFGYDVQVEQHGDTLKITSK (SEQ ID NO: 324) |
| HB1G2.5651.1 | TSTSQVRMPFAAWIAAKIMADFGYDVQVEQHGDTLKITSK (SEQ ID NO: 325) |
| HB1G2.6857.1 | TYTITSHSSFAAEIAARILKEFNIPFELHKKNGTVQVQNE (SEQ ID NO: 326) |
| HB1G2.6066.1 | TYTITSHSSFAAAIAAKILKEFNIPFELHKKNGTVQVQNE (SEQ ID NO: 327) |
| HB1G2.6516.1 | TFTSQARSDFAAQIAADILAEFGIKFHLTQNGDTYKVTSH (SEQ ID NO: 328) |
| HB1G2.5587.1 | TFTMQARSTFAAAIAAEILREFGIKFKLTQNGDTYKVISH (SEQ ID NO: 329) |
| HB1G2.7749.1 | TTFRKAPSLFAALIAAQILAEFNVEVHITQRNGTYLVEKR (SEQ ID NO: 330) |
| HB1G2.4752.1 | TDQSVCHSEFAARIAAKIAKEFNLEVHITQKNGTWKITVK (SEQ ID NO: 331) |
| HB1G2.6534.1 | TYTSVATSEFAARIAAEIAREFGYEVHVTKKNGQFQVTVK (SEQ ID NO: 332) |
| HB1G2.7834.1 | TQQSHAADSFAAEIAARINKEFGYEVHVTQVNGTFTVKTK (SEQ ID NO: 333) |
| HB1G2.7232.1 | TAVVQAKSPFAAAIAVEIARQFNLPVTVEKHGKTLKVTIH (SEQ ID NO: 334) |
| HB1G2.7182.1 | TLESTAASPFAAAIAAEIWKEFGYKVTTHKKGDTLTVKIE (SEQ ID NO: 335) |
| HB1G2.6512.1 | TFTIHAPSKFAAKIAADILKEFNIPVTVTKKNGTWEVKCK (SEQ ID NO: 336) |
| HB1G2.5768.1 | KIELTAYSPFAAWIAAEILKEFNYDVQVHTDGDTITVKVK (SEQ ID NO: 337) |
| HB1G2.5203.1 | TYTSHTNSPFAAAILAEILRQFNIPVQVHQKNGEVTVTEH (SEQ ID NO: 338) |
| HB1G2.6754.1 | TEHSEVRSKFAAAIAAEIARSFNWEVHLTKTNGYWEVRVK (SEQ ID NO: 339) |
| HB1G2.5967.1 | TYTVVANSPFAAEIVKRILAEFNIPVTVQKHGGTYHITSH (SEQ ID NO: 340) |
| HB1G2.5236.1 | TYTVVAQSPFAAQIVKDILAEFNIPVTVQKHGGTYHITSH (SEQ ID NO: 341) |
| HB1G2.5320.1 | TYTVVANSPFAAAIVAKILWEFNIPVTVQKHGGTYHITSH (SEQ ID NO: 342) |
| HB1G2.5968.1 | TYTSTTAAKFAAQIAADIAAEFGIPVTLTKKNGKWQVHEN (SEQ ID NO: 343) |
| HB2.8292.3 | TTTVTTTSPFSCKMRAMWAEAFGRTFEVRTEGTTCEVRFH (SEQ ID NO: 344) |

TABLE 1-continued

| ID | Sequence |
|---|---|
| HB2.7064.3 | TCQEIQPTSFDDCMKLLWKAVFTGTCRVELRPGGNCRVRCCG (SEQ ID NO: 345) |
| HB2.10520.3 | EDYKAENDFDKCMKLMWIAAFKGCKIIFNGTRCRVIC (SEQ ID NO: 346) |
| HB1.6752.3 | TFRSVATSEFAAEIAKRILAEFGYTVHIQRHGTTITVESR (SEQ ID NO: 347) |
| HB1.5118.3 | TYTVESATRFAAEIAREIAREFGYDAQIREENGTFKLHVG (SEQ ID NO: 348) |
| HB1.5852.3 | TAYIEAPSKFAADIAAQILAEFGMTVTVTDDNGKFKVTVG (SEQ ID NO: 349) |
| HB1.6811.3 | TMTSITTSPFAAEIAARIWAEFGYTVRIETRGKTVHVTVD (SEQ ID NO: 350) |
| HB1.5702.3 | TSRVRATSKFAALIAAEIAREFGYTVDVQEVNGQWEVTFD (SEQ ID NO: 351) |
| HB1.5702.3.3 | TSGVRATSKFAALIAAEIAREFGYTVDVQEKNGEWRVVFD (SEQ ID NO: 352) |
| HB1.6093.3 | TFTSKASDRFAADIAAEIMKEFGYDVRVTKVGTTWKVESE (SEQ ID NO: 353) |
| HB1.5227.3 | TYEFEARSPFAAAIARDILLEFGQTVTVEERNGRFRVRAD (SEQ ID NO: 354) |
| HB1.7852.3 | TMTSVAYSDFAAEIAAQIAREFGYTVRKEKRNGTITLEVH (SEQ ID NO: 355) |
| HB1.5103.3 | TYTSEVWTPFAAAIAYEIARQFGIPVESNTHGPEFRFNMK (SEQ ID NO: 356) |
| HB1.11596.3 | TIESTTRSEFAAAIACEIARQFGWTVTCEKRGTTLTVRTT (SEQ ID NO: 357) |
| HB1.11591.3 | TLHITSYSPFAAAIACEIAREFGYTVECRKDGTRLEVHSK (SEQ ID NO: 358) |
| HB1.10854.3 | TATSTANDSFACKIAKKIILEFNLTVEVTKSNGYCEVRCK (SEQ ID NO: 359) |
| HB1.10511.3 | SFACKIAAEILRQFGKSEEEIKRALKKAGCSPDEAEEAIRALR (SEQ ID NO: 360) |
| HB1.10775.3 | CPYCEEAKEAAKEGNFARIIAAAIRAEFAGDQECAKCAKKV (SEQ ID NO: 361) |
| HB1.8855.3 | TCEEIRGNFAECIRAEIEARFQGCEFEKHGDQCRRCC (SEQ ID NO: 362) |
| HB1.11432.3 | ECRRWTDNFAKCIAAKILAEFQGCEFREDGHRCELCC (SEQ ID NO: 363) |
| HB1.10027.3 | TTTCVRNNFAEAIRLKIECEFKGLEIREENGEVCCHG (SEQ ID NO: 364) |
| HB1.5280.3 | TFCVDCNSPFACQIAKDIADEFNPTGRCTVTNGRVCCQF (SEQ ID NO: 365) |
| HB1.4899.3 | TEDCERECRKMSKTMSFADEIACQIMVEFWGSSQCEKMKRDLKR (SEQ ID NO: 366) |
| HB1.8724.3 | TCKRWEDRFADCIAAEILAEFWGCEYRRHGWTCELCC (SEQ ID NO: 367) |
| HB1.5481.3 | CTTIEATSFAECIALEILAEFNNCEVRKHGDRCEVTCC (SEQ ID NO: 368) |
| HB1.6211.3 | CTCGATTFAELIACKIMLDFGWCVETQDGTQKIKVCCG (SEQ ID NO: 369) |
| HB1.11457.3 | TCKRWENRFADCIAAEIEAEFKGCEYRRHGYTCELCC (SEQ ID NO: 370) |
| HB1.9730.3 | PSSVAQAGTFACQIACKIAAEFGCTCTTDGDTCKVTC (SEQ ID NO: 371) |
| HB1.8771.3 | RSSVAQAGQFACEVACRIAASFGCTCTTDGDTCKVTC (SEQ ID NO: 372) |
| HB1.7749.2 | TYELEVTSKFAAEIARQILEEFGITATVEKVNGQYRIKYD (SEQ ID NO: 373) |
| HB1.9549.2 | PFACRIAAKIAAEFGYSEEQIKELLKNAGCSEDEARDAVEYLR (SEQ ID NO: 374) |
| HB1.10414.2 | GFACEIAAKIAREFGRSKDQIKEILQKCGVSEDEAEEILRRLG (SEQ ID NO: 375) |
| HB1.9905.2 | KYTSTNSSKFACAIAKQILAEFGFTVTCTHENGTCTCTYG (SEQ ID NO: 376) |
| HB1.9048.2 | TYWAQSPSSFAAEIAAQICREFRQTVEVTKENGTYKVRCE (SEQ ID NO: 377) |
| HB1.6928.2 | CIEISVTTPFACQIAAEIWRAFGYEVKIDDDNGNCRLHVC (SEQ ID NO: 378) |
| HB1.6928.2.3 | CIEQSFTTLFACQTAAEIWRAFGYTVKIMVDNGNCRLHVC (SEQ ID NO: 379) |
| HB1.4840.2 | CETRTYTSFAAAIRARIEAEFEGRFCEEEVRGREFRFTCC (SEQ ID NO: 380) |
| HB1.6394.2 | CQDYTFTDPFACQIAAEILRDFGYDCTVQTNNGECRVRCC (SEQ ID NO: 381) |
| HB1.6394.2.3 | CQEYRFTNPFACQIALEILRDFGYACTVQTINGECRVRCC (SEQ ID NO: 382) |
| HB1.9985.2 | EKQKTRSSFAECIAMKIEAEFRGCEFYQDGEWCVIVC (SEQ ID NO: 383) |

TABLE 1-continued

| ID | Sequence |
|---|---|
| HB1.7921.2 | CYEFQSKAKFACKIAELILREFGQEVRRQDDGNTCRIESC (SEQ ID NO: 384) |
| HB1.9682.2 | PTSVAQAGSFACWIACEIAREFGCTCTTDGDTCKVTC (SEQ ID NO: 385) |
| HB1.5724.2 | CTEQYHCTRFAECIAIQIRAEFEGKECTIDLENQRVECHC (SEQ ID NO: 386) |
| HB1.4681.1 | TTRYHYTNFDLAMEAMWRAVFKGLRVTLKQENGQWFVEID (SEQ ID NO: 387) |
| HB1.7242.1 | TERIKVDSFDAAMRAAWELAFRGQQYRITKHNGTWFVERG (SEQ ID NO: 388) |
| HB1.11116.1 | TTKIRVTSFDNCMRLAWKATFKGLTVTIRRHGKTCEVESR (SEQ ID NO: 389) |
| HB1.10063.1 | TCKCLENPTFDLKMRLIWLCAFAKECRNHGNRVCVCE (SEQ ID NO: 390) |
| HB1.6779.1 | TCQTLQPTSFDDCMKALWLAAFTGTCRFEFRPGGKCRVTCCG (SEQ ID NO: 391) |
| HB1.5706.1 | PFAVRIAAQIAADFGYSEEQIKELLKNAGASEDEARDAVEYLR (SEQ ID NO: 392) |
| HB1.7707.1 | PFAAKIAAAILAEFGYSPEQIKRSLKKQGVSEDEAEKILRDLL (SEQ ID NO: 393) |
| HB1.7935.1 | PFAAKIAVKILIEFGVTPDEIKKIAKKLGLSEDTVEEIIRRIY (SEQ ID NO: 394) |
| HB1.6935.1 | PTFANLIAAKIAAEFGYRDKARELAKRAGLSDDQADQFVRDLG (SEQ ID NO: 395) |
| HB1.7256.1 | APFALKIAAKILAEFGNKDKARKVLEKAGLSPDQAEEFIRRVD (SEQ ID NO: 396) |
| HB1.5841.1 | TSTIVCYSEFAARIAEKILREFGYTVTVRTHGTEFRLEVH (SEQ ID NO: 397) |
| HB1.5486.1 | TYESVARAKFAADIARDIAAEFGYDLEVREENGNFRLKTK (SEQ ID NO: 398) |
| HB1.5649.1 | RFRIEARSKFAAEIAARILAEFGLDVTVTKKNGYYFVESG (SEQ ID NO: 399) |
| HB1.6190.1 | TMHITSYSPRAAKIAALIALEFGYTVELRKDGTRLEVHSK (SEQ ID NO: 400) |
| HB1.6278.1 | TTEQEARSEFAAAIAAEIARQFGYTVTVQKSGTRLRVRVG (SEQ ID NO: 401) |
| HB1.4854.1 | TFTSTAWNRFSAEIARKIAEEFGYTVTIEDRNGDFHVRVT (SEQ ID NO: 402) |
| HB1.6056.1 | TQRVRASSRFSAMIAAKILKEFGYTVHVYEDNGRFEIESR (SEQ ID NO: 403) |
| HB1.6876.1 | TVTTVTLSEFAARIAEKILREFGITVEVTQENGTWKVRTE (SEQ ID NO: 404) |
| HB1.7380.1 | TIEVTVRAEFAARIAYKIMKEFGWDVRVRQENGTWKIESD (SEQ ID NO: 405) |
| HB1.5621.1 | TYTIIAKSEFAARIAAKILASFRYRVELRKHNGTVTIRFD (SEQ ID NO: 406) |
| HB1.7462.1 | TSRCVTRSSFAAQIAKDILAEFGYRVEVEEHNGNFEVRYD (SEQ ID NO: 407) |
| HB1.6987.1 | TYTTVVCSEFAAKIAAEIAREFGYTVTIRQENGKWHVEVR (SEQ ID NO: 408) |
| HB1.4439.1 | PFALEIAAKIMAEFGVSSEEIKRELKKQGASDDTAEELARRAG (SEQ ID NO: 409) |
| HB1.7912.1 | LFAARIAAKIAAEFGASPDEIKEILKRAGVSEDEAEQIVQELF (SEQ ID NO: 410) |
| HB1.10604.1 | RFACAIAFKILWEFGYSPEEIREILKRAGCSPKEAEEAEREAL (SEQ ID NO: 411) |
| HB1.9152.1 | TYTSIVRAEFACRIACEIMREFGWQVHCRKHGTTCKVESR (SEQ ID NO: 412) |
| HB1.8242.1 | TYTVETVSDFSCWIAAEIAREFGYEVELRKHGTKCKVRIG (SEQ ID NO: 413) |
| HB1.9107.1 | TCTTESATRFACEIAREIAREFGYDAQIREENGTCKLHVG (SEQ ID NO: 414) |
| HB1.9960.1 | TRELIAYSDFACRIAEEILAEFGQTVTVEKRNGTCHIRVD (SEQ ID NO: 415) |
| HB1.8600.1 | TFTSHAKQDFACEIAARIAAEFGWDVQVRKHGTTCEVEVR (SEQ ID NO: 416) |
| HB1.10917.1 | GQRMVVPSEFACEIARQILEEFGQTVTVRKTGGYCEIESN (SEQ ID NO: 417) |
| HB1.11180.1 | TDTSTTVSPFAAKIACDIIREFNWDVRCTQENGQWKVERR (SEQ ID NO: 418) |
| HB1.10731.1 | TYTIIAYAPFACEIARQILEEFNYTVTRTTDGTTCTLSYE (SEQ ID NO: 419) |
| HB1.10944.1 | TQRVRAWSRFACEIAREILREFGYTVHVYEDNGRCEIESR (SEQ ID NO: 420) |
| HB1.10953.1 | TMTSLAYSQFACDIARRIAAEFGYTVTIEDRNGECHLTVD (SEQ ID NO: 421) |
| HB1.9912.1 | TFISVTRSSFACAIAAQILQEFNIPYEVETRGTTCRIRSE (SEQ ID NO: 422) |

TABLE 1-continued

| ID | Sequence |
|---|---|
| HB1.10493.1 | TYEFEAYSPFACTIAELILREFGQTVTVEERNGRCRVRAD (SEQ ID NO: 423) |
| HB1.11458.1 | TMTSVSYSDFACEIAAKIAWEFGYTVRKEKRNGTCTLEVH (SEQ ID NO: 424) |
| HB1.10904.1 | PFALCIAAKILLEFGKNPDEIREFLRNAGYDQSQAEEALKCAL (SEQ ID NO: 425) |
| HB1.8150.1 | RFACEIAAKILSEFGKSTKEIERVLRECGVSDDEAEEILRRYG (SEQ ID NO: 426) |
| HB1.7567.1 | CYETEVHSPFACKIAEDILREFGQRVERQDDGTSCRIRVC (SEQ ID NO: 427) |
| HB1.6521.1 | CETRTYTNFAAEIAARIEAYFRGQPCEFRDDGGKVERRCC (SEQ ID NO: 428) |
| HB1.6012.1 | CWETTVSSEFAARIAQKIAKAFGWDVQFEDNGDKFRLRNC (SEQ ID NO: 429) |
| HB1.10567.1 | SEELKRLCKEGNFAELIRFAIEAEFNRNPEEAERAKKC (SEQ ID NO: 430) |
| HB1.11478.1 | QRRRTEASEFACRIAQEILREFGWQWTQDGRTCEIHA (SEQ ID NO: 431) |
| HB1.10091.1 | CPYCEWAKEAAKNGNFAQAIAWAIKASFQGDPSCAQCALDV (SEQ ID NO: 432) |
| HB1.11115.1 | SCTTCDCNNFACKIAAKIAAEFGATSSCSGGLLTFCF (SEQ ID NO: 433) |
| HB1.9135.1 | TRYTVCWGSFACKIAYEIAREFGCQCQHSGGTVECEC (SEQ ID NO: 434) |
| HB1.9973.1 | STNSCEGCNFACQIAAEIARDFGCDVRCTGGHVEIHC (SEQ ID NO: 435) |
| HB1.9183.1 | PELRFQAGNFACEIACRIAKEFGCTCTREGNTCRVSC (SEQ ID NO: 436) |
| HB1.10408.1 | TCECCDNPSFAEKIACEIKREFARKTRDHGNKVCNCF (SEQ ID NO: 437) |
| HB1.8668.1 | ETREVQNDFARCIAEKILAEFRGCQFKLDGTTCYVYC (SEQ ID NO: 438) |
| HB1.9937.1 | TTECVTDDFAKIIALKIQCEFWGCEVHESNGKICCHC (SEQ ID NO: 439) |
| HB1.5061.1 | TTCQEFSDGTFAEIIRLKIEAEFKGCRVEERPLEGRVRVCCG (SEQ ID NO: 440) |
| HB1.6481.1 | TCEEVQATNFAEKIAVEIKAQFKGCPYTTDGDKVTICC (SEQ ID NO: 441) |
| HB1.5933.1 | TQCFQNCSSPFACRIAAEILKAFGWDCQEEPDNNRICCQEG (SEQ ID NO: 442) |
| HB1.7094.1 | CDQMEASCPFACRIAAEINREFGYRVEIHDDNGRCHLKRC (SEQ ID NO: 443) |
| HB1.7200.1 | CQELTLWAPFACEIAARIMWEFGLDVDRQEEGNHCRLRSC (SEQ ID NO: 444) |
| HB1.10268.1 | PQRTWTTAPFACAIAEQILAEFGMQWENRNNKECRAQA (SEQ ID NO: 445) |
| HB1.5137.1 | PCDDCKEELERRGCSFAVKIAVDIACEFNMSSEYCERMRRWCS (SEQ ID NO: 446) |
| HB1.11497.1 | TTIKITNDFAKCIAAKILAEFWGCKFEENGHECYVYC (SEQ ID NO: 447) |
| HB1.7425.1 | TECYTVTNFAEEIAVKILCEFKGYQCFEERESGTTRTVCCSC (SEQ ID NO: 448) |
| HB1.6809.1 | CQRVTATSFAECIALKILAEFWGCPITEQPGKDTCELRCC (SEQ ID NO: 449) |
| HB1.10233.1 | PCARIDSNTFAAQIACEICKDFGAECRDDGNVVRCCL (SEQ ID NO: 450) |
| HB1.9439.1 | RTETYEHDAQFAVEIMCEILAQLKGCKLEKDGKRCRLHC (SEQ ID NO: 451) |
| HB1.4707.1 | TTAKMSSAQFACKIAAEIAREFGCRCTIDGTECYCVC (SEQ ID NO: 452) |
| HB1.7056.1 | ETRRCKGFAECIRCEIEAEFKKGCTSKRHGEYCEVFC (SEQ ID NO: 453) |
| HB1.10269.1 | PCTQVDKSFAEAIALCIEAEFRGCQCRMDGLVVEVCC (SEQ ID NO: 454) |

In specific embodiments, the isolated polypeptide comprises an amino acid sequence, having a amino acid sequence having at least 70%, 75% 80%, 85%, 90%, 91%, 92%, 93%, 94%, 95%, 96%, 97%, 98%, 99%, or 100% sequence identity over its length to the amino acid sequence of any one of SEQ ID NOS SEQ ID NOS: 1,351-352 378-379, 381-382, and 455-462.

(SEQ ID NO: 1)
CIE(Q/I)S(F/V)TT(L/P)FACQ(T/I)AAEIWRAFGY (T/E)VKI(M/D)(VD)DNGNCRLHVC (SEQ ID NO: 351)
TSRVRATSKFAALIAAEIAREEGYTVDVQEVNGQWEVTFD (SEQ ID NO: 352)
TSGVRATSKFAALIAAEIAREFGYTVDVQEKNGEWRVVFD (SEQ ID NO: 379)
CIEQSFTT1FACQTAAEIWRAFGYTVKIMVDNGNCRLHVC (SEQ ID NO: 378)
CIEISVTTPFACQIAAEIWRAFGYEVKIDDDNGNCRLHVC (SEQ ID NO: 381)
CQDYTFTDPPFACQIAAEILRDFGYDCTVQTNNGECRVRCC (SEQ ID NO: 382)
CQEYRFTNPFACQIALEILRDFGYACTVQTINGECRVRCC

SEQ ID NO: 455
TS(R/G)VRATSKFAALIAAEIAREFGYTVDVQE(V/K)N

G(Q/E)W(E/R)V(T/V)FD (SEQ ID NO: 456)
CQ(D/E)Y(T/R)FT(D/N)PFACQIA(A/L)EILRDFGY (D/A)CTVQT(N/I)NGECRVRCC (SEQ ID NO: 457)
*(C/T/pE/G)*IEQSFTTLFA(*C/A*)QTAAEIWRAFGYTVK

IM(V/Q)DNGN(*C/W*)RLHV(*C/T/G-NH2/P*)

CS15989 A13_r31_AWQ C-40-C
(SEQ ID NO: 459)
*C*IEQSFTTLFAAQTAAEIWRAFGYTVKIMQDNGN<u>W</u>RLHV*C*

CS15990 A13_r31_TAWQT T-40-T
(SEQ ID NO: 460)
*T*IEQSFTTLFAAQTAAEIWRAFGYTVKIMQDNGN<u>W</u>RLHV*T*

CS16342 A13-NpE-CG-NH2
(SEQ ID NO: 461)
pEIEQSFTTLFA<u>C</u>QTAAEIWRAFGYTVKIMVDNGN<u>C</u>RLHV

G-NH2

CS16343 A13-NG_CP
(SEQ ID NO: 462)
GIEQSFTTLFA<u>C</u>QTAAEIWRAFGYTVKIMVDNGN<u>C</u>RLHVP

In a specific embodiment, the isolated polypeptide comprises an amino acid sequence having an amino acid sequence having at least 70% 75%, 80%, 85%, 90%, 91%, 92%, 93%, 94%, 95%, 96%, 97%, 98%, 99%, or 100% sequence identity over its length to the amino acid sequence of SEQ ID NO: 379 and 459-462.

In various further embodiments, the polypeptide is 75, 70, 65, 60, 55, or fewer amino add residues in length. In other embodiments, the polypeptide is at least 30, 35, or 40 amino acids in length The polypeptides of the disclosure may include additional residues at the N-terminus, C-terminus, or both. Such residues may be any residues suitable for an intended use, including but not limited to tags. As used herein, "tags" include general detectable moieties (i.e.: fluorescent proteins, antibody epitope tags, etc.), therapeutic agent, purification tags (His tags, etc.), linkers, ligands suitable for purposes of purification and peptide domains that add functionality to the polypeptides, etc.

In a further aspect, the present disclosure provides isolated nucleic acids encoding a polypeptide of the present disclosure. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein; including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In another aspect, the present disclosure provides recombinant expression vectors comprising the isolated nucleic acid of any aspect of the disclosure operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting host cells is well known in the art, and thus can be accomplished via standard techniques, (See, for example, Sambrook, Fritsch, and. Maniatis, in Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In various embodiments, the expression vector may comprise a plasmid, viral-based vector, or any other suitable expression vector.

In a further aspect, the present disclosure, provides host cells that comprise the recombinant expression vectors disclosed herein, wherein the host cells can be either prokaryotic or eukaryotic. The cells can be transiently or stably engineered to incorporate the expression vector of the disclosure, using standard techniques in the art, including but not limited to standard bacterial transformations, calcium phosphate co-precipitation, electroporation, or liposome mediated-, DEAE, dextran mediated-, polycationic mediated-, or viral mediated transfection. (See, for example, *Molecular Cloning: A Laboratory Manual* (Sambrook, et. al, 1989, Cold Spring Harbor Laboratory Press; *Culture of Animal Cells: A Manual of Basic Technique,* $2^{nd}$ Ed. (R. I. Freshney. 1987. Liss, Inc. New York, N.Y.). A method of producing a polypeptide according to the disclosure is an additional part of the disclosure. In one embodiment, the method comprises the steps of (a) culturing a host according to this aspect of the disclosure under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the person skilled in the art. In another embodiment, the method comprises chemically synthesizing the polypeptides.

In a further aspect, the present disclosure provides antibodies that selectively bind to the polypeptides of the disclosure. The antibodies can be polyclonal, monoclonal antibodies, humanized antibodies, and fragments thereof, and can be made using techniques known to those of skill in the art. As used herein, "selectively bind" means preferential binding of the antibody to the polypeptide of the disclosure, as opposed to one or more other biological molecules, structures, cells, tissues, etc., as is well understood by those of skill in the art, In another aspect, the present disclosure provides pharmaceutical compositions, comprising one or more polypeptides of the disclosure and a pharmaceutically acceptable carrier. The pharmaceutical compositions of the disclosure can be used, for example, in the methods of the disclosure described below. The pharmaceutical composition may comprise in addition to the polypeptide of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmacentical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other active agents suitable for an intended use.

In a further aspect, the present disclosure provides methods for treating and/or limiting an influenza infection, comprising administering to a subject in need thereof a therapeutically effective amount of one or more polypeptides of the disclosure, salts thereof, conjugates thereof, or pharmaceutical compositions thereof, to treat and/or limit the influenza infection. When the method comprises treating an influenza infection, the one or more polypeptides are administered to a subject that has already been infected with the influenza virus, and/or who is suffering from symptoms (including but not limited to chills, fever, sore throat, muscle pains, coughing, weakness, fatigue, and general discomfort) indicating that the subject, is likely to have been infected with the influenza virus. As used herein, "treat" or "treating" means accomplishing one or more of the following: (a) reducing influenza viral titer in the subject; (b) limiting any increase of influenza viral titer in the subject; (c) reducing the severity of flu symptoms; (d) limiting or preventing development of flu symptoms after infection; (e) inhibiting worsening of flu symptoms; (1) limiting or preventing recurrence of flu symptoms in subjects that were previously symptomatic for influenza infection.

When the method comprises limiting an influenza infection, the one or more polypeptides are administered prophylactically to a subject that is not known to have been infected, but may be at risk of exposure to the influenza virus. As used herein, "limiting" means to limit influenza infection in subjects at risk of influenza infection. Given the nature of seasonal influenza outbreaks, virtually all subjects are at risk of exposure, at least at certain times of the year. Groups at particularly high risk include children under age 18, adults over the age of 65, and individuals suffering from one or more of asthma, diabetes, heart disease, or any type of immunodeficiency.

While not being bound by any mechanism of action, it is believe that prophylactic protection by the polypeptides of the disclosure appears to be mediated by limiting or blocking viral replication at the respiratory site of exposure whereas therapeutic protection may be achieved by curtailing the spread of the virus into the lower respiratory tract and limiting inflammation and disease.

In one embodiment, the subject is immune-compromised (including, but not limited, to, subjects taking immumosuppressants, subjects with a disease that compromises the immune system, such as acquired immune deficiency syndrome, etc.) and/or is 65 years of age or older. The therapeutic and prophylactic activity of the polypeptides of the disclosure is not dependent on the subject having a properly functioning immune system, and thus the methods are of particular benefit from any subject that does not have a properly functioning immune system.

The methods of the disclosure ran be used to treat any individual infected with influenza virus, including but not limited to influenza virus A group 1.

As used herein, a "therapeutically effective amount" refers to an amount of the polypeptide that is effective for treating and/or limiting influenza infection. The polypeptides are typically formulated as a pharmaceutical composition, such as those disclosed above, and can be administered via any suitable route, including orally, by inhalation spray, ocularly, in dosage unit formulations containing conventional pharmaceutically acceptable carriers, adjuvants, and vehicles. In one particular embodiment, the polypeptides are administered mucosally, including but not limited to intraocular, inhaled, or intranasal administration. In another particular embodiment, the polypeptides are administered orally. Such particular embodiments can be administered via droplets, nebulizers, sprays, or other suitable formulations.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the disclosure neutralize influenza virus infectivity. In various embodiments, the polypeptides of the disclosure prevent influenza virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by influenza virus in the absence of the polypeptides. Neutralization can, for instance, be measured as described in "Laboratory techniques in influenza," edited by F.-X. Meslin, M. M. Kaplan and H. Koprowski (1996), 4th edition, Chapters 15-17, World Health Organization, Geneva.

The polypeptides according to the disclosure can bind to the HA protein with any suitable affinity constant ($K_d$ value) that provides therapeutic or prophylactic benefit. In various embodiments, the $K_d$ value is lower than $0.2*10^{-4}$ M, $1.0*10^{-5}$ M, $1.0*10^{-6}$ M, $1.0*10^{-7}$ M, $1.0*10^{-8}$ M, $1.0*10^{-9}$ M, $1.0*10^{-10}$ M, $1.0*10^{-11}$ M, or $1.0*10^{-12}$ M. Affinity constants can for instance be measured using surface plasmon resonance, i.e., an optical phenomenon that allows for the analysis of real-time biospecific interactions by detection of alterations in protein concentrations within a biosensor matrix for example, using the BIACORE system (Pharmacia Biosensor AB, Uppsala, Sweden).

The polypeptides made be administered as the sole prophylactic or therapeutic agent, or may be administered together with (i.e.: combined or separately) one or more other prophylactic or therapeutic agents, including but not limited to oseltamivir, zanamivir, and laninamivir.

In another aspect, the present disclosure provides methods for diagnosing an influenza infection, or monitoring progression of an influenza infection, comprising
  (a) contacting a biological sample from a subject suspected of having an influenza infection with a diagnostically effective amount of one or more polypeptides the disclosure under conditions suitable for binding of the polypeptide to a viral HA protein present in the sample; and
  (b) detecting polypeptide-viral HA binding complexes, where the presence of such binding complexes indicates that the subject has an influenza infection, or provides a measure progression an influenza infection.

The methods of this aspect of the disclosure can be used to more accurately identify patients that may be suffering from an influenza infection and to thus provide more informed determination of treatment options by an attending caregiver. Individuals at risk of an influenza infection are as described above. The methods can also be used to monitor progression of an influenza infection; in this embodiment, the subject is known to be infected, and the methods can be used, for example, as a data point for an attending caregiver to determine whether to initiate, modify or continue a particular course of therapy.

The biological sample may be any suitable biological sample including, but not limited to blood, serum, nasal secretions, tissue or other biological material from a subject at risk of infection.

The sample may first be manipulated to make it more suitable for the method of detection. "Manipulation" includes, but is not limited to treating the sample in such a way that any influenza virus in the sample will disintegrate into antigenic components such as proteins, polypeptides or other antigenic fragments. The polypeptides of the disclosure are contacted with the sample under conditions which allow the formation of an complex between the human polypeptides and influenza virus or antigenic components thereof that may be present in the sample. The formation of such complexes, if any, indicating the presence of influenza virus in the sample, is then detected and measured by suitable means. Such methods include, but are not limited to homogeneous and heterogeneous binding immunoassays, such as radioimmunoassays (RIA), ELISA, immunofluorescence, immunohistochemistry, FACS, BIACORE and Western blot analyses. Suitable conditions to promote binding of the test compounds to one or more polypeptide of the disclosure can be determined by those of skill in the art, based on the teachings herein.

The polypeptides of the disclosure for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the disclosure may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. In one embodiment, conditions are selected to identify test compounds that hind to the polypeptide of the disclosure with a $K_d$ value lower than $0.2*10^{-4}$ M, $1.0*10^{-5}$ M, $1.0*10^{-6}$ M, $1.0*10^{-7}$ M, $1.0*10^{-8}$ M, $1.0*10^{-9}$M, $1.0*10^{-10}$ M, $1.0*10^{-11}$ M, or $1.0*10^{-12}$ M.

In a further aspect, the present disclosure provides methods for identifying candidate influenza vaccines, comprising
  (a) contacting test compounds with a polypeptide of the present disclosure under conditions suitable for polypeptide binding and
  (b) identifying those test compounds that bind to the polypeptide of the disclosure, wherein such test compounds are candidate influenza vaccines.

As discussed above, the polypeptides of the present disclosure were designed to target the HA protein. Thus, the polypeptides of the disclosure can be viewed as specific binders to HA epitope, similar to antibody binding to a specific epitope. Vaccines can be produced, for example, by selecting small molecules (ie: mimotopes) that bind to an antibody specific to a viral epitope. Thus, the present methods involve substituting one or more polypeptides of the present disclosure for the antibody in such assay to identify candidate influenza vaccines.

Suitable conditions to promote binding of the test compounds to one or more polypeptide of the disclosure can be determined by those of skill in the art, based on the teachings herein. The polypeptides of the disclosure for use in this aspect may comprise a conjugate as disclosed above, to provide a tag useful for any detection technique suitable for a given assay. The tag used will depend cut the specific detection/analysis/diagnosis techniques and/or methods used, as discussed above. The methods may be carried in solution, the polypeptide(s) of the disclosure may be bound or attached to a carrier or substrate, as discussed above. Based on the teachings herein, it is within the level of skill in the art to determine specific conditions for the various types of diagnostic assays disclosed in this aspect of the disclosure. In one embodiment, conditions are selected to identity test compounds that bind to the polypeptide of the disclosure with a $K_d$ value lower than $0.2*10^{-4}$ M, $1.0*10^{-5}$ M, $1.0*1.0^{-6}$ M, $1.0*10^{-7}$ M, $1.0*10^{-8}$ M, $1.0*10^{-9}$ M, $1.0*10^{-10}$ M, $1.0*10^{11}$ M, or $1.0*10^{-12}$ M.

Any suitable test compound may be used, including but not limited to polypeptides, antibodies, nucleic acids, etc.

In another aspect, the present disclosure provides methods for identifying candidate compounds for treating, limiting, and/or diagnosing influenza infection, comprising (a) contacting an influenza HA protein with (i) test compounds and (ii) a polypeptide of the present disclosure, under conditions suitable for binding of the HA protein to the polypeptide of the present disclosure; and (b) identifying those test compounds that outcompete the polypeptide for binding to HA protein, wherein such test compounds are candidate compounds for treating, limiting, and/or diagnosing influenza infection.

In this aspect, the methods identify test compounds that compete with the polypeptides of the disclosure for binding to HA, and thus such candidate compounds may be useful in any of the other methods of the disclosure disclosed herein. Any suitable test compound can be used, as disclosed above in the eleventh aspect of the disclosure.

In general, competitive inhibition is measured by means of an assay, wherein an HA composition is admixed with the polypeptide(s) of the disclosure and the test compounds to be screened. In one embodiment, the test compounds to be screened are present in excess. Protocols based upon ELISAs are suitable for use in such competition studies. In certain embodiments, one may pre-mix the polypeptide(s) of the disclosure with varying amounts of test compounds to be screened (e.g., 1:10, 1:20, 1:30, 1:40, 1:50, 1:60, 1:70, 1:80, 1:90 or 1:100) for a period of time prior to applying to the HA composition. In other embodiments, the polypeptide(s) of the disclosure and varying amounts of test compounds to be screened are admixed during exposure to the HA composition. Any suitable detection means can be used binding. In one embodiment, the polypeptide(s) of the disclosure are tagged for detection, as discussed above. In this embodiment, the detectable label will decrease in the presence of competitive test compounds. The reactivity of the (labeled) polypeptide of the disclosure in the absence of test compound could serve as one suitable control. Preferably, competitive test compounds when present in excess, inhibit specific binding of the polypeptide(s) of the disclosure to HA by at least 10%, preferably by at least 25%, more preferably by at least 50%, and most preferably by at least 75% to 90% or even greater.

Exemplary conditions for HA binding, studies can be carried out as disclosed in the examples that follow.

Example 1

De novo design bolds promise for creating small stable proteins with shapes customized to bind therapeutic targets. We describe a massively parallel approach for designing, manufacturing and screening mini-protein binders that integrate large-scale computational design, oligonucleotide synthesis, yeast display screening and next generation sequencing. We designed and tested thousands of ~40-residue proteins targeting influenza hemagglutinin, along with 6,286 control sequences probing contributions to folding and binding, and identified high affinity binders. Biophysical characterization of a subset showed they are extremely stable and, unlike antibodies, do not lose activity following high temperature exposure. Comparison of the sets of binding and non-binding designs, two orders of magnitude larger than any before, enables systematic improvement of the computational model. The designs elicit little or no immune response, and provide potent prophylactic and therapeutic protection against influenza even after extensive repeated dosing.

Here, we describe an integrated computational and experimental approach that enables the rapid design and testing of tens of thousands of de novo mini-protein binders. Our approach exploits advances in both DNA manufacturing and protein design that have led to a fortunate convergence between the upper limit of the size of oligonucleotides (230 bp) that can be synthesized as pools of 10,000 or larger, and the lower limit of the size of genetically encodable computationally designed proteins (~40 ammo acids). To generate binders for a given target, we use Rosetta™ to design thousands of protein scaffolds with varying shapes, dock these onto the target, optimize the residues at the interface for high affinity binding, and identify, from the resulting pool of hundreds of thousands of designs, ~10,000 with high predicted stability and affinity. This large pool of computational designs, together with controls probing different aspects of the design procedure, are then experimentally evaluated by encoding each individual sequence in a single oligonueleotide, manufacturing the oligonucleotides in parallel, sorting yeast libraries displaying the designs labeled with fluorescent target, and identifying the designs most enriched for binding using deep sequencing.

High-Throughput Computational Design of Mini-Protein Binders

We selected Influenza H1 hemagglutinin (HA) as a target, as this virus remains a serious public health concern. We generated virtual scaffold libraries with over 4000 backbone geometries in five different topologies (HHH, EHEE, HEE, EEHE, and HEEH; where H indicates α-helix and E β-strand) with or without a diversity of disulfide connectivities, and then designed binding interlaces into these. The core of the interface was seeded with 4-9 hotspot residues, while the remainder of the binding residues were designed de novo. The different designs interact with the targets in a myriad of different ways, resulting in a wide range of interface buried surface area.

We selected for experimental characterization 3,594 disulfide and 3,682 non-disulfide containing HA-binding designs with an average sequence identity of ~24% (see Methods). To probe the contribution of different aspects of the design process, we also included versions with the amino acids outside the helical interface motif randomly permuted. Oligo pools encoding the design and control sequences were synthesized, amplified, and co-transformed into yeast along with a linearized yeast display vector. The resulting yeast libraries displaying the proteins were incubated with different concentrations of fluorescently labeled target, in some cases after protease treatment to remove poorly folded designs, and cells displaying designs which bound target were retrieved by Fluorescence-Activated Cell Sorting (FACS). After deep sequencing, of the various pools, each binder was categorized based on the stringency of the condition under which it was maximally enriched.

Deep sequencing of the initial yeast transformed pools showed near complete representation of full length genes; the HA pool contained 11,002 of the 11,657 sequences ordered (94.4%). Sorting of the library under conditions of increasing stringency (decreasing concentration of target) sharply reduced the number of distinct sequences recovered. For HA, the population following sorting against A/PuertoRico/8/1934 HA concentrations of 1000, 100 and 10 nM contained 115, 41 and 29 distinct sequences. The population fraction of the computational designs increased over that of the scrambled control sequences with increasing selection stringency; computational design considerably increased the probability of binding the target with high affinity. The simplest explanation of this increase is that a significant fraction of the proteins fold as designed.

The design population included 3,594 HA designs with multiple disulfides in geometrically-allowed positions. Disulfide containing designs did not have a higher success rate than the non-disulfide designs (0.5% vs 0.8%), consistent with a late non-instructive role for disulfides in protein folding. However, when the design libraries were treated with trypsin before binding selection, only disulfide-stabilized designs were recovered; while not guiding folding, the disulfides clearly confer stability against proteolysis, Assessment of Computational Model The measured binding activity of a design reflects both the extent to which the protein is folded and the binding affinity of the folded state to the target. Sequences with binding activity in general had lower computed folding energies and binding energies. This is perhaps the largest-scale confirmation of the ability of a computational model to recapitulate protein-protein interaction to date. The second-order features most strongly associated with binding were: local sequence-structure compatibility and the numbers of contacts across the interface. Based on these results, we updated the design protocol (see Methods), and generated 11,420 new HA designs for a second round experimental testing in which the success rate increased from 1.4% to 3.1% (342 new HA binders). The improvement was particularly dramatic in the subset of HB2 seeded designs, improving the success rate 10-fold from 0.19% to 1.9%.

The large dataset provides an opportunity to determine whether extensive molecular dynamics (MD) simulations in explicit solvent can reproducibly distinguish binding and nonbinding designs. We simulated randomly selected non-binders and binders for a total simulation time of 108 μs (see Methods). There was a strong, correlation between the extent of fluctuations of residues at the binding interface and experimental binding activity, suggesting that binding site pre-organization is important for binding and that MD simulations capture this property reasonably well.

To interrogate the sequence dependence of folding and function, we also tested designs containing every single point mutant variant of 6 HA active designs. Residues at the binding interface and in the protein core were more conserved than surface residues and cysteines tend to be highly conserved in proteins containing disulfides. The contributions of the non-hotspot designed contacts differentiated the highest affinity designs from the remainder. For example, mutation of non-hotspot HB1.6928.2 residues Ala11. Trp19, and Tyr24 drastically decreased binding affinity. The effects of the SSMs were also computationally modeled considering both changes in binding energy and monomer stability. A reasonable correlation was found between the predicted and experimentally determined susceptibility of positions to mutation for three of the six designs for HB1, suggesting that they adopt structures close to the designed model. This low resolution structure validation is powerful considering that no protein purification or traditional biochemical characterization is required. Finally, the single-site saturation mutagenesis (SSM) datasets were used to guide generation of higher affinity HA binders (see Methods).

Individual Characterization Of Designed Binders

Six HA binders, a mix of affinity-matured and original designs, were chemically synthesized or expressed in *E. coli*, purified, and characterized in solution. All designs had circular dichroism spectra consistent with the design models, and melting temperatures greater than 70° C. For designs containing disulfides, there was little unfolding at 95° C., while in the presence of the reducing agent TCEP their stability and thermal reversibility were seriously compromised (data not shown), suggesting correctly formed disulfide bonds. These disulfide containing designs were resistant to trypsin (data not shown). The HA binders bound to HA proteins from two H1N1 influenza strains, A/PuertoRico/8/1934 (PR8) and A/California/04/2009 (Cal09), and the three affinity-matured binders had affinities against Cal09 below 10 nM. Co-crystal structures were determined for a binder HB1.6928.2.3 and were found to be in excellent agreement with the computational models (monomer-$C_\alpha$RMSD=0.94+for HB1.6928.2.3.

To compare the ability of the designs to survive high temperature exposure with that of antibodies, we incubated HB1.6928.2.3 and mAb FI6v3 at 80° C. for various times prior to performing binding assays. The mini-protein binder showed no detectable loss of binding after 1 hr at high temperature, while FI6v3 binding activity was reduced ~74% (data not shown). These results suggest small protein-based therapeutics could overcome the current requirement of cold chain management for monoclonal antibodies.

In vitro assays were carried out for HB1.6928.2.3, an affinity-matured, disulfide-containing design. HB1.6928.2.3 strongly neutralized PR8 and CA09 influenza viruses after 48 hours in culture with $EC_{50}$ values more than 100-fold lower than the broadly neutralizing antibody FI6v3[18] and HB36.6 on a mass basis (data not shown; the $EC_{50}$ are comparable on a molar basis). The increase in protection likely reflects both the reduction in conformational entropy of the binding motif and additional designed interface contacts.

HB1.6928.2.3 protected mice from influenza both pre- and post- exposure. Intranasal administration (i.n.) of HB1.6928.2.3 24 hrs prior to lethal challenge with CA09 influenza gave 100% survival at doses as low as 0.03 mg/kg, 100-fold lower on a mass basis than the FI6v3 dose required for equivalent protection (data not shown). Therapeutic administration of HB1.6928.2.3 24 hrs post virus challenge resulted in 100% survival and little (<10%) weight loss (data not shown), and a single 3 mg/kg dose administered 72 hours post-challenge gave complete protection and 100% survival (data not shown). Intravenous administration of HB1.6928.2.3 exhibited little protection (not shown), indicating that similar to the on-market drug Zanamivir intranasal administration is likely the optimal delivery route for these mini-proteins.

Immunogenicity studies showed that 3 sequential doses of the mini-proteins administered by i.n. or intravenous (i.v.) delivery every two weeks induced little or no antibody response (data not shown). The low level of antibody detected was comparable to levels induced by a mouse IgG (negative control) and substantially less than human IgG (positive control). The influenza mini-protein binders retained 100% prophylactic efficacy even after four repeat i.n or i.v doses over a six week period prior to virus challenge (data not shown) indicating that any immune response and clearance is mimimal and not sufficient to interfere with antiviral potency. The low immunogenicity is likely due to a. combination of the very small size and hyperstability of the mini-proteins, and suggests that the binders could be used for prophylactic protection against influenza over an extended period of time. To our knowledge this is the first investigation of the immunogenicity of de nova designed proteins.

Conclusions

Our high throughput computational design-experimental testing pipeline enables the characterization of computationally designed binding proteins on a scale orders of magnitude greater than previous studies, and generated hundreds of potential anti Flu drug leads. This approach enables probing of individual contributions to folding and binding on thousands of test cases simultaneously. For example, the finding that substitution of designed loop sequences with generic gly-ser linkers reduces binding fitness more than scrambling the order of the designed core residues or substituting them all with valine suggests a perhaps underappreciated instructive role for loops in the folding of proteins in this size range. Different topologies were found to be optimal for the HA interfaces, supporting the hypothesis that no single protein topology/shape is ideally suited to best fit all interfaces. The massively parallel enabled success despite uncertainties in the design of 40 residue proteins with multiple surface hydrophobic residues potentially complicating folding. Iteration between data-driven model improvement and experimental testing should improve both the computational design methodology and our understanding of the determinants of folding and binding—the limited number of native protein structures from which much of current knowledge is derived is dwarfed by the nearly unlimited number of de novo proteins that can be designed and tested.

De novo protein design has the promise to generate pharmaceutically superior molecules that combine the specificity of antibodies with the high stability and manufacturability of small molecules. The de novo designed binders described here exhibit much greater stability to incubation at elevated temperatures and better neutralization than the FI6v3 mAb, have ~1/30th of the molecular weight, and are readily chemically synthesizable, which enables the introduction of a wide variety of chemical functionalizations. Likely due to their small size and very high stability, they elicit little immune response even without explicit negative design[20], and the best of the HA designs provides prophylactic and therapeutic protection against influenza infection in vivo with potency rivaling or surpassing antibodies. The antibody Fc region is clearly not required for potent protection against influenza, and lack of the Fc could reduce problems with antibody enhanced infectivity. More generally, hyperstable designed mini-proteins show promise for both therapeutic and diagnostic applications.

Methods

Mini-protein binders design: Mini-protein design began by defining a variety of mixed αβ and α-only scaffold topologies using the RosettaRemodel™ 'blueprint' format[21] with the requirement of at least one 10-14 residue helix. The blueprints were used to generate backbones using the Rosetta Monte Carlo-based fragment assembly protocol[22,23]. One to three disulfides were added to a subset of these backbones at geometrically allowed positions. Sequence design was performed using the Fast Design™ protocol with layer control active, alternating between side-chain rotamer optimization and gradient-descent based energy minimization. For each topology, over 10,000 structures were generated and filtered on overall energy per residue and score terms related to backbone quality, compactness, and disulfide quality.

To match the mini-protein-scaffolds into the desired target helix-binding motifs, we used the Rosetta MotifGraft™ Mover[7,24]. The inputs were composed of: (1) HB36, HB80 or Syt-II helical binding motifs (PDB IDs 3R2X, 4EEF and 2NM1, respectively); (2) The context target protein (Flu-HA or BoNT $H_C$B), and (3) the above described library of de novo mini-protein scaffolds. Matching parameters were set to perform full backbone alignment of the input motif, with a maximum backbone RMSD=1.0Å, endpoints RMSD=1.0Å, clash_score_cutoff=5 and enabling revert-_graft_to_native_sequence. In the case of BoNT/B's Syt-II binding domain, the hotspots were defined as: Met-1, Phe-2, Leu-5, Lys-6, Lys-8, Phe-9, Phe-10, Glu-12, Ile-13 (see Extended Data FIG. 1), while for Flu-HA HB80.4 (HB1) binding domain, the hotspots were defined as: Phe-1, Ile-5, Ile-9, Phe-13, and for Flu-HA HB36.6 (HB2) binding domain, the hotspots were defined as: Phe-1, Met-5, Trp-9, Phe-13. MotifGraft™ was followed by Rosetta's sequence repack of interface neighboring residues (except hotspots), cartesian minimization and filtering using the scoring function Talaris2013 or Talaris2014.

After the first round of HA design and testing the Kolmogorov-Smirnov 2-sample test was used to determine p-values for the null hypothesis that the computational metrics of the binding vs non-binding designs were drawn from the same underlying distribution. Based on the metrics that correlated strongly with success (such as those shown FIG. 3b) a second round of HA design was performed which incorporated more stringent filtering on a broader range of metrics. The metrics used to select the first round of HA designs were delta G of binding(ddg filter), shape complementarity(sc), and interface buried surface area(SASA). The additional metrics used to select the second generation HA designs and shown to be highly predictive of round one success in the logistic regression model(FIG. 3c inset) were: average degree (degree), side-chain probability given phi-psi (p_aa_pp), percent core by side chain neighbors, phi-psi probability given side-chain (rama) and more stringent shape-complementarily.

Software analysis: All amino-acid sequences were reverse translated and codon optimized for yeast using DNA-works™ 2.0[25]. Sequence identity calculations were performed with a subset of designs using PRALINE[26] after PSI-BLAST global alignment. Sequencing pairing alter Illumina deep sequencing was performed by PEAR[27]. Plots and visualizations were created using Seaborn statistical visualization tools[28], Python (Python Software Foundation), and python's scikit-learn (INRIA).

Gene pools: Oligo library pools ordered from either CustomArray or Agilent with all genes 3' and 5' flanked with common 20 bp adaptor segments to allow for amplification. We obtained conventional oligonucleotides (PCR primers and sequencing primers) from Integrated DNA Technologies. The raw oligonucleotide pools were amplified with Kapa HiFi Hotstart™ Ready Mix (Kapa Biosystems) using extension primers to add pETCON™ yeast homologous recombination segments (40bp) to each end. All amplifications were performed using real-time PCR on a MiniOpticon™ (Bio-Rad) for between 9-20 cycles. qPCR amplification was critical as over-amplification of gene pools resulted in low transformation efficiency. Amplified pools were size selected on a 2% agarose gel and cleaned (Qiagen QIAquick™ Gel Extraction Kit). A second round of qPCR amplification was performed with the same primers on the size-selected pools to generate 2-4 μg of DNA. Yeast EBY100 cells were transformed with library DNA and linearized pETCON™ plasmid[29] using an established protocol[30]. After transformation (minimum 1E7 transformants), cells were grown overnight in SDCAA media in 30 ml cultures at 30° C., passaged once, and stored in 20 mM HEPES 150 mM NaCl pH 7.5, 20% (w/v) glycerol in 1e7 aliquots at −80° C.

Yeast display and deep sequencing: Cell aliquots were thawed on ice, centrifuged at 13,000 r.p.m. for 30 s, resuspended in 1e7 cells per ml of C-Trp-Ura media and grown at 30° C. for 16 h. Cells were then centrifuged for 13,000 r.p.m. and resuspended at 1e7 cells per ml SGCAA media and induced at 30° C. for 16-24 h. Cells were labeled with either PR8 hemagglutinin, CA/04/09 hemagglutinin, washed, secondary labeled with SAPE (Invitrogen) and anti-cmyc FITC (Miltenyi Biotech), and sorted by fluorescent gates under various stringency conditions using a Sony SH800. HA target proteins were produced as previously described[16]. Cells were recovered overnight at 2.5e5 collected cells per ml SDCAA media, whereupon at least 1e7 cells were spun down at 13,000 r.p.m. for 1 min and stored as cell pellets at −80° C. before library prep for deep sequencing. Between 1e7 and 4e7 yeasts cells were barcoded and prepared for deep sequencing for each library as previously described[16].

SSM and affinity maturation: SSM libraries for 8 designs were constructed from Agilent gene pools and yeast display selections performed as described above. Upon deep sequencing the 5 most beneficial mutations at 9 positions in each of the HA designs predicted to result in higher affinity were combined into high-diversity libraries (<1E7) using wobble bases as guided by SwiftLib[31]. A DNA library for each design was constructed from assembly PCR using Ultramer™ oligonucleotides (Integrated DNA Technology) to encode the variable region. These libraries went through three increasing stringency sorts rd1 100 nM, rd2 10nM, and rd3 1 nM against CA/04/09. Promising constructs were identified through sanger sequencing of a subset of the final rd3 pool.

Mini-protein expression and peptide synthesis: Genes encoding the designed protein sequences were synthesized and cloned into pET-28b(+) *E. coli* plasmid expression vectors (GenScript, N-terminal 6xHis tag and thrombin cleavage site). Plasmids were then transformed into chemically competent *E. coli* Lemo21™ cells (NEB). Protein expression was then induced with 1 mM of isopropyl β-D-thiogalactopyranoside (IPTG) at 18° C. After overnight expression, cells were collected and purified by nickel affinity followed by FPLC size-exclusion chromatography (Superdex™ 75 10/300 GL, GE Healthcare) and Mass Spectrum (MS) verification of the molecular weight of the species in solution (Thermo Scientific). Peptide sequences were synthesized from commercial vendors Biomatik or CS Bio in 50 mg quantities with 70% purity requirements. Sequences containing cysteines underwent standard natural oxidation performed by vendor.

Circular dichroism (CD) Far-ultraviolet CD measurements were carried out with an AVIV spectrometer model 420 in PBS buffer (pH 7.4) in a 1 mm path-length cuvette with protein concentration of ~0.25 mg/ml (unless otherwise mentioned in the text). Temperature melts where from 25 to 95° C. and monitored absorption signal at 222 nm (steps of 2° C./min, 30 s of equilibration by step). Wavelength scans (195-260 nm) were collected at 25° C. and 95° C., and again at 25° C. after fast refolding (~5 min). Four chemically-synthesized, disulfide-containing, mini-proteins were also characterized at a concentration of ~0.2 mg/ml in the absence or presence of 2.5 mM of the reducing agent TCEP[5].

Biolayer Interferometry: Binding data were collected in a Octet RED96™ (ForteBio, Menlo Park, Calif.) and processed using the instrument's integrated software using a 1:1 binding model. For influenza binding proteins, streptavidin-coated biosensors were dipped in wells containing biotinylated HA proteins (100 nM) in binding buffer for immobilization for 300 seconds, while the binding proteins to assay were diluted from a concentrated stock into binding buffer (1× PBS pH 7.4, 0.01% BSA, 0.002% Tween 20). After baseline measurement in binding buffer alone, the binding kinetics were monitored by dipping the biosensors in wells containing defined concentrations of the designed protein (association) and then dipping the sensors back into baseline wells (dissociation). For heat-time courses, the proteins were incubated for defined times at a concentration of 160 nM in PBS buffer (150 nM NaCl, pH-7.4 ) and then diluted to 8 nM in the final buffer and assayed as described above.

Influenza H1 co-crystal structure: For the HA-MB1.6928.2.3 complex, A/PuertoRico/8/1934 HA and HB1.6928.2.3 peptide (in 25 mM Tris pH 8.0, 150 mM NaCl) were mixed at a 1:4 molar ratio at a final concentration of 10 mg/ml HA, in 25 mM Tris pH 8.0, 150 mM NaCl. Crystals were grown with a well solution of 5% PEG 3000, 30% PEG 200, 100 mM MES pH 6.0 using the sitting drop vapor diffusion method and directly flash cooled in liquid nitrogen. Data were collected at ALS beamline 5.0.3 and processed with HKL200[38]. Phaser™[38,39] was used for molecular replacement within Phenix™[40] using a single protomer of H1 PR8 HA (PDB ID: 1RVX[41]) as a search model. The HB1.6928.2.3 peptide was manually built into $F_O$-$F_C$ and $2F_O$-$F_C$ maps using clearly defined aromatic residues and disulfide bonds to confirm the register. The model was refined through iterative rounds of model building in COOT[34] and refinement in Phenix. TLS groups were automatically identified by Phenix. Glycans and waters were manually added and edited in COOT. The final model was assessed with quality metrics within the Phenix.refine interface which utilizes MolProbity™[37].

Molecular dynamics simulations: A total 146 independent mini-protein binders were simulated (see Extended Data FIG. 3) using Gromacs™ 5.04[42] and Amber99sb-ILDN force field[43]. Each protein was simulated in a triclinic box with explicit water solvent (TIP3P[44]), with box edges at least 10 Å from the protein. Counterions (Na+/Cl −) were used to neutralize the system. Integration time step was 2.0 ps and LINCS[45] was applied to constrain all the bonds. Long-range electrostatics (>12 Å) were treated with the Particle-Mesh Ewald method[46]. Van der Waals interactions were smoothly switched off between 10 Å-12 Å. After minimization (10,000 steps), the system was position restrained for 200 ps in an NVT ensemble (only heavy atoms, restraint=10 kJ×mol$^{-1}$×Å$^{-2}$, T=310 K), followed by 500 ps of NPT (T=310 K, restraint-10 kJ×mol$^{-1}$×Å$^{-2}$, 1 bar) using Berendsen thermostat and barostat[47]. For each protein, we then performed 5 independent NPT production simulations (T=310 K, 1 bar) with 500 ps of initial temperature annealing (T$_0$=50, T$_{final}$=310 K) using V-rescale thermostat[48] and Parrinello-Rahman Barostat[49]. Each production simulation was in the length of 50 ns for Flu binders. Snapshots were recorded every 50 ps, and all of them were used for subsequent data analysis.

Influenza neutralization assays: 100 TCID$_{50}$ units of virus and half-log dilutions of binders were incubated in quadruplicate at 37° for two hours in 200 ul of neutralization assay media ("NAM"- media 199, 0.3% BSA, 10 mM HEPES, 1 mM CaCl$_2$ pen/strep). 96 well plates with confluent monolayers of Madin-Darby Canine Kidney Epithelial Cells (ATCC) cells were washed twice with PBS followed by addition of 50 ul of 5 ug/ml TPCK-Trypsin in NAM and the virus/binder neutralization mix. Plates were incubated 48 hours and virus detected by combining 50 ul each of assay supernatants and 0.5% turkey red blood cells (TRBC). Virus positive wells that hemagglutinate the TRBC were identified and the EC$_{50}$ was calculated using Reed-Muench method.

In vivo immunogenicity and influenza challenge: Animal studies approved by the University of Washington Institutional Animal Care and Use Committee. Female, 6-8 week-old BALB/c mice (female, 6-8 weeks old, n=5-10 group) were randomly separated into groups, anesthetized and were dosed either intranasally (i.n.) or intravenously (i.v.) with PBS (negative control), the broadly neutralizing antibody F16 (SFFV-F16v3 IgG, Molecular design & Therapeutics, Fred Hutch, Seattle, Wash.) or mini-protein binders (HB1.6928.2.3 or HB36.6). 24-96 hours afterwards the mice were anesthetized with 2.5% isoflurane and challenged i.n. with 2 MLD$_{50}$ (fifty percent mouse lethal dose) of A/California/04/09 (H1N1) (CA09). Following challenge, the mice were monitored twice daily for weight loss and survival until up to 14 days post-infection. Animals that reached 30% of weight lost (respect of their initial body weight) were euthanized by carbon dioxide in accordance with our animal protocols. For the immunogenicity experiment, female, 6-8 week-old BALB/c mice (n=5/group) were randomly separated into groups, anesthetized and dosed with (i.n. or i.v) PBS, or mini-proteins (HB1.5702.3.3, HB1.6928.2.3, HB1.6394.2.3, HB36.6, Bot2110.4 or Bot3194.4), or monoclonal antibodies mIgG (Innovative IR-MSBC-GF) or hIgG (Innovative IR-HU-GF-ED). A total of three 3 or 4 doses were administered two weeks apart for i.n. and i.v. administration. Blood was collected two weeks alter each dose by retro orbital bleed using micro-hematocrit capillary tubes (Fisher). Serum was separated by centrifuging the blood samples in polymer gel chemistry tubes (BD). For mouse experiments, researchers were not blinded to animal identity.

Enzyme-linked immunosorbent assay (ELISA): HB36.6, HB1.6928.2.3, HB1.6394.2.3, mIgG, hIgG and BSA-specific IgG antibody levels mouse serum were assessed by ELISA. Maxisorp™ (Thermo Scientific-Nunc) were coated with 100 ng/well of HB36.6, HB1.5702.3.3, HB1.6928.2.3, HB1.6394.2.3, mIgG (Innovative IR-MSBC-GF), hIgG (Innovative IR-HU-GF-ED) or BSA (LAMPIRE Biological laboratories, cat no. 7500804) in PBS overnight at 4° C. Plates were blocked with 5% nonfat milk powder in PBS for 1 h at room temperature, and then washed three times with wash buffer (PBS-T; phosphate-buffered saline containing 0.05% Tween 20). Samples were diluted in a buffer containing 1% nonfat milk powder in PBS-T, added to the wells, and incubated for 1 hr at room temperature. Following three washes with PBS-T, plates were incubated with horseradish-peroxidase conjugated goat anti-mouse IgG (1/5,000 dilution) secondary antibodies (ThermoFisher 62-6520) for 1 h at room temperature. After five washes with PBS-T, TMB substrate (KPL 52-00-03) was added to the wells for 30 min at room temperature. Color development was stopped by the addition of 50 uL HCl (1 M), and the plates were read at 450 nm to measure relative optical densities (O.D.). The average O.D. of blank wells was subtracted to calculate the reported values.

Statistical and power analyses: Survival analyses were performed by using the Kaplan-Meier log-rank test. A P value of <0.05 was considered to be significant. For mice, the minimum group size was determined using weight loss data with 70% of control mice becoming infected with CA09. Comparisons in antibody responses were performed using unpaired student t-test. Based on a standard deviation of 2% in weight loss, a group size of n=5 yields >80% power to detect a minimum of a 10% difference between groups in weight loss using a two-sided t-test with an alpha value of 0.05.

Example 2

Four novel derivatives of anti-influenza minibinder HB1.6928.2.3 (aka A13) have been designed, manufactured/synthesized, purified, and characterized in vitro for their anti-viral activity. In addition, protocols to purify and formulate the lead peptide A13 to have been developed to support multiple routes of delivery (intranasal, intratracheal, subcutaneous and intravenous) and have been validated in a ferret challenge model of infection for HB1.6928.2.3.

A13 Anti-Flu Peptide:

The amino acid sequence for HB1.6928.2.3 (aka A13) is as follows:

```
CS15134 A13_rd31 Cys-40-Cys
                                    (SEQ ID NO: 379)
Cys-Ile-Glu-Gln-Ser-Phe-Thr-Thr-Leu-Phe-Ala-

Cys-Gln-Thr-Ala-Ala-Glu-Ile-Trp-Arg-Ala-Phe-

Gly-Tyr-Thr-Val-Lys-Ile-Met-Val-Asp-Asn-Gly-

Asn-Cys-Arg-Leu-His-Val-Cys
Where Cys1 is disulfide bonded to Cys40,
and Cys12 is disulfide bonded to Cys35
```

The production of this peptide was achieved by solid phase peptide synthesis and air oxidation, followed by HPLC purification. Extensive purification, formulation and mass spectrometry analysis of A13 revealed that the majority of the synthetic A13 peptide was properly configured with both disulfides formed Cys1-Cys40 and Cys12-Cys35. However, minor quantities of alternatively disulfide bonded forms of A13 could also be detected, and the quantities of such alternate forms of A13 appeared to vary between independent synthesis and purification of different lots of A13. These observations, together with bio-potency data on A13 for blocking influenza virus infection led to the design of A13 variants that could retain anti-flu activity, yet had a reduced number of disulfide bonds. The following four (4) A13 derivatives have been synthesized.

Two (2) A13 Analogues:
The sequences of two (2) A13 derivatives are listed below.

```
CS15989 A13_r31_AWQ Cys-40-Cys
Cys-Ile-Glu-Gln-Ser-Phe-Thr-Thr-Leu-Phe-Ala-

Ala-Gln-Thr-Ala-Ala-Glu-Ile-Trp-Arg-Ala-Phe-

Gly-Tyr-Thr-Val-Lys-Ile-Met-Gln-Asp-Asn-Gly-

Asn-Trp-Arg-Leu-His-Val-Cys
``` where C1 is disulfide bonded to C40 (SEQ ID NO: 459).
This design eliminates the Cys12-Cys35 disulfide by replacing Cys12 with Ala and Cys35 with Trp.

```
CS15990 A13_r31_TAWQT Thr-40-Thr
                                  (SEQ ID NO: 460)
Thr-Ile-Glu Gln-Ser-Phe-Thr-Thr-Leu-Phe-Ala-

Ala-Gln-Thr-Ala-Ala-Glu-Ile-Trp-Arg-Ala-Phe-

Gly-Tyr-Thr-Val-Lys-Ile-Met-Gln-Asp-Asn-Gly-

Asn-Trp-Arg-Leu-His-Val-Thr
```

This design eliminates both disulfides by replacing Cys1 with Thr, Cys12 with Ala, Cys35 with Trp, and Cys40 with Thr.
The in vitro anti-flu activity of these two (2) A13 derivatives is as follows (See Table 2).

In vitro formulation and anti-flu testing of the activities of A13_r31_AWQ Cys-40-Cys and A13_r31_TAWQT Thr-40-Thr revealed that they had reasonable potency against flu virus strains Ca0409 and Ft. Monmout with IC50's ranging from 0.01 to 0.002 ug/ml. While these two peptides were not as potent as A13 (IC50 ~$2\times10^{-5}$, measured for two independent A13 lots), they have the have the feature of fewer (1) or no disulfide bonds; with A13 _r31_AWQ Cys-40-Cys having only a single (1) disulfide bond (confirmed by mass spectrometry), and A13_r31_TAWQT Thr-40-Thr has no disulfide bonds.

TABLE 2

In vitro bio-efficacy of A13 and Analogues. EC50 values for inhibition of viral replication in vitro reported at ug/ml for each Test Aiticle.

| Test Article | Virus Ca0409 | Virus Ft. Monmouth |
|---|---|---|
| A13r31 CS15134 | 2-3 × $10^{-5}$ | 2 × $10^{-5}$ |
| AQW CS15989 | 0.01 | 0.01 |
| TAWQT CS15990 | 0.02 | 0.002 |
| FI6-Anti-HA mAb | 3.1 | 3.1 |
| Anti-Ca0409 serum | 1/1500 dilution | 1/15 dilution |
| Anti-Ft. Monmouth serum | 1/1500 dilution | 1/150000 dilution |

Two (2) Additional A13 Analogues:

Two additional A13 derivatives were designed, CS16342 A13-NpGlu-CGly-NH2 and CS16343 A13-NGly_CPro.

Both of the following A13 dedvatives preserve the internal Cys12-Cys35 disulfide which is predicted to be most important to stabilize the binding helix of A13 to influenza hemagglutinin. However, since the N- and C-terminal ends are no longer "protected" with the Cys1-Cys40, we designed natural modifications pGlu on N-term and Gly-NH2 on C-term (CS16342), which are common natural modifications to bioactive peptides that improve their resistance to degradation by exoproteases and can be used on any of the amino acid sequences described herein. In addition, we designed a companion A13 derivative with designed Gly1 and Pro40 (CS16343) residues expected to stabilize the ends by folding/stacking.

CS16342 A13-NpGlu-CGly-NH2 pGlu-Ile-Glu-Gln-Ser-Phe-Thr-Thr-Leu-Phe-Ala-Cys-Gln-Thr-Ala-Ala-Glu-Ile-Trp-Arg -Ala-Phe-Gly-Tyr-Thr-Val-Lys-Ile-Met-Val-Asp-Asn-Gly-Asn-Cys-Arg-Leu-His-Val-Gly -NH2 (SEQ ID NO: 461), wherein C12 is disulfide bonded to C35.

This design eliminates the Cys1-Cys40 disulfide by replacing Cys1 with pyroglutamic acid p(11n, and Cys40 with glyeinatnide Gly-M-12. Both modifications ane natural modifications of proteins, commonly found in bioactive neuropeptides thought to stabilize peptides from digestion by exoproteases.

CS16343 A13-NGly_CPro

Gly-Ile-Glu-Gln-Ser-Phe-Thr-Thr-Leu-Phe-Ala-Cys-Gln-Thr-Ala-Ala-Glu-Ile-Trp-Arg-Ala -Phe-Gly-Tyr-Thr-Val-Lys-Ile-Met-Val-Asp-Asn-Gly-Asn-Cys-Arg-Leu-His-Val-Pro (SEQ ID NO: 462), wherein C12 is disulfide bonded to C35.

This design eliminates the Cys1-Cys40 disulfide by replacing Cys1 with Gly, and Cys40 with Pro, natural amino acids predicted to stabilize the N- an C-termini of the peptide.

These two peptides CS16342 A13-NpGLu-CGly-NH2 and CS16343 A13-NGly_CPro were synthesized and formulated.

Summary of A13 and the Four (4) Analogue Sequences:

TABLE 3

Amino Acid Sequences of A13 and Four (4) Analogues.

| | |
|---|---|
| CS15134 A13_rd31 C-40-C A13 parent) | CIEQSFTTLFACQTAA EIWRAFGYTVKIMVDN GNCRLHVC (SEQ ID NO: 379) |
| CS15989 A13_r31_AWQ C-40-C | CIEQSFTTLFAAQTAA EIWRAFGYTVKIMQDN GNWRLHVC (SEQ ID NO: 459) |
| CS15990 A13_r31_TAWQT T-40-T | TIEQSFTTLFAAQTAA EIWRAFGYTVKIMQDN GNWRLHVT (SEQ ID NO: 460) |
| CS16342 A13-NpE-CG-NH2 | pE-IEQSFTTLFACQT AAEIWRAFGYTVKIMV DNGNCRLHV-GNH2 (SEQ ID NO: 461) |
| CS16343 A13-NG_CP | GIEQSFTTLFACQTAA EIWRAFGYTVKIMVDN GNCRLHVP (SEQ ID NO: 462) |

Mass Spectrometry Analysis of the Disulfides of A13:

Two independent lots of synthesized and purified A13 CS159134 have been characterized by HPLC, and mass spectrometry; both prior to and after exposure to reducing agent dithiothreitol (DTT). These studies confirm that the majority of A13 peptide behaves as if it has two disulfides prior to reducing with DTT and that these disulfides are reduced after exposure to DTT. Furthermore, attempts to oxidize any free thiols in CS159134 A13 revealed that only a very minor amount of the peptide contains any free Cys residues, which is consistent with MS/MS analysis of intact and trypsin chymotrypsin digested A13.

MS/MS analysis of A13, A13_r31_TAWQT Thr-40-Thr, CS15990 A13_r31_TAWQT Thr-40-Thr:

A13 CS15134), A13_r31_TAWQT Thr-40-Thr (CS15990), and A13_r31_AWQ Cys-40-Cys (CS15989), were all analyzed by trypsin digest MS/MS with and without prior reducing agent treatment. The results are primarily consistent with A13 having two disulfides Cys1-Cys40 and Cys12-Cys35. A13_r31_Thr-40-Thr has no disulfides as expected. CS15989 A13_r31_AWQ Cys-40-Cys has a single disulfide as Cys1-Cys40. These data are consistent with the predicted structures of these peptides.

SDS-PAGE and HPLC Analysis of A13:

A13 from different lots of formulated peptide have been analyzed by SDS-PAGE both prior to and after exposure to reducing agent dithiothreitol (DTT). These results demonstrate that the majority of A13 contains disulfide bonds which make the peptide more compact and run in SDS-PAGE with higher mobility than when it is reduced. The majority of the peptide runs as a single band with minor contaminants. Similar results were observed by HPLC analysis of A13 before and after reduction with DTT where a clear mobility shift in bulk peak elution is observed.

The SEC-HPLC of the lots of A13 formulated followed by dilution indicates a single monomeric peak, corresponding to the expected retention time of a 4.5 kDA peptide. The SDS-PAGE results demonstrate a shift in molecular weight in reducing versus non-reducing conditions, indicating formation of the disulfide bonds.

CD Analysis of A13:

Two independent lots of synthesized and purified A13 were formulated by diluting from 5 mg/ml in water to 0.2 mg/ml in PBS, and then analyzed by circular dichroisin (CD) including thermal melt study, with identical CD properties observed tbr the two lots (DS).

Ferret Study A13:

A13 was investigated for the ability to protect ferrets from influenza challenge. Ferrets are the standard preclinical model for evaluating new influenza antivirals and success in this model generally translates to success in human clinical testing. Ferrets were challenged by aerosol exposure to H1N1 (CA09) and then 24 hours after challenge, a total of 10 mg of A 13 was administered via both intranasal (5 mg) and intratracheal inoculation (5 mg) to mimic routes of delivery achieved by nose/oral nebulizers used in humans. The results in FIG. 1 show that A13 afforded profound protection from clinical signs of disease in ferrets. Control annuals that received only saline exhibited significant clinical signs of disease (lethargy, sneezing/coughing, labored breath, reduced appetite, FIG. 1 Left Panel) and weight loss (FIG. 1 Right Panel). In contrast, animals that received A13 exhibited minimal clinical signs of disease (FIG. 1 Left Panel) and no significant weight loss (FIG. 1 Right Panel). Evaluation of effects of the A13 in reducing viral replication in lung tissue and nasal secretions and reducing lung inflammation is in progress. These data provide strong evidence that A13 anti-flu minibinder mediates profound protection from influenza disease in the standardized preclinical ferret model for influenza infection.

REFERENCES

1. Kintzing, J. R. & Cochran, J. R. Engineered knottin peptides as diagnostics, therapeutics, and drug delivery vehicles, *Curr. Opin. Chem. Biol.* 34, 143-150 (2016).
2. Gebauer, M. & Skerra, A. Engineered protein scaffolds as next-generation antibody therapeutics. *Curr. Opin. Chem. Biol.* 13, 245-255 (2009).
3. Zahnd, C. et al. Efficient tumor targeting with high-affinity designed ankyrin repeat proteins: effects of affinity and molecular size. *Cancer Res.* 70. 1595-1605 (2010).
4. Vazquez-Lombardi, R. et al. Challenges and opportunities for non-antibody scaffold drugs. *Drug Discov. Today* 20, 1271-1283 (2015).
5. Bhardwaj, G. et al. Accurate de novo design of hyperstable constrained peptides. *Nature* 538, 329-335 (2016).
6. Rocklin, G. J. et at Global analysis of protein folding using massively parallel design, synthesis, and testing. *Science* 357, 168-175 (2017).
7. Berger, S. et al. Computationally designed high specificity inhibitors delineate the roles of BCL2 family proteins in cancer, *Elife* 5, (2016).
8. Procko, E. et al. A computationally designed inhibitor of an Epstein-Barr viral Bcl-2 protein induces apoptosis in infected cells. *Cell* 157, 1644-1656 (2014).
9. Cleary, M. A. et al. Production of complex nucleic acid libraries using highly parallel in situ oligonucleotide synthesis. *Nat. Methods* 1, 241-248 (2004).
10. Sun, M. G. F., Seo, M.-H., Nim, S., Corbi-Verge, C. & Kim, P. M. Protein engineering by highly parallel screening of computationally designed variants. *Sci Adv* 2, e1600692 (2016).
11. Fleishman, S. J. et al. RosettaScripts: a scripting language interface to the Rosetta macromolecular modeling suite. *PLoS One* 6, e20161 (2011).
12. Hurt, A. C. et al. Antiviral resistance during the 2009 influenza A H1N1 pandemic: public health, laboratory, and clinical perspectives. *Lancet Infect. Dis.* 12, 240-248 (2012).
13. Blitzer, A. Spasmodic dysphonia and botulinum toxin: experience from the largest treatment series. *Eur. J. Neurol.* 17, 28-30 (2010).
14. Koday, M. T. et al. A Computationally Designed Hemagglutinin Stem-Binding Protein Provides In Vivo Protection from Influenza Independent of a Host Immune Response. *PLoS Pathog.* 12, e1005409 (2016).
15. Whitehead, T. A. et al. Optimization of affinity, specificity and function of designed influenza inhibitors using deep sequencing. *Nat. Biotechnol.* 30, 543-548 (2012).
16. Fleishman, S. J. et al. Computational design of proteins targeting the conserved stem region of influenza hemagglutinin. *Science* 332. 816-821 (2011).
17. Berntsson, R. P. A., Peng, L., Dong, M. & Stenmark, P. Structure of Botulinum neurotoxin B binding domain in complex with both synaptotagmin II and GD1a. (2013). doi: 10.2210/pdb4kbb/pdb
18. Corti, D. et al. A antibody selected from plasma cells that binds to group 1 and group 2 influenza A hemagglutinis. *Science* 333, 850-856 (2011).
19. Cass, L. M. R., Efthymiopoulos, C. & Bye, A. Pharmacokinetics of Zanamivir After Intravenous, Oral, Inhaled of Intranasal Administration to Healthy Volunteers. *Clin. Pharmacokinet* 36, 1-11 (1999).
20. King, C. et al. Removing T-cell epitopes with computational protein design. *Proc. Natl. Acad. Sci: U.S.A.* 111, 8577-8582 (2014).
21. Huang, P.-S. et al. RosettaRemodel: a generalized framework for flexible backbone protein design. *PLoS One* 6, e24109 (2011).
22. Lin, Y.-R. et al. Control over overall shape and size in de novo designed proteins. *Proc. Natl. Acad. Sci. U.S.A.* 112, E5478-85 (2015).
23. Koga, N. et al. Prineiples for designing ideal protein structures. *Nature* 491, 222-227 (2012).

24. Silva, D.-A., Correia, B. E, & Procko, E. Motif-Driven Design of Protein-Protein Interfaces, in Methods in Molecular Biology 285-304 (2016).

25. Hoover, D. M. DNAWorks: an automated method for designing oligonucleotides for PCR-based gene synthesis. Nucleic Acids Res. 30, 43e-43 (2002).

26. Bawono, P. &. Heringa, J. PRALINE: A Versatile Multiple Sequence Alignment Toolkit. in Methods in Molecular Biology 245-262 (2013).

27. Zhang, J., Kobert, K., Flouri, T. & Stamatakis, A. PEAR: a fast and accurate Illumina Paired-End reAd mergeR. Bioinformatics 30, 614-620 (2013).

28. Waskom, M. et al. seaborn; v0.7.1 (June 2016). doi:10.5281/zenodo.54844

29. Chao, G. el al. Isolating and engineering human antibodies using yeast surface display. Nat. Protoc. 1, 755-768 (2006).

30. Benatuil, L., Perez, J. M., Belk, J. & Hsieh, C.-M. An improved yeast transformation method for the generation of very large human antibody libraries, Protein Eng. Des. Sel. 23, 155-159 (2010).

31. Jacobs, T. M., Yumerefendi, H., Kuhlman, B. & Leaver-Fay, A. SwiftLib: rapid degenerate-codon-library optimization through dynamic programming. Nucleic Acids Res. 43, e34 (2015).

32. Jin, R., Rummel, A., Binz, T. & Brungt, T. A. Botalinum neurotoxin B recognizes its protein receptor with high affinity and specificity. Nature 444, 1092-1095 (2006).

32. Kabsch, W. XDS. Acta Crystallogr. 66, 125-132 (2010).

34. Emsley, P. & Cowtan, K. Coot: model-building tools for molecular graphics. Acta Crystallogr. D Biol. Crystalloger. 60, 2126-2132 (2004).

35. McCoy, A. J. et al. Phasercrystallographic software. J. Appl. Crystalloger. 40, 658-674 (2007).

36. Brünger, A. T. Free R value: a novel statistical quantity for assessing the accuracy of crystal structures. Nature 355, 472-475 (1992).

37. Chen, V. B. et al. MolProbity; all-atom structure validation for macromolecular crystallography. Acta Crystallogr. D Biol Crystallogr. 66, 12-21 (2010).

38. Otwinowski, Z. & Minor, W. [20] Processing of X-ray diffraction data collected in oscillation mode, in Methods in Enzymology 307-326 (1997).

39. McCoy, A. J. at al. Phaser crystallographic softsware. J. Appl. Crystallogr. 40, 658-674 (2007).

40. Adams, P. D. et al. The Phenix software for automated determination of macromolecular structures. Methods 55, 94-106 (2011).

41. Gamblin, S. J. et al. The structure and receptor binding properties of the 1918 influenza hemagglutinin, Science 303, 1838-1842 (2004).

42. Van Der Spoel, D. et al GROMACS: fast, flexible, and free. J. Comput. Chem. 26, 1701-1718 (2005).

43. Lindorff-Larsen, K. et al. Improved side-chain torsion potentials for the Amber ff99SB protein force field. Proteins. 78, 1950-1958 (2010).

44. Jorgensen, W. I., Chandrasekhar, J., Madura, J. D., Impey, R. W. & Klein, M. I. Comparison of simple potential functions for simulating liquid water. J. Chem. Phys. 79, 926 (1983).

45. Hess, B., Bekker, H., Berendsen, H. J. C. & Johannes G E. LINCS. A linear constraint solver for molecular simulations. J. Comput. Chem. 18, 1463-1472 (1997).

46. Essmann, U. et al. A smooth particle mesh Ewald method. J. Clim. Phys. 103, 8577 (1995).

47. Berendsen, H. J. C. Transport Properties Computed by Linear Response through Weak Couplin to a Bath, in Computer Simulation in Materiais Science 139-155 (1991).

48. Bussi, G., Donadio. D. & Parrinello, M. Canonical sampling through velocity resealing. J. Chem. Phys. 126, 014101 (2007).

49. Nosé, S. & Klein, M. L. Constant pressure molecular dynamics for molecular systems. Mol. Phys. 50, 1055-1076 (1983).

We claim:

1. An isolated polypeptide, comprising an amino acid sequence having the amino acid sequence of any one of SEQ ID NOS: 1, 351-352, 378-379, 381-382, and 455-462.

2. The isolated polypeptide of claim 1, comprising the amino acid sequence of SEQ ID NO:379 or 459-462.

3. An isolated nucleic acid encoding the polypeptide of claim 1.

4. A recombinant expression vector comprising the nucleic acid of claim 3, operatively linked to a suitable control sequence.

5. A recombinant host cell comprising the recombinant expression vector of claim 4.

6. An antibody that selectively binds to the polypeptide of claim 1.

7. A pharmaceutical composition, comprising one or more polypeptides according to claim 1 and a pharmaceutically acceptable carrier.

8. A method for limiting and/or treating an influenza infection, comprising administering to a subject in need thereof aft therapeutically effective amount of one or more polypeptides of claim 1, salts thereof, conjugates thereof, or pharmaceutical compositions thereof, to treat and/or limit the influenza infection.

9. The method of claim 8, wherein an effective amount of one or more polypeptides are administered mucosally, intranasally, or orally.

10. A method for diagnosing an influenza infection, or monitoring progression of an influenza infection, comprising (a) contacting a biological sample from a subject suspected of having an influenza infection with a diagnostically effective amount of one or more polypeptides of claim 7, under conditions suitable for binding of the polypeptide to a viral hemagglutinin protein present in the sample; and (b) detecting polypeptide-viral hemagglutinin binding complexes, where the presence of such binding complexes indicates that the subject has an influenza infection, or provides a measure progression of an influenza infection.

11. The isolated polypeptide of claim 1, comprising the amino acid sequence of SEQ ID NO:1.

12. The isolated polypeptide of claim 1, comprising the amino acid sequence of SEQ ID NO:379.

13. The isolated polypeptide of claim 1, comprising the amino acid sequence of SEQ ID NO:459.

14. The isolated polypeptide of claim 1, comprising the amino acid sequence of SEQ ID NO:460.

15. The isolated polypeptide of claim 1, comprising the amino acid sequence of SEQ ID NO:461.

16. The isolated polypeptide of claim 1, comprising the amino acid sequence of SEQ ID NO:462.

17. An isolated nucleic acid encoding the polypeptide of claim 2.

18. A recombinant expression vector comprising the nucleic acid of claim 17, operatively linked to a suitable control sequence.

19. A recombinant host cell comprising the recombinant expression vector of claim 18.

* * * * *

SEQUENCE LISTING

```
<160> NUMBER OF SEQ ID NOS: 462

<210> SEQ ID NO 1
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is Q or I
<220> FEATURE:
<221> NAME/KEY: MISC_FEATURE
<222> LOCATION: (6)..(6)
<223> OTHER INFORMATION: X is F or V
<220> FEATURE:
<221> NAME/KEY: MISC_FEATURE
<222> LOCATION: (9)..(9)
<223> OTHER INFORMATION: X is L or P
<220> FEATURE:
<221> NAME/KEY: MISC_FEATURE
<222> LOCATION: (14)..(14)
<223> OTHER INFORMATION: X is T or I
<220> FEATURE:
<221> NAME/KEY: MISC_FEATURE
<222> LOCATION: (25)..(25)
<223> OTHER INFORMATION: X is T or E
<220> FEATURE:
<221> NAME/KEY: MISC_FEATURE
```

<222> LOCATION: (29)..(29)
<223> OTHER INFORMATION: X is M or D
<220> FEATURE:
<221> NAME/KEY: MISC_FEATURE
<222> LOCATION: (30)..(30)
<223> OTHER INFORMATION: X is V or D

<400> SEQUENCE: 1

Cys Ile Glu Xaa Ser Xaa Thr Thr Xaa Phe Ala Cys Gln Xaa Ala Ala
1               5                   10                  15

Glu Ile Trp Arg Ala Phe Gly Tyr Xaa Val Lys Ile Xaa Xaa Asp Asn
            20                  25                  30

Gly Asn Cys Arg Leu His Val Cys
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic

<400> SEQUENCE: 2

Lys Lys Lys Ile Thr Val Glu Ser Pro Phe Thr Ala Trp Met Leu Ala
1               5                   10                  15

Met Trp Leu Trp Ala Phe Gly Thr Pro Val Thr Cys Thr Thr His Gly
            20                  25                  30

Thr Lys Ile Thr Cys Lys Glu Glu
        35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic

<400> SEQUENCE: 3

Thr Ile Glu Phe Asn Val Tyr Ser Pro Phe Ser Ala Lys Met Ala Ala
1               5                   10                  15

Met Trp Cys Glu Val Phe Gly Ala Pro Tyr Thr Val His Lys His Gly
            20                  25                  30

Thr Lys Ile Thr Val Lys Cys Glu
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic

<400> SEQUENCE: 4

Thr Glu Thr Tyr His Phe Thr Ser Phe Asp Leu Ala Met Arg Ala Ala
1               5                   10                  15

Trp Lys Ala Ala Phe Asn Asn Leu Glu Val His Cys Glu Asn His Asn
            20                  25                  30

Gly Thr Val Gln Cys His Val Lys
        35                  40

<210> SEQ ID NO 5
<211> LENGTH: 40
<212> TYPE: PRT

```
<213> ORGANISM: Artificial Sequence
<220> FEATURE:
<223> OTHER INFORMATION: Synthetic

<400> SEQUENCE: 5

Ser Thr Thr Val Thr Ile Glu Cys Pro Phe Asn Ala Trp Met Phe Ala
1               5                   10                  15

Met Trp Ala Arg Ala Phe Gly Arg Glu Val His Cys Glu Lys His Gly
            20                  25                  30

Asp Lys Val Thr Cys Thr Phe Glu
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic

<400> SEQUENCE: 6

Thr Ile His Ile Gln Glu Thr Ser Arg Phe Asn Cys Ala Met Arg Ala
1               5                   10                  15

Met Trp Ala Trp Ala Phe Gly Ala Pro Val Glu Ile Gln Glu His Asn
            20                  25                  30

Gly Gln Cys Gln Val His Ile Lys
        35                  40

<210> SEQ ID NO 7
<211> LENGTH: 40
<212> TYPE: PRT
<213> ORGANISM: Artificial Sequence
<220> FEATURE:
<223> OTHER INFORMATION: Synthetic

<400> SEQUENCE: 7

Thr Glu Lys Tyr Thr Trp His Ser Pro Phe Ala Cys Lys Met Ala Ala
1               5                   10                  15

Met Trp Trp Arg Ala Phe Gly Arg Asp Val Gln Val His Gln Lys Asn
            20                  25                  30

Gly Thr Cys Thr Val Glu Val His
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic

<400> SEQUENCE: 8

Thr Glu His Ser Val Ala Arg Ser Ile Phe Ser Ala Trp Ile Ala Ala
1               5                   10                  15

Lys Ile Ala Ala Glu Phe Gly Leu Asp Val Thr Cys Thr Leu Lys Asn
            20                  25                  30

Gly Lys Val Thr Cys Gln Val Asn
        35                  40

<210> SEQ ID NO 9
<211> LENGTH: 40
<212> TYPE: PRT
<213> ORGANISM: Artificial Sequence
<220> FEATURE:
<223> OTHER INFORMATION: Synthetic
```

<400> SEQUENCE: 9

Thr Cys His Thr Thr Ser Asn Ala Pro Phe Ala Cys Ala Ile Ala Arg
1               5                   10                  15

Asp Ile Ala Ile Glu Phe Asn Leu Glu Val His Ile Thr Gln Lys Asn
            20                  25                  30

Gly Lys Cys Thr Leu Glu Ile Arg
        35                  40

<210> SEQ ID NO 10
<211> LENGTH: 40
<212> TYPE: PRT
<213> ORGANISM: Artificial Sequence
<220> FEATURE:
<223> OTHER INFORMATION: Synthetic

<400> SEQUENCE: 10

Cys Tyr Lys Ser Gln Ala Lys Met Pro Phe Ala Ala Gln Ile Ala Ala
1               5                   10                  15

Glu Ile Ala Arg Glu Phe Asn Ile Pro Val Lys Val Gln Gln His Gly
            20                  25                  30

Asp Thr Leu Lys Val Glu His Cys
        35                  40

<210> SEQ ID NO 11
<211> LENGTH: 40
<212> TYPE: PRT
<213> ORGANISM: Artificial Sequence
<220> FEATURE:
<223> OTHER INFORMATION: Synthetic

<400> SEQUENCE: 11

Cys Val Thr Ser Gln Ala Arg Gln Pro Phe Ala Ala Glu Ile Ala Ala
1               5                   10                  15

Gln Ile Met Lys Glu Phe Asn Ile Glu Val His Cys Glu Lys Lys Gly
            20                  25                  30

Pro Thr Leu Lys Cys Thr Ser Cys
        35                  40

<210> SEQ ID NO 12
<211> LENGTH: 40
<212> TYPE: PRT
<213> ORGANISM: Artificial Sequence
<220> FEATURE:
<223> OTHER INFORMATION: Synthetic

<400> SEQUENCE: 12

Cys Tyr Thr Thr Ile Ala His Thr Pro Phe Ala Ala Lys Ile Ala Ala
1               5                   10                  15

Lys Ile Ala Ala Glu Phe Gly Tyr Glu Val His Val Gln Gln His Gly
            20                  25                  30

Pro Thr Val Lys Leu Gln Val Cys
        35                  40

<210> SEQ ID NO 13
<211> LENGTH: 40
<212> TYPE: PRT
<213> ORGANISM: Artificial Sequence
<220> FEATURE:
<223> OTHER INFORMATION: Synthetic

<400> SEQUENCE: 13

-continued

Thr Tyr Thr Lys Glu Ser Asn Met Pro Phe Ala Ala Ile Ala Ala
1               5                   10                  15

Lys Ile Trp Trp Glu Phe Gly Ile Pro Val Thr Cys Ser Gln His Gly
            20                  25                  30

Asn Thr Val Lys Cys His Val Asn
            35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic

<400> SEQUENCE: 14

Thr Thr Thr Tyr Thr Trp Asp Ser Phe Asp Ala Ala Met Lys Ala Met
1               5                   10                  15

Trp Leu Leu Val Phe Lys Gly Ile Pro Val Gln Ile Thr Ala Lys Asn
            20                  25                  30

Gly Lys Trp Gln Val Lys Glu His
            35                  40

<210> SEQ ID NO 15
<211> LENGTH: 40
<212> TYPE: PRT
<213> ORGANISM: Artificial Sequence
<220> FEATURE:
<223> OTHER INFORMATION: Synthetic

<400> SEQUENCE: 15

Thr Glu Glu Tyr Thr Phe Asp Thr Phe Asp Glu Ala Met Arg Ala Ala
1               5                   10                  15

Trp Glu Ala Val Phe Lys Gly Leu Glu Val His Val Arg Ser Lys Asn
            20                  25                  30

Gly Lys Trp Thr Val His Val Lys
            35                  40

<210> SEQ ID NO 16
<211> LENGTH: 40
<212> TYPE: PRT
<213> ORGANISM: Artificial Sequence
<220> FEATURE:
<223> OTHER INFORMATION: Synthetic

<400> SEQUENCE: 16

Thr Ile Asn Ile Glu Ile His Cys Phe Asp Ala Ala Met Arg Ala Met
1               5                   10                  15

Trp Trp Ala Ala Phe Ala Gly Lys Gln Val Ile Ile Thr Gln Thr Asn
            20                  25                  30

Gly Gln Trp His Val Gln Val Gln
            35                  40

<210> SEQ ID NO 17
<211> LENGTH: 40
<212> TYPE: PRT
<213> ORGANISM: Artificial Sequence
<220> FEATURE:
<223> OTHER INFORMATION: Synthetic

<400> SEQUENCE: 17

Thr Val Asp Leu Glu Asn Tyr Ser Pro Phe Ala Ala Glu Met Ala Arg
1               5                   10                  15

Met Trp Ala Gln Ala Phe Asn Ala Pro Tyr Thr Val Glu Lys His Asn
            20                  25                  30

Gly Arg Phe His Val Lys Val Ala
        35                  40

<210> SEQ ID NO 18
<211> LENGTH: 40
<212> TYPE: PRT
<213> ORGANISM: Artificial Sequence
<220> FEATURE:
<223> OTHER INFORMATION: Synthetic

<400> SEQUENCE: 18

Thr Thr Thr Ile Gln Phe Asp Arg Phe Asp Asn Ala Met Lys Ala Ala
1               5                   10                  15

Trp Lys Leu Ala Phe Leu Gly Ile Pro Tyr Lys Val Thr Gln Val Asn
            20                  25                  30

Gly Ser Trp Thr Val Thr Gln Lys
        35                  40

<210> SEQ ID NO 19
<211> LENGTH: 40
<212> TYPE: PRT
<213> ORGANISM: Artificial Sequence
<220> FEATURE:
<223> OTHER INFORMATION: Synthetic

<400> SEQUENCE: 19

Thr Glu Thr Val Thr Val His Ser Phe Asp Glu Ala Met Arg Leu Met
1               5                   10                  15

Trp Tyr Ala Val Phe His Asn Leu Asp Val Thr Phe His Lys His Gly
            20                  25                  30

Asn Lys Ile Lys Val Glu Ile Asn
        35                  40

<210> SEQ ID NO 20
<211> LENGTH: 40
<212> TYPE: PRT
<213> ORGANISM: Artificial Sequence
<220> FEATURE:
<223> OTHER INFORMATION: Synthetic

<400> SEQUENCE: 20

Thr Arg Thr Ile Thr Val Val Ser Pro Phe Ala Ala Trp Met Ala Met
1               5                   10                  15

Met Trp Ala Ala Ala Phe Gly Ala Pro Phe Thr Val Glu Thr His Gly
            20                  25                  30

Asp Thr Phe Lys Val Thr Ile His
        35                  40

<210> SEQ ID NO 21
<211> LENGTH: 40
<212> TYPE: PRT
<213> ORGANISM: Artificial Sequence
<220> FEATURE:
<223> OTHER INFORMATION: Synthetic

<400> SEQUENCE: 21

Ser Thr Gln Ile Asn Val Glu Ser Pro Phe Ala Ala Trp Met Ala Lys
1               5                   10                  15

Met Trp Ala Leu Ala Phe Gly Ala Glu Val His Val Thr Gln Lys Asn
            20                  25                  30

```
Gly Thr Trp His Ile Gln Leu Lys
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic

<400> SEQUENCE: 22

Gly Lys Glu Ile Lys Val Gln Asn Pro Phe Ser Ala Trp Met Ala Ala
1               5                   10                  15

Met Trp Ala Lys Ala Phe Gly Thr Pro Val Thr Leu Lys Gln Asp Gly
            20                  25                  30

Asn Thr Phe His Leu His Gln His
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic

<400> SEQUENCE: 23

Thr Ile Thr Ile Lys Val Asp Cys Phe Asp Gln Ala Met Arg Ala Met
1               5                   10                  15

Trp Ala Ala Val Phe Ala Gly Leu Glu Leu Glu Gln Gln Thr His Asn
            20                  25                  30

Gly Thr Ile His Val His Leu Lys
        35                  40

<210> SEQ ID NO 24
<211> LENGTH: 40
<212> TYPE: PRT
<213> ORGANISM: Artificial Sequence
<220> FEATURE:
<223> OTHER INFORMATION: Synthetic

<400> SEQUENCE: 24

Thr Gln Thr Phe Lys Tyr Asp Ser Phe Ser Lys Ala Ile Ala Ala Ala
1               5                   10                  15

Ile Lys Ala Glu Phe Lys Gly Leu Pro Phe Lys Val Lys Met Asn Gly
            20                  25                  30

Asp Trp Val Glu Val Glu Ile Thr
        35                  40

<210> SEQ ID NO 25
<211> LENGTH: 40
<212> TYPE: PRT
<213> ORGANISM: Artificial Sequence
<220> FEATURE:
<223> OTHER INFORMATION: Synthetic

<400> SEQUENCE: 25

Glu Ile Thr Arg Thr Ser Ser Lys Glu Phe Ala Ala Trp Ile Ala Ala
1               5                   10                  15

Glu Ile Asn Arg Glu Phe Gly Tyr Asp Val Gln Val Arg Lys Lys Asn
            20                  25                  30

Gly Lys Tyr His Val His Val Lys
        35                  40
```

<210> SEQ ID NO 26
<211> LENGTH: 40
<212> TYPE: PRT
<213> ORGANISM: Artificial Sequence
<220> FEATURE:
<223> OTHER INFORMATION: Synthetic

<400> SEQUENCE: 26

Lys Ile Thr Arg Glu Ala Lys Cys Pro Phe Ala Ala Glu Ile Ala Ala
1               5                   10                  15

Arg Ile Leu Arg Glu Phe Gly Lys Asp Ala Thr Val Thr Thr Leu Asn
            20                  25                  30

Gly His Val Val Val Thr Phe Thr
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic

<400> SEQUENCE: 27

Thr Tyr Glu Thr Asn Ala Pro Ser Pro Phe Ala Ala Ala Ile Ala Ala
1               5                   10                  15

Glu Ile Ala Arg Gln Phe Gly Trp Glu Val Thr Leu Lys Lys Lys Asn
            20                  25                  30

Gly Lys Leu Thr Val His Val Glu
        35                  40

<210> SEQ ID NO 28
<211> LENGTH: 40
<212> TYPE: PRT
<213> ORGANISM: Artificial Sequence
<220> FEATURE:
<223> OTHER INFORMATION: Synthetic

<400> SEQUENCE: 28

Thr Thr Thr Ser Asp Ala Lys Ala Pro Phe Ala Ala Arg Ile Ala Ala
1               5                   10                  15

Glu Ile Ala Arg Glu Phe Gly Tyr Asp Val Gln Leu Thr Lys His Asn
            20                  25                  30

Gly Gln Leu Gln Ile Thr Leu Lys
        35                  40

<210> SEQ ID NO 29
<211> LENGTH: 40
<212> TYPE: PRT
<213> ORGANISM: Artificial Sequence
<220> FEATURE:
<223> OTHER INFORMATION: Synthetic

<400> SEQUENCE: 29

Thr Tyr Thr Ser Tyr Ala His Ser Pro Phe Ala Ala Gln Ile Ala Ala
1               5                   10                  15

Glu Ile Ala Arg Glu Phe Gly Trp Asp Val Thr Tyr Thr Gln His Gly
            20                  25                  30

Asp Thr Leu Lys Val His Val Asn
        35                  40

<210> SEQ ID NO 30
<211> LENGTH: 40

```
<212> TYPE: PRT
<213> ORGANISM: Artificial Sequence
<220> FEATURE:
<223> OTHER INFORMATION: Synthetic

<400> SEQUENCE: 30

Thr Ile Lys Gln Thr Ala Arg Ser Pro Phe Ala Ala Gln Ile Ala Ala
1               5                   10                  15

Asp Ile Ala Ala Glu Phe Gly Tyr Thr Val Lys Leu Ser Gln Lys Asn
                20                  25                  30

Gly Lys Trp His Leu His Val Asn
            35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic

<400> SEQUENCE: 31

Thr Arg Glu Ile Asn Ala Arg Ser Pro Phe Ala Ala Trp Ile Ala Ala
1               5                   10                  15

Glu Ile Ala Lys Glu Phe Gly Tyr Glu Val Glu Val His Lys Lys Asn
                20                  25                  30

Gly Lys Phe Thr Leu His Ser Gln
            35                  40

<210> SEQ ID NO 32
<211> LENGTH: 40
<212> TYPE: PRT
<213> ORGANISM: Artificial Sequence
<220> FEATURE:
<223> OTHER INFORMATION: Synthetic

<400> SEQUENCE: 32

Thr Leu Glu Ile Asn Ala Arg Ser Pro Phe Ala Ala Ala Ile Ala Ala
1               5                   10                  15

Glu Ile Ala Arg Gln Phe Gly Tyr Glu Val Glu Val His Lys Lys Asn
                20                  25                  30

Gly Lys Phe Thr Leu His Ser Gln
            35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic

<400> SEQUENCE: 33

Lys Ile Thr Ile Lys Val Thr Met Phe Ala Gln Ala Ile Ala Ala Val
1               5                   10                  15

Ile Lys Ala Leu Phe Trp Gly Leu Pro Val Thr Val Gln Glu His Gly
                20                  25                  30

Asn Thr Ile Lys Ile Gln Val Lys
            35                  40

<210> SEQ ID NO 34
<211> LENGTH: 40
<212> TYPE: PRT
<213> ORGANISM: Artificial Sequence
<220> FEATURE:
```

<223> OTHER INFORMATION: Synthetic

<400> SEQUENCE: 34

Lys Thr Thr Tyr His Ala Pro Ser Lys Phe Ala Ala Gln Ile Ala Ala
1               5                   10                  15

Glu Ile Leu Arg Glu Phe Gly Ile Pro Val Thr Val Thr Lys Ala Gly
            20                  25                  30

Asp Thr Tyr Val Leu Gln Glu Lys
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic

<400> SEQUENCE: 35

Thr Arg His Thr Thr Ala Pro Ser Glu Phe Ala Ala Glu Ile Ala Arg
1               5                   10                  15

Gln Ile Ala Ala Ser Phe Arg Ile Pro Val Thr Val Thr Lys Lys Asn
            20                  25                  30

Gly Lys Leu Thr Val Lys Val His
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic

<400> SEQUENCE: 36

Thr Thr His Leu Thr Tyr Arg Ser Pro Phe Ala Ala Gln Ile Ala Ala
1               5                   10                  15

Glu Ile Leu Arg Glu Phe Gly Leu Pro Val Asn Val Gln Lys Asn Gly
            20                  25                  30

Pro Thr Leu Thr Val Gln Val Asn
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthetic

<400> SEQUENCE: 37

Thr Lys Thr Ile Lys Val Pro Asp Phe Ser Lys Ala Ile Ala Glu Ala
1               5                   10                  15

Ile Arg Ala Glu Phe Lys Gly Leu Asp Val Lys Val His Ala Leu Asn
            20                  25                  30

Gly Val Ala Val Val Thr Phe Ser
        35                  40

<210> SEQ ID NO 38
<211> LENGTH: 40
<212> TYPE: PRT
<213> ORGANISM: Artificial Sequence
<220> FEATURE:
<223> OTHER INFORMATION: Synthetic

<400> SEQUENCE: 38

```
Thr Ser Thr Ser Glu Ala Ser Lys Asn Phe Ala Ala Ile Ala Ala
1               5                   10                  15

Lys Ile Leu Ala Glu Phe Gly Ile Lys Phe Lys Leu Thr Gln Asn Gly
                20                  25                  30

Asp Thr Tyr Lys Val Thr Ala His
            35                  40
```

<210> SEQ ID NO 39
<211> LENGTH: 40
<212> TYPE: PRT
<213> ORGANISM: Artificial Sequence
<220> FEATURE:
<223> OTHER INFORMATION: Synthetic

<400> SEQUENCE: 39

```
Thr Trp Thr Ser Thr Ala Ala Ser Glu Phe Ala Ala Ile Ala Ala
1               5                   10                  15

Glu Ile Ala Arg Glu Phe Gly Tyr Glu Val His Val Thr Lys Lys Asn
                20                  25                  30

Gly Gln Phe Gln Val Thr Val Lys
            35                  40
```

<210> SEQ ID NO 40
<211> LENGTH: 40
<212> TYPE: PRT
<213> ORGANISM: Artificial Sequence
<220> FEATURE:
<223> OTHER INFORMATION: Synthetic

<400> SEQUENCE: 40

```
Thr Tyr Thr Ser Val Ala Lys Ser Glu Phe Ala Ala Glu Ile Ala Ala
1               5                   10                  15

Arg Ile Ala Ala Glu Phe Gly Tyr Glu Val His Val Thr Lys Lys Asn
                20                  25                  30

Gly Gln Phe Gln Val Thr Val Lys
            35                  40
```

<210> SEQ ID NO 41
<211> LENGTH: 40
<212> TYPE: PRT
<213> ORGANISM: Artificial Sequence
<220> FEATURE:
<223> OTHER INFORMATION: Synthetic

<400> SEQUENCE: 41

```
Thr Gln Thr Ser Gln Ser Ser Pro Phe Ala Ala Trp Ile Ala Ala
1               5                   10                  15

Glu Ile Leu Lys Glu Phe Gly Ile Pro Val Thr Val Gln Arg His Gly
                20                  25                  30

Asp Thr Val Lys Val Lys Gln Lys
            35                  40
```

<210> SEQ ID NO 42
<211> LENGTH: 40
<212> TYPE: PRT
<213> ORGANISM: Artificial Sequence
<220> FEATURE:
<223> OTHER INFORMATION: Synthetic

<400> SEQUENCE: 42

```
Thr Ile Gln Thr Thr Ala Trp Tyr Pro Phe Ala Ala Trp Ile Tyr Ala
1               5                   10                  15
```

```
Lys Ile Leu Lys Glu Phe Asn Ile Pro Leu Gln Val His Val Lys Asn
            20                  25                  30

Gly Lys Val Thr Val His Lys Glu
        35                  40
```

<210> SEQ ID NO 43
<211> LENGTH: 40
<212> TYPE: PRT
<213> ORGANISM: Artificial Sequence
<220> FEATURE:
<223> OTHER INFORMATION: Synthetic

<400> SEQUENCE: 43

```
Thr Trp Thr Ser Val Ala Ser Lys Glu Phe Ala Ala Gln Ile Ala Ala
1               5                   10                  15

Asp Ile Ala Ala Glu Phe Gly Trp Pro Val Thr Val Lys Lys Asn Gly
            20                  25                  30

Asn Tyr Tyr Thr Val His Phe Asp
        35                  40
```

<210> SEQ ID NO 44
<211> LENGTH: 40
<212> TYPE: PRT
<213> ORGANISM: Artificial Sequence
<220> FEATURE:
<223> OTHER INFORMATION: Synthetic

<400> SEQUENCE: 44

```
Thr Tyr Thr Ser Val Ala Arg Ser Pro Phe Ala Ala Gln Ile Ala Ala
1               5                   10                  15

Glu Ile Leu Lys Glu Phe Gly Tyr Asp Val Thr Val Thr Gln His Gly
            20                  25                  30

Asp Gln Leu Lys Val Thr Val Glu
        35                  40
```

<210> SEQ ID NO 45
<211> LENGTH: 40
<212> TYPE: PRT
<213> ORGANISM: Artificial Sequence
<220> FEATURE:
<223> OTHER INFORMATION: Synthetic

<400> SEQUENCE: 45

```
Thr Gln Thr Thr Val Ala Lys Ser Pro Phe Ala Ala Glu Ile Ala Ala
1               5                   10                  15

Arg Ile Trp Ala Glu Phe Gly Tyr Asp Val Thr Val Thr Gln His Gly
            20                  25                  30

Asp Gln Leu Lys Val Thr Val Glu
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Synthetic

<400> SEQUENCE: 46

```
Thr Thr Thr Val Thr Val Glu Asp Phe Ala Lys Ala Ile Ala Ala Ala
1               5                   10                  15

Ile Leu Leu Glu Phe Asn Gly Lys Asp Val Gln Val Glu His His Gly
            20                  25                  30
```

Lys Tyr Val Thr Leu Gln Gln His
        35                  40

<210> SEQ ID NO 47
<211> LENGTH: 40
<212> TYPE: PRT
<213> ORGANISM: Artificial Sequence
<220> FEATURE:
<223> OTHER INFORMATION: Synthetic

<400> SEQUENCE: 47

Thr Val Thr Ile Lys Val Glu Asp Lys Phe Ser Cys Glu Met Ala Ile
1               5                   10                  15

Met Trp Leu Lys Ala Phe Gly Gln Asp Cys Thr Phe Glu Leu His Gly
            20                  25                  30

Asn Thr Cys His Ile Gln Cys Lys
        35                  40

<210> SEQ ID NO 48
<211> LENGTH: 40
<212> TYPE: PRT
<213> ORGANISM: Artificial Sequence
<220> FEATURE:
<223> OTHER INFORMATION: Synthetic

<400> SEQUENCE: 48

Thr Ile His Ser Thr Ala Asn Ala Pro Phe Ala Cys Arg Ile Ala Ala
1               5                   10                  15

Glu Ile Ala Arg Glu Phe Asn Ile Pro Val Thr Leu Arg Glu His Gly
            20                  25                  30

Asp Thr Cys Thr Ile Gln Asn Lys
        35                  40

<210> SEQ ID NO 49
<211> LENGTH: 40
<212> TYPE: PRT
<213> ORGANISM: Artificial Sequence
<220> FEATURE:
<223> OTHER INFORMATION: Synthetic

<400> SEQUENCE: 49

Thr Glu Thr Ser Val Ala His Ala Pro Phe Ala Ala Gln Ile Ala Ala
1               5                   10                  15

Glu Ile Trp Arg Glu Phe Gly Tyr Lys Val Thr Cys Thr Glu Lys Asn
            20                  25                  30

Gly Thr Val Thr Cys Lys Val Gln
        35                  40

<210> SEQ ID NO 50
<211> LENGTH: 40
<212> TYPE: PRT
<213> ORGANISM: Artificial Sequence
<220> FEATURE:
<223> OTHER INFORMATION: Synthetic

<400> SEQUENCE: 50

Thr Tyr His Ser Thr Ala Arg Ala Pro Phe Ala Cys Lys Ile Ala Ala
1               5                   10                  15

Glu Ile Ala Arg Gln Phe Asn Trp Glu Val His Leu His Glu Lys Asn
            20                  25                  30

Gly Lys Cys Thr Leu Gln Ile Lys
        35                  40

<210> SEQ ID NO 51
<211> LENGTH: 40
<212> TYPE: PRT
<213> ORGANISM: Artificial Sequence
<220> FEATURE:
<223> OTHER INFORMATION: Synthetic

<400> SEQUENCE: 51

Cys Met Thr Ser His Thr Tyr Ala Pro Phe Ala Ala Ala Ile Ala Ala
1               5                   10                  15

Lys Ile Ala Ala Glu Phe Gly Tyr Asp Val Gln Leu Gln His Asp Gly
            20                  25                  30

Thr Lys Leu Thr Val His Ser Cys
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic

<400> SEQUENCE: 52

Cys Met Thr Ser His Thr Thr Ala Pro Phe Ala Ala Trp Ile Ala Ala
1               5                   10                  15

Glu Ile Ala Lys Glu Phe Gly Tyr Asp Val Gln Leu Gln His Asp Gly
            20                  25                  30

Thr Lys Leu Thr Val His Ser Cys
        35                  40

<210> SEQ ID NO 53
<211> LENGTH: 40
<212> TYPE: PRT
<213> ORGANISM: Artificial Sequence
<220> FEATURE:
<223> OTHER INFORMATION: Synthetic

<400> SEQUENCE: 53

Cys Tyr His Ser Thr Thr Ala Ser Pro Phe Ala Ala Lys Ile Ala Ala
1               5                   10                  15

Glu Ile Leu Arg Gln Phe Asn Gln Glu Val Thr Val Thr Gln His Gly
            20                  25                  30

Asp Lys Leu Thr Val Gln Trp Cys
        35                  40

<210> SEQ ID NO 54
<211> LENGTH: 40
<212> TYPE: PRT
<213> ORGANISM: Artificial Sequence
<220> FEATURE:
<223> OTHER INFORMATION: Synthetic

<400> SEQUENCE: 54

Cys Tyr His Ser Thr Thr Arg Ser Pro Phe Ala Ala Lys Ile Ala Ala
1               5                   10                  15

Asp Ile Leu Lys Glu Phe Asn Gln Glu Val Thr Val Thr Gln His Gly
            20                  25                  30

Asp Lys Leu Thr Val Gln Trp Cys
        35                  40

<210> SEQ ID NO 55

```
<211> LENGTH: 40
<212> TYPE: PRT
<213> ORGANISM: Artificial Sequence
<220> FEATURE:
<223> OTHER INFORMATION: Synthetic

<400> SEQUENCE: 55

Cys Val Thr Ser His Ser Asn Ser Thr Phe Ala Ala Glu Ile Ala Ala
1               5                   10                  15

Arg Ile Ala Ala Glu Phe Gly Leu Glu Val His Val Gln Lys Asn Gly
            20                  25                  30

Pro Arg Val Glu Val Thr Val Cys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Synthetic

<400> SEQUENCE: 56

Cys Tyr Lys Ser Val Ser Ser Ala Pro Phe Ala Ala Ala Ile Ser Gln
1               5                   10                  15

Glu Ile Ala Arg Gln Phe Asn Trp Asp Val Gln Cys Thr Gln His Gly
            20                  25                  30

Asp Thr Ile Thr Cys His Met Cys
        35                  40

<210> SEQ ID NO 57
<211> LENGTH: 40
<212> TYPE: PRT
<213> ORGANISM: Artificial Sequence
<220> FEATURE:
<223> OTHER INFORMATION: Synthetic

<400> SEQUENCE: 57

Thr Tyr Thr Thr Trp Thr Ala Met Pro Phe Ser Ala Glu Ile Val Arg
1               5                   10                  15

Gln Ile Ala Glu Glu Phe Gly Tyr Glu Val His Cys Thr Gln His Gly
            20                  25                  30

Arg Tyr Val Glu Cys Lys Val Lys
        35                  40

<210> SEQ ID NO 58
<211> LENGTH: 40
<212> TYPE: PRT
<213> ORGANISM: Artificial Sequence
<220> FEATURE:
<223> OTHER INFORMATION: Synthetic

<400> SEQUENCE: 58

Thr Trp Thr Ser Gln Ala Arg Ser Glu Phe Ala Ala Gln Ile Ala Ala
1               5                   10                  15

Asp Ile Ala Asn Ser Phe Gly Leu Pro Cys Thr Val Lys Gln Asn Gly
            20                  25                  30

Pro Thr Tyr Lys Val His Cys Asn
        35                  40

<210> SEQ ID NO 59
<211> LENGTH: 40
<212> TYPE: PRT
<213> ORGANISM: Artificial Sequence
```

<220> FEATURE:
<223> OTHER INFORMATION: Synthetic

<400> SEQUENCE: 59

Thr Trp Thr Ser Val Ala Thr Ala Pro Phe Ala Cys Lys Ile Ala Ala
1               5                   10                  15

Glu Ile Ala Arg Glu Phe Asn Trp Asp Val Thr Val Thr Gln His Gly
            20                  25                  30

Arg Thr Cys Lys Val His Val Glu
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic

<400> SEQUENCE: 60

Thr Cys Tyr Ile Glu Ala Lys Ala Pro Phe Ala Cys Ala Ile Val Ala
1               5                   10                  15

Glu Ile Asn Arg Gln Phe Arg Leu Glu Val His Val Thr Lys Lys Asn
            20                  25                  30

Gly Thr Cys His Val Glu Ile Lys
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic

<400> SEQUENCE: 61

Thr Trp Lys Ser Val Ser His Ser Pro Phe Ala Cys Gln Ile Ala Ala
1               5                   10                  15

Glu Ile Trp Arg Glu Phe Gly Tyr Asp Val Gln Val His Gln Lys Asn
            20                  25                  30

Gly Thr Cys Thr Val Glu Val His
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic

<400> SEQUENCE: 62

Thr Trp Lys Thr Val Ala His Ser Pro Phe Ala Cys Trp Ile Ala Ala
1               5                   10                  15

Lys Ile Trp Lys Glu Phe Gly Tyr Asp Val Gln Val His Gln Lys Asn
            20                  25                  30

Gly Thr Cys Thr Val Glu Val His
        35                  40

<210> SEQ ID NO 63
<211> LENGTH: 40
<212> TYPE: PRT
<213> ORGANISM: Artificial Sequence
<220> FEATURE:
<223> OTHER INFORMATION: Synthetic

```
<400> SEQUENCE: 63

Thr Tyr Lys Val Val Ser His Ser Pro Phe Ala Cys Gln Ile Ala Ala
1               5                   10                  15

Glu Ile Trp Arg Glu Phe Asn Tyr Asp Val Gln Val His Gln Lys Asn
            20                  25                  30

Gly Thr Cys Thr Val Glu Val His
        35                  40

<210> SEQ ID NO 64
<211> LENGTH: 40
<212> TYPE: PRT
<213> ORGANISM: Artificial Sequence
<220> FEATURE:
<223> OTHER INFORMATION: Synthetic

<400> SEQUENCE: 64

Thr Trp Lys Thr Val Ala His Ser Pro Phe Ala Cys Glu Ile Ala Ala
1               5                   10                  15

Arg Ile Trp Ala Glu Phe Gly Tyr Asp Val Gln Val His Gln Lys Asn
            20                  25                  30

Gly Thr Cys Thr Val Glu Val His
        35                  40

<210> SEQ ID NO 65
<211> LENGTH: 40
<212> TYPE: PRT
<213> ORGANISM: Artificial Sequence
<220> FEATURE:
<223> OTHER INFORMATION: Synthetic

<400> SEQUENCE: 65

Thr Tyr Lys Thr Tyr Ala His Ser Pro Phe Ala Cys Glu Ile Ala Ala
1               5                   10                  15

Arg Ile Trp Lys Glu Phe Gly Tyr Asp Val Gln Val His Gln Lys Asn
            20                  25                  30

Gly Thr Cys Thr Val Glu Val His
        35                  40

<210> SEQ ID NO 66
<211> LENGTH: 40
<212> TYPE: PRT
<213> ORGANISM: Artificial Sequence
<220> FEATURE:
<223> OTHER INFORMATION: Synthetic

<400> SEQUENCE: 66

Cys Trp Ile Ser Val Ser His Ser Pro Phe Ala Ala Glu Ile Val Arg
1               5                   10                  15

Glu Ile Val Arg Gln Phe Gly Tyr Glu Val His Val Gln His Gly
            20                  25                  30

Asp Thr Val Lys Val Gln Val Cys
        35                  40

<210> SEQ ID NO 67
<211> LENGTH: 40
<212> TYPE: PRT
<213> ORGANISM: Artificial Sequence
<220> FEATURE:
<223> OTHER INFORMATION: Synthetic

<400> SEQUENCE: 67

Thr Tyr Thr Ser Val Ala Trp Ser Asp Phe Ala Cys Lys Ile Ala Ala
```

```
                1               5                   10                  15
Asp Ile Ala Ala Glu Phe Gly Trp Glu Val His Leu Glu Asn His Asn
            20                  25                  30

Gly Lys Cys Lys Val Thr Val Lys
        35                  40

<210> SEQ ID NO 68
<211> LENGTH: 40
<212> TYPE: PRT
<213> ORGANISM: Artificial Sequence
<220> FEATURE:
<223> OTHER INFORMATION: Synthetic

<400> SEQUENCE: 68

Thr Tyr Thr Ser Val Ala Trp Ser Glu Phe Ala Cys Lys Ile Ala Ala
1               5                   10                  15

Glu Ile Ala Ala Glu Phe Gly Trp Glu Val His Leu Glu Asn His Asn
            20                  25                  30

Gly Lys Cys Lys Val Thr Val Lys
        35                  40

<210> SEQ ID NO 69
<211> LENGTH: 40
<212> TYPE: PRT
<213> ORGANISM: Artificial Sequence
<220> FEATURE:
<223> OTHER INFORMATION: Synthetic

<400> SEQUENCE: 69

Thr Ile Lys Tyr Thr Ala Arg Ser Pro Phe Ala Ala Glu Ile Ser Ala
1               5                   10                  15

Arg Ile Leu Trp Glu Phe Gly Ala Glu Val His Cys Thr Gln His Gly
            20                  25                  30

Asp Arg Val Glu Cys Arg Glu Lys
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic

<400> SEQUENCE: 70

Thr Val Thr Leu His Val Thr Asn Phe Ala Gln Ala Ile Ala Ala Ile
1               5                   10                  15

Ile Lys Cys Glu Phe Leu Gly Leu Pro Val Thr Val Glu Asp His Gly
            20                  25                  30

Asn Thr Ile Lys Ile Gln Cys Thr
        35                  40

<210> SEQ ID NO 71
<211> LENGTH: 40
<212> TYPE: PRT
<213> ORGANISM: Artificial Sequence
<220> FEATURE:
<223> OTHER INFORMATION: Synthetic

<400> SEQUENCE: 71

Thr Thr Lys Leu Lys Phe His Ser Phe Asp Lys Ala Met Glu Ala Leu
1               5                   10                  15

Trp Arg Leu Ala Phe Leu Gly Ile Pro Ala Gln Ala Thr Gln Glu Asn
```

```
                    20                  25                  30

Gly Thr Trp Leu Val Lys Lys His
        35                  40

<210> SEQ ID NO 72
<211> LENGTH: 40
<212> TYPE: PRT
<213> ORGANISM: Artificial Sequence
<220> FEATURE:
<223> OTHER INFORMATION: Synthetic

<400> SEQUENCE: 72

Arg Thr Lys Phe Thr Phe Asp Ser Phe Asp Lys Ala Met Arg Ala Ala
1               5                   10                  15

Trp Lys Ala Val Phe Asn Asn Leu Thr Val His Gln Thr Lys Lys Asn
            20                  25                  30

Gly Lys Tyr His Val Glu Leu Gln
        35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic

<400> SEQUENCE: 73

Thr Ile His Ile Gln Val Thr Ala Phe Asp Glu Ala Met Glu Ala Ala
1               5                   10                  15

Trp Arg Ala Ala Phe Asn Gly Leu Pro Val Glu Ile Gln Ser His Asn
            20                  25                  30

Gly Gln Tyr Gln Val His Ile Lys
        35                  40

<210> SEQ ID NO 74
<211> LENGTH: 40
<212> TYPE: PRT
<213> ORGANISM: Artificial Sequence
<220> FEATURE:
<223> OTHER INFORMATION: Synthetic

<400> SEQUENCE: 74

Lys Thr Thr Tyr Thr Phe Asp Ser Phe Asp Glu Ala Met Arg Ala Ala
1               5                   10                  15

Trp Glu Ala Val Phe Arg Gly Leu Pro Val Gln Leu His Met Lys Asn
            20                  25                  30

Gly Lys Trp Gln Val Thr Val Glu
        35                  40

<210> SEQ ID NO 75
<211> LENGTH: 40
<212> TYPE: PRT
<213> ORGANISM: Artificial Sequence
<220> FEATURE:
<223> OTHER INFORMATION: Synthetic

<400> SEQUENCE: 75

Thr Lys Thr Ile Lys Val Asp Ser Phe Asp Ala Ala Met Lys Thr Ala
1               5                   10                  15

Trp Asp Leu Ala Phe Lys Gly Ile Pro Phe Lys Ile Thr Gln Leu Asn
            20                  25                  30

Gly Thr Trp Val Val Gln Gln Gly
```

<210> SEQ ID NO 76
<211> LENGTH: 40
<212> TYPE: PRT
<213> ORGANISM: Artificial Sequence
<220> FEATURE:
<223> OTHER INFORMATION: Synthetic

<400> SEQUENCE: 76

Thr Lys Thr Ile Lys Val Asp Ser Phe Asp Ala Ala Met Glu Thr Ala
1               5                   10                  15

Trp Arg Leu Ala Phe Lys Gly Ile Pro Phe Lys Ile Thr Gln Leu Asn
            20                  25                  30

Gly Thr Trp Val Val Gln Gln Gly
        35                  40

<210> SEQ ID NO 77
<211> LENGTH: 40
<212> TYPE: PRT
<213> ORGANISM: Artificial Sequence
<220> FEATURE:
<223> OTHER INFORMATION: Synthetic

<400> SEQUENCE: 77

Thr Glu Thr Ile Lys Val Gln Asp Phe Asp Asn Ala Met Arg Ala Met
1               5                   10                  15

Trp Glu Ala Val Phe Arg Asn Ile Pro Val Glu Val Glu Ile His Gly
            20                  25                  30

Pro Thr Leu Lys Val His Ile Lys
        35                  40

<210> SEQ ID NO 78
<211> LENGTH: 40
<212> TYPE: PRT
<213> ORGANISM: Artificial Sequence
<220> FEATURE:
<223> OTHER INFORMATION: Synthetic

<400> SEQUENCE: 78

Thr Ile Thr Ile Val Val Asp Ser Pro Phe Ala Ala Lys Met Ala Ala
1               5                   10                  15

Met Trp Ala Lys Ala Phe Gly Ser Glu Val Glu Val His Arg His Gly
            20                  25                  30

Asp Leu Ile Lys Ile Gln Leu His
        35                  40

<210> SEQ ID NO 79
<211> LENGTH: 40
<212> TYPE: PRT
<213> ORGANISM: Artificial Sequence
<220> FEATURE:
<223> OTHER INFORMATION: Synthetic

<400> SEQUENCE: 79

Lys Gln Thr Ile Gln Phe Pro Ser Phe Asp Ala Ala Met Glu Ala Val
1               5                   10                  15

Trp Arg Ala Ala Phe Lys Gly Leu Pro Val Thr Met Thr Lys Val Asn
            20                  25                  30

Gly Thr Trp Lys Val Lys Ile Lys
        35                  40

```
<210> SEQ ID NO 80
<211> LENGTH: 40
<212> TYPE: PRT
<213> ORGANISM: Artificial Sequence
<220> FEATURE:
<223> OTHER INFORMATION: Synthetic

<400> SEQUENCE: 80

Thr Thr Tyr Gln Lys Val Glu Ala Pro Phe Ser Ala Trp Met Val Ala
1               5                   10                  15

Met Trp Leu Ala Ala Phe Gly Ile Pro Phe Lys Val Gln Lys Lys Asn
            20                  25                  30

Gly Thr Trp His Ile Gln Lys Gln
        35                  40

<210> SEQ ID NO 81
<211> LENGTH: 40
<212> TYPE: PRT
<213> ORGANISM: Artificial Sequence
<220> FEATURE:
<223> OTHER INFORMATION: Synthetic

<400> SEQUENCE: 81

Ser Thr Lys Tyr His Val Lys Ser Phe Asp Glu Ala Met Lys Gln Ala
1               5                   10                  15

Trp Lys Ala Ala Phe Lys Gly Leu Glu Val His Leu Arg Ser Lys Asn
            20                  25                  30

Gly Thr Trp Thr Val Glu Val Arg
        35                  40

<210> SEQ ID NO 82
<211> LENGTH: 40
<212> TYPE: PRT
<213> ORGANISM: Artificial Sequence
<220> FEATURE:
<223> OTHER INFORMATION: Synthetic

<400> SEQUENCE: 82

Thr Thr Thr Tyr Thr Leu Asp Ser Phe Asp Ala Ala Met Lys Ala Met
1               5                   10                  15

Trp Lys Ala Val Phe Asn Gly Ile Pro Val Thr Cys Thr Gln Lys Asn
            20                  25                  30

Gly Lys Trp Gln Val Thr Ile Gln
        35                  40

<210> SEQ ID NO 83
<211> LENGTH: 40
<212> TYPE: PRT
<213> ORGANISM: Artificial Sequence
<220> FEATURE:
<223> OTHER INFORMATION: Synthetic

<400> SEQUENCE: 83

Lys Ala Thr Ser Gln Ser Ser Ser Phe Ala Ala Gln Ile Ala Ala
1               5                   10                  15

Glu Ile Ala Lys Glu Phe Gly Ile Pro Val Thr Val Glu Asp Val Gly
            20                  25                  30

Asp Thr Tyr Lys Val His Asn Glu
        35                  40

<210> SEQ ID NO 84
<211> LENGTH: 40
<212> TYPE: PRT
```

<213> ORGANISM: Artificial Sequence
<220> FEATURE:
<223> OTHER INFORMATION: Synthetic

<400> SEQUENCE: 84

```
Glu Ile Thr Val Thr Ser Asp Lys Ser Phe Ala Ala Ala Ile Ala Ala
1               5                   10                  15
Glu Ile Trp Arg Gln Phe Gly Tyr Asp Val Gln Val Arg Lys Lys Asn
            20                  25                  30
Gly Lys Tyr His Val His Val Lys
        35                  40
```

<210> SEQ ID NO 85
<211> LENGTH: 40
<212> TYPE: PRT
<213> ORGANISM: Artificial Sequence
<220> FEATURE:
<223> OTHER INFORMATION: Synthetic

<400> SEQUENCE: 85

```
Glu Ile Thr Arg Thr Ser Ser Lys Ser Phe Ala Ala Lys Ile Ala Ala
1               5                   10                  15
Asp Ile Asn Lys Glu Phe Gly Tyr Asp Val Gln Val Arg Lys Lys Asn
            20                  25                  30
Gly Lys Tyr His Val His Val Lys
        35                  40
```

<210> SEQ ID NO 86
<211> LENGTH: 40
<212> TYPE: PRT
<213> ORGANISM: Artificial Sequence
<220> FEATURE:
<223> OTHER INFORMATION: Synthetic

<400> SEQUENCE: 86

```
Thr Tyr Thr Ser Lys Ala Cys Lys Pro Phe Ala Ala Gln Ile Ala Ala
1               5                   10                  15
Asp Ile Ala Lys Glu Phe Gly Tyr Glu Val His Val Thr Gln Lys Gly
            20                  25                  30
Gly Thr Val Val Val Thr Arg Lys
        35                  40
```

<210> SEQ ID NO 87
<211> LENGTH: 40
<212> TYPE: PRT
<213> ORGANISM: Artificial Sequence
<220> FEATURE:
<223> OTHER INFORMATION: Synthetic

<400> SEQUENCE: 87

```
Thr Pro Gln Ser Thr Ala Arg Ser Pro Phe Ala Ala Glu Ile Ala Ala
1               5                   10                  15
Arg Ile Leu Lys Glu Phe Asn Ile Pro Tyr Asp Val Gln Thr His Gly
            20                  25                  30
Asp Lys Val Thr Val Thr Ala His
        35                  40
```

<210> SEQ ID NO 88
<211> LENGTH: 40
<212> TYPE: PRT
<213> ORGANISM: Artificial Sequence
<220> FEATURE:
<223> OTHER INFORMATION: Synthetic

<400> SEQUENCE: 88

Thr Pro Gln Ser Thr Ala Tyr Ser Pro Phe Ala Ala Trp Ile Ala Ala
1               5                   10                  15

Lys Ile Leu Glu Glu Phe Asn Ile Pro Tyr Asp Val Gln Thr His Gly
            20                  25                  30

Asp Lys Val Thr Val Thr Ala His
        35                  40

<210> SEQ ID NO 89
<211> LENGTH: 40
<212> TYPE: PRT
<213> ORGANISM: Artificial Sequence
<220> FEATURE:
<223> OTHER INFORMATION: Synthetic

<400> SEQUENCE: 89

Thr Gln Thr Ile Lys Ala Gln Ser Ser Phe Ala Ala Trp Ile Ala Ala
1               5                   10                  15

Glu Ile Leu Arg Gln Phe Asn Ile Pro Val Thr Leu Gln Thr His Gly
            20                  25                  30

Ser Thr Tyr Lys Val Glu Gln His
        35                  40

<210> SEQ ID NO 90
<211> LENGTH: 40
<212> TYPE: PRT
<213> ORGANISM: Artificial Sequence
<220> FEATURE:
<223> OTHER INFORMATION: Synthetic

<400> SEQUENCE: 90

Thr Phe His Ser Val Ala Tyr Ser Pro Phe Ala Ala Glu Ile Ala Arg
1               5                   10                  15

Gln Ile Leu Glu Glu Phe Gly Ile Pro Val Glu Val His Val Lys Asn
            20                  25                  30

Gly Lys Val Glu Val Lys Ser Lys
        35                  40

<210> SEQ ID NO 91
<211> LENGTH: 40
<212> TYPE: PRT
<213> ORGANISM: Artificial Sequence
<220> FEATURE:
<223> OTHER INFORMATION: Synthetic

<400> SEQUENCE: 91

Thr Tyr Thr Ser Ile Ser His Ser Pro Phe Ala Ala Gln Ile Ala Ala
1               5                   10                  15

Asp Ile Ala Ala Glu Phe Gly Trp Asp Val Thr Tyr Thr Gln His Gly
            20                  25                  30

Asp Thr Leu Lys Val His Val Asn
        35                  40

<210> SEQ ID NO 92
<211> LENGTH: 40
<212> TYPE: PRT
<213> ORGANISM: Artificial Sequence
<220> FEATURE:
<223> OTHER INFORMATION: Synthetic

<400> SEQUENCE: 92

Thr Lys Thr Val Thr Ala Arg Ser Lys Phe Ala Ala Asp Ile Ala Ala
1               5                   10                  15

Glu Ile Leu Arg Glu Phe Gly Ile Asp Val Gln Ile Thr Thr Lys Asn
            20                  25                  30

Gly Lys Tyr Gln Leu Gln Asn Lys
        35                  40

<210> SEQ ID NO 93
<211> LENGTH: 40
<212> TYPE: PRT
<213> ORGANISM: Artificial Sequence
<220> FEATURE:
<223> OTHER INFORMATION: Synthetic

<400> SEQUENCE: 93

Lys Ile Thr Phe His Val Thr Arg Phe Ala Glu Ala Ile Ala Ala Ala
1               5                   10                  15

Ile Lys Ala Gln Phe Leu Gly Leu Pro Tyr Thr Val Glu Val His Gly
            20                  25                  30

Thr Glu Ile Lys Ile Lys Val Glu
        35                  40

<210> SEQ ID NO 94
<211> LENGTH: 40
<212> TYPE: PRT
<213> ORGANISM: Artificial Sequence
<220> FEATURE:
<223> OTHER INFORMATION: Synthetic

<400> SEQUENCE: 94

Thr Glu Thr Tyr Thr Ala Pro Ser Glu Phe Ser Ala Ala Ile Ala Ala
1               5                   10                  15

Glu Ile Ala Arg Glu Phe Gly Tyr Asp Leu Gln Val Thr Lys Leu Asn
            20                  25                  30

Gly Lys Trp Val Val His Gln Lys
        35                  40

<210> SEQ ID NO 95
<211> LENGTH: 40
<212> TYPE: PRT
<213> ORGANISM: Artificial Sequence
<220> FEATURE:
<223> OTHER INFORMATION: Synthetic

<400> SEQUENCE: 95

Thr Gln Thr Ile Gln Val Asp Ser Phe Ala Asn Ala Ile Ala Ala Ala
1               5                   10                  15

Ile Leu Ala Leu Phe Lys Asn Leu Pro Val Thr Cys His Arg Asp Gly
            20                  25                  30

Asp Thr Val Lys Leu His Val Lys
        35                  40

<210> SEQ ID NO 96
<211> LENGTH: 40
<212> TYPE: PRT
<213> ORGANISM: Artificial Sequence
<220> FEATURE:
<223> OTHER INFORMATION: Synthetic

<400> SEQUENCE: 96

Thr Trp Thr Thr His Thr Lys Gly Pro Phe Ala Ala Trp Ile Ala Ala
1               5                   10                  15

Gln Ile Leu Glu Phe Asn Leu Asp Val Gln Val Glu Asp His Asn
            20                  25                  30

Gly Lys Phe Thr Leu His Ser Lys
        35                  40

<210> SEQ ID NO 97
<211> LENGTH: 40
<212> TYPE: PRT
<213> ORGANISM: Artificial Sequence
<220> FEATURE:
<223> OTHER INFORMATION: Synthetic

<400> SEQUENCE: 97

Thr Asn Lys Phe Asp Ala Pro Ser Pro Phe Ala Ala Lys Ile Ala Ala
1               5                   10                  15

Glu Ile Leu Lys Glu Phe Gly Tyr Asp Val Thr Val Lys Gln Lys Asn
            20                  25                  30

Gly Gln Val Trp Val Glu Gln Lys
        35                  40

<210> SEQ ID NO 98
<211> LENGTH: 40
<212> TYPE: PRT
<213> ORGANISM: Artificial Sequence
<220> FEATURE:
<223> OTHER INFORMATION: Synthetic

<400> SEQUENCE: 98

Thr Tyr Thr Ile His Ala Ser Ser Pro Phe Ala Ala Trp Ile Ala Ala
1               5                   10                  15

Glu Ile Ala Arg Glu Phe Arg Ile Pro Val Gln Val Gln Gln His Gly
            20                  25                  30

Asp Thr Val Gln Val His Glu His
        35                  40

<210> SEQ ID NO 99
<211> LENGTH: 40
<212> TYPE: PRT
<213> ORGANISM: Artificial Sequence
<220> FEATURE:
<223> OTHER INFORMATION: Synthetic

<400> SEQUENCE: 99

Thr Gln His Thr Gln Ala Lys Ser Glu Phe Ala Ala Gln Ile Ala Ala
1               5                   10                  15

Glu Ile Leu Lys Glu Phe Gly Ile Asp Ala Gln Val Val Lys Val Gly
            20                  25                  30

Pro Thr Tyr Lys Val Lys Glu Thr
        35                  40

<210> SEQ ID NO 100
<211> LENGTH: 40
<212> TYPE: PRT
<213> ORGANISM: Artificial Sequence
<220> FEATURE:
<223> OTHER INFORMATION: Synthetic

<400> SEQUENCE: 100

Thr Tyr His Thr Gln Thr Lys Ser Glu Phe Ala Ala Glu Ile Ala Ala
1               5                   10                  15

Arg Ile Leu Lys Glu Phe Gly Ile Asp Ala Gln Val Val Lys Val Gly
            20                  25                  30

```
Pro Thr Tyr Lys Val Lys Glu Thr
        35                  40

<210> SEQ ID NO 101
<211> LENGTH: 40
<212> TYPE: PRT
<213> ORGANISM: Artificial Sequence
<220> FEATURE:
<223> OTHER INFORMATION: Synthetic

<400> SEQUENCE: 101

Thr Ser Thr Ser Gln Val Arg Met Pro Phe Ala Ala Ile Ala Ala
1               5                   10                  15

Glu Ile Met Arg Gln Phe Gly Tyr Asp Val Gln Val Glu Gln His Gly
                20                  25                  30

Asp Thr Leu Lys Ile Thr Ser Lys
        35                  40

<210> SEQ ID NO 102
<211> LENGTH: 40
<212> TYPE: PRT
<213> ORGANISM: Artificial Sequence
<220> FEATURE:
<223> OTHER INFORMATION: Synthetic

<400> SEQUENCE: 102

Thr Ile Lys Ser Val Thr Lys Ser Ser Phe Ala Ala Ile Ala Ala
1               5                   10                  15

Lys Ile Trp Ala Glu Phe Gly Tyr Asp Val Gln Val Thr Gln Asn Gly
                20                  25                  30

Asp Gln Tyr Thr Val His Val Lys
        35                  40

<210> SEQ ID NO 103
<211> LENGTH: 40
<212> TYPE: PRT
<213> ORGANISM: Artificial Sequence
<220> FEATURE:
<223> OTHER INFORMATION: Synthetic

<400> SEQUENCE: 103

Glu Thr Thr Phe Glu Ala Pro Ser Pro Phe Ala Ala Glu Ile Ala Ala
1               5                   10                  15

Arg Ile Ala Ala Glu Phe Gly Ile Lys Leu Thr Leu Lys Lys Val Asn
                20                  25                  30

Gly Val Leu Val Val Thr Lys Lys
        35                  40

<210> SEQ ID NO 104
<211> LENGTH: 40
<212> TYPE: PRT
<213> ORGANISM: Artificial Sequence
<220> FEATURE:
<223> OTHER INFORMATION: Synthetic

<400> SEQUENCE: 104

Thr Met Lys Ile Thr Ser Arg Ser Lys Phe Ala Ala Leu Ile Ala Ala
1               5                   10                  15

Glu Ile Trp Arg Gln Phe Gly Tyr Glu Val His Ile Leu Thr His Gly
                20                  25                  30

Asp Thr Tyr Gln Val Glu Val Asn
        35                  40
```

<210> SEQ ID NO 105
<211> LENGTH: 40
<212> TYPE: PRT
<213> ORGANISM: Artificial Sequence
<220> FEATURE:
<223> OTHER INFORMATION: Synthetic

<400> SEQUENCE: 105

Thr Met Lys Ile Thr Thr Glu Ser Lys Phe Ser Ala Asp Ile Ala Ala
1               5                   10                  15

Lys Ile Trp Ala Glu Phe Gly Tyr Glu Val His Ile Leu Thr His Gly
            20                  25                  30

Asp Thr Tyr Gln Val Glu Val Asn
        35                  40

<210> SEQ ID NO 106
<211> LENGTH: 40
<212> TYPE: PRT
<213> ORGANISM: Artificial Sequence
<220> FEATURE:
<223> OTHER INFORMATION: Synthetic

<400> SEQUENCE: 106

Thr Thr Thr Tyr Gln Tyr Pro Asn Phe Ala Leu Ala Ile Ala Ala Ala
1               5                   10                  15

Ile Lys Ala Glu Phe Lys Gly Leu Glu Val His Thr Thr Ser Asp Gly
            20                  25                  30

Asp Thr Tyr Lys Ile Thr Val His
        35                  40

<210> SEQ ID NO 107
<211> LENGTH: 40
<212> TYPE: PRT
<213> ORGANISM: Artificial Sequence
<220> FEATURE:
<223> OTHER INFORMATION: Synthetic

<400> SEQUENCE: 107

Lys Arg Thr Leu Lys Ala Asn Ser Asn Phe Ala Ala Gln Ile Ala Ala
1               5                   10                  15

Lys Ile Asn Lys Glu Phe Gly Tyr Glu Val His Val Thr Gln Gln Asn
            20                  25                  30

Gly Thr Trp Gln Val Thr Val Lys
        35                  40

<210> SEQ ID NO 108
<211> LENGTH: 40
<212> TYPE: PRT
<213> ORGANISM: Artificial Sequence
<220> FEATURE:
<223> OTHER INFORMATION: Synthetic

<400> SEQUENCE: 108

Thr Phe Thr Ser Thr Ala Ala Lys Ser Phe Ala Ala Glu Ile Ala Ala
1               5                   10                  15

Arg Ile Met Lys Glu Phe Gly Ile Glu Val Lys Leu Gln Lys Lys Asn
            20                  25                  30

Gly Lys Val Gln Val Gln Ala His
        35                  40

<210> SEQ ID NO 109
<211> LENGTH: 40

<212> TYPE: PRT
<213> ORGANISM: Artificial Sequence
<220> FEATURE:
<223> OTHER INFORMATION: Synthetic

<400> SEQUENCE: 109

Thr Tyr Thr Ser Val Ala Ala Ser Glu Phe Ala Ala Gln Ile Ala Ala
1               5                   10                  15

Glu Ile Ala Arg Glu Phe Gly Trp Glu Val His Val Thr Lys Lys Asn
            20                  25                  30

Gly Gln Phe Gln Val Thr Val Lys
        35                  40

<210> SEQ ID NO 110
<211> LENGTH: 40
<212> TYPE: PRT
<213> ORGANISM: Artificial Sequence
<220> FEATURE:
<223> OTHER INFORMATION: Synthetic

<400> SEQUENCE: 110

Thr Lys Thr Val Lys Val Asp Arg Phe Ala Glu Ala Ile Ala Glu Ala
1               5                   10                  15

Ile Arg Ala Leu Phe Lys Gly Leu Glu Val His Ile Thr Gln Ile Asn
            20                  25                  30

Gly Thr Ala His Val Gln Ile Lys
        35                  40

<210> SEQ ID NO 111
<211> LENGTH: 40
<212> TYPE: PRT
<213> ORGANISM: Artificial Sequence
<220> FEATURE:
<223> OTHER INFORMATION: Synthetic

<400> SEQUENCE: 111

Thr Gln Gln Ser His Ala Ala Asp Ser Phe Ala Ala Trp Ile Ala Ala
1               5                   10                  15

Glu Ile Asn Arg Glu Phe Gly Tyr Glu Val His Val Thr Gln Val Asn
            20                  25                  30

Gly Thr Phe Thr Val Lys Thr Lys
        35                  40

<210> SEQ ID NO 112
<211> LENGTH: 40
<212> TYPE: PRT
<213> ORGANISM: Artificial Sequence
<220> FEATURE:
<223> OTHER INFORMATION: Synthetic

<400> SEQUENCE: 112

Arg Gln Lys Ile Gln Ala Arg Ala Pro Phe Ala Ala Ile Ala Val
1               5                   10                  15

Lys Ile Ala Ala Glu Phe Gly Trp Thr Leu Thr Val Thr Lys His Gly
            20                  25                  30

Asp Thr Leu Thr Val His Glu Glu
        35                  40

<210> SEQ ID NO 113
<211> LENGTH: 40
<212> TYPE: PRT
<213> ORGANISM: Artificial Sequence
<220> FEATURE:

<223> OTHER INFORMATION: Synthetic

<400> SEQUENCE: 113

Thr Met Thr Thr Lys Ser Ser Pro Phe Ala Ala Lys Ile Ala Tyr
1               5                   10                  15

Glu Ile Ala Arg Glu Phe Gly Trp Asp Ala His Ile Thr Gln Lys Asn
            20                  25                  30

Gly Thr Trp His Val Thr Val Lys
        35                  40

<210> SEQ ID NO 114
<211> LENGTH: 40
<212> TYPE: PRT
<213> ORGANISM: Artificial Sequence
<220> FEATURE:
<223> OTHER INFORMATION: Synthetic

<400> SEQUENCE: 114

Thr Lys Thr Phe Gln Ala Arg Ser Glu Phe Ala Ala Ala Ile Ala Ala
1               5                   10                  15

Gln Ile Ala Lys Glu Phe Gly Tyr Glu Val His Leu His Lys Ser Gly
            20                  25                  30

Asn Thr Leu Lys Val Glu Val Arg
        35                  40

<210> SEQ ID NO 115
<211> LENGTH: 40
<212> TYPE: PRT
<213> ORGANISM: Artificial Sequence
<220> FEATURE:
<223> OTHER INFORMATION: Synthetic

<400> SEQUENCE: 115

Thr Trp Thr Ser Val Ala Ser Lys Tyr Phe Ala Ala Glu Ile Ala Arg
1               5                   10                  15

Gln Ile Ala Glu Glu Phe Gly Trp Pro Val Thr Val Lys Lys Asn Gly
            20                  25                  30

Asn Tyr Tyr Thr Val His Phe Asp
        35                  40

<210> SEQ ID NO 116
<211> LENGTH: 40
<212> TYPE: PRT
<213> ORGANISM: Artificial Sequence
<220> FEATURE:
<223> OTHER INFORMATION: Synthetic

<400> SEQUENCE: 116

Thr Lys Thr Ile Lys Val Asp Ser Phe Ala Glu Ala Ile Ala Ala Ala
1               5                   10                  15

Ile Arg Ala Trp Phe Lys Gly Ile Glu Val His Val Thr Arg Val Asn
            20                  25                  30

Gly Thr Ala Ser Val Lys Gln His
        35                  40

<210> SEQ ID NO 117
<211> LENGTH: 40
<212> TYPE: PRT
<213> ORGANISM: Artificial Sequence
<220> FEATURE:
<223> OTHER INFORMATION: Synthetic

<400> SEQUENCE: 117

```
Thr Tyr Thr Ser Val Ala Arg Ser Pro Phe Ala Ala Gln Ile Ala Ala
1               5                   10                  15

Asp Ile Leu Arg Glu Phe Gly Tyr Asp Val Thr Val Thr Gln His Gly
            20                  25                  30

Asp Gln Leu Lys Val Thr Val Glu
        35                  40

<210> SEQ ID NO 118
<211> LENGTH: 40
<212> TYPE: PRT
<213> ORGANISM: Artificial Sequence
<220> FEATURE:
<223> OTHER INFORMATION: Synthetic

<400> SEQUENCE: 118

Thr Tyr Thr Ser Val Ala Arg Ser Pro Phe Ala Ala Gln Ile Ala Ala
1               5                   10                  15

Glu Ile Leu Arg Glu Phe Gly Tyr Asp Val Thr Val Thr Gln His Gly
            20                  25                  30

Asp Gln Leu Lys Val Thr Val Glu
        35                  40

<210> SEQ ID NO 119
<211> LENGTH: 40
<212> TYPE: PRT
<213> ORGANISM: Artificial Sequence
<220> FEATURE:
<223> OTHER INFORMATION: Synthetic

<400> SEQUENCE: 119

Thr Thr Gln Ile Gln Val Lys Ser Phe Ala Glu Ala Ile Ala Glu Ala
1               5                   10                  15

Ile Arg Ala Gln Phe Lys Gly Leu Pro Ala Thr Val Lys Ser Asp Gly
            20                  25                  30

Lys Thr Ala His Val Glu Phe Glu
        35                  40

<210> SEQ ID NO 120
<211> LENGTH: 40
<212> TYPE: PRT
<213> ORGANISM: Artificial Sequence
<220> FEATURE:
<223> OTHER INFORMATION: Synthetic

<400> SEQUENCE: 120

Thr Tyr Thr Ser Gln Ser His Ser Pro Phe Ala Ala Asn Ile Ala Ala
1               5                   10                  15

Glu Ile Leu Lys Glu Phe Gly Ile Glu Phe Thr Gln Thr Lys Val Gly
            20                  25                  30

Asp Thr Leu Lys Ile Thr Ser His
        35                  40

<210> SEQ ID NO 121
<211> LENGTH: 40
<212> TYPE: PRT
<213> ORGANISM: Artificial Sequence
<220> FEATURE:
<223> OTHER INFORMATION: Synthetic

<400> SEQUENCE: 121

Thr Glu Thr Val Gln Val Asp Ser Phe Ala Ala Ala Ile Ala Ala Ser
1               5                   10                  15
```

Ile Lys Ile Glu Phe Arg Gly Leu Glu Val Lys Ile Gln Glu Val Gly
            20                  25                  30

Asp Thr Val Lys Val Glu Leu His
        35                  40

<210> SEQ ID NO 122
<211> LENGTH: 40
<212> TYPE: PRT
<213> ORGANISM: Artificial Sequence
<220> FEATURE:
<223> OTHER INFORMATION: Synthetic

<400> SEQUENCE: 122

Thr Trp Gln Ser Val Ser Val Lys Lys Phe Ala Ala Ile Ala Arg
1               5                   10                  15

Asp Ile Ala Leu Glu Phe Gly Trp Asp Val Gln Leu Thr Gln Gln Asn
            20                  25                  30

Gly Lys Trp Thr Leu His Ile Asn
        35                  40

<210> SEQ ID NO 123
<211> LENGTH: 40
<212> TYPE: PRT
<213> ORGANISM: Artificial Sequence
<220> FEATURE:
<223> OTHER INFORMATION: Synthetic

<400> SEQUENCE: 123

Thr Glu Thr Val Asn Val Thr Cys Pro Phe Trp Cys Trp Met Ala Ala
1               5                   10                  15

Met Trp Trp Lys Ala Phe Gly Ser Glu Val His Val His Gln Asp Gly
            20                  25                  30

Asn Lys Cys Thr Ile Gln Ile Lys
        35                  40

<210> SEQ ID NO 124
<211> LENGTH: 40
<212> TYPE: PRT
<213> ORGANISM: Artificial Sequence
<220> FEATURE:
<223> OTHER INFORMATION: Synthetic

<400> SEQUENCE: 124

Thr Thr Glu Thr Thr Phe Asp Ser Phe Asp Glu Ala Met Gln Ala Met
1               5                   10                  15

Trp Asp Ala Ala Phe Lys Gly Leu Glu Val His Cys Thr Gln Lys Asn
            20                  25                  30

Gly Thr Val Thr Cys Lys Ile His
        35                  40

<210> SEQ ID NO 125
<211> LENGTH: 40
<212> TYPE: PRT
<213> ORGANISM: Artificial Sequence
<220> FEATURE:
<223> OTHER INFORMATION: Synthetic

<400> SEQUENCE: 125

Glu Ile His Ile His Glu Thr Ala Pro Phe Asp Cys Trp Met Arg Tyr
1               5                   10                  15

Met Trp Leu Ala Ala Phe Gly Ser Asn Val Thr Val Thr Glu Arg Gly
            20                  25                  30

```
Asn Lys Cys Thr Val Thr Val Thr
        35              40
```

```
<210> SEQ ID NO 126
<211> LENGTH: 40
<212> TYPE: PRT
<213> ORGANISM: Artificial Sequence
<220> FEATURE:
<223> OTHER INFORMATION: Synthetic

<400> SEQUENCE: 126

Cys Lys Lys Val Gln Val Glu Ser Pro Phe Ser Ala Trp Met Glu Ala
1               5                   10                  15

Met Trp Ala Lys Ala Phe Asn Ile Pro Val Lys Val Gln Gln His Gly
            20                  25                  30

Asp Thr Leu Lys Val Glu His Cys
        35              40
```

```
<210> SEQ ID NO 127
<211> LENGTH: 40
<212> TYPE: PRT
<213> ORGANISM: Artificial Sequence
<220> FEATURE:
<223> OTHER INFORMATION: Synthetic

<400> SEQUENCE: 127

Thr Ile Thr Ile Lys Arg Glu Ser Pro Phe Ala Cys Trp Met Ala Ile
1               5                   10                  15

Met Trp Ala Lys Ala Phe Gly Ala Thr Phe Glu Leu Lys Gln His Gly
            20                  25                  30

Leu Thr Cys Lys Leu His Val Lys
        35              40
```

```
<210> SEQ ID NO 128
<211> LENGTH: 40
<212> TYPE: PRT
<213> ORGANISM: Artificial Sequence
<220> FEATURE:
<223> OTHER INFORMATION: Synthetic

<400> SEQUENCE: 128

Cys Thr Thr Leu Lys Val Asp Ser Phe Asp Lys Ala Met Arg Ile Ala
1               5                   10                  15

Trp Glu Leu Ala Phe Arg Gly Val Arg Ala Tyr Val Arg Leu Cys Asn
            20                  25                  30

Gly Thr Ala Phe Val Gln Lys Cys
        35              40
```

```
<210> SEQ ID NO 129
<211> LENGTH: 40
<212> TYPE: PRT
<213> ORGANISM: Artificial Sequence
<220> FEATURE:
<223> OTHER INFORMATION: Synthetic

<400> SEQUENCE: 129

Thr Ile Thr Phe His Val Val Cys Pro Phe Ser Ala Lys Met Val Ala
1               5                   10                  15

Met Trp Cys Ala Ala Phe Gly Ser Pro Phe Glu Val Gln Thr His Asn
            20                  25                  30

Gly Thr Leu Thr Ile His Cys Asp
        35              40
```

<210> SEQ ID NO 130
<211> LENGTH: 40
<212> TYPE: PRT
<213> ORGANISM: Artificial Sequence
<220> FEATURE:
<223> OTHER INFORMATION: Synthetic

<400> SEQUENCE: 130

Lys Glu Glu Tyr Thr Tyr Glu Ser Pro Phe Glu Cys Trp Met Ala Ala
1               5                   10                  15

Met Trp Leu Arg Ala Phe Gly Leu Asp Val Gln Val His Thr Asp Gly
            20                  25                  30

Leu Thr Cys Thr Val Lys Val Lys
        35                  40

<210> SEQ ID NO 131
<211> LENGTH: 40
<212> TYPE: PRT
<213> ORGANISM: Artificial Sequence
<220> FEATURE:
<223> OTHER INFORMATION: Synthetic

<400> SEQUENCE: 131

Cys Ser His Ile Thr Ser Asn Ser Glu Phe Ala Ala Trp Ile Ala Ala
1               5                   10                  15

Glu Ile Ala Lys Glu Phe Gly Leu Glu Val His Leu His Lys Lys Asn
            20                  25                  30

Gly Thr Tyr Thr Val Gln Val Cys
        35                  40

<210> SEQ ID NO 132
<211> LENGTH: 40
<212> TYPE: PRT
<213> ORGANISM: Artificial Sequence
<220> FEATURE:
<223> OTHER INFORMATION: Synthetic

<400> SEQUENCE: 132

Thr Tyr His Thr Val Ser Arg Ala Pro Phe Ala Cys Gln Ile Val Ala
1               5                   10                  15

Glu Ile Ala Arg Glu Phe Asn Ile Glu Val Lys Val Glu Thr His Asn
            20                  25                  30

Gly Thr Cys Glu Ile Gln Ala Lys
        35                  40

<210> SEQ ID NO 133
<211> LENGTH: 40
<212> TYPE: PRT
<213> ORGANISM: Artificial Sequence
<220> FEATURE:
<223> OTHER INFORMATION: Synthetic

<400> SEQUENCE: 133

Arg Tyr Lys Ser Thr Asn Trp Thr Pro Phe Ala Cys Glu Ile Ala Lys
1               5                   10                  15

Arg Ile Ile Asp Glu Phe Asn Ile Pro Val Glu Ile His Ile Thr Asn
            20                  25                  30

Gly Lys Cys Thr Ile His Val Ser
        35                  40

<210> SEQ ID NO 134

<211> LENGTH: 40
<212> TYPE: PRT
<213> ORGANISM: Artificial Sequence
<220> FEATURE:
<223> OTHER INFORMATION: Synthetic

<400> SEQUENCE: 134

Arg Phe Lys Ser Thr Asn Trp Asn Pro Phe Ala Cys Glu Ile Ala Arg
1               5                   10                  15

Gln Ile Ile Glu Glu Phe Asn Ile Pro Val Glu Ile His Ile Thr Asn
            20                  25                  30

Gly Lys Cys Thr Ile His Thr Ser
        35                  40

<210> SEQ ID NO 135
<211> LENGTH: 40
<212> TYPE: PRT
<213> ORGANISM: Artificial Sequence
<220> FEATURE:
<223> OTHER INFORMATION: Synthetic

<400> SEQUENCE: 135

Arg Trp Lys Ser Thr Cys Trp Ser Pro Phe Ala Cys Ala Ile Ala Ala
1               5                   10                  15

Lys Ile Ile Lys Glu Phe Asn Ile Pro Val Glu Ile His Ile Thr Asn
            20                  25                  30

Gly Lys Cys Thr Ile His Val Ser
        35                  40

<210> SEQ ID NO 136
<211> LENGTH: 40
<212> TYPE: PRT
<213> ORGANISM: Artificial Sequence
<220> FEATURE:
<223> OTHER INFORMATION: Synthetic

<400> SEQUENCE: 136

Thr Trp Thr Ser Val Ala Val Ser Asp Phe Ala Cys Thr Ile Ala Ala
1               5                   10                  15

Glu Ile Ala Arg Gln Phe Gly Trp Glu Val His Val Glu Lys His Asn
            20                  25                  30

Gly Thr Cys Lys Val Lys Ile His
        35                  40

<210> SEQ ID NO 137
<211> LENGTH: 40
<212> TYPE: PRT
<213> ORGANISM: Artificial Sequence
<220> FEATURE:
<223> OTHER INFORMATION: Synthetic

<400> SEQUENCE: 137

Cys Ile Thr Ile Asp Val Asp Arg Phe Ala Asn Ala Ile Ala Cys Lys
1               5                   10                  15

Ile Glu Ala Glu Phe Arg Gly Leu Asp Val Gln Leu Glu Asn His Asn
            20                  25                  30

Gly Lys Leu Lys Leu His Leu Cys
        35                  40

<210> SEQ ID NO 138
<211> LENGTH: 40
<212> TYPE: PRT
<213> ORGANISM: Artificial Sequence
<220> FEATURE:
<223> OTHER INFORMATION: Synthetic

<400> SEQUENCE: 138

Thr Trp Thr Ser His Ala Lys Ala Pro Phe Ala Cys Gln Ile Ala Ala
1               5                   10                  15

Asp Ile Ala Ala Glu Phe Gly Trp Thr Cys Thr Val Glu Lys His Asn
            20                  25                  30

Gly Thr Cys Glu Ile Asn Cys Gln
        35                  40

<210> SEQ ID NO 139
<211> LENGTH: 40
<212> TYPE: PRT
<213> ORGANISM: Artificial Sequence
<220> FEATURE:
<223> OTHER INFORMATION: Synthetic

<400> SEQUENCE: 139

Thr Trp Thr Ser His Ala Asn Ala Pro Phe Ala Cys Glu Ile Ala Arg
1               5                   10                  15

Gln Ile Ala Glu Glu Phe Gly Trp Thr Cys Thr Val Glu Lys His Asn
            20                  25                  30

Gly Thr Cys Glu Ile Asn Cys Gln
        35                  40

<210> SEQ ID NO 140
<211> LENGTH: 40
<212> TYPE: PRT
<213> ORGANISM: Artificial Sequence
<220> FEATURE:
<223> OTHER INFORMATION: Synthetic

<400> SEQUENCE: 140

Thr Trp Thr Ser His Ala Asn Ala Pro Phe Ala Cys Glu Ile Ala Arg
1               5                   10                  15

Arg Ile Ala Glu Glu Phe Gly Trp Thr Cys Thr Val Glu Lys His Asn
            20                  25                  30

Gly Thr Cys Glu Ile Asn Cys Gln
        35                  40

<210> SEQ ID NO 141
<211> LENGTH: 40
<212> TYPE: PRT
<213> ORGANISM: Artificial Sequence
<220> FEATURE:
<223> OTHER INFORMATION: Synthetic

<400> SEQUENCE: 141

Thr Trp Thr Ser His Ala Lys Ala Pro Phe Ala Cys Arg Ile Ala Ala
1               5                   10                  15

Glu Ile Ala Arg Glu Phe Gly Trp Thr Cys Thr Val Glu Lys His Asn
            20                  25                  30

Gly Thr Cys Glu Ile Asn Cys Gln
        35                  40

<210> SEQ ID NO 142
<211> LENGTH: 40
<212> TYPE: PRT
<213> ORGANISM: Artificial Sequence
<220> FEATURE:
<223> OTHER INFORMATION: Synthetic

```
<400> SEQUENCE: 142

Glu Met His Val His Ser Met Ala Pro Phe Ala Cys Glu Ile Ala Arg
1               5                   10                  15

Gln Ile Leu Glu Glu Phe Asn Gln Asn Val Thr Val Thr Glu Arg Gly
            20                  25                  30

Asn Lys Cys Thr Val Thr Val Thr
        35                  40

<210> SEQ ID NO 143
<211> LENGTH: 40
<212> TYPE: PRT
<213> ORGANISM: Artificial Sequence
<220> FEATURE:
<223> OTHER INFORMATION: Synthetic

<400> SEQUENCE: 143

Glu Met His Ile His Ala Arg Ala Pro Phe Ala Cys Gln Ile Ala Tyr
1               5                   10                  15

Glu Ile Leu Arg Glu Phe Gly Gln Asn Val Thr Val Thr Glu Arg Gly
            20                  25                  30

Asn Lys Cys Thr Val Thr Val Thr
        35                  40

<210> SEQ ID NO 144
<211> LENGTH: 40
<212> TYPE: PRT
<213> ORGANISM: Artificial Sequence
<220> FEATURE:
<223> OTHER INFORMATION: Synthetic

<400> SEQUENCE: 144

Lys Lys Lys Ile Gln Val Asp Arg Phe Ala Glu Ala Ile Ala Val Ala
1               5                   10                  15

Ile Lys Cys Glu Phe Asn Asn Leu Gly Val His Gln Thr Phe Ile Asn
            20                  25                  30

Gly Tyr Ile Val Leu Thr Cys Lys
        35                  40

<210> SEQ ID NO 145
<211> LENGTH: 40
<212> TYPE: PRT
<213> ORGANISM: Artificial Sequence
<220> FEATURE:
<223> OTHER INFORMATION: Synthetic

<400> SEQUENCE: 145

Cys Phe Thr Ser Val Ala His Ser Lys Phe Ala Cys Asp Ile Ile Ala
1               5                   10                  15

Gln Ile Leu Ala Glu Phe Asn Gln Glu Val His Val Glu Thr His Gly
            20                  25                  30

Asp Glu Cys Arg Val Thr Ser Cys
        35                  40

<210> SEQ ID NO 146
<211> LENGTH: 40
<212> TYPE: PRT
<213> ORGANISM: Artificial Sequence
<220> FEATURE:
<223> OTHER INFORMATION: Synthetic

<400> SEQUENCE: 146

Cys Phe Thr Ser Val Ala His Ser Glu Phe Ala Cys Arg Ile Ile Val
```

```
1               5                   10                  15
Glu Ile Leu Arg Gln Phe Gly Gln Glu Val His Val Glu Thr His Gly
                20                  25                  30

Asp Glu Cys Arg Val Thr Ser Cys
            35                  40
```

<210> SEQ ID NO 147
<211> LENGTH: 40
<212> TYPE: PRT
<213> ORGANISM: Artificial Sequence
<220> FEATURE:
<223> OTHER INFORMATION: Synthetic

<400> SEQUENCE: 147

```
Thr Ser His Ile Thr Ser Asn Ala Pro Phe Ala Cys Gln Ile Ala Ala
1               5                   10                  15

Asp Ile Ala Ala Glu Phe Asn Trp Glu Val His Leu His Glu Lys Asn
                20                  25                  30

Gly Lys Cys Thr Leu Gln Ile Lys
            35                  40
```

<210> SEQ ID NO 148
<211> LENGTH: 40
<212> TYPE: PRT
<213> ORGANISM: Artificial Sequence
<220> FEATURE:
<223> OTHER INFORMATION: Synthetic

<400> SEQUENCE: 148

```
Thr Tyr His Ser Thr Ala Asn Ala Pro Phe Ala Cys Gln Ile Ala Ala
1               5                   10                  15

Glu Ile Ala Lys Ser Phe Asn Trp Glu Val His Leu His Glu Lys Asn
                20                  25                  30

Gly Lys Cys Thr Leu Gln Ile Lys
            35                  40
```

<210> SEQ ID NO 149
<211> LENGTH: 40
<212> TYPE: PRT
<213> ORGANISM: Artificial Sequence
<220> FEATURE:
<223> OTHER INFORMATION: Synthetic

<400> SEQUENCE: 149

```
Thr Ser His Ser Thr Ala Lys Ala Pro Phe Ala Cys Ala Ile Ala Ala
1               5                   10                  15

Glu Ile Ala Ala Arg Phe Asn Trp Glu Val His Leu His Glu Lys Asn
                20                  25                  30

Gly Lys Cys Thr Leu Gln Ile Lys
            35                  40
```

<210> SEQ ID NO 150
<211> LENGTH: 40
<212> TYPE: PRT
<213> ORGANISM: Artificial Sequence
<220> FEATURE:
<223> OTHER INFORMATION: Synthetic

<400> SEQUENCE: 150

```
Cys Met Thr Ser His Thr Tyr Ala Pro Phe Ala Trp Ile Ala Ala
1               5                   10                  15

Glu Ile Ala Lys Glu Phe Gly Tyr Asp Val Gln Leu Gln His Asp Gly
```

```
                20                  25                  30

Thr Lys Leu Thr Val His Ser Cys
        35                  40

<210> SEQ ID NO 151
<211> LENGTH: 40
<212> TYPE: PRT
<213> ORGANISM: Artificial Sequence
<220> FEATURE:
<223> OTHER INFORMATION: Synthetic

<400> SEQUENCE: 151

Cys Met Thr Ser His Thr Arg Ser Pro Phe Ala Ala Glu Ile Ala Ala
1               5                   10                  15

Arg Ile Ala Ala Glu Phe Gly Tyr Asp Val Gln Leu Gln His Asp Gly
            20                  25                  30

Thr Lys Leu Thr Val His Ser Cys
        35                  40

<210> SEQ ID NO 152
<211> LENGTH: 40
<212> TYPE: PRT
<213> ORGANISM: Artificial Sequence
<220> FEATURE:
<223> OTHER INFORMATION: Synthetic

<400> SEQUENCE: 152

Thr Ile Thr Phe His Cys Lys Ala Pro Phe Ala Ala Lys Ile Ser Ala
1               5                   10                  15

Glu Ile Leu Lys Ser Phe Arg Leu Glu Val His Cys Gln Gln His Gly
            20                  25                  30

Asn Gln Val Thr Cys Lys Val Ser
        35                  40

<210> SEQ ID NO 153
<211> LENGTH: 40
<212> TYPE: PRT
<213> ORGANISM: Artificial Sequence
<220> FEATURE:
<223> OTHER INFORMATION: Synthetic

<400> SEQUENCE: 153

Cys Asn Lys Ser Val Cys Asp Ala Pro Phe Ala Ala Ile Ala Ala
1               5                   10                  15

Lys Ile Ala Ala Glu Phe Asn Trp Asp Val Gln Phe Thr Gln His Gly
            20                  25                  30

Ser Thr Ile Thr Leu His Cys Cys
        35                  40

<210> SEQ ID NO 154
<211> LENGTH: 40
<212> TYPE: PRT
<213> ORGANISM: Artificial Sequence
<220> FEATURE:
<223> OTHER INFORMATION: Synthetic

<400> SEQUENCE: 154

Cys Tyr Lys Ser Val Thr Lys Ser Pro Phe Ala Ala Glu Ile Ala Arg
1               5                   10                  15

Gln Ile Ala Glu Glu Phe Asn Trp Asp Val Gln Cys Thr Gln His Gly
            20                  25                  30

Asp Thr Ile Thr Cys His Met Cys
```

```
<210> SEQ ID NO 155
<211> LENGTH: 40
<212> TYPE: PRT
<213> ORGANISM: Artificial Sequence
<220> FEATURE:
<223> OTHER INFORMATION: Synthetic

<400> SEQUENCE: 155

Cys Thr Thr Ser Val Ala Thr Ser Pro Phe Ala Ala Trp Ile Ala Ala
1               5                   10                  15

Lys Ile Leu Ala Glu Phe Asn Tyr Glu Val His Val His Gln His Gly
            20                  25                  30

Thr Gln Val Thr Val Glu Met Cys
        35                  40

<210> SEQ ID NO 156
<211> LENGTH: 40
<212> TYPE: PRT
<213> ORGANISM: Artificial Sequence
<220> FEATURE:
<223> OTHER INFORMATION: Synthetic

<400> SEQUENCE: 156

Thr Tyr Thr Ser Ile Val Ser Ser Pro Phe Ala Ala Glu Ile Val Arg
1               5                   10                  15

Gln Ile Ala Ala Glu Phe Gly Tyr Glu Val His Cys Thr Gln His Gly
            20                  25                  30

Asn Tyr Val Glu Cys Lys Val Lys
        35                  40

<210> SEQ ID NO 157
<211> LENGTH: 40
<212> TYPE: PRT
<213> ORGANISM: Artificial Sequence
<220> FEATURE:
<223> OTHER INFORMATION: Synthetic

<400> SEQUENCE: 157

Thr Tyr Thr Thr Trp Val Gln Ser Pro Phe Ala Ala Glu Ile Val Arg
1               5                   10                  15

Gln Ile Ala Glu Glu Phe Gly Tyr Glu Val His Cys Thr Gln His Gly
            20                  25                  30

Asn Tyr Val Glu Cys Lys Val Lys
        35                  40

<210> SEQ ID NO 158
<211> LENGTH: 40
<212> TYPE: PRT
<213> ORGANISM: Artificial Sequence
<220> FEATURE:
<223> OTHER INFORMATION: Synthetic

<400> SEQUENCE: 158

Lys Thr Gln Phe Lys Val Asp Ser Phe Ala Asn Ala Ile Ala Gln Ala
1               5                   10                  15

Ile Lys Cys Glu Phe Asn Asn Leu Pro Phe Thr Val Glu Ile His Gly
            20                  25                  30

Arg Thr Ile Lys Ile Lys Cys Lys
        35                  40
```

```
<210> SEQ ID NO 159
<211> LENGTH: 40
<212> TYPE: PRT
<213> ORGANISM: Artificial Sequence
<220> FEATURE:
<223> OTHER INFORMATION: Synthetic

<400> SEQUENCE: 159

Cys Val Thr Ser Gln Ala Lys Thr Pro Phe Ala Ala Gln Ile Ala Ala
1               5                   10                  15

Glu Ile Met Arg Glu Phe Asn Ile Glu Val His Cys Glu Lys Lys Gly
            20                  25                  30

Pro Thr Leu Lys Cys Thr Ser Cys
        35                  40

<210> SEQ ID NO 160
<211> LENGTH: 40
<212> TYPE: PRT
<213> ORGANISM: Artificial Sequence
<220> FEATURE:
<223> OTHER INFORMATION: Synthetic

<400> SEQUENCE: 160

Thr Trp Thr Ser Val Ser Ala Ala Pro Phe Ala Cys Lys Ile Ala Ala
1               5                   10                  15

Glu Ile Ala Arg Glu Phe Asn Trp Asp Val Thr Val Thr Gln His Gly
            20                  25                  30

Arg Thr Cys Lys Val His Val Glu
        35                  40

<210> SEQ ID NO 161
<211> LENGTH: 40
<212> TYPE: PRT
<213> ORGANISM: Artificial Sequence
<220> FEATURE:
<223> OTHER INFORMATION: Synthetic

<400> SEQUENCE: 161

Thr Asn Gln Ser Gln Ala Ser Ser Lys Phe Ala Ala Leu Ile Ala Ala
1               5                   10                  15

Asp Ile Cys Arg Glu Phe Gly Leu Glu Val His Leu His Lys Lys Asn
            20                  25                  30

Gly Thr Trp Thr Val Glu Cys Asn
        35                  40

<210> SEQ ID NO 162
<211> LENGTH: 40
<212> TYPE: PRT
<213> ORGANISM: Artificial Sequence
<220> FEATURE:
<223> OTHER INFORMATION: Synthetic

<400> SEQUENCE: 162

Cys Val Thr Ser Gln Cys His Ser Pro Phe Ala Cys Ala Ile Ala Ala
1               5                   10                  15

Lys Ile Met Lys Glu Phe Gly Trp Glu Val His Val Glu Glu His Asn
            20                  25                  30

Gly Thr Cys His Leu Gln Val Cys
        35                  40

<210> SEQ ID NO 163
<211> LENGTH: 40
<212> TYPE: PRT
```

```
<213> ORGANISM: Artificial Sequence
<220> FEATURE:
<223> OTHER INFORMATION: Synthetic

<400> SEQUENCE: 163

Thr Tyr Lys Ser Tyr Ala His Ser Pro Phe Ala Cys Gln Ile Ala Ala
1               5                   10                  15

Asp Ile Phe Ala Glu Phe Gly Tyr Asp Val Gln Val His Gln Lys Asn
            20                  25                  30

Gly Thr Cys Thr Val Glu Val His
        35                  40

<210> SEQ ID NO 164
<211> LENGTH: 40
<212> TYPE: PRT
<213> ORGANISM: Artificial Sequence
<220> FEATURE:
<223> OTHER INFORMATION: Synthetic

<400> SEQUENCE: 164

Thr Trp Lys Ser Val Ser His Ser Pro Phe Ala Cys Glu Ile Ala Ala
1               5                   10                  15

Lys Ile Phe Lys Glu Phe Gly Tyr Asp Val Gln Val His Gln Lys Asn
            20                  25                  30

Gly Thr Cys Thr Val Glu Val His
        35                  40

<210> SEQ ID NO 165
<211> LENGTH: 40
<212> TYPE: PRT
<213> ORGANISM: Artificial Sequence
<220> FEATURE:
<223> OTHER INFORMATION: Synthetic

<400> SEQUENCE: 165

Thr Tyr Lys Ser Tyr Ser His Ser Pro Phe Ala Cys Gln Ile Ala Ala
1               5                   10                  15

Glu Ile Phe Arg Glu Phe Gly Phe Asp Val Gln Val His Gln Lys Asn
            20                  25                  30

Gly Thr Cys Thr Val Glu Val His
        35                  40

<210> SEQ ID NO 166
<211> LENGTH: 40
<212> TYPE: PRT
<213> ORGANISM: Artificial Sequence
<220> FEATURE:
<223> OTHER INFORMATION: Synthetic

<400> SEQUENCE: 166

Thr Trp Lys Ser Val Ser His Ser Pro Phe Ala Cys Ala Ile Ala Ala
1               5                   10                  15

Lys Ile Phe Lys Glu Phe Gly Tyr Asp Val Gln Val His Gln Lys Asn
            20                  25                  30

Gly Thr Cys Thr Val Glu Val His
        35                  40

<210> SEQ ID NO 167
<211> LENGTH: 40
<212> TYPE: PRT
<213> ORGANISM: Artificial Sequence
<220> FEATURE:
<223> OTHER INFORMATION: Synthetic
```

<400> SEQUENCE: 167

Thr Trp Lys Ser Val Ser His Ser Pro Phe Ala Cys Ala Ile Ala Ala
1               5                   10                  15

Glu Ile Phe Arg Gln Phe Gly Tyr Asp Val Gln Val His Gln Lys Asn
            20                  25                  30

Gly Thr Cys Thr Val Glu Val His
        35                  40

<210> SEQ ID NO 168
<211> LENGTH: 40
<212> TYPE: PRT
<213> ORGANISM: Artificial Sequence
<220> FEATURE:
<223> OTHER INFORMATION: Synthetic

<400> SEQUENCE: 168

Thr Trp Lys Thr Val Ser His Ser Pro Phe Ala Cys Trp Ile Ala Ala
1               5                   10                  15

Gln Ile Trp Leu Glu Phe Gly Tyr Asp Val Gln Val His Gln Lys Asn
            20                  25                  30

Gly Thr Cys Thr Val Glu Val His
        35                  40

<210> SEQ ID NO 169
<211> LENGTH: 40
<212> TYPE: PRT
<213> ORGANISM: Artificial Sequence
<220> FEATURE:
<223> OTHER INFORMATION: Synthetic

<400> SEQUENCE: 169

Thr Trp Lys Ser Val Ser His Ser Pro Phe Ala Cys Gln Ile Ala Ala
1               5                   10                  15

Glu Ile Phe Arg Glu Phe Gly Tyr Asp Val Gln Val His Gln Lys Asn
            20                  25                  30

Gly Thr Cys Thr Val Glu Val His
        35                  40

<210> SEQ ID NO 170
<211> LENGTH: 40
<212> TYPE: PRT
<213> ORGANISM: Artificial Sequence
<220> FEATURE:
<223> OTHER INFORMATION: Synthetic

<400> SEQUENCE: 170

Thr Trp Lys Ser Tyr Ala His Ser Pro Phe Ala Cys Gln Ile Ala Ala
1               5                   10                  15

Glu Ile Phe Arg Glu Phe Gly Tyr Asp Val Gln Val His Gln Lys Asn
            20                  25                  30

Gly Thr Cys Thr Val Glu Val His
        35                  40

<210> SEQ ID NO 171
<211> LENGTH: 40
<212> TYPE: PRT
<213> ORGANISM: Artificial Sequence
<220> FEATURE:
<223> OTHER INFORMATION: Synthetic

<400> SEQUENCE: 171

```
Thr Phe Lys Ser Tyr Ser His Ser Pro Phe Ala Cys Ala Ile Ala Ala
1               5                   10                  15

Lys Ile Ala Lys Glu Phe Gly Trp Asp Val Gln Val His Gln Lys Asn
                20                  25                  30

Gly Thr Cys Thr Val Glu Val His
            35                  40
```

<210> SEQ ID NO 172
<211> LENGTH: 40
<212> TYPE: PRT
<213> ORGANISM: Artificial Sequence
<220> FEATURE:
<223> OTHER INFORMATION: Synthetic

<400> SEQUENCE: 172

```
Cys Tyr Lys Ile Val Ala Arg Ala Pro Phe Ala Cys Glu Ile Ala Ala
1               5                   10                  15

Arg Ile Ala Ala Glu Phe Arg Trp Asp Val Lys Ile His Gln His Gly
                20                  25                  30

Asp His Cys Thr Val Glu Val Cys
            35                  40
```

<210> SEQ ID NO 173
<211> LENGTH: 40
<212> TYPE: PRT
<213> ORGANISM: Artificial Sequence
<220> FEATURE:
<223> OTHER INFORMATION: Synthetic

<400> SEQUENCE: 173

```
Thr Arg Lys Val Glu Val Asp Asp Phe Ser Asn Ala Ile Ala Val Gln
1               5                   10                  15

Ile Lys Cys Glu Phe Lys Gly Leu Pro Tyr Thr Val Thr Ile His Gly
                20                  25                  30

Lys Arg Val Thr Val His Cys Lys
            35                  40
```

<210> SEQ ID NO 174
<211> LENGTH: 40
<212> TYPE: PRT
<213> ORGANISM: Artificial Sequence
<220> FEATURE:
<223> OTHER INFORMATION: Synthetic

<400> SEQUENCE: 174

```
Thr Asn Gln Ser Phe Ala Arg Ser Thr Phe Ala Cys Gln Ile Ala Ala
1               5                   10                  15

Glu Ile Cys Lys Glu Phe Gly Leu Asp Val Gln Ile Gln Lys His Asn
                20                  25                  30

Gly Thr Cys His Val His Cys Asn
            35                  40
```

<210> SEQ ID NO 175
<211> LENGTH: 40
<212> TYPE: PRT
<213> ORGANISM: Artificial Sequence
<220> FEATURE:
<223> OTHER INFORMATION: Synthetic

<400> SEQUENCE: 175

```
Glu Thr Thr Tyr Thr Phe Asp Arg Phe Asp Glu Ala Met Arg Phe Ala
1               5                   10                  15
```

```
Trp Glu Ala Val Phe Lys Gly Ile Pro Val Gln Trp Thr Thr Lys Asn
            20                  25                  30

Gly Lys Phe Gln Val Thr Gln His
        35                  40
```

<210> SEQ ID NO 176
<211> LENGTH: 40
<212> TYPE: PRT
<213> ORGANISM: Artificial Sequence
<220> FEATURE:
<223> OTHER INFORMATION: Synthetic

<400> SEQUENCE: 176

```
Thr Thr Thr Tyr Thr Val Tyr Ser Pro Phe Asp Ala Trp Met Arg Ala
1               5                   10                  15

Met Trp Leu Lys Val Phe Gly Arg Thr Val Thr Leu His Glu Lys Asn
            20                  25                  30

Gly Lys Val Lys Leu Glu Thr Lys
        35                  40
```

<210> SEQ ID NO 177
<211> LENGTH: 40
<212> TYPE: PRT
<213> ORGANISM: Artificial Sequence
<220> FEATURE:
<223> OTHER INFORMATION: Synthetic

<400> SEQUENCE: 177

```
Thr Thr Lys Tyr Thr Tyr Glu Ser Phe Asp Glu Ala Met Arg Ala Met
1               5                   10                  15

Trp Lys Leu Ala Phe Lys Gly Leu Asp Val Arg Leu Thr Val Val Asn
            20                  25                  30

Gly Lys Trp Val Leu Glu Thr His
        35                  40
```

<210> SEQ ID NO 178
<211> LENGTH: 40
<212> TYPE: PRT
<213> ORGANISM: Artificial Sequence
<220> FEATURE:
<223> OTHER INFORMATION: Synthetic

<400> SEQUENCE: 178

```
Lys Thr Thr Tyr Thr Phe Pro Arg Phe Asp Leu Ala Met Glu Ala Met
1               5                   10                  15

Trp Arg Ala Val Phe Asn Asn Ile Pro Val Thr Val Thr Trp Lys Asn
            20                  25                  30

Gly Lys Trp Gln Val Thr Val Lys
        35                  40
```

<210> SEQ ID NO 179
<211> LENGTH: 40
<212> TYPE: PRT
<213> ORGANISM: Artificial Sequence
<220> FEATURE:
<223> OTHER INFORMATION: Synthetic

<400> SEQUENCE: 179

```
Thr Pro Gln Ile Thr Ile Lys Ser Pro Phe Ser Ala Trp Met Ala Ala
1               5                   10                  15

Met Trp Leu Gln Ala Phe Asn Ile Pro Tyr Asp Val Gln Thr His Gly
            20                  25                  30
```

```
Asp Lys Val Thr Val Thr Gln His
        35                  40

<210> SEQ ID NO 180
<211> LENGTH: 40
<212> TYPE: PRT
<213> ORGANISM: Artificial Sequence
<220> FEATURE:
<223> OTHER INFORMATION: Synthetic

<400> SEQUENCE: 180

Thr Lys Leu Ile Lys Val Asp Ser Phe Asp Ala Ala Met Arg Val Ala
1               5                   10                  15

Trp Lys Leu Val Phe Leu Gly Ile Pro Val Lys Ile Thr Gln Val Asn
            20                  25                  30

Gly Thr Trp Val Val Gln Lys Gly
        35                  40

<210> SEQ ID NO 181
<211> LENGTH: 40
<212> TYPE: PRT
<213> ORGANISM: Artificial Sequence
<220> FEATURE:
<223> OTHER INFORMATION: Synthetic

<400> SEQUENCE: 181

Thr Glu Thr Leu Thr Phe Thr Asn Phe Asp Glu Ala Met Arg Ala Met
1               5                   10                  15

Trp Glu Tyr Ala Phe Lys Gly Ile Pro Val Thr Val Thr Val Lys Asn
            20                  25                  30

Gly Lys Trp Gln Val Gln Ile Asn
        35                  40

<210> SEQ ID NO 182
<211> LENGTH: 40
<212> TYPE: PRT
<213> ORGANISM: Artificial Sequence
<220> FEATURE:
<223> OTHER INFORMATION: Synthetic

<400> SEQUENCE: 182

Lys Lys Thr Ile Thr Val Asp Cys Phe Asp Ala Ala Met Arg Gln Ala
1               5                   10                  15

Trp Lys Ala Ala Phe Asn Asn Ile Pro Val Thr Ala Thr Lys Lys Asn
            20                  25                  30

Gly Lys Phe Gln Val His Gln Lys
        35                  40

<210> SEQ ID NO 183
<211> LENGTH: 40
<212> TYPE: PRT
<213> ORGANISM: Artificial Sequence
<220> FEATURE:
<223> OTHER INFORMATION: Synthetic

<400> SEQUENCE: 183

Thr Glu Thr Val Lys Val Pro Ser Phe Asp Glu Ala Met Arg Gln Ala
1               5                   10                  15

Trp Ala Ala Val Phe Lys Gly Ile Asp Val Arg Ile Thr Asn Leu Asn
            20                  25                  30

Gly Thr Trp Val Leu Gln Lys Asn
        35                  40
```

<210> SEQ ID NO 184
<211> LENGTH: 40
<212> TYPE: PRT
<213> ORGANISM: Artificial Sequence
<220> FEATURE:
<223> OTHER INFORMATION: Synthetic

<400> SEQUENCE: 184

Thr Thr Thr Ile Val Val Leu Ala Pro Phe Ser Ala Asp Met Ala Arg
1               5                   10                  15

Met Trp Ala Trp Val Phe Gly Ser Pro Val Glu Val Gln Lys His Asn
            20                  25                  30

Gly Thr Phe Lys Ile His Ile His
        35                  40

<210> SEQ ID NO 185
<211> LENGTH: 40
<212> TYPE: PRT
<213> ORGANISM: Artificial Sequence
<220> FEATURE:
<223> OTHER INFORMATION: Synthetic

<400> SEQUENCE: 185

Thr Lys Thr Ile Thr Val Leu Ser Pro Phe Asp Ala Ala Met Arg Ala
1               5                   10                  15

Met Trp Leu Lys Val Phe Gly Ile Pro Val Glu Val His Thr His Gly
            20                  25                  30

Asp Lys Ile Lys Leu Gln Lys Lys
        35                  40

<210> SEQ ID NO 186
<211> LENGTH: 40
<212> TYPE: PRT
<213> ORGANISM: Artificial Sequence
<220> FEATURE:
<223> OTHER INFORMATION: Synthetic

<400> SEQUENCE: 186

Thr Thr Thr Ile Gln Phe Asp Met Phe Asp Glu Ala Met Arg Ala Ala
1               5                   10                  15

Trp Glu Leu Ala Phe Leu Gly Ile Pro Tyr Lys Val Thr Gln Val Asn
            20                  25                  30

Gly Ser Trp Thr Val Thr Gln Lys
        35                  40

<210> SEQ ID NO 187
<211> LENGTH: 40
<212> TYPE: PRT
<213> ORGANISM: Artificial Sequence
<220> FEATURE:
<223> OTHER INFORMATION: Synthetic

<400> SEQUENCE: 187

Gly Thr Lys Tyr Thr Phe Asp Ser Phe Asp Glu Ala Met Arg Phe Ala
1               5                   10                  15

Trp Lys Leu Asp Phe Lys Gly Ile Pro Tyr Thr Ile Thr Lys Lys Asn
            20                  25                  30

Gly Lys Phe Gln Val Glu Glu Lys
        35                  40

<210> SEQ ID NO 188
<211> LENGTH: 40

<212> TYPE: PRT
<213> ORGANISM: Artificial Sequence
<220> FEATURE:
<223> OTHER INFORMATION: Synthetic

<400> SEQUENCE: 188

Thr Gln His Ile Gln Val Asp Ser Phe Asp Glu Ala Met Arg Ala Met
1               5                   10                  15

Trp Ala Trp Val Phe Gln Gly Val Pro Val Thr Phe His Met Ser Gly
            20                  25                  30

Gly Glu Phe His Val Glu Val Asn
        35                  40

<210> SEQ ID NO 189
<211> LENGTH: 40
<212> TYPE: PRT
<213> ORGANISM: Artificial Sequence
<220> FEATURE:
<223> OTHER INFORMATION: Synthetic

<400> SEQUENCE: 189

Thr Pro Thr Thr Thr Val Tyr Ala Pro Phe Asn Ala Trp Met Leu Ala
1               5                   10                  15

Met Trp Leu Gln Ala Phe Gly Ile Asp Ala Glu Ile His Thr His Gly
            20                  25                  30

Leu Thr Ile Thr Ile Lys Phe Glu
        35                  40

<210> SEQ ID NO 190
<211> LENGTH: 40
<212> TYPE: PRT
<213> ORGANISM: Artificial Sequence
<220> FEATURE:
<223> OTHER INFORMATION: Synthetic

<400> SEQUENCE: 190

Lys Gln Thr Ile Gln Phe Pro Ser Phe Asp Ala Met Lys Ala Val
1               5                   10                  15

Trp Lys Ala Ala Phe Lys Gly Leu Pro Val Thr Met Thr Lys Val Asn
            20                  25                  30

Gly Thr Trp Lys Val Lys Ile Lys
        35                  40

<210> SEQ ID NO 191
<211> LENGTH: 40
<212> TYPE: PRT
<213> ORGANISM: Artificial Sequence
<220> FEATURE:
<223> OTHER INFORMATION: Synthetic

<400> SEQUENCE: 191

Thr Thr Glu Ile Lys Val Asp Ser Phe Asp Lys Ala Met Arg Glu Ala
1               5                   10                  15

Trp Arg Glu Ala Phe Asn Gly Lys Val Val His Phe His Cys Lys Asn
            20                  25                  30

Gly Thr Val Thr Leu His Ile Lys
        35                  40

<210> SEQ ID NO 192
<211> LENGTH: 40
<212> TYPE: PRT
<213> ORGANISM: Artificial Sequence
<220> FEATURE:

<223> OTHER INFORMATION: Synthetic

<400> SEQUENCE: 192

Glu Thr Lys Val Lys Val Asp Ser Phe Asp Leu Ala Met Tyr Leu Ala
1               5                   10                  15

Trp Met Tyr Ala Phe Asn Gly Leu Pro Val Glu Ile Gln Gln His Asn
            20                  25                  30

Gly Thr Phe Thr Leu His Val Lys
        35                  40

<210> SEQ ID NO 193
<211> LENGTH: 40
<212> TYPE: PRT
<213> ORGANISM: Artificial Sequence
<220> FEATURE:
<223> OTHER INFORMATION: Synthetic

<400> SEQUENCE: 193

Lys Thr Thr Tyr Thr Leu Thr Ala Pro Phe Asp Ala Trp Met Phe Ala
1               5                   10                  15

Met Trp Ala Ala Ala Phe Gly Arg Glu Val His Leu Thr Lys His Gly
            20                  25                  30

Asp His Leu Lys Ile Thr Val Gly
        35                  40

<210> SEQ ID NO 194
<211> LENGTH: 40
<212> TYPE: PRT
<213> ORGANISM: Artificial Sequence
<220> FEATURE:
<223> OTHER INFORMATION: Synthetic

<400> SEQUENCE: 194

Gly Arg Lys Ile Thr Val Glu Ala Pro Phe Ala Ala Lys Met Val Lys
1               5                   10                  15

Met Trp Val Leu Ala Phe Gly Ser Glu Val His Val Gln Glu Lys Asn
            20                  25                  30

Gly Lys Phe Thr Ile Glu Ser Arg
        35                  40

<210> SEQ ID NO 195
<211> LENGTH: 40
<212> TYPE: PRT
<213> ORGANISM: Artificial Sequence
<220> FEATURE:
<223> OTHER INFORMATION: Synthetic

<400> SEQUENCE: 195

Thr Thr Thr Tyr Thr Leu Asp Ser Phe Asp Ala Ala Met Glu Ala Met
1               5                   10                  15

Trp Arg Ala Val Phe Asn Gly Ile Pro Val Thr Cys Thr Gln Lys Asn
            20                  25                  30

Gly Lys Trp Gln Val Thr Ile Gln
        35                  40

<210> SEQ ID NO 196
<211> LENGTH: 40
<212> TYPE: PRT
<213> ORGANISM: Artificial Sequence
<220> FEATURE:
<223> OTHER INFORMATION: Synthetic

<400> SEQUENCE: 196

```
Thr Lys Thr Phe Thr Trp Gln Asn Phe Asp Asn Ala Met Lys Phe Ala
1               5                   10                  15

Trp Trp Ala Ala Phe His Gly Ile Pro Val Thr Val Thr Trp Lys Asn
            20                  25                  30

Gly Thr Ala Gln Val Thr Gln His
        35                  40
```

<210> SEQ ID NO 197
<211> LENGTH: 40
<212> TYPE: PRT
<213> ORGANISM: Artificial Sequence
<220> FEATURE:
<223> OTHER INFORMATION: Synthetic

<400> SEQUENCE: 197

```
Thr Tyr Thr Ser Thr Ser Tyr Ser Ser Phe Ala Ala Ala Ile Ala Ala
1               5                   10                  15

Glu Ile Leu Arg Gln Phe Gly Leu Glu Val His Val Thr Lys Lys Asn
            20                  25                  30

Gly Thr Tyr Gln Val Glu Glu Asn
        35                  40
```

<210> SEQ ID NO 198
<211> LENGTH: 40
<212> TYPE: PRT
<213> ORGANISM: Artificial Sequence
<220> FEATURE:
<223> OTHER INFORMATION: Synthetic

<400> SEQUENCE: 198

```
Thr Tyr Thr Ser Thr Ser Tyr Ser Ser Phe Ala Ala Ala Ile Ala Ala
1               5                   10                  15

Glu Ile Leu Arg Glu Phe Gly Leu Glu Val His Val Thr Lys Lys Asn
            20                  25                  30

Gly Thr Tyr Gln Val Glu Glu Asn
        35                  40
```

<210> SEQ ID NO 199
<211> LENGTH: 40
<212> TYPE: PRT
<213> ORGANISM: Artificial Sequence
<220> FEATURE:
<223> OTHER INFORMATION: Synthetic

<400> SEQUENCE: 199

```
Lys Ile Thr Ser Thr Cys Ser Ser Phe Ala Ala Ala Ile Ala Val
1               5                   10                  15

Glu Ile Leu Arg Gln Phe Asn Ile Pro Ala Thr Val Thr Gln His Gly
            20                  25                  30

Asp Lys Trp Gln Val Thr Ala Glu
        35                  40
```

<210> SEQ ID NO 200
<211> LENGTH: 40
<212> TYPE: PRT
<213> ORGANISM: Artificial Sequence
<220> FEATURE:
<223> OTHER INFORMATION: Synthetic

<400> SEQUENCE: 200

```
Thr Lys Thr Leu His Val Pro Ser Phe Ala Leu Ala Ile Ala Ala Ala
1               5                   10                  15
```

Ile Lys Ala Glu Phe Lys Gly Leu Glu Val His Leu Thr Ser Arg Asn
                20                  25                  30

Gly Glu Ala Gln Val Lys Ile Lys
        35                  40

<210> SEQ ID NO 201
<211> LENGTH: 40
<212> TYPE: PRT
<213> ORGANISM: Artificial Sequence
<220> FEATURE:
<223> OTHER INFORMATION: Synthetic

<400> SEQUENCE: 201

Thr Thr Thr Ser Asp Ala Lys Ala Pro Phe Ala Ala Gln Ile Ala Ala
1               5                   10                  15

Glu Ile Ala Arg Glu Phe Gly Tyr Asp Val Gln Leu Thr Lys His Asn
                20                  25                  30

Gly Gln Leu Gln Ile Thr Leu Lys
        35                  40

<210> SEQ ID NO 202
<211> LENGTH: 40
<212> TYPE: PRT
<213> ORGANISM: Artificial Sequence
<220> FEATURE:
<223> OTHER INFORMATION: Synthetic

<400> SEQUENCE: 202

Thr Trp His Thr Thr Val Leu Ser Pro Phe Ala Ala Arg Ile Ala Ala
1               5                   10                  15

Asp Ile Ala Lys Glu Phe Gly Ile Pro Val Thr Leu Arg Glu His Gly
                20                  25                  30

Asp Thr Ile Thr Ile Gln Met Lys
        35                  40

<210> SEQ ID NO 203
<211> LENGTH: 40
<212> TYPE: PRT
<213> ORGANISM: Artificial Sequence
<220> FEATURE:
<223> OTHER INFORMATION: Synthetic

<400> SEQUENCE: 203

Thr Cys Val Val Thr Ala Ser Ser Glu Phe Ala Ala Arg Ile Ala Ala
1               5                   10                  15

Glu Ile Ala Arg Gln Phe Gly Tyr Glu Val His Val His Lys Lys Asn
                20                  25                  30

Gly Thr Tyr Gln Val Glu Val Arg
        35                  40

<210> SEQ ID NO 204
<211> LENGTH: 40
<212> TYPE: PRT
<213> ORGANISM: Artificial Sequence
<220> FEATURE:
<223> OTHER INFORMATION: Synthetic

<400> SEQUENCE: 204

Thr Tyr Thr Ser Phe Ala His Ser Pro Phe Ala Ala Gln Ile Ala Ala
1               5                   10                  15

Lys Ile Ala Ala Glu Phe Gly Trp Asp Val Thr Tyr Thr Gln His Gly
                20                  25                  30

Asp Thr Leu Lys Val His Val Asn
        35                  40

<210> SEQ ID NO 205
<211> LENGTH: 40
<212> TYPE: PRT
<213> ORGANISM: Artificial Sequence
<220> FEATURE:
<223> OTHER INFORMATION: Synthetic

<400> SEQUENCE: 205

Thr Thr Thr Ser Gln Ala Ala Lys Phe Ala Ala Asp Ile Ala Ala
1               5                   10                  15

Glu Ile Ala Arg Gln Phe Gly Tyr Glu Leu His Val Thr Lys Val Asn
            20                  25                  30

Gly Thr Tyr Lys Val Thr Gln His
        35                  40

<210> SEQ ID NO 206
<211> LENGTH: 40
<212> TYPE: PRT
<213> ORGANISM: Artificial Sequence
<220> FEATURE:
<223> OTHER INFORMATION: Synthetic

<400> SEQUENCE: 206

Thr Val His Ile Thr Val Thr Arg Phe Ala Ala Ile Ala Gln
1               5                   10                  15

Ile Leu Ala Glu Phe Trp Asn Leu Pro Tyr Thr Val Glu Ile His Gly
            20                  25                  30

Thr Gln Ile Thr Val Gln Val Gln
        35                  40

<210> SEQ ID NO 207
<211> LENGTH: 40
<212> TYPE: PRT
<213> ORGANISM: Artificial Sequence
<220> FEATURE:
<223> OTHER INFORMATION: Synthetic

<400> SEQUENCE: 207

Glu Ser His Thr Thr Arg Ser Glu Phe Ala Ala Trp Ile Ala Ala
1               5                   10                  15

Glu Ile Trp Arg Glu Phe Gly Lys Glu Val His Val Lys Lys Asn Gly
            20                  25                  30

Asp Gln Tyr Thr Val Thr Val Lys
        35                  40

<210> SEQ ID NO 208
<211> LENGTH: 40
<212> TYPE: PRT
<213> ORGANISM: Artificial Sequence
<220> FEATURE:
<223> OTHER INFORMATION: Synthetic

<400> SEQUENCE: 208

Lys Thr Thr Tyr His Met Pro Ser Lys Phe Ala Ala Ile Ala Ala
1               5                   10                  15

Lys Ile Leu Ala Glu Phe Gly Ile Pro Val Thr Val Thr Lys Ala Gly
            20                  25                  30

Asp Thr Tyr Val Leu Gln Glu Lys
        35                  40

<210> SEQ ID NO 209
<211> LENGTH: 40
<212> TYPE: PRT
<213> ORGANISM: Artificial Sequence
<220> FEATURE:
<223> OTHER INFORMATION: Synthetic

<400> SEQUENCE: 209

Thr Asn Thr Leu Tyr Ala Ser Ser Lys Phe Ala Ala Leu Ile Ala Ala
1               5                   10                  15

Glu Ile Ala Arg Gln Phe Asn Trp Asp Val Thr Val Ser Gln Ile Asn
            20                  25                  30

Gly Thr Trp Val Val Thr Val His
        35                  40

<210> SEQ ID NO 210
<211> LENGTH: 40
<212> TYPE: PRT
<213> ORGANISM: Artificial Sequence
<220> FEATURE:
<223> OTHER INFORMATION: Synthetic

<400> SEQUENCE: 210

Thr Thr His Leu Thr Tyr Arg Ser Pro Phe Ala Ala Arg Ile Ala Ala
1               5                   10                  15

Glu Ile Leu Arg Glu Phe Gly Leu Pro Val Asn Val Gln Lys Asn Gly
            20                  25                  30

Pro Thr Leu Thr Val Gln Val Asn
        35                  40

<210> SEQ ID NO 211
<211> LENGTH: 40
<212> TYPE: PRT
<213> ORGANISM: Artificial Sequence
<220> FEATURE:
<223> OTHER INFORMATION: Synthetic

<400> SEQUENCE: 211

Thr Thr His Leu Thr Tyr Arg Ser Pro Phe Ala Ala Ala Ile Ala Ala
1               5                   10                  15

Glu Ile Leu Arg Gln Phe Gly Leu Pro Val Asn Val Gln Lys Asn Gly
            20                  25                  30

Pro Thr Leu Thr Val Gln Val Asn
        35                  40

<210> SEQ ID NO 212
<211> LENGTH: 40
<212> TYPE: PRT
<213> ORGANISM: Artificial Sequence
<220> FEATURE:
<223> OTHER INFORMATION: Synthetic

<400> SEQUENCE: 212

Thr Tyr Thr Ser Thr Ala Thr Ser Lys Phe Ala Ala Glu Ile Ala Ala
1               5                   10                  15

Gln Ile Ala Ala Glu Phe Gly Ile Lys Val Glu Val His Gln Lys Asn
            20                  25                  30

Asn Arg Trp Gln Val Thr Glu Lys
        35                  40

<210> SEQ ID NO 213

```
<211> LENGTH: 40
<212> TYPE: PRT
<213> ORGANISM: Artificial Sequence
<220> FEATURE:
<223> OTHER INFORMATION: Synthetic

<400> SEQUENCE: 213

Thr Trp His Ser Thr Ser Ser Lys Glu Phe Ala Ala Asp Ile Ala Arg
1               5                   10                  15

Gln Ile Phe Glu Glu Phe Gly Tyr Asp Val Gln Val His Glu Lys Asn
            20                  25                  30

Gly Gln Tyr Glu Val Gln Val His
        35                  40

<210> SEQ ID NO 214
<211> LENGTH: 40
<212> TYPE: PRT
<213> ORGANISM: Artificial Sequence
<220> FEATURE:
<223> OTHER INFORMATION: Synthetic

<400> SEQUENCE: 214

Thr Trp His Ser His Ala Tyr Ser Gln Phe Ala Ala Glu Ile Ala Ala
1               5                   10                  15

Arg Ile Ala Lys Glu Phe Asn Ile Pro Val Gln Leu His Glu Lys Asn
            20                  25                  30

Gly Lys Val Glu Val Gln Met His
        35                  40

<210> SEQ ID NO 215
<211> LENGTH: 40
<212> TYPE: PRT
<213> ORGANISM: Artificial Sequence
<220> FEATURE:
<223> OTHER INFORMATION: Synthetic

<400> SEQUENCE: 215

Thr Tyr Thr Ile Thr Ser His Ser Ser Phe Ala Ala Lys Ile Ala Ala
1               5                   10                  15

Asp Ile Leu Lys Glu Phe Asn Ile Pro Phe Glu Leu His Lys Lys Asn
            20                  25                  30

Gly Thr Val Gln Val Gln Asn Glu
        35                  40

<210> SEQ ID NO 216
<211> LENGTH: 40
<212> TYPE: PRT
<213> ORGANISM: Artificial Sequence
<220> FEATURE:
<223> OTHER INFORMATION: Synthetic

<400> SEQUENCE: 216

Glu Val Thr Arg Asn Ala Ala Ser Lys Phe Ala Ala Asp Ile Ala Ala
1               5                   10                  15

Lys Ile Ala Ala Glu Phe Gly Leu Lys Val Thr Val Thr Gln Lys Asn
            20                  25                  30

Gly Gln Phe Phe Val Thr Glu Lys
        35                  40

<210> SEQ ID NO 217
<211> LENGTH: 40
<212> TYPE: PRT
<213> ORGANISM: Artificial Sequence
```

<220> FEATURE:
<223> OTHER INFORMATION: Synthetic

<400> SEQUENCE: 217

Thr Gln Thr Cys Thr Ser Lys Asp Ser Phe Ala Ala Arg Ile Ala Ala
1               5                   10                  15

Glu Ile Leu Arg Glu Phe Asn Ile Pro Val Ser Phe Thr Gln His Gly
            20                  25                  30

Asp Thr Phe Gln Val Thr Cys His
        35                  40

<210> SEQ ID NO 218
<211> LENGTH: 40
<212> TYPE: PRT
<213> ORGANISM: Artificial Sequence
<220> FEATURE:
<223> OTHER INFORMATION: Synthetic

<400> SEQUENCE: 218

Thr Leu Glu Ser Thr Ala Glu Ser Pro Phe Ala Ala Glu Ile Ala Ala
1               5                   10                  15

Arg Ile Met Ala Glu Phe Gly Tyr Lys Val Thr Thr His Lys Lys Gly
            20                  25                  30

Asp Thr Leu Thr Val Lys Ile Glu
        35                  40

<210> SEQ ID NO 219
<211> LENGTH: 40
<212> TYPE: PRT
<213> ORGANISM: Artificial Sequence
<220> FEATURE:
<223> OTHER INFORMATION: Synthetic

<400> SEQUENCE: 219

Thr Thr Thr Ser Thr Ala Arg Asn Pro Phe Ala Ala Trp Ile Ala Ala
1               5                   10                  15

Glu Ile Ala Lys Glu Phe Asn Trp Glu Val His Leu Glu Asp Thr Asn
            20                  25                  30

Gly Thr Leu Thr Val His Ile His
        35                  40

<210> SEQ ID NO 220
<211> LENGTH: 40
<212> TYPE: PRT
<213> ORGANISM: Artificial Sequence
<220> FEATURE:
<223> OTHER INFORMATION: Synthetic

<400> SEQUENCE: 220

Thr Gln Thr Ile Thr Ala Arg Ala Ser Phe Ala Ala Arg Ile Ala Ala
1               5                   10                  15

Glu Ile Leu Arg Glu Phe Gly Tyr Glu Val His Val Glu Gln His Gly
            20                  25                  30

Ser Thr Tyr Thr Val His Glu Lys
        35                  40

<210> SEQ ID NO 221
<211> LENGTH: 40
<212> TYPE: PRT
<213> ORGANISM: Artificial Sequence
<220> FEATURE:
<223> OTHER INFORMATION: Synthetic

```
<400> SEQUENCE: 221

Thr Leu Lys Ile Gln Ala His Ser Pro Phe Ala Ala Gln Ile Ala Ala
1               5                   10                  15

Asp Ile Trp Lys Glu Phe Gly Tyr Asp Val Gln Val His Gln Lys Asn
            20                  25                  30

Gly Thr Phe Thr Val Glu Val His
        35                  40

<210> SEQ ID NO 222
<211> LENGTH: 40
<212> TYPE: PRT
<213> ORGANISM: Artificial Sequence
<220> FEATURE:
<223> OTHER INFORMATION: Synthetic

<400> SEQUENCE: 222

Thr Val Thr Ser Thr Ala Asn Asp Lys Phe Ala Ala Glu Ile Ala Arg
1               5                   10                  15

Gln Ile Leu Glu Glu Phe Gly Ile Pro Val Lys Ile His Lys Lys Asn
            20                  25                  30

Gly Thr Trp Gln Val Glu Ser His
        35                  40

<210> SEQ ID NO 223
<211> LENGTH: 40
<212> TYPE: PRT
<213> ORGANISM: Artificial Sequence
<220> FEATURE:
<223> OTHER INFORMATION: Synthetic

<400> SEQUENCE: 223

Thr Thr Lys Ser Thr Ala Lys Ser Pro Phe Ala Ala Ile Ala Ala
1               5                   10                  15

Glu Ile Ala Arg Gln Phe Gly Trp Glu Val His Val Thr Gln His Gly
            20                  25                  30

Asp Lys Val Thr Val Lys Ile Gly
        35                  40

<210> SEQ ID NO 224
<211> LENGTH: 40
<212> TYPE: PRT
<213> ORGANISM: Artificial Sequence
<220> FEATURE:
<223> OTHER INFORMATION: Synthetic

<400> SEQUENCE: 224

Thr Tyr Gln Thr Gln Ala Arg Ser Glu Phe Ala Ala Arg Ile Ala Ala
1               5                   10                  15

Glu Ile Asn Arg Glu Phe Gly Tyr Glu Val His Val Thr Gln Val Gly
            20                  25                  30

Pro Thr Tyr Lys Val Thr Val Lys
        35                  40

<210> SEQ ID NO 225
<211> LENGTH: 40
<212> TYPE: PRT
<213> ORGANISM: Artificial Sequence
<220> FEATURE:
<223> OTHER INFORMATION: Synthetic

<400> SEQUENCE: 225

Thr Ile Glu Phe Asp Val Glu Ser Pro Phe Ser Ala Lys Met Ala Gln
```

```
                1               5                  10                  15
Met Trp Cys Ala Ala Phe Gly Ala Pro Tyr Thr Val His Lys His Gly
                20                  25                  30

Thr Lys Ile Thr Val Lys Cys Glu
        35                  40
```

<210> SEQ ID NO 226
<211> LENGTH: 40
<212> TYPE: PRT
<213> ORGANISM: Artificial Sequence
<220> FEATURE:
<223> OTHER INFORMATION: Synthetic

<400> SEQUENCE: 226

```
Thr Glu Lys Ile Gln Val Glu Ser Pro Phe Ala Ala Lys Met Val Ala
1               5                  10                  15

Met Trp Cys Leu Ala Phe Gly Ala Pro Phe Thr Val Lys Gln His Gly
                20                  25                  30

Asp Thr Val Thr Ile His Cys Ser
        35                  40
```

<210> SEQ ID NO 227
<211> LENGTH: 40
<212> TYPE: PRT
<213> ORGANISM: Artificial Sequence
<220> FEATURE:
<223> OTHER INFORMATION: Synthetic

<400> SEQUENCE: 227

```
Gly Val Thr Tyr Thr Tyr His Ser Pro Phe Asp Ala Glu Met Ala Arg
1               5                  10                  15

Met Trp Cys Trp Ala Phe Gly Ser Pro Val Glu Ile Gln Glu His Gly
                20                  25                  30

Asp Lys Ile Gln Val Thr Cys Gly
        35                  40
```

<210> SEQ ID NO 228
<211> LENGTH: 40
<212> TYPE: PRT
<213> ORGANISM: Artificial Sequence
<220> FEATURE:
<223> OTHER INFORMATION: Synthetic

<400> SEQUENCE: 228

```
Thr Ile His Leu His Leu Thr His Phe Asp Ile Val Met Arg Ala Met
1               5                  10                  15

Trp Lys Cys Val Phe Asn Gly Leu Lys Val Gln Thr Lys Lys Lys Asn
                20                  25                  30

Gly Thr Ile Thr Leu Glu Cys His
        35                  40
```

<210> SEQ ID NO 229
<211> LENGTH: 40
<212> TYPE: PRT
<213> ORGANISM: Artificial Sequence
<220> FEATURE:
<223> OTHER INFORMATION: Synthetic

<400> SEQUENCE: 229

```
Lys Lys Lys Val Gln Val Glu Ser Pro Phe Ser Ala Trp Met Arg Ala
1               5                  10                  15

Met Trp Ala Leu Val Phe Gly Thr Pro Val Thr Cys Glu Gln His Gly
```

```
                20                  25                  30

Asp Thr Val Thr Cys His Ile Lys
        35                  40

<210> SEQ ID NO 230
<211> LENGTH: 40
<212> TYPE: PRT
<213> ORGANISM: Artificial Sequence
<220> FEATURE:
<223> OTHER INFORMATION: Synthetic

<400> SEQUENCE: 230

Glu Thr Thr Val Lys Val Asp Ser Phe Asp Ala Ala Met Arg Ala Met
1               5                   10                  15

Trp Lys Ala Ala Phe Lys Gly Leu Glu Val His Cys Glu Gln His Gly
                20                  25                  30

Asp Thr Val Lys Cys Thr Ile His
        35                  40

<210> SEQ ID NO 231
<211> LENGTH: 40
<212> TYPE: PRT
<213> ORGANISM: Artificial Sequence
<220> FEATURE:
<223> OTHER INFORMATION: Synthetic

<400> SEQUENCE: 231

Glu Thr Thr Val Lys Val Asp Ser Phe Asp Ala Ala Met Arg Ala Met
1               5                   10                  15

Trp Lys Ala Ala Phe Leu Gly Leu Glu Val His Cys Glu Gln His Gly
                20                  25                  30

Asp Thr Val Lys Cys Thr Ile His
        35                  40

<210> SEQ ID NO 232
<211> LENGTH: 40
<212> TYPE: PRT
<213> ORGANISM: Artificial Sequence
<220> FEATURE:
<223> OTHER INFORMATION: Synthetic

<400> SEQUENCE: 232

Glu Thr Thr Val Lys Val Asp Ser Phe Asp Asn Ala Met Arg Ala Met
1               5                   10                  15

Trp Lys Ala Ala Phe Lys Gly Leu Glu Val His Cys Glu Gln His Gly
                20                  25                  30

Asp Thr Val Lys Cys Thr Ile His
        35                  40

<210> SEQ ID NO 233
<211> LENGTH: 40
<212> TYPE: PRT
<213> ORGANISM: Artificial Sequence
<220> FEATURE:
<223> OTHER INFORMATION: Synthetic

<400> SEQUENCE: 233

Lys Lys Thr Val Thr Val His Ser Pro Phe Glu Ala Trp Met Arg Ala
1               5                   10                  15

Met Trp Ala Lys Ala Phe Gly Leu Glu Val His Cys Thr Gln His Gly
                20                  25                  30

Asp Gln Ile Thr Cys His Ile Glu
```

-continued

```
                35                  40

<210> SEQ ID NO 234
<211> LENGTH: 40
<212> TYPE: PRT
<213> ORGANISM: Artificial Sequence
<220> FEATURE:
<223> OTHER INFORMATION: Synthetic

<400> SEQUENCE: 234

Cys Thr Thr Tyr His Val Glu Cys Pro Phe Asn Cys Trp Met Arg Tyr
1               5                   10                  15

Met Trp Ala Ala Ala Phe Gly Ala Glu Val His Leu His Gln His Gly
            20                  25                  30

Asp Thr Cys Gln Val Thr Val Cys
        35                  40

<210> SEQ ID NO 235
<211> LENGTH: 40
<212> TYPE: PRT
<213> ORGANISM: Artificial Sequence
<220> FEATURE:
<223> OTHER INFORMATION: Synthetic

<400> SEQUENCE: 235

Arg Glu Lys Ile Val Val His Ser Pro Phe Asp Ala Ala Met Ala Lys
1               5                   10                  15

Met Trp Cys Glu Val Phe Gly Val Pro Val Glu Ile Arg Lys Lys Asn
            20                  25                  30

Gly Thr Tyr Thr Val His Cys Gly
        35                  40

<210> SEQ ID NO 236
<211> LENGTH: 40
<212> TYPE: PRT
<213> ORGANISM: Artificial Sequence
<220> FEATURE:
<223> OTHER INFORMATION: Synthetic

<400> SEQUENCE: 236

Thr Glu Thr Tyr Glu Phe Asp Ser Pro Phe Asp Ala Trp Met Arg Ala
1               5                   10                  15

Met Trp Trp Gln Ala Phe Gly Ile Pro Val Thr Cys Ser Gln His Gly
            20                  25                  30

Asn Thr Val Lys Cys His Val Asn
        35                  40

<210> SEQ ID NO 237
<211> LENGTH: 40
<212> TYPE: PRT
<213> ORGANISM: Artificial Sequence
<220> FEATURE:
<223> OTHER INFORMATION: Synthetic

<400> SEQUENCE: 237

Glu Glu Thr Ser Thr Ser Tyr Ala Pro Phe Ala Cys Glu Ile Ala Arg
1               5                   10                  15

Gln Ile Ala Glu Glu Phe Asn Trp Lys Val Arg Cys Thr Gln His Gly
            20                  25                  30

Asn Gln Cys Thr Cys His Val His
        35                  40
```

```
<210> SEQ ID NO 238
<211> LENGTH: 40
<212> TYPE: PRT
<213> ORGANISM: Artificial Sequence
<220> FEATURE:
<223> OTHER INFORMATION: Synthetic

<400> SEQUENCE: 238

Thr Ile His Ser Thr Ala Tyr Ala Pro Phe Ala Cys Arg Ile Ala Ala
1               5                   10                  15

Lys Ile Ala Lys Glu Phe Asn Ile Pro Val Thr Leu Arg Glu His Gly
            20                  25                  30

Asp Thr Cys Thr Ile Gln Met Lys
        35                  40

<210> SEQ ID NO 239
<211> LENGTH: 40
<212> TYPE: PRT
<213> ORGANISM: Artificial Sequence
<220> FEATURE:
<223> OTHER INFORMATION: Synthetic

<400> SEQUENCE: 239

Cys Gln His Ile Thr Ser Asn Ser Glu Phe Ala Ala Glu Ile Ala Ala
1               5                   10                  15

Arg Ile Ala Ala Glu Phe Gly Leu Glu Val His Leu His Lys Lys Asn
            20                  25                  30

Gly Thr Tyr Thr Val Gln Val Cys
        35                  40

<210> SEQ ID NO 240
<211> LENGTH: 40
<212> TYPE: PRT
<213> ORGANISM: Artificial Sequence
<220> FEATURE:
<223> OTHER INFORMATION: Synthetic

<400> SEQUENCE: 240

Arg Tyr Lys Ser Thr Ala Trp Ser Pro Phe Ala Cys Glu Ile Ala Arg
1               5                   10                  15

Gln Ile Ile Glu Lys Phe Asn Ile Pro Val Glu Ile His Ile Thr Asn
            20                  25                  30

Gly Lys Cys Thr Ile His Val Ser
        35                  40

<210> SEQ ID NO 241
<211> LENGTH: 40
<212> TYPE: PRT
<213> ORGANISM: Artificial Sequence
<220> FEATURE:
<223> OTHER INFORMATION: Synthetic

<400> SEQUENCE: 241

Arg Tyr Lys Ser Thr Asn Trp Asn Pro Phe Ala Cys Glu Ile Ala Lys
1               5                   10                  15

Arg Ile Ile Leu Glu Phe Asn Ile Pro Val Glu Ile His Ile Thr Asn
            20                  25                  30

Gly Lys Cys Thr Ile His Val Ser
        35                  40

<210> SEQ ID NO 242
<211> LENGTH: 40
<212> TYPE: PRT
```

-continued

<213> ORGANISM: Artificial Sequence
<220> FEATURE:
<223> OTHER INFORMATION: Synthetic

<400> SEQUENCE: 242

Arg Phe Lys Ser Thr Asn Trp Ser Pro Phe Ala Cys Glu Ile Ala Arg
1               5                   10                  15

Gln Ile Ile Glu Lys Phe Asn Ile Pro Val Glu Ile His Ile Thr Asn
            20                  25                  30

Gly Lys Cys Thr Ile His Val Ser
        35                  40

<210> SEQ ID NO 243
<211> LENGTH: 40
<212> TYPE: PRT
<213> ORGANISM: Artificial Sequence
<220> FEATURE:
<223> OTHER INFORMATION: Synthetic

<400> SEQUENCE: 243

Arg Trp Lys Ser Thr Ala Trp Ser Pro Phe Ala Cys Lys Ile Ala Glu
1               5                   10                  15

Lys Ile Ile Arg Glu Phe Asn Ile Pro Val Glu Ile His Ile Thr Asn
            20                  25                  30

Gly Lys Cys Thr Ile His Val Ser
        35                  40

<210> SEQ ID NO 244
<211> LENGTH: 40
<212> TYPE: PRT
<213> ORGANISM: Artificial Sequence
<220> FEATURE:
<223> OTHER INFORMATION: Synthetic

<400> SEQUENCE: 244

Arg Tyr Lys Ser Thr Asn Trp Thr Pro Phe Ala Cys Glu Ile Ala Arg
1               5                   10                  15

Gln Ile Ile Glu Glu Phe Asn Ile Pro Val Glu Ile His Ile Thr Asn
            20                  25                  30

Gly Lys Cys Thr Ile His Val Ser
        35                  40

<210> SEQ ID NO 245
<211> LENGTH: 40
<212> TYPE: PRT
<213> ORGANISM: Artificial Sequence
<220> FEATURE:
<223> OTHER INFORMATION: Synthetic

<400> SEQUENCE: 245

Thr Phe Thr Ser Val Ala Tyr Ser Ser Phe Ala Cys Ala Ile Ala Ala
1               5                   10                  15

Glu Ile Ala Arg Gln Phe Gly Trp Glu Val His Val Glu Lys His Asn
            20                  25                  30

Gly Thr Cys Lys Val Lys Ile His
        35                  40

<210> SEQ ID NO 246
<211> LENGTH: 40
<212> TYPE: PRT
<213> ORGANISM: Artificial Sequence
<220> FEATURE:
<223> OTHER INFORMATION: Synthetic

<400> SEQUENCE: 246

Thr Trp Thr Thr Val Ser Asn Ser Pro Phe Ala Ala Trp Ile Ala Ala
1               5                   10                  15

Glu Ile Ala Arg Gln Phe Asn Leu Glu Val His Cys Glu Thr His Asn
            20                  25                  30

Gly Thr Val Thr Cys His Thr Lys
        35                  40

<210> SEQ ID NO 247
<211> LENGTH: 40
<212> TYPE: PRT
<213> ORGANISM: Artificial Sequence
<220> FEATURE:
<223> OTHER INFORMATION: Synthetic

<400> SEQUENCE: 247

Thr Trp Thr Ser His Ala Lys Ala Pro Phe Ala Cys Glu Ile Ala Arg
1               5                   10                  15

Gln Ile Ala Glu Glu Phe Gly Trp Thr Cys Thr Val Glu Lys His Asn
            20                  25                  30

Gly Thr Cys Glu Ile Asn Cys Gln
        35                  40

<210> SEQ ID NO 248
<211> LENGTH: 40
<212> TYPE: PRT
<213> ORGANISM: Artificial Sequence
<220> FEATURE:
<223> OTHER INFORMATION: Synthetic

<400> SEQUENCE: 248

Thr Tyr Thr Ser His Ala Arg Ala Pro Phe Ala Cys Glu Ile Ala Arg
1               5                   10                  15

Gln Ile Ala Glu Glu Phe Gly Trp Thr Cys Thr Val Glu Lys His Asn
            20                  25                  30

Gly Thr Cys Glu Ile Asn Cys Gln
        35                  40

<210> SEQ ID NO 249
<211> LENGTH: 40
<212> TYPE: PRT
<213> ORGANISM: Artificial Sequence
<220> FEATURE:
<223> OTHER INFORMATION: Synthetic

<400> SEQUENCE: 249

Thr Tyr Thr Ser His Ala Ala Ala Pro Phe Ala Cys Glu Ile Ala Lys
1               5                   10                  15

Gln Ile Ala Ala Glu Phe Gly Trp Thr Cys Thr Val Glu Lys His Asn
            20                  25                  30

Gly Thr Cys Glu Ile Asn Cys Gln
        35                  40

<210> SEQ ID NO 250
<211> LENGTH: 40
<212> TYPE: PRT
<213> ORGANISM: Artificial Sequence
<220> FEATURE:
<223> OTHER INFORMATION: Synthetic

<400> SEQUENCE: 250

```
Thr Trp Thr Ser His Ala Lys Ala Pro Phe Ala Cys Glu Ile Ala Arg
1               5                   10                  15

Arg Ile Ala Glu Glu Phe Gly Trp Thr Cys Thr Val Glu Lys His Asn
            20                  25                  30

Gly Thr Cys Glu Ile Asn Cys Gln
        35                  40
```

<210> SEQ ID NO 251
<211> LENGTH: 40
<212> TYPE: PRT
<213> ORGANISM: Artificial Sequence
<220> FEATURE:
<223> OTHER INFORMATION: Synthetic

<400> SEQUENCE: 251

```
Glu Met His Ile His Ala Arg Ala Pro Phe Ala Cys Gln Ile Ala Tyr
1               5                   10                  15

Asp Ile Leu Lys Glu Phe Gly Gln Asn Val Thr Val Thr Glu Arg Gly
            20                  25                  30

Asn Lys Cys Thr Val Thr Val Thr
        35                  40
```

<210> SEQ ID NO 252
<211> LENGTH: 40
<212> TYPE: PRT
<213> ORGANISM: Artificial Sequence
<220> FEATURE:
<223> OTHER INFORMATION: Synthetic

<400> SEQUENCE: 252

```
Thr Ser Lys Ser Thr Ser Met Ser Glu Phe Ala Ala Glu Ile Ala Ala
1               5                   10                  15

Arg Ile Cys Lys Glu Phe Gly Trp Pro Val Arg Val Arg Lys Asn Gly
            20                  25                  30

Asp Lys Tyr Thr Val Glu Cys Glu
        35                  40
```

<210> SEQ ID NO 253
<211> LENGTH: 40
<212> TYPE: PRT
<213> ORGANISM: Artificial Sequence
<220> FEATURE:
<223> OTHER INFORMATION: Synthetic

<400> SEQUENCE: 253

```
Cys Phe Thr Ser Val Ala His Ser Glu Phe Ala Cys Arg Ile Ile Ala
1               5                   10                  15

Lys Ile Leu Trp Glu Phe Gly Gln Glu Val His Val Glu Thr His Gly
            20                  25                  30

Asp Glu Cys Arg Val Thr Ser Cys
        35                  40
```

<210> SEQ ID NO 254
<211> LENGTH: 40
<212> TYPE: PRT
<213> ORGANISM: Artificial Sequence
<220> FEATURE:
<223> OTHER INFORMATION: Synthetic

<400> SEQUENCE: 254

```
Cys Phe Thr Ser Val Ala His Ser Gln Phe Ala Cys Glu Ile Ile Ala
1               5                   10                  15
```

Glu Ile Leu Arg Gln Phe Gly Gln Glu Val His Val Glu Thr His Gly
            20                  25                  30

Asp Glu Cys Arg Val Thr Ser Cys
            35                  40

<210> SEQ ID NO 255
<211> LENGTH: 40
<212> TYPE: PRT
<213> ORGANISM: Artificial Sequence
<220> FEATURE:
<223> OTHER INFORMATION: Synthetic

<400> SEQUENCE: 255

Thr Ser His Ile Thr Ser Asn Ala Pro Phe Ala Cys Ala Ile Ala Ala
1               5                   10                  15

Lys Ile Ala Ala Glu Phe Asn Trp Glu Val His Leu His Glu Lys Asn
            20                  25                  30

Gly Lys Cys Thr Leu Gln Ile Lys
            35                  40

<210> SEQ ID NO 256
<211> LENGTH: 40
<212> TYPE: PRT
<213> ORGANISM: Artificial Sequence
<220> FEATURE:
<223> OTHER INFORMATION: Synthetic

<400> SEQUENCE: 256

Thr Tyr His Ser Thr Ser Asn Ala Pro Phe Ala Cys Gln Ile Ala Ala
1               5                   10                  15

Glu Ile Ala Lys Glu Phe Arg Trp Glu Val His Leu His Glu Lys Asn
            20                  25                  30

Gly Lys Cys Thr Leu Gln Ile Lys
            35                  40

<210> SEQ ID NO 257
<211> LENGTH: 40
<212> TYPE: PRT
<213> ORGANISM: Artificial Sequence
<220> FEATURE:
<223> OTHER INFORMATION: Synthetic

<400> SEQUENCE: 257

Thr Ala His Ile Thr Ala Arg Ala Pro Phe Ala Cys Arg Ile Ala Ala
1               5                   10                  15

Glu Ile Ala Arg Glu Phe Asn Trp Glu Val His Leu His Glu Lys Asn
            20                  25                  30

Gly Lys Cys Thr Leu Gln Ile Lys
            35                  40

<210> SEQ ID NO 258
<211> LENGTH: 40
<212> TYPE: PRT
<213> ORGANISM: Artificial Sequence
<220> FEATURE:
<223> OTHER INFORMATION: Synthetic

<400> SEQUENCE: 258

Thr Ser His Ile Thr Ser Glu Ala Pro Phe Ala Cys Gln Ile Ala Ala
1               5                   10                  15

Glu Ile Ala Lys Glu Phe Asn Trp Glu Val His Leu His Glu Lys Asn
            20                  25                  30

```
Gly Lys Cys Thr Leu Gln Ile Lys
        35                  40
```

<210> SEQ ID NO 259
<211> LENGTH: 40
<212> TYPE: PRT
<213> ORGANISM: Artificial Sequence
<220> FEATURE:
<223> OTHER INFORMATION: Synthetic

<400> SEQUENCE: 259

```
Thr Ser His Ile Thr Ser Glu Ser Pro Phe Ala Cys Gln Ile Ala Ala
1               5                   10                  15

Glu Ile Ala Lys Glu Phe Asn Trp Glu Val His Leu His Glu Lys Asn
            20                  25                  30

Gly Lys Cys Thr Leu Gln Ile Lys
        35                  40
```

<210> SEQ ID NO 260
<211> LENGTH: 40
<212> TYPE: PRT
<213> ORGANISM: Artificial Sequence
<220> FEATURE:
<223> OTHER INFORMATION: Synthetic

<400> SEQUENCE: 260

```
Thr Asp His Ser Thr Ser Arg Ala Pro Phe Ala Cys Gln Ile Ala Ala
1               5                   10                  15

Glu Ile Ala Lys Glu Phe Asn Trp Glu Val His Leu His Glu Lys Asn
            20                  25                  30

Gly Lys Cys Thr Leu Gln Ile Lys
        35                  40
```

<210> SEQ ID NO 261
<211> LENGTH: 40
<212> TYPE: PRT
<213> ORGANISM: Artificial Sequence
<220> FEATURE:
<223> OTHER INFORMATION: Synthetic

<400> SEQUENCE: 261

```
Cys Met Thr Thr His Thr Arg Ala Pro Phe Ala Ala Gln Ile Ala Ala
1               5                   10                  15

Asp Ile Ala Ala Lys Phe Gly Tyr Asp Val Gln Leu Gln His Asp Gly
            20                  25                  30

Thr Lys Leu Thr Val His Ser Cys
        35                  40
```

<210> SEQ ID NO 262
<211> LENGTH: 40
<212> TYPE: PRT
<213> ORGANISM: Artificial Sequence
<220> FEATURE:
<223> OTHER INFORMATION: Synthetic

<400> SEQUENCE: 262

```
Cys Met Thr Ile His Thr Tyr Ala Pro Phe Ala Ala Glu Ile Ala Ala
1               5                   10                  15

Arg Ile Ala Ala Glu Phe Gly Tyr Asp Val Gln Leu Gln His Asp Gly
            20                  25                  30

Thr Lys Leu Thr Val His Ser Cys
        35                  40
```

<210> SEQ ID NO 263
<211> LENGTH: 40
<212> TYPE: PRT
<213> ORGANISM: Artificial Sequence
<220> FEATURE:
<223> OTHER INFORMATION: Synthetic

<400> SEQUENCE: 263

```
Cys Met Thr Ile His Thr Arg Met Pro Phe Ala Ala Glu Ile Ala Ala
1               5                   10                  15

Arg Ile Ala Lys Glu Phe Gly Tyr Asp Val Gln Leu Gln His Asp Gly
            20                  25                  30

Thr Lys Leu Thr Val His Ser Cys
        35                  40
```

<210> SEQ ID NO 264
<211> LENGTH: 40
<212> TYPE: PRT
<213> ORGANISM: Artificial Sequence
<220> FEATURE:
<223> OTHER INFORMATION: Synthetic

<400> SEQUENCE: 264

```
Cys Thr Thr Ile Glu Val Thr Arg Phe Ala Gln Ala Ile Ala Ala Ala
1               5                   10                  15

Ile Lys Cys Glu Phe Lys Gly Lys Lys Ile Thr Thr His Ala His Gly
            20                  25                  30

Asp Thr Ile Lys Leu Thr Cys Cys
        35                  40
```

<210> SEQ ID NO 265
<211> LENGTH: 40
<212> TYPE: PRT
<213> ORGANISM: Artificial Sequence
<220> FEATURE:
<223> OTHER INFORMATION: Synthetic

<400> SEQUENCE: 265

```
Thr Gln Thr Ser Ile Ser Trp Cys Pro Phe Ala Cys Gln Ile Ala Val
1               5                   10                  15

Asp Ile Ala Ala Ser Phe Asn Trp Asp Val Thr Val Thr Gln His Gly
            20                  25                  30

Asp Lys Cys Thr Val His Ile Asn
        35                  40
```

<210> SEQ ID NO 266
<211> LENGTH: 40
<212> TYPE: PRT
<213> ORGANISM: Artificial Sequence
<220> FEATURE:
<223> OTHER INFORMATION: Synthetic

<400> SEQUENCE: 266

```
Thr Gln Thr Ser Ile Ser Trp Cys Pro Phe Ala Cys Glu Ile Ala Arg
1               5                   10                  15

Gln Ile Ala Glu Ser Phe Asn Trp Asp Val Thr Val Thr Gln His Gly
            20                  25                  30

Asp Lys Cys Thr Val His Ile Asn
        35                  40
```

<210> SEQ ID NO 267
<211> LENGTH: 40

```
<212> TYPE: PRT
<213> ORGANISM: Artificial Sequence
<220> FEATURE:
<223> OTHER INFORMATION: Synthetic

<400> SEQUENCE: 267

Thr Glu Thr Ser Ile Ser Tyr Cys Pro Phe Ala Cys Arg Ile Ala Val
1               5                   10                  15

Glu Ile Ala Arg Ser Phe Asn Trp Asp Val Thr Val Thr Gln His Gly
            20                  25                  30

Asp Lys Cys Thr Val His Ile Asn
        35                  40

<210> SEQ ID NO 268
<211> LENGTH: 40
<212> TYPE: PRT
<213> ORGANISM: Artificial Sequence
<220> FEATURE:
<223> OTHER INFORMATION: Synthetic

<400> SEQUENCE: 268

Cys Arg Thr Ser Lys Cys Tyr Ser Pro Phe Ala Ala Ala Ile Ala Ala
1               5                   10                  15

Glu Ile Ala Arg Gln Phe Asn Trp Lys Val Thr Val His Gln His Gly
            20                  25                  30

Asp Thr Ile His Val Thr Ile Cys
        35                  40

<210> SEQ ID NO 269
<211> LENGTH: 40
<212> TYPE: PRT
<213> ORGANISM: Artificial Sequence
<220> FEATURE:
<223> OTHER INFORMATION: Synthetic

<400> SEQUENCE: 269

Cys Tyr Lys Ser Val Thr Lys Ser Pro Phe Ala Ala Glu Ile Ala Arg
1               5                   10                  15

Gln Ile Ala Glu Glu Phe Asn Trp Asp Val Gln Cys Thr Gln His Gly
            20                  25                  30

Thr Thr Ile Thr Cys His Met Cys
        35                  40

<210> SEQ ID NO 270
<211> LENGTH: 40
<212> TYPE: PRT
<213> ORGANISM: Artificial Sequence
<220> FEATURE:
<223> OTHER INFORMATION: Synthetic

<400> SEQUENCE: 270

Thr Tyr Thr Thr Trp Thr Ser Ser Pro Phe Ser Ala Glu Ile Val Arg
1               5                   10                  15

Gln Ile Ala Glu Glu Phe Gly Tyr Glu Val His Cys Thr Gln His Gly
            20                  25                  30

Asn Arg Val Glu Cys Lys Val Lys
        35                  40

<210> SEQ ID NO 271
<211> LENGTH: 40
<212> TYPE: PRT
<213> ORGANISM: Artificial Sequence
<220> FEATURE:
```

<223> OTHER INFORMATION: Synthetic

<400> SEQUENCE: 271

Lys Thr Gln Phe Lys Val Asp Ser Phe Ala Asn Ala Ile Ala Gln Ala
1               5                   10                  15

Ile Leu Cys Glu Phe Asn Asn Leu Pro Phe Thr Val Glu Ile His Gly
            20                  25                  30

Arg Thr Ile Lys Ile Lys Cys Lys
        35                  40

<210> SEQ ID NO 272
<211> LENGTH: 40
<212> TYPE: PRT
<213> ORGANISM: Artificial Sequence
<220> FEATURE:
<223> OTHER INFORMATION: Synthetic

<400> SEQUENCE: 272

Cys Ile Thr Ser Gln Ala Lys Thr Pro Phe Ala Ala Gln Ile Ala Ala
1               5                   10                  15

Glu Ile Met Arg Glu Phe Asn Ile Glu Val His Cys Glu Lys Lys Gly
            20                  25                  30

Pro Thr Leu Lys Cys Thr Ser Cys
        35                  40

<210> SEQ ID NO 273
<211> LENGTH: 40
<212> TYPE: PRT
<213> ORGANISM: Artificial Sequence
<220> FEATURE:
<223> OTHER INFORMATION: Synthetic

<400> SEQUENCE: 273

Thr Cys Arg Ala Gln Ser Lys Ser Lys Phe Ala Ala Leu Ile Ala Ala
1               5                   10                  15

Glu Ile Cys Arg Gln Phe Gly Leu Glu Val His Leu His Lys Lys Asn
            20                  25                  30

Gly Thr Trp Thr Val Glu Cys Asn
        35                  40

<210> SEQ ID NO 274
<211> LENGTH: 40
<212> TYPE: PRT
<213> ORGANISM: Artificial Sequence
<220> FEATURE:
<223> OTHER INFORMATION: Synthetic

<400> SEQUENCE: 274

Thr Ala Val Ala Cys Ser Arg Ser Ser Phe Ser Ala Ala Ile Ala Ala
1               5                   10                  15

Glu Ile Cys Arg Gln Phe Arg Trp Glu Trp His Ile Glu Thr His Gly
            20                  25                  30

Asp Val Tyr Lys Val Thr Cys Lys
        35                  40

<210> SEQ ID NO 275
<211> LENGTH: 40
<212> TYPE: PRT
<213> ORGANISM: Artificial Sequence
<220> FEATURE:
<223> OTHER INFORMATION: Synthetic

<400> SEQUENCE: 275

```
Thr Tyr Lys Leu Val Ser His Ser Pro Phe Ala Cys Ala Ile Ala Ala
1               5                   10                  15

Glu Ile Phe Arg Gln Phe Asn Tyr Asp Val Gln Val His Gln Lys Asn
            20                  25                  30

Gly Thr Cys Thr Val Glu Val His
        35                  40

<210> SEQ ID NO 276
<211> LENGTH: 40
<212> TYPE: PRT
<213> ORGANISM: Artificial Sequence
<220> FEATURE:
<223> OTHER INFORMATION: Synthetic

<400> SEQUENCE: 276

Thr Tyr Lys Leu Val Ser His Ser Pro Phe Ala Cys Lys Ile Ala Ala
1               5                   10                  15

Glu Ile Phe Lys Glu Phe Asn Tyr Asp Val Gln Val His Gln Lys Asn
            20                  25                  30

Gly Thr Cys Thr Val Glu Val His
        35                  40

<210> SEQ ID NO 277
<211> LENGTH: 40
<212> TYPE: PRT
<213> ORGANISM: Artificial Sequence
<220> FEATURE:
<223> OTHER INFORMATION: Synthetic

<400> SEQUENCE: 277

Thr Trp Lys Ser Tyr Ser His Ser Pro Phe Ala Cys Gln Ile Ala Ala
1               5                   10                  15

Glu Ile Leu Arg Glu Phe Gly Phe Asp Val Gln Val His Gln Lys Asn
            20                  25                  30

Gly Thr Cys Thr Val Glu Val His
        35                  40

<210> SEQ ID NO 278
<211> LENGTH: 40
<212> TYPE: PRT
<213> ORGANISM: Artificial Sequence
<220> FEATURE:
<223> OTHER INFORMATION: Synthetic

<400> SEQUENCE: 278

Thr Trp Lys Thr Tyr Ala His Ser Pro Phe Ala Cys Trp Ile Ala Ala
1               5                   10                  15

Glu Ile Phe Lys Glu Phe Gly Phe Asp Val Gln Val His Gln Lys Asn
            20                  25                  30

Gly Thr Cys Thr Val Glu Val His
        35                  40

<210> SEQ ID NO 279
<211> LENGTH: 40
<212> TYPE: PRT
<213> ORGANISM: Artificial Sequence
<220> FEATURE:
<223> OTHER INFORMATION: Synthetic

<400> SEQUENCE: 279

Thr Trp Lys Ser Val Ser His Ser Pro Phe Ala Cys Lys Ile Ala Ala
1               5                   10                  15
```

Glu Ile Phe Lys Glu Phe Gly Tyr Asp Val Gln Val His Gln Lys Asn
            20                  25                  30

Gly Thr Cys Thr Val Glu Val His
        35                  40

<210> SEQ ID NO 280
<211> LENGTH: 40
<212> TYPE: PRT
<213> ORGANISM: Artificial Sequence
<220> FEATURE:
<223> OTHER INFORMATION: Synthetic

<400> SEQUENCE: 280

Thr Trp Lys Ser Tyr Ser His Ser Pro Phe Ala Cys Glu Ile Ala Ala
1               5                   10                  15

Arg Ile Phe Lys Glu Phe Gly Tyr Asp Val Gln Val His Gln Lys Asn
            20                  25                  30

Gly Thr Cys Thr Val Glu Val His
        35                  40

<210> SEQ ID NO 281
<211> LENGTH: 40
<212> TYPE: PRT
<213> ORGANISM: Artificial Sequence
<220> FEATURE:
<223> OTHER INFORMATION: Synthetic

<400> SEQUENCE: 281

Thr Trp Lys Thr Val Ser His Ser Pro Phe Ala Cys Glu Ile Ala Ala
1               5                   10                  15

Arg Ile Trp Lys Glu Phe Gly Tyr Asp Val Gln Val His Gln Lys Asn
            20                  25                  30

Gly Thr Cys Thr Val Glu Val His
        35                  40

<210> SEQ ID NO 282
<211> LENGTH: 40
<212> TYPE: PRT
<213> ORGANISM: Artificial Sequence
<220> FEATURE:
<223> OTHER INFORMATION: Synthetic

<400> SEQUENCE: 282

Thr Arg Thr Ser Gln Gln Glu Ser Glu Phe Ala Cys Arg Ile Ala Ala
1               5                   10                  15

Glu Ile Ala Arg Gln Phe Gly Leu Glu Val His Leu Thr Lys His Gly
            20                  25                  30

Pro Gln Cys Lys Ile Thr Val Lys
        35                  40

<210> SEQ ID NO 283
<211> LENGTH: 40
<212> TYPE: PRT
<213> ORGANISM: Artificial Sequence
<220> FEATURE:
<223> OTHER INFORMATION: Synthetic

<400> SEQUENCE: 283

Thr Thr Thr Tyr Lys Phe Gln Ser Phe Ala Leu Ala Ile Ala Ala Ala
1               5                   10                  15

Ile Lys Cys Glu Phe Asn Gln Val Pro Tyr Glu Val Gln Asn His Gly
            20                  25                  30

Thr Thr Tyr Lys Val Lys Cys Thr
        35                  40

<210> SEQ ID NO 284
<211> LENGTH: 40
<212> TYPE: PRT
<213> ORGANISM: Artificial Sequence
<220> FEATURE:
<223> OTHER INFORMATION: Synthetic

<400> SEQUENCE: 284

Thr Tyr Thr Ser Thr Ala Ser Tyr Asp Phe Ala Cys Gln Ile Ile Ala
1               5                   10                  15

Glu Ile Cys Arg Gln Phe Gly Trp Pro Val Asp Val Glu Thr His Gly
            20                  25                  30

Lys Thr Cys His Val Lys Cys His
        35                  40

<210> SEQ ID NO 285
<211> LENGTH: 40
<212> TYPE: PRT
<213> ORGANISM: Artificial Sequence
<220> FEATURE:
<223> OTHER INFORMATION: Synthetic

<400> SEQUENCE: 285

Thr Ser Thr Ser Thr Ala Ser Ser Phe Ala Cys Gln Ile Ile Ala
1               5                   10                  15

Asp Ile Cys Ala Asn Phe Gly Trp Pro Val Asp Val Glu Thr His Gly
            20                  25                  30

Lys Thr Cys His Val Lys Cys His
        35                  40

<210> SEQ ID NO 286
<211> LENGTH: 40
<212> TYPE: PRT
<213> ORGANISM: Artificial Sequence
<220> FEATURE:
<223> OTHER INFORMATION: Synthetic

<400> SEQUENCE: 286

Thr Tyr Glu Ser Arg Ala Arg Ser Pro Phe Ala Cys Trp Ile Leu Ala
1               5                   10                  15

Glu Ile Leu Arg Glu Phe Gly Gly Glu Val His Cys Thr Glu Gln Asn
            20                  25                  30

Gly Thr Cys Thr Cys Lys Val Gln
        35                  40

<210> SEQ ID NO 287
<211> LENGTH: 40
<212> TYPE: PRT
<213> ORGANISM: Artificial Sequence
<220> FEATURE:
<223> OTHER INFORMATION: Synthetic

<400> SEQUENCE: 287

Thr Thr Thr Tyr Thr Trp Asp Ser Phe Asp Ala Ala Met Glu Ala Met
1               5                   10                  15

Trp Arg Leu Ala Phe Asn Gly Ile Pro Val Gln Ile Thr Met Lys Asn
            20                  25                  30

Gly Lys Trp Gln Val Lys Glu His
        35                  40

<210> SEQ ID NO 288
<211> LENGTH: 40
<212> TYPE: PRT
<213> ORGANISM: Artificial Sequence
<220> FEATURE:
<223> OTHER INFORMATION: Synthetic

<400> SEQUENCE: 288

Thr Glu Thr Leu His Phe Gln Ser Phe Asp Glu Ala Met Glu Ala Ala
1               5                   10                  15

Trp Arg Ala Ala Phe Lys Gly Val Pro Tyr Glu Val Gln Val His Gly
            20                  25                  30

Lys Thr Tyr Thr Val His Ile Lys
        35                  40

<210> SEQ ID NO 289
<211> LENGTH: 40
<212> TYPE: PRT
<213> ORGANISM: Artificial Sequence
<220> FEATURE:
<223> OTHER INFORMATION: Synthetic

<400> SEQUENCE: 289

Thr Pro Gln Ile Thr Ile Lys Ser Pro Phe Ser Ala Trp Met Ala Ala
1               5                   10                  15

Met Trp Leu Glu Ala Phe Asn Ile Pro Tyr Asp Val Gln Thr His Gly
            20                  25                  30

Asp Lys Val Thr Val Thr Gln His
        35                  40

<210> SEQ ID NO 290
<211> LENGTH: 40
<212> TYPE: PRT
<213> ORGANISM: Artificial Sequence
<220> FEATURE:
<223> OTHER INFORMATION: Synthetic

<400> SEQUENCE: 290

Thr Lys Thr Val Gln Val Asp Ser Phe Asp Glu Ala Met Arg Val Ala
1               5                   10                  15

Trp Lys Ala Ala Phe Asn Asn Ile Lys Val Gln Ile Gln Lys Val Gly
            20                  25                  30

Thr Thr Val Lys Leu His Leu His
        35                  40

<210> SEQ ID NO 291
<211> LENGTH: 40
<212> TYPE: PRT
<213> ORGANISM: Artificial Sequence
<220> FEATURE:
<223> OTHER INFORMATION: Synthetic

<400> SEQUENCE: 291

Thr Glu Thr Leu Thr Phe Thr Asn Phe Asp Glu Ala Met Arg Ala Met
1               5                   10                  15

Trp Glu Trp Val Phe Lys Gly Ile Pro Val Thr Val Thr Val Lys Asn
            20                  25                  30

Gly Lys Trp Gln Val Gln Ile Asn
        35                  40

<210> SEQ ID NO 292

```
<211> LENGTH: 40
<212> TYPE: PRT
<213> ORGANISM: Artificial Sequence
<220> FEATURE:
<223> OTHER INFORMATION: Synthetic

<400> SEQUENCE: 292

Thr Thr Thr Tyr Thr Tyr Leu Ser Pro Phe Asn Ala Trp Met Arg Ala
1               5                   10                  15

Met Trp Lys Gln Ala Phe Gly Ile Pro Val Thr Trp Lys Lys His Gly
            20                  25                  30

Asp Thr Leu Thr Val His Glu His
        35                  40

<210> SEQ ID NO 293
<211> LENGTH: 40
<212> TYPE: PRT
<213> ORGANISM: Artificial Sequence
<220> FEATURE:
<223> OTHER INFORMATION: Synthetic

<400> SEQUENCE: 293

Thr Glu Lys Ile Gln Val Tyr Ala Pro Phe Asn Ala Trp Met Arg Ala
1               5                   10                  15

Met Trp Ala Leu Val Phe Gly Val Pro Val Lys Val Thr Gln Lys Asn
            20                  25                  30

Gly Thr Leu Thr Leu His Leu Asn
        35                  40

<210> SEQ ID NO 294
<211> LENGTH: 40
<212> TYPE: PRT
<213> ORGANISM: Artificial Sequence
<220> FEATURE:
<223> OTHER INFORMATION: Synthetic

<400> SEQUENCE: 294

Glu Thr Thr Tyr Thr Tyr Glu Ser Pro Phe Glu Ala Ala Met Ala Ala
1               5                   10                  15

Met Trp Trp Arg Ala Phe Gly Val Pro Val Thr Val His Thr His Gly
            20                  25                  30

Thr Lys Ile Lys Val Thr Thr Lys
        35                  40

<210> SEQ ID NO 295
<211> LENGTH: 40
<212> TYPE: PRT
<213> ORGANISM: Artificial Sequence
<220> FEATURE:
<223> OTHER INFORMATION: Synthetic

<400> SEQUENCE: 295

Lys Lys Glu Val Val Val Tyr Ser Pro Phe Ser Ala Lys Met Val Ala
1               5                   10                  15

Met Trp Ala Gln Val Phe Gly Val Pro Tyr Glu Val His Gln His Gly
            20                  25                  30

Thr Thr Ile Thr Val Lys Ile Asp
        35                  40

<210> SEQ ID NO 296
<211> LENGTH: 40
<212> TYPE: PRT
<213> ORGANISM: Artificial Sequence
```

<220> FEATURE:
<223> OTHER INFORMATION: Synthetic

<400> SEQUENCE: 296

Thr Gln Lys Phe Thr Tyr Asp Ser Phe Asp Glu Ala Met Arg Ala Met
1               5                   10                  15

Trp Lys Leu Val Phe Asn Gly Val Pro Ala Arg Val Thr Ile Leu Asn
            20                  25                  30

Gly Lys Trp Gln Val Glu Lys Lys
        35                  40

<210> SEQ ID NO 297
<211> LENGTH: 40
<212> TYPE: PRT
<213> ORGANISM: Artificial Sequence
<220> FEATURE:
<223> OTHER INFORMATION: Synthetic

<400> SEQUENCE: 297

Thr Lys Gln Ile Lys Val Asp Ser Phe Asp Ala Ala Met Lys Ala Met
1               5                   10                  15

Trp Glu Ala Val Phe Arg Asn Leu Asp Val Gln Ile Gln Gln Glu Asn
            20                  25                  30

Gly Thr Trp Thr Val Lys Thr Lys
        35                  40

<210> SEQ ID NO 298
<211> LENGTH: 40
<212> TYPE: PRT
<213> ORGANISM: Artificial Sequence
<220> FEATURE:
<223> OTHER INFORMATION: Synthetic

<400> SEQUENCE: 298

Thr Glu His Ile Thr Val Asp Ser Phe Asp Lys Ala Met Asp Thr Ala
1               5                   10                  15

Trp Arg Tyr Val Phe Gln Gly Ile Pro Ala Thr Val Thr Trp Lys Asn
            20                  25                  30

Gly Gln Trp Thr Val Lys Val His
        35                  40

<210> SEQ ID NO 299
<211> LENGTH: 40
<212> TYPE: PRT
<213> ORGANISM: Artificial Sequence
<220> FEATURE:
<223> OTHER INFORMATION: Synthetic

<400> SEQUENCE: 299

Thr Thr Thr Tyr Thr Tyr Asp Ser Phe Asp Glu Ala Met Arg Ala Met
1               5                   10                  15

Trp Glu Ala Val Phe Lys Gly Leu Glu Val His Ile Glu Ile His Gly
            20                  25                  30

Lys Gln Phe Gln Val Thr Val His
        35                  40

<210> SEQ ID NO 300
<211> LENGTH: 40
<212> TYPE: PRT
<213> ORGANISM: Artificial Sequence
<220> FEATURE:
<223> OTHER INFORMATION: Synthetic -continued

<400> SEQUENCE: 300

Thr Gln His Ile Thr Lys Glu Ala Lys Phe Ala Ala Lys Met Ala Met
1               5                   10                  15

Met Trp Ala Lys Val Phe Gly Ser Glu Val Arg Val Thr Gln His Gly
            20                  25                  30

Thr Gln Leu Thr Ile Glu Leu His
        35                  40

<210> SEQ ID NO 301
<211> LENGTH: 40
<212> TYPE: PRT
<213> ORGANISM: Artificial Sequence
<220> FEATURE:
<223> OTHER INFORMATION: Synthetic

<400> SEQUENCE: 301

Thr Lys Phe Ile Lys Tyr Asp Ser Lys Phe Ala Ala Glu Met Ala Arg
1               5                   10                  15

Met Trp Tyr Glu Val Phe Gly Ser Glu Val His Val Ser Gln Ile Asn
            20                  25                  30

Gly Thr Trp Val Val Lys Glu Asn
        35                  40

<210> SEQ ID NO 302
<211> LENGTH: 40
<212> TYPE: PRT
<213> ORGANISM: Artificial Sequence
<220> FEATURE:
<223> OTHER INFORMATION: Synthetic

<400> SEQUENCE: 302

Thr Thr Thr Tyr Thr Leu Asp Ser Phe Asp Ala Ala Met Arg Ala Met
1               5                   10                  15

Trp Lys Ala Val Phe Lys Gly Ile Pro Val Thr Cys Thr Gln Lys Asn
            20                  25                  30

Gly Lys Trp Gln Val Thr Ile Gln
        35                  40

<210> SEQ ID NO 303
<211> LENGTH: 40
<212> TYPE: PRT
<213> ORGANISM: Artificial Sequence
<220> FEATURE:
<223> OTHER INFORMATION: Synthetic

<400> SEQUENCE: 303

Thr Thr Thr Tyr Thr Leu Asp Ser Phe Asp Ala Ala Met Arg Ala Met
1               5                   10                  15

Trp Lys Ala Val Phe Lys Gly Ile Pro Val Thr Cys Thr Met Lys Asn
            20                  25                  30

Gly Lys Trp Gln Val Thr Ile Gln
        35                  40

<210> SEQ ID NO 304
<211> LENGTH: 40
<212> TYPE: PRT
<213> ORGANISM: Artificial Sequence
<220> FEATURE:
<223> OTHER INFORMATION: Synthetic

<400> SEQUENCE: 304

Thr Thr Thr Tyr Thr Leu Asp Ser Phe Asp Ala Ala Met Lys Ala Met

```
  1               5                   10                  15
Trp Glu Ala Val Phe Asn Gly Ile Pro Val Thr Cys Thr Gln Lys Asn
                20                  25                  30
Gly Lys Trp Gln Val Thr Ile Gln
            35                  40
```

<210> SEQ ID NO 305
<211> LENGTH: 40
<212> TYPE: PRT
<213> ORGANISM: Artificial Sequence
<220> FEATURE:
<223> OTHER INFORMATION: Synthetic

<400> SEQUENCE: 305

```
Gly Thr Thr Tyr Gln Phe His Ser Phe Thr Glu Ala Met Arg Ala Ala
1               5                   10                  15
Trp Lys Ala Val Phe Leu Asn Leu Pro Tyr Glu Ile Thr Gln Val Gly
                20                  25                  30
Asp Thr Phe Gln Val Thr Ile Lys
            35                  40
```

<210> SEQ ID NO 306
<211> LENGTH: 40
<212> TYPE: PRT
<213> ORGANISM: Artificial Sequence
<220> FEATURE:
<223> OTHER INFORMATION: Synthetic

<400> SEQUENCE: 306

```
Thr Met His Ser Trp Ala Ser Asp Gln Phe Ala Ala Glu Ile Ala Ala
1               5                   10                  15
Arg Ile Ala Arg Glu Phe Gly Tyr Asp Val Thr Phe Thr Glu Lys Asn
                20                  25                  30
Gly His Val Glu Val Glu Val Asn
            35                  40
```

<210> SEQ ID NO 307
<211> LENGTH: 40
<212> TYPE: PRT
<213> ORGANISM: Artificial Sequence
<220> FEATURE:
<223> OTHER INFORMATION: Synthetic

<400> SEQUENCE: 307

```
Thr Ile His Ser Trp Ala Ser Asp Gln Phe Ala Ala Lys Ile Ala Ala
1               5                   10                  15
Asp Ile Ala Arg Glu Phe Gly Tyr Asp Val Thr Phe Thr Glu Lys Asn
                20                  25                  30
Gly His Val Glu Val Glu Val Asn
            35                  40
```

<210> SEQ ID NO 308
<211> LENGTH: 40
<212> TYPE: PRT
<213> ORGANISM: Artificial Sequence
<220> FEATURE:
<223> OTHER INFORMATION: Synthetic

<400> SEQUENCE: 308

```
Thr Ala Thr Val Thr Thr Arg Ser Glu Phe Ala Ala Lys Ile Ala Ala
1               5                   10                  15
Glu Ile Trp Arg Glu Phe Gly Tyr Glu Val His Val His Lys Lys Asn
```

```
            20                  25                  30

Gly Thr Tyr Gln Val Glu Val Arg
        35                  40

<210> SEQ ID NO 309
<211> LENGTH: 40
<212> TYPE: PRT
<213> ORGANISM: Artificial Sequence
<220> FEATURE:
<223> OTHER INFORMATION: Synthetic

<400> SEQUENCE: 309

Thr Ala Thr Asn Thr Thr Arg Ser Lys Phe Ala Ala Leu Ile Ala Ala
1               5                   10                  15

Lys Ile Trp Ala Glu Phe Gly Tyr Glu Val His Val His Lys Lys Asn
            20                  25                  30

Gly Thr Tyr Gln Val Glu Val Arg
        35                  40

<210> SEQ ID NO 310
<211> LENGTH: 40
<212> TYPE: PRT
<213> ORGANISM: Artificial Sequence
<220> FEATURE:
<223> OTHER INFORMATION: Synthetic

<400> SEQUENCE: 310

Thr Pro Gln Thr Thr Ala Tyr Ser Pro Phe Ala Ala Glu Ile Ala Ala
1               5                   10                  15

Lys Ile Leu Arg Asp Phe Asn Ile Pro Tyr Asp Val Gln Thr His Gly
            20                  25                  30

Asp Lys Val Thr Val Thr Ala His
        35                  40

<210> SEQ ID NO 311
<211> LENGTH: 40
<212> TYPE: PRT
<213> ORGANISM: Artificial Sequence
<220> FEATURE:
<223> OTHER INFORMATION: Synthetic

<400> SEQUENCE: 311

Thr Pro Gln Thr Thr Ala Tyr Ser Pro Phe Ala Ala Trp Ile Ala Ala
1               5                   10                  15

Lys Ile Leu Glu Glu Phe Asn Ile Pro Tyr Asp Val Gln Thr His Gly
            20                  25                  30

Asp Lys Val Thr Val Thr Ala His
        35                  40

<210> SEQ ID NO 312
<211> LENGTH: 40
<212> TYPE: PRT
<213> ORGANISM: Artificial Sequence
<220> FEATURE:
<223> OTHER INFORMATION: Synthetic

<400> SEQUENCE: 312

Thr Gln Thr Cys Glu Ala Arg Met Pro Phe Ala Ala Glu Ile Ala Ala
1               5                   10                  15

Arg Ile Ala Ala Glu Phe Asn Trp Pro Val Lys Leu His His His Gly
            20                  25                  30

Asp Thr Ile Thr Val Gln Val Asn
```

```
              35                  40

<210> SEQ ID NO 313
<211> LENGTH: 40
<212> TYPE: PRT
<213> ORGANISM: Artificial Sequence
<220> FEATURE:
<223> OTHER INFORMATION: Synthetic

<400> SEQUENCE: 313

Lys Tyr Thr Ser Thr Ala Ser Asp Ser Phe Ala Ala Lys Ile Ala Ala
1               5                   10                  15

Leu Ile Leu Lys Glu Phe Asn Ile Pro Phe Glu Val Gln Thr His Asn
            20                  25                  30

Gly Thr Tyr Lys Val Thr Ser Lys
        35                  40

<210> SEQ ID NO 314
<211> LENGTH: 40
<212> TYPE: PRT
<213> ORGANISM: Artificial Sequence
<220> FEATURE:
<223> OTHER INFORMATION: Synthetic

<400> SEQUENCE: 314

Thr Ile Lys Ser Thr Ala Arg Ser Pro Phe Ala Ala Ala Ile Ala Ala
1               5                   10                  15

Lys Ile Ala Ala Glu Phe Gly Tyr Thr Val Lys Leu Ser Gln Lys Asn
            20                  25                  30

Gly Lys Trp His Leu His Val Asn
        35                  40

<210> SEQ ID NO 315
<211> LENGTH: 40
<212> TYPE: PRT
<213> ORGANISM: Artificial Sequence
<220> FEATURE:
<223> OTHER INFORMATION: Synthetic

<400> SEQUENCE: 315

Thr Asp Thr Ser His Ala Lys Ser Lys Phe Ala Ala Glu Ile Ala Ala
1               5                   10                  15

Arg Ile Leu Ala Glu Phe Gly Ile Pro Ala Lys Val Ser Lys Leu Asn
            20                  25                  30

Gly Thr Trp Val Val His Glu Asn
        35                  40

<210> SEQ ID NO 316
<211> LENGTH: 40
<212> TYPE: PRT
<213> ORGANISM: Artificial Sequence
<220> FEATURE:
<223> OTHER INFORMATION: Synthetic

<400> SEQUENCE: 316

Thr Lys Thr Ile Thr Ala Arg Ser Glu Phe Ala Ala Arg Ile Ala Ala
1               5                   10                  15

Glu Ile Leu Arg Gln Phe Gly Ile Asp Val Gln Ile Thr Thr Lys Asn
            20                  25                  30

Gly Lys Tyr Gln Leu Gln Asn Lys
        35                  40
```

```
<210> SEQ ID NO 317
<211> LENGTH: 40
<212> TYPE: PRT
<213> ORGANISM: Artificial Sequence
<220> FEATURE:
<223> OTHER INFORMATION: Synthetic

<400> SEQUENCE: 317

Ser Tyr Phe Ser Thr Ala Asn Ser Pro Phe Ala Ala Gln Ile Ala Ala
1               5                   10                  15

Glu Ile Leu Ala Ser Phe Asn Ile Pro Val Thr Leu Arg Thr Leu Asn
            20                  25                  30

Gly Lys Val Gln Val Glu Arg His
        35                  40

<210> SEQ ID NO 318
<211> LENGTH: 40
<212> TYPE: PRT
<213> ORGANISM: Artificial Sequence
<220> FEATURE:
<223> OTHER INFORMATION: Synthetic

<400> SEQUENCE: 318

Thr Ala Glu Val Asn Ala Arg Ser Pro Phe Ala Ala Lys Ile Ala Ala
1               5                   10                  15

Leu Ile Trp Lys Glu Phe Gly Tyr Glu Val Glu Val His Lys Lys Asn
            20                  25                  30

Gly Lys Phe Thr Leu His Ser Gln
        35                  40

<210> SEQ ID NO 319
<211> LENGTH: 40
<212> TYPE: PRT
<213> ORGANISM: Artificial Sequence
<220> FEATURE:
<223> OTHER INFORMATION: Synthetic

<400> SEQUENCE: 319

Gln Thr Thr Ser Thr Ser Asn Met Pro Phe Ala Ala Glu Ile Ala Ala
1               5                   10                  15

Arg Ile Ala Trp Glu Phe Asn Ile Pro Val Glu Phe Thr Gln His Gly
            20                  25                  30

Thr Lys Val Lys Leu Thr Val Lys
        35                  40

<210> SEQ ID NO 320
<211> LENGTH: 40
<212> TYPE: PRT
<213> ORGANISM: Artificial Sequence
<220> FEATURE:
<223> OTHER INFORMATION: Synthetic

<400> SEQUENCE: 320

Lys Thr Thr Tyr His Met Pro Ser Lys Phe Ala Ala Arg Ile Ala Ala
1               5                   10                  15

Glu Ile Leu Arg Glu Phe Gly Ile Pro Val Thr Val Thr Lys Ala Gly
            20                  25                  30

Asp Thr Tyr Val Leu Gln Glu Lys
        35                  40

<210> SEQ ID NO 321
<211> LENGTH: 40
<212> TYPE: PRT
```

```
<213> ORGANISM: Artificial Sequence
<220> FEATURE:
<223> OTHER INFORMATION: Synthetic

<400> SEQUENCE: 321

Thr Arg Thr Leu Tyr Ala Ser Ser Asp Phe Ala Ala Lys Ile Ala Ala
1               5                   10                  15

Lys Ile Ala Ala Ser Phe Asn Trp Asp Val Thr Val Ser Gln Ile Asn
            20                  25                  30

Gly Thr Trp Val Val Thr Val His
        35                  40

<210> SEQ ID NO 322
<211> LENGTH: 40
<212> TYPE: PRT
<213> ORGANISM: Artificial Sequence
<220> FEATURE:
<223> OTHER INFORMATION: Synthetic

<400> SEQUENCE: 322

Thr Tyr Thr Ala Glu Ala Ser Ala Lys Phe Ala Ala Arg Ile Ala Ala
1               5                   10                  15

Glu Ile Phe Arg Glu Phe Gly Tyr Glu Val His Ile Thr Gln Lys Asn
            20                  25                  30

Gly Lys Trp Gln Val Thr Val Lys
        35                  40

<210> SEQ ID NO 323
<211> LENGTH: 40
<212> TYPE: PRT
<213> ORGANISM: Artificial Sequence
<220> FEATURE:
<223> OTHER INFORMATION: Synthetic

<400> SEQUENCE: 323

Thr Tyr Thr Ile Val Val Asn Ser Pro Phe Ala Ala Trp Ile Ala Ala
1               5                   10                  15

Glu Ile Ala Arg Glu Phe Asn Trp Glu Val Gln Val Glu Asp His Gly
            20                  25                  30

Asn Thr Phe Lys Leu Lys Val Asn
        35                  40

<210> SEQ ID NO 324
<211> LENGTH: 40
<212> TYPE: PRT
<213> ORGANISM: Artificial Sequence
<220> FEATURE:
<223> OTHER INFORMATION: Synthetic

<400> SEQUENCE: 324

Thr Ser Thr Ser Gln Val Arg Met Pro Phe Ala Ala Trp Ile Ala Ala
1               5                   10                  15

Glu Ile Met Lys Glu Phe Gly Tyr Asp Val Gln Val Glu Gln His Gly
            20                  25                  30

Asp Thr Leu Lys Ile Thr Ser Lys
        35                  40

<210> SEQ ID NO 325
<211> LENGTH: 40
<212> TYPE: PRT
<213> ORGANISM: Artificial Sequence
<220> FEATURE:
<223> OTHER INFORMATION: Synthetic
```

-continued

<400> SEQUENCE: 325

Thr Ser Thr Ser Gln Val Arg Met Pro Phe Ala Ala Trp Ile Ala Ala
1               5                   10                  15

Lys Ile Met Ala Asp Phe Gly Tyr Asp Val Gln Val Glu Gln His Gly
            20                  25                  30

Asp Thr Leu Lys Ile Thr Ser Lys
        35                  40

<210> SEQ ID NO 326
<211> LENGTH: 40
<212> TYPE: PRT
<213> ORGANISM: Artificial Sequence
<220> FEATURE:
<223> OTHER INFORMATION: Synthetic

<400> SEQUENCE: 326

Thr Tyr Thr Ile Thr Ser His Ser Ser Phe Ala Ala Glu Ile Ala Ala
1               5                   10                  15

Arg Ile Leu Lys Glu Phe Asn Ile Pro Phe Glu Leu His Lys Lys Asn
            20                  25                  30

Gly Thr Val Gln Val Gln Asn Glu
        35                  40

<210> SEQ ID NO 327
<211> LENGTH: 40
<212> TYPE: PRT
<213> ORGANISM: Artificial Sequence
<220> FEATURE:
<223> OTHER INFORMATION: Synthetic

<400> SEQUENCE: 327

Thr Tyr Thr Ile Thr Ser His Ser Ser Phe Ala Ala Ala Ile Ala Ala
1               5                   10                  15

Lys Ile Leu Lys Glu Phe Asn Ile Pro Phe Glu Leu His Lys Lys Asn
            20                  25                  30

Gly Thr Val Gln Val Gln Asn Glu
        35                  40

<210> SEQ ID NO 328
<211> LENGTH: 40
<212> TYPE: PRT
<213> ORGANISM: Artificial Sequence
<220> FEATURE:
<223> OTHER INFORMATION: Synthetic

<400> SEQUENCE: 328

Thr Phe Thr Ser Gln Ala Arg Ser Asp Phe Ala Ala Gln Ile Ala Ala
1               5                   10                  15

Asp Ile Leu Ala Glu Phe Gly Ile Lys Phe Lys Leu Thr Gln Asn Gly
            20                  25                  30

Asp Thr Tyr Lys Val Thr Ser His
        35                  40

<210> SEQ ID NO 329
<211> LENGTH: 40
<212> TYPE: PRT
<213> ORGANISM: Artificial Sequence
<220> FEATURE:
<223> OTHER INFORMATION: Synthetic

<400> SEQUENCE: 329

-continued

```
Thr Phe Thr Met Gln Ala Arg Ser Thr Phe Ala Ala Ile Ala Ala
1               5                   10                  15

Glu Ile Leu Arg Glu Phe Gly Ile Lys Phe Lys Leu Thr Gln Asn Gly
            20                  25                  30

Asp Thr Tyr Lys Val Thr Ser His
        35                  40

<210> SEQ ID NO 330
<211> LENGTH: 40
<212> TYPE: PRT
<213> ORGANISM: Artificial Sequence
<220> FEATURE:
<223> OTHER INFORMATION: Synthetic

<400> SEQUENCE: 330

Thr Thr Phe Arg Lys Ala Pro Ser Leu Phe Ala Ala Leu Ile Ala Ala
1               5                   10                  15

Gln Ile Leu Ala Glu Phe Asn Val Glu Val His Ile Thr Gln Arg Asn
            20                  25                  30

Gly Thr Tyr Leu Val Glu Lys Arg
        35                  40

<210> SEQ ID NO 331
<211> LENGTH: 40
<212> TYPE: PRT
<213> ORGANISM: Artificial Sequence
<220> FEATURE:
<223> OTHER INFORMATION: Synthetic

<400> SEQUENCE: 331

Thr Asp Gln Ser Val Cys His Ser Glu Phe Ala Ala Arg Ile Ala Ala
1               5                   10                  15

Lys Ile Ala Lys Glu Phe Asn Leu Glu Val His Ile Thr Gln Lys Asn
            20                  25                  30

Gly Thr Trp Lys Ile Thr Val Lys
        35                  40

<210> SEQ ID NO 332
<211> LENGTH: 40
<212> TYPE: PRT
<213> ORGANISM: Artificial Sequence
<220> FEATURE:
<223> OTHER INFORMATION: Synthetic

<400> SEQUENCE: 332

Thr Tyr Thr Ser Val Ala Thr Ser Glu Phe Ala Ala Arg Ile Ala Ala
1               5                   10                  15

Glu Ile Ala Arg Glu Phe Gly Tyr Glu Val His Val Thr Lys Lys Asn
            20                  25                  30

Gly Gln Phe Gln Val Thr Val Lys
        35                  40

<210> SEQ ID NO 333
<211> LENGTH: 40
<212> TYPE: PRT
<213> ORGANISM: Artificial Sequence
<220> FEATURE:
<223> OTHER INFORMATION: Synthetic

<400> SEQUENCE: 333

Thr Gln Gln Ser His Ala Ala Asp Ser Phe Ala Ala Glu Ile Ala Ala
1               5                   10                  15
```

Arg Ile Asn Lys Glu Phe Gly Tyr Glu Val His Val Thr Gln Val Asn
            20                  25                  30

Gly Thr Phe Thr Val Lys Thr Lys
        35                  40

<210> SEQ ID NO 334
<211> LENGTH: 40
<212> TYPE: PRT
<213> ORGANISM: Artificial Sequence
<220> FEATURE:
<223> OTHER INFORMATION: Synthetic

<400> SEQUENCE: 334

Thr Ala Val Val Gln Ala Lys Ser Pro Phe Ala Ala Ile Ala Val
1               5                   10                  15

Glu Ile Ala Arg Gln Phe Asn Leu Pro Val Thr Val Glu Lys His Gly
            20                  25                  30

Lys Thr Leu Lys Val Thr Ile His
        35                  40

<210> SEQ ID NO 335
<211> LENGTH: 40
<212> TYPE: PRT
<213> ORGANISM: Artificial Sequence
<220> FEATURE:
<223> OTHER INFORMATION: Synthetic

<400> SEQUENCE: 335

Thr Leu Glu Ser Thr Ala Ala Ser Pro Phe Ala Ala Ala Ile Ala Ala
1               5                   10                  15

Glu Ile Trp Lys Glu Phe Gly Tyr Lys Val Thr Thr His Lys Lys Gly
            20                  25                  30

Asp Thr Leu Thr Val Lys Ile Glu
        35                  40

<210> SEQ ID NO 336
<211> LENGTH: 40
<212> TYPE: PRT
<213> ORGANISM: Artificial Sequence
<220> FEATURE:
<223> OTHER INFORMATION: Synthetic

<400> SEQUENCE: 336

Thr Phe Thr Ile His Ala Pro Ser Lys Phe Ala Ala Lys Ile Ala Ala
1               5                   10                  15

Asp Ile Leu Lys Glu Phe Asn Ile Pro Val Thr Val Thr Lys Lys Asn
            20                  25                  30

Gly Thr Trp Glu Val Lys Cys Lys
        35                  40

<210> SEQ ID NO 337
<211> LENGTH: 40
<212> TYPE: PRT
<213> ORGANISM: Artificial Sequence
<220> FEATURE:
<223> OTHER INFORMATION: Synthetic

<400> SEQUENCE: 337

Lys Ile Glu Leu Thr Ala Tyr Ser Pro Phe Ala Ala Trp Ile Ala Ala
1               5                   10                  15

Glu Ile Leu Lys Glu Phe Asn Tyr Asp Val Gln Val His Thr Asp Gly
            20                  25                  30

Asp Thr Ile Thr Val Lys Val Lys
            35                  40

<210> SEQ ID NO 338
<211> LENGTH: 40
<212> TYPE: PRT
<213> ORGANISM: Artificial Sequence
<220> FEATURE:
<223> OTHER INFORMATION: Synthetic

<400> SEQUENCE: 338

Thr Tyr Thr Ser His Thr Asn Ser Pro Phe Ala Ala Ala Ile Leu Ala
1               5                   10                  15

Glu Ile Leu Arg Gln Phe Asn Ile Pro Val Gln Val His Gln Lys Asn
            20                  25                  30

Gly Glu Val Thr Val Thr Glu His
            35                  40

<210> SEQ ID NO 339
<211> LENGTH: 40
<212> TYPE: PRT
<213> ORGANISM: Artificial Sequence
<220> FEATURE:
<223> OTHER INFORMATION: Synthetic

<400> SEQUENCE: 339

Thr Glu His Ser Glu Val Arg Ser Lys Phe Ala Ala Ile Ala Ala
1               5                   10                  15

Glu Ile Ala Arg Ser Phe Asn Trp Glu Val His Leu Thr Lys Thr Asn
            20                  25                  30

Gly Tyr Trp Glu Val Arg Val Lys
            35                  40

<210> SEQ ID NO 340
<211> LENGTH: 40
<212> TYPE: PRT
<213> ORGANISM: Artificial Sequence
<220> FEATURE:
<223> OTHER INFORMATION: Synthetic

<400> SEQUENCE: 340

Thr Tyr Thr Val Val Ala Asn Ser Pro Phe Ala Ala Glu Ile Val Lys
1               5                   10                  15

Arg Ile Leu Ala Glu Phe Asn Ile Pro Val Thr Val Gln Lys His Gly
            20                  25                  30

Gly Thr Tyr His Ile Thr Ser His
            35                  40

<210> SEQ ID NO 341
<211> LENGTH: 40
<212> TYPE: PRT
<213> ORGANISM: Artificial Sequence
<220> FEATURE:
<223> OTHER INFORMATION: Synthetic

<400> SEQUENCE: 341

Thr Tyr Thr Val Val Ala Gln Ser Pro Phe Ala Ala Gln Ile Val Lys
1               5                   10                  15

Asp Ile Leu Ala Glu Phe Asn Ile Pro Val Thr Val Gln Lys His Gly
            20                  25                  30

Gly Thr Tyr His Ile Thr Ser His
            35                  40

```
<210> SEQ ID NO 342
<211> LENGTH: 40
<212> TYPE: PRT
<213> ORGANISM: Artificial Sequence
<220> FEATURE:
<223> OTHER INFORMATION: Synthetic

<400> SEQUENCE: 342

Thr Tyr Thr Val Val Ala Asn Ser Pro Phe Ala Ala Ala Ile Val Ala
1               5                   10                  15

Lys Ile Leu Trp Glu Phe Asn Ile Pro Val Thr Val Gln Lys His Gly
            20                  25                  30

Gly Thr Tyr His Ile Thr Ser His
        35                  40

<210> SEQ ID NO 343
<211> LENGTH: 40
<212> TYPE: PRT
<213> ORGANISM: Artificial Sequence
<220> FEATURE:
<223> OTHER INFORMATION: Synthetic

<400> SEQUENCE: 343

Thr Tyr Thr Ser Thr Thr Ala Ala Lys Phe Ala Ala Gln Ile Ala Ala
1               5                   10                  15

Asp Ile Ala Ala Glu Phe Gly Ile Pro Val Thr Leu Thr Lys Lys Asn
            20                  25                  30

Gly Lys Trp Gln Val His Glu Asn
        35                  40

<210> SEQ ID NO 344
<211> LENGTH: 40
<212> TYPE: PRT
<213> ORGANISM: Artificial Sequence
<220> FEATURE:
<223> OTHER INFORMATION: Synthetic

<400> SEQUENCE: 344

Thr Thr Thr Val Thr Thr Thr Ser Pro Phe Ser Cys Lys Met Arg Ala
1               5                   10                  15

Met Trp Ala Glu Ala Phe Gly Arg Thr Phe Glu Val Arg Thr Glu Gly
            20                  25                  30

Thr Thr Cys Glu Val Arg Phe His
        35                  40

<210> SEQ ID NO 345
<211> LENGTH: 42
<212> TYPE: PRT
<213> ORGANISM: Artificial Sequence
<220> FEATURE:
<223> OTHER INFORMATION: Synthetic

<400> SEQUENCE: 345

Thr Cys Gln Glu Ile Gln Pro Thr Ser Phe Asp Asp Cys Met Lys Leu
1               5                   10                  15

Leu Trp Lys Ala Val Phe Thr Gly Thr Cys Arg Val Glu Leu Arg Pro
            20                  25                  30

Gly Gly Asn Cys Arg Val Arg Cys Cys Gly
        35                  40

<210> SEQ ID NO 346
<211> LENGTH: 37
```

```
<212> TYPE: PRT
<213> ORGANISM: Artificial Sequence
<220> FEATURE:
<223> OTHER INFORMATION: Synthetic

<400> SEQUENCE: 346

Glu Asp Tyr Lys Ala Glu Asn Asp Phe Asp Lys Cys Met Lys Leu Met
1               5                   10                  15

Trp Ile Ala Ala Phe Lys Gly Cys Lys Ile Ile Phe Asn Gly Thr Arg
            20                  25                  30

Cys Arg Val Ile Cys
        35

<210> SEQ ID NO 347
<211> LENGTH: 40
<212> TYPE: PRT
<213> ORGANISM: Artificial Sequence
<220> FEATURE:
<223> OTHER INFORMATION: Synthetic

<400> SEQUENCE: 347

Thr Phe Arg Ser Val Ala Thr Ser Glu Phe Ala Ala Glu Ile Ala Lys
1               5                   10                  15

Arg Ile Leu Ala Glu Phe Gly Tyr Thr Val His Ile Gln Arg His Gly
            20                  25                  30

Thr Thr Ile Thr Val Glu Ser Arg
        35                  40

<210> SEQ ID NO 348
<211> LENGTH: 40
<212> TYPE: PRT
<213> ORGANISM: Artificial Sequence
<220> FEATURE:
<223> OTHER INFORMATION: Synthetic

<400> SEQUENCE: 348

Thr Tyr Thr Val Glu Ser Ala Thr Arg Phe Ala Ala Glu Ile Ala Arg
1               5                   10                  15

Glu Ile Ala Arg Glu Phe Gly Tyr Asp Ala Gln Ile Arg Glu Glu Asn
            20                  25                  30

Gly Thr Phe Lys Leu His Val Gly
        35                  40

<210> SEQ ID NO 349
<211> LENGTH: 40
<212> TYPE: PRT
<213> ORGANISM: Artificial Sequence
<220> FEATURE:
<223> OTHER INFORMATION: Synthetic

<400> SEQUENCE: 349

Thr Ala Tyr Ile Glu Ala Pro Ser Lys Phe Ala Ala Asp Ile Ala Ala
1               5                   10                  15

Gln Ile Leu Ala Glu Phe Gly Met Thr Val Thr Val Thr Asp Asp Asn
            20                  25                  30

Gly Lys Phe Lys Val Thr Val Gly
        35                  40

<210> SEQ ID NO 350
<211> LENGTH: 40
<212> TYPE: PRT
<213> ORGANISM: Artificial Sequence
<220> FEATURE:
```

<223> OTHER INFORMATION: Synthetic

<400> SEQUENCE: 350

Thr Met Thr Ser Ile Thr Thr Ser Pro Phe Ala Ala Glu Ile Ala Ala
1               5                   10                  15

Arg Ile Trp Ala Glu Phe Gly Tyr Thr Val Arg Ile Glu Thr Arg Gly
            20                  25                  30

Lys Thr Val His Val Thr Val Asp
        35                  40

<210> SEQ ID NO 351
<211> LENGTH: 40
<212> TYPE: PRT
<213> ORGANISM: Artificial Sequence
<220> FEATURE:
<223> OTHER INFORMATION: Synthetic

<400> SEQUENCE: 351

Thr Ser Arg Val Arg Ala Thr Ser Lys Phe Ala Ala Leu Ile Ala Ala
1               5                   10                  15

Glu Ile Ala Arg Glu Phe Gly Tyr Thr Val Asp Val Gln Glu Val Asn
            20                  25                  30

Gly Gln Trp Glu Val Thr Phe Asp
        35                  40

<210> SEQ ID NO 352
<211> LENGTH: 40
<212> TYPE: PRT
<213> ORGANISM: Artificial Sequence
<220> FEATURE:
<223> OTHER INFORMATION: Synthetic

<400> SEQUENCE: 352

Thr Ser Gly Val Arg Ala Thr Ser Lys Phe Ala Ala Leu Ile Ala Ala
1               5                   10                  15

Glu Ile Ala Arg Glu Phe Gly Tyr Thr Val Asp Val Gln Glu Lys Asn
            20                  25                  30

Gly Glu Trp Arg Val Val Phe Asp
        35                  40

<210> SEQ ID NO 353
<211> LENGTH: 40
<212> TYPE: PRT
<213> ORGANISM: Artificial Sequence
<220> FEATURE:
<223> OTHER INFORMATION: Synthetic

<400> SEQUENCE: 353

Thr Phe Thr Ser Lys Ala Ser Asp Arg Phe Ala Ala Asp Ile Ala Ala
1               5                   10                  15

Glu Ile Met Lys Glu Phe Gly Tyr Asp Val Arg Val Thr Lys Val Gly
            20                  25                  30

Thr Thr Trp Lys Val Glu Ser Glu
        35                  40

<210> SEQ ID NO 354
<211> LENGTH: 40
<212> TYPE: PRT
<213> ORGANISM: Artificial Sequence
<220> FEATURE:
<223> OTHER INFORMATION: Synthetic

<400> SEQUENCE: 354

```
Thr Tyr Glu Phe Glu Ala Arg Ser Pro Phe Ala Ala Ala Ile Ala Arg
1               5                   10                  15

Asp Ile Leu Leu Glu Phe Gly Gln Thr Val Thr Val Glu Arg Asn
                20                  25                  30

Gly Arg Phe Arg Val Arg Ala Asp
        35                  40
```

<210> SEQ ID NO 355
<211> LENGTH: 40
<212> TYPE: PRT
<213> ORGANISM: Artificial Sequence
<220> FEATURE:
<223> OTHER INFORMATION: Synthetic

<400> SEQUENCE: 355

```
Thr Met Thr Ser Val Ala Tyr Ser Asp Phe Ala Ala Glu Ile Ala Ala
1               5                   10                  15

Gln Ile Ala Arg Glu Phe Gly Tyr Thr Val Arg Lys Glu Lys Arg Asn
                20                  25                  30

Gly Thr Ile Thr Leu Glu Val His
        35                  40
```

<210> SEQ ID NO 356
<211> LENGTH: 40
<212> TYPE: PRT
<213> ORGANISM: Artificial Sequence
<220> FEATURE:
<223> OTHER INFORMATION: Synthetic

<400> SEQUENCE: 356

```
Thr Tyr Thr Ser Glu Val Trp Thr Pro Phe Ala Ala Ala Ile Ala Tyr
1               5                   10                  15

Glu Ile Ala Arg Gln Phe Gly Ile Pro Val Glu Ser Asn Thr His Gly
                20                  25                  30

Pro Glu Phe Arg Phe Asn Met Lys
        35                  40
```

<210> SEQ ID NO 357
<211> LENGTH: 40
<212> TYPE: PRT
<213> ORGANISM: Artificial Sequence
<220> FEATURE:
<223> OTHER INFORMATION: Synthetic

<400> SEQUENCE: 357

```
Thr Ile Glu Ser Thr Thr Arg Ser Glu Phe Ala Ala Ala Ile Ala Cys
1               5                   10                  15

Glu Ile Ala Arg Gln Phe Gly Trp Thr Val Thr Cys Glu Lys Arg Gly
                20                  25                  30

Thr Thr Leu Thr Val Arg Thr Thr
        35                  40
```

<210> SEQ ID NO 358
<211> LENGTH: 40
<212> TYPE: PRT
<213> ORGANISM: Artificial Sequence
<220> FEATURE:
<223> OTHER INFORMATION: Synthetic

<400> SEQUENCE: 358

```
Thr Leu His Ile Thr Ser Tyr Ser Pro Phe Ala Ala Ala Ile Ala Cys
1               5                   10                  15
```

Glu Ile Ala Arg Glu Phe Gly Tyr Thr Val Glu Cys Arg Lys Asp Gly
            20                  25                  30

Thr Arg Leu Glu Val His Ser Lys
        35                  40

<210> SEQ ID NO 359
<211> LENGTH: 40
<212> TYPE: PRT
<213> ORGANISM: Artificial Sequence
<220> FEATURE:
<223> OTHER INFORMATION: Synthetic

<400> SEQUENCE: 359

Thr Ala Thr Ser Thr Ala Asn Asp Ser Phe Ala Cys Lys Ile Ala Lys
1               5                   10                  15

Lys Ile Ile Leu Glu Phe Asn Leu Thr Val Glu Val Thr Lys Ser Asn
            20                  25                  30

Gly Tyr Cys Glu Val Arg Cys Lys
        35                  40

<210> SEQ ID NO 360
<211> LENGTH: 43
<212> TYPE: PRT
<213> ORGANISM: Artificial Sequence
<220> FEATURE:
<223> OTHER INFORMATION: Synthetic

<400> SEQUENCE: 360

Ser Phe Ala Cys Lys Ile Ala Ala Glu Ile Leu Arg Gln Phe Gly Lys
1               5                   10                  15

Ser Glu Glu Glu Ile Lys Arg Ala Leu Lys Lys Ala Gly Cys Ser Pro
            20                  25                  30

Asp Glu Ala Glu Glu Ala Ile Arg Ala Leu Arg
        35                  40

<210> SEQ ID NO 361
<211> LENGTH: 41
<212> TYPE: PRT
<213> ORGANISM: Artificial Sequence
<220> FEATURE:
<223> OTHER INFORMATION: Synthetic

<400> SEQUENCE: 361

Cys Pro Tyr Cys Glu Glu Ala Lys Glu Ala Ala Lys Glu Gly Asn Phe
1               5                   10                  15

Ala Arg Ile Ile Ala Ala Ala Ile Arg Ala Glu Phe Ala Gly Asp Gln
            20                  25                  30

Glu Cys Ala Lys Cys Ala Lys Lys Val
        35                  40

<210> SEQ ID NO 362
<211> LENGTH: 37
<212> TYPE: PRT
<213> ORGANISM: Artificial Sequence
<220> FEATURE:
<223> OTHER INFORMATION: Synthetic

<400> SEQUENCE: 362

Thr Cys Glu Glu Ile Arg Gly Asn Phe Ala Glu Cys Ile Arg Ala Glu
1               5                   10                  15

Ile Glu Ala Arg Phe Gln Gly Cys Glu Phe Glu Lys His Gly Asp Gln
            20                  25                  30

-continued

Cys Arg Arg Cys Cys
        35

<210> SEQ ID NO 363
<211> LENGTH: 37
<212> TYPE: PRT
<213> ORGANISM: Artificial Sequence
<220> FEATURE:
<223> OTHER INFORMATION: Synthetic

<400> SEQUENCE: 363

Glu Cys Arg Arg Trp Thr Asp Asn Phe Ala Lys Cys Ile Ala Ala Lys
1               5                   10                  15

Ile Leu Ala Glu Phe Gln Gly Cys Glu Phe Arg Glu Asp Gly His Arg
            20                  25                  30

Cys Glu Leu Cys Cys
        35

<210> SEQ ID NO 364
<211> LENGTH: 37
<212> TYPE: PRT
<213> ORGANISM: Artificial Sequence
<220> FEATURE:
<223> OTHER INFORMATION: Synthetic

<400> SEQUENCE: 364

Thr Thr Thr Cys Val Arg Asn Asn Phe Ala Glu Ala Ile Arg Leu Lys
1               5                   10                  15

Ile Glu Cys Glu Phe Lys Gly Leu Glu Ile Arg Glu Glu Asn Gly Glu
            20                  25                  30

Val Cys Cys His Gly
        35

<210> SEQ ID NO 365
<211> LENGTH: 39
<212> TYPE: PRT
<213> ORGANISM: Artificial Sequence
<220> FEATURE:
<223> OTHER INFORMATION: Synthetic

<400> SEQUENCE: 365

Thr Phe Cys Val Asp Cys Asn Ser Pro Phe Ala Cys Gln Ile Ala Lys
1               5                   10                  15

Asp Ile Ala Asp Glu Phe Asn Pro Thr Gly Arg Cys Thr Val Thr Asn
            20                  25                  30

Gly Arg Val Cys Cys Gln Phe
        35

<210> SEQ ID NO 366
<211> LENGTH: 44
<212> TYPE: PRT
<213> ORGANISM: Artificial Sequence
<220> FEATURE:
<223> OTHER INFORMATION: Synthetic

<400> SEQUENCE: 366

Thr Glu Asp Cys Glu Arg Glu Cys Arg Lys Met Ser Lys Thr Met Ser
1               5                   10                  15

Phe Ala Asp Glu Ile Ala Cys Gln Ile Met Val Glu Phe Trp Gly Ser
            20                  25                  30

Ser Gln Cys Glu Lys Met Lys Arg Asp Leu Lys Arg
        35                  40

<210> SEQ ID NO 367
<211> LENGTH: 37
<212> TYPE: PRT
<213> ORGANISM: Artificial Sequence
<220> FEATURE:
<223> OTHER INFORMATION: Synthetic

<400> SEQUENCE: 367

Thr Cys Lys Arg Trp Glu Asp Arg Phe Ala Asp Cys Ile Ala Ala Glu
1               5                   10                  15

Ile Leu Ala Glu Phe Trp Gly Cys Gly Tyr Arg Arg His Gly Trp Thr
            20                  25                  30

Cys Glu Leu Cys Cys
        35

<210> SEQ ID NO 368
<211> LENGTH: 38
<212> TYPE: PRT
<213> ORGANISM: Artificial Sequence
<220> FEATURE:
<223> OTHER INFORMATION: Synthetic

<400> SEQUENCE: 368

Cys Thr Thr Ile Glu Ala Thr Ser Phe Ala Glu Cys Ile Ala Leu Glu
1               5                   10                  15

Ile Leu Ala Glu Phe Asn Asn Cys Glu Val Arg Lys His Gly Asp Arg
            20                  25                  30

Cys Glu Val Thr Cys Cys
        35

<210> SEQ ID NO 369
<211> LENGTH: 38
<212> TYPE: PRT
<213> ORGANISM: Artificial Sequence
<220> FEATURE:
<223> OTHER INFORMATION: Synthetic

<400> SEQUENCE: 369

Cys Thr Cys Gly Ala Thr Thr Phe Ala Glu Leu Ile Ala Cys Lys Ile
1               5                   10                  15

Met Leu Asp Phe Gly Trp Cys Val Glu Thr Gln Asp Gly Thr Gln Lys
            20                  25                  30

Ile Lys Val Cys Cys Gly
        35

<210> SEQ ID NO 370
<211> LENGTH: 37
<212> TYPE: PRT
<213> ORGANISM: Artificial Sequence
<220> FEATURE:
<223> OTHER INFORMATION: Synthetic

<400> SEQUENCE: 370

Thr Cys Lys Arg Trp Glu Asn Arg Phe Ala Asp Cys Ile Ala Ala Glu
1               5                   10                  15

Ile Glu Ala Glu Phe Lys Gly Cys Glu Tyr Arg Arg His Gly Tyr Thr
            20                  25                  30

Cys Glu Leu Cys Cys
        35

<210> SEQ ID NO 371

<211> LENGTH: 37
<212> TYPE: PRT
<213> ORGANISM: Artificial Sequence
<220> FEATURE:
<223> OTHER INFORMATION: Synthetic

<400> SEQUENCE: 371

Pro Ser Ser Val Ala Gln Ala Gly Thr Phe Ala Cys Gln Ile Ala Cys
1               5                   10                  15

Lys Ile Ala Ala Glu Phe Gly Cys Thr Cys Thr Thr Asp Gly Asp Thr
            20                  25                  30

Cys Lys Val Thr Cys
        35

<210> SEQ ID NO 372
<211> LENGTH: 37
<212> TYPE: PRT
<213> ORGANISM: Artificial Sequence
<220> FEATURE:
<223> OTHER INFORMATION: Synthetic

<400> SEQUENCE: 372

Arg Ser Ser Val Ala Gln Ala Gly Gln Phe Ala Cys Glu Val Ala Cys
1               5                   10                  15

Arg Ile Ala Ala Ser Phe Gly Cys Thr Cys Thr Thr Asp Gly Asp Thr
            20                  25                  30

Cys Lys Val Thr Cys
        35

<210> SEQ ID NO 373
<211> LENGTH: 40
<212> TYPE: PRT
<213> ORGANISM: Artificial Sequence
<220> FEATURE:
<223> OTHER INFORMATION: Synthetic

<400> SEQUENCE: 373

Thr Tyr Glu Leu Glu Val Thr Ser Lys Phe Ala Ala Glu Ile Ala Arg
1               5                   10                  15

Gln Ile Leu Glu Glu Phe Gly Ile Thr Ala Thr Val Glu Lys Val Asn
            20                  25                  30

Gly Gln Tyr Arg Ile Lys Tyr Asp
        35                  40

<210> SEQ ID NO 374
<211> LENGTH: 43
<212> TYPE: PRT
<213> ORGANISM: Artificial Sequence
<220> FEATURE:
<223> OTHER INFORMATION: Synthetic

<400> SEQUENCE: 374

Pro Phe Ala Cys Arg Ile Ala Ala Lys Ile Ala Glu Phe Gly Tyr
1               5                   10                  15

Ser Glu Glu Gln Ile Lys Glu Leu Leu Lys Asn Ala Gly Cys Ser Glu
            20                  25                  30

Asp Glu Ala Arg Asp Ala Val Glu Tyr Leu Arg
        35                  40

<210> SEQ ID NO 375
<211> LENGTH: 43
<212> TYPE: PRT
<213> ORGANISM: Artificial Sequence
<220> FEATURE:
<223> OTHER INFORMATION: Synthetic

<400> SEQUENCE: 375

Gly Phe Ala Cys Glu Ile Ala Ala Lys Ile Ala Arg Glu Phe Gly Arg
1               5                   10                  15

Ser Lys Asp Gln Ile Lys Glu Ile Leu Gln Lys Cys Gly Val Ser Glu
            20                  25                  30

Asp Glu Ala Glu Glu Ile Leu Arg Arg Leu Gly
        35                  40

<210> SEQ ID NO 376
<211> LENGTH: 40
<212> TYPE: PRT
<213> ORGANISM: Artificial Sequence
<220> FEATURE:
<223> OTHER INFORMATION: Synthetic

<400> SEQUENCE: 376

Lys Tyr Thr Ser Thr Asn Ser Ser Lys Phe Ala Cys Ala Ile Ala Lys
1               5                   10                  15

Gln Ile Leu Ala Glu Phe Gly Phe Thr Val Thr Cys Thr His Glu Asn
            20                  25                  30

Gly Thr Cys Thr Cys Thr Tyr Gly
        35                  40

<210> SEQ ID NO 377
<211> LENGTH: 40
<212> TYPE: PRT
<213> ORGANISM: Artificial Sequence
<220> FEATURE:
<223> OTHER INFORMATION: Synthetic

<400> SEQUENCE: 377

Thr Tyr Trp Ala Gln Ser Pro Ser Ser Phe Ala Ala Glu Ile Ala Ala
1               5                   10                  15

Gln Ile Cys Arg Glu Phe Arg Gln Thr Val Glu Val Thr Lys Glu Asn
            20                  25                  30

Gly Thr Tyr Lys Val Arg Cys Glu
        35                  40

<210> SEQ ID NO 378
<211> LENGTH: 40
<212> TYPE: PRT
<213> ORGANISM: Artificial Sequence
<220> FEATURE:
<223> OTHER INFORMATION: Synthetic

<400> SEQUENCE: 378

Cys Ile Glu Ile Ser Val Thr Thr Pro Phe Ala Cys Gln Ile Ala Ala
1               5                   10                  15

Glu Ile Trp Arg Ala Phe Gly Tyr Glu Val Lys Ile Asp Asp Asp Asn
            20                  25                  30

Gly Asn Cys Arg Leu His Val Cys
        35                  40

<210> SEQ ID NO 379
<211> LENGTH: 40
<212> TYPE: PRT
<213> ORGANISM: Artificial Sequence
<220> FEATURE:
<223> OTHER INFORMATION: Synthetic

<400> SEQUENCE: 379

Cys Ile Glu Gln Ser Phe Thr Thr Leu Phe Ala Cys Gln Thr Ala Ala
1               5                   10                  15

Glu Ile Trp Arg Ala Phe Gly Tyr Thr Val Lys Ile Met Val Asp Asn
            20                  25                  30

Gly Asn Cys Arg Leu His Val Cys
        35                  40

<210> SEQ ID NO 380
<211> LENGTH: 40
<212> TYPE: PRT
<213> ORGANISM: Artificial Sequence
<220> FEATURE:
<223> OTHER INFORMATION: Synthetic

<400> SEQUENCE: 380

Cys Glu Thr Arg Thr Tyr Thr Ser Phe Ala Ala Ile Arg Ala Arg
1               5                   10                  15

Ile Glu Ala Glu Phe Glu Gly Arg Asp Cys Glu Glu Val Arg Gly
            20                  25                  30

Arg Glu Phe Arg Phe Thr Cys Cys
        35                  40

<210> SEQ ID NO 381
<211> LENGTH: 40
<212> TYPE: PRT
<213> ORGANISM: Artificial Sequence
<220> FEATURE:
<223> OTHER INFORMATION: Synthetic

<400> SEQUENCE: 381

Cys Gln Asp Tyr Thr Phe Thr Asp Pro Phe Ala Cys Gln Ile Ala Ala
1               5                   10                  15

Glu Ile Leu Arg Asp Phe Gly Tyr Asp Cys Thr Val Gln Thr Asn Asn
            20                  25                  30

Gly Glu Cys Arg Val Arg Cys Cys
        35                  40

<210> SEQ ID NO 382
<211> LENGTH: 40
<212> TYPE: PRT
<213> ORGANISM: Artificial Sequence
<220> FEATURE:
<223> OTHER INFORMATION: Synthetic

<400> SEQUENCE: 382

Cys Gln Glu Tyr Arg Phe Thr Asn Pro Phe Ala Cys Gln Ile Ala Leu
1               5                   10                  15

Glu Ile Leu Arg Asp Phe Gly Tyr Ala Cys Thr Val Gln Thr Ile Asn
            20                  25                  30

Gly Glu Cys Arg Val Arg Cys Cys
        35                  40

<210> SEQ ID NO 383
<211> LENGTH: 37
<212> TYPE: PRT
<213> ORGANISM: Artificial Sequence
<220> FEATURE:
<223> OTHER INFORMATION: Synthetic

<400> SEQUENCE: 383

Glu Lys Gln Lys Thr Arg Ser Ser Phe Ala Glu Cys Ile Ala Met Lys

```
1               5                   10                  15
Ile Glu Ala Glu Phe Arg Gly Cys Glu Phe Tyr Gln Asp Gly Glu Trp
                20                  25                  30

Cys Val Ile Val Cys
        35

<210> SEQ ID NO 384
<211> LENGTH: 40
<212> TYPE: PRT
<213> ORGANISM: Artificial Sequence
<220> FEATURE:
<223> OTHER INFORMATION: Synthetic

<400> SEQUENCE: 384

Cys Tyr Glu Phe Gln Ser Lys Ala Lys Phe Ala Cys Lys Ile Ala Glu
1               5                   10                  15

Leu Ile Leu Arg Glu Phe Gly Gln Glu Val Arg Arg Gln Asp Asp Gly
                20                  25                  30

Asn Thr Cys Arg Ile Glu Ser Cys
        35                  40

<210> SEQ ID NO 385
<211> LENGTH: 37
<212> TYPE: PRT
<213> ORGANISM: Artificial Sequence
<220> FEATURE:
<223> OTHER INFORMATION: Synthetic

<400> SEQUENCE: 385

Pro Thr Ser Val Ala Gln Ala Gly Ser Phe Ala Cys Trp Ile Ala Cys
1               5                   10                  15

Glu Ile Ala Arg Glu Phe Gly Cys Thr Cys Thr Thr Asp Gly Asp Thr
                20                  25                  30

Cys Lys Val Thr Cys
        35

<210> SEQ ID NO 386
<211> LENGTH: 40
<212> TYPE: PRT
<213> ORGANISM: Artificial Sequence
<220> FEATURE:
<223> OTHER INFORMATION: Synthetic

<400> SEQUENCE: 386

Cys Thr Glu Gln Tyr His Cys Thr Arg Phe Ala Glu Cys Ile Ala Ile
1               5                   10                  15

Gln Ile Arg Ala Glu Phe Glu Gly Lys Glu Cys Thr Ile Asp Leu Glu
                20                  25                  30

Asn Gln Arg Val Glu Cys His Cys
        35                  40

<210> SEQ ID NO 387
<211> LENGTH: 40
<212> TYPE: PRT
<213> ORGANISM: Artificial Sequence
<220> FEATURE:
<223> OTHER INFORMATION: Synthetic

<400> SEQUENCE: 387

Thr Thr Arg Tyr His Tyr Thr Asn Phe Asp Leu Ala Met Glu Ala Met
1               5                   10                  15

Trp Arg Ala Val Phe Lys Gly Leu Arg Val Thr Leu Lys Gln Glu Asn
```

```
                20                  25                  30

Gly Gln Trp Phe Val Glu Ile Asp
        35                  40

<210> SEQ ID NO 388
<211> LENGTH: 40
<212> TYPE: PRT
<213> ORGANISM: Artificial Sequence
<220> FEATURE:
<223> OTHER INFORMATION: Synthetic

<400> SEQUENCE: 388

Thr Glu Arg Ile Lys Val Asp Ser Phe Asp Ala Ala Met Arg Ala Ala
1               5                   10                  15

Trp Glu Leu Ala Phe Arg Gly Gln Gln Tyr Arg Ile Thr Lys His Asn
            20                  25                  30

Gly Thr Trp Phe Val Glu Arg Gly
        35                  40

<210> SEQ ID NO 389
<211> LENGTH: 40
<212> TYPE: PRT
<213> ORGANISM: Artificial Sequence
<220> FEATURE:
<223> OTHER INFORMATION: Synthetic

<400> SEQUENCE: 389

Thr Thr Lys Ile Arg Val Thr Ser Phe Asp Asn Cys Met Arg Leu Ala
1               5                   10                  15

Trp Lys Ala Thr Phe Lys Gly Leu Thr Val Thr Ile Arg Arg His Gly
            20                  25                  30

Lys Thr Cys Glu Val Glu Ser Arg
        35                  40

<210> SEQ ID NO 390
<211> LENGTH: 37
<212> TYPE: PRT
<213> ORGANISM: Artificial Sequence
<220> FEATURE:
<223> OTHER INFORMATION: Synthetic

<400> SEQUENCE: 390

Thr Cys Lys Cys Leu Glu Asn Pro Thr Phe Asp Leu Lys Met Arg Leu
1               5                   10                  15

Ile Trp Leu Cys Ala Phe Ala Lys Glu Cys Arg Asn His Gly Asn Arg
            20                  25                  30

Val Cys Val Cys Glu
        35

<210> SEQ ID NO 391
<211> LENGTH: 42
<212> TYPE: PRT
<213> ORGANISM: Artificial Sequence
<220> FEATURE:
<223> OTHER INFORMATION: Synthetic

<400> SEQUENCE: 391

Thr Cys Gln Thr Leu Gln Pro Thr Ser Phe Asp Asp Cys Met Lys Ala
1               5                   10                  15

Leu Trp Leu Ala Ala Phe Thr Gly Thr Cys Arg Phe Glu Phe Arg Pro
            20                  25                  30

Gly Gly Lys Cys Arg Val Thr Cys Cys Gly
```

```
                    35                  40

<210> SEQ ID NO 392
<211> LENGTH: 43
<212> TYPE: PRT
<213> ORGANISM: Artificial Sequence
<220> FEATURE:
<223> OTHER INFORMATION: Synthetic

<400> SEQUENCE: 392

Pro Phe Ala Val Arg Ile Ala Ala Gln Ile Ala Asp Phe Gly Tyr
1               5                   10                  15

Ser Glu Glu Gln Ile Lys Glu Leu Leu Lys Asn Ala Gly Ala Ser Glu
            20                  25                  30

Asp Glu Ala Arg Asp Ala Val Glu Tyr Leu Arg
            35                  40

<210> SEQ ID NO 393
<211> LENGTH: 43
<212> TYPE: PRT
<213> ORGANISM: Artificial Sequence
<220> FEATURE:
<223> OTHER INFORMATION: Synthetic

<400> SEQUENCE: 393

Pro Phe Ala Ala Lys Ile Ala Ala Ala Ile Leu Ala Glu Phe Gly Tyr
1               5                   10                  15

Ser Pro Glu Gln Ile Lys Arg Ser Leu Lys Lys Gln Gly Val Ser Glu
            20                  25                  30

Asp Glu Ala Glu Lys Ile Leu Arg Asp Leu Leu
            35                  40

<210> SEQ ID NO 394
<211> LENGTH: 43
<212> TYPE: PRT
<213> ORGANISM: Artificial Sequence
<220> FEATURE:
<223> OTHER INFORMATION: Synthetic

<400> SEQUENCE: 394

Pro Phe Ala Ala Lys Ile Ala Val Lys Ile Leu Ile Glu Phe Gly Val
1               5                   10                  15

Thr Pro Asp Glu Ile Lys Lys Ile Ala Lys Lys Leu Gly Leu Ser Glu
            20                  25                  30

Asp Thr Val Glu Glu Ile Ile Arg Arg Ile Tyr
            35                  40

<210> SEQ ID NO 395
<211> LENGTH: 43
<212> TYPE: PRT
<213> ORGANISM: Artificial Sequence
<220> FEATURE:
<223> OTHER INFORMATION: Synthetic

<400> SEQUENCE: 395

Pro Thr Phe Ala Asn Leu Ile Ala Ala Lys Ile Ala Ala Glu Phe Gly
1               5                   10                  15

Tyr Arg Asp Lys Ala Arg Glu Leu Ala Lys Arg Ala Gly Leu Ser Asp
            20                  25                  30

Asp Gln Ala Asp Gln Phe Val Arg Asp Leu Gly
            35                  40
```

```
<210> SEQ ID NO 396
<211> LENGTH: 43
<212> TYPE: PRT
<213> ORGANISM: Artificial Sequence
<220> FEATURE:
<223> OTHER INFORMATION: Synthetic

<400> SEQUENCE: 396

Ala Pro Phe Ala Leu Lys Ile Ala Ala Lys Ile Leu Ala Glu Phe Gly
1               5                   10                  15

Asn Lys Asp Lys Ala Arg Lys Val Leu Glu Lys Ala Gly Leu Ser Pro
            20                  25                  30

Asp Gln Ala Glu Glu Phe Ile Arg Arg Val Asp
        35                  40

<210> SEQ ID NO 397
<211> LENGTH: 40
<212> TYPE: PRT
<213> ORGANISM: Artificial Sequence
<220> FEATURE:
<223> OTHER INFORMATION: Synthetic

<400> SEQUENCE: 397

Thr Ser Thr Ile Val Cys Tyr Ser Glu Phe Ala Ala Arg Ile Ala Glu
1               5                   10                  15

Lys Ile Leu Arg Glu Phe Gly Tyr Thr Val Thr Val Arg Thr His Gly
            20                  25                  30

Thr Glu Phe Arg Leu Glu Val His
        35                  40

<210> SEQ ID NO 398
<211> LENGTH: 40
<212> TYPE: PRT
<213> ORGANISM: Artificial Sequence
<220> FEATURE:
<223> OTHER INFORMATION: Synthetic

<400> SEQUENCE: 398

Thr Tyr Glu Ser Val Ala Arg Ala Lys Phe Ala Ala Asp Ile Ala Arg
1               5                   10                  15

Asp Ile Ala Ala Glu Phe Gly Tyr Asp Leu Glu Val Arg Glu Glu Asn
            20                  25                  30

Gly Asn Phe Arg Leu Lys Thr Lys
        35                  40

<210> SEQ ID NO 399
<211> LENGTH: 40
<212> TYPE: PRT
<213> ORGANISM: Artificial Sequence
<220> FEATURE:
<223> OTHER INFORMATION: Synthetic

<400> SEQUENCE: 399

Arg Phe Arg Ile Glu Ala Arg Ser Lys Phe Ala Ala Glu Ile Ala Ala
1               5                   10                  15

Arg Ile Leu Ala Glu Phe Gly Leu Asp Val Thr Val Thr Lys Lys Asn
            20                  25                  30

Gly Tyr Tyr Phe Val Glu Ser Gly
        35                  40

<210> SEQ ID NO 400
<211> LENGTH: 40
<212> TYPE: PRT
```

```
<213> ORGANISM: Artificial Sequence
<220> FEATURE:
<223> OTHER INFORMATION: Synthetic

<400> SEQUENCE: 400

Thr Met His Ile Thr Ser Tyr Ser Pro Phe Ala Ala Lys Ile Ala Ala
1               5                   10                  15

Leu Ile Ala Leu Glu Phe Gly Tyr Thr Val Glu Leu Arg Lys Asp Gly
            20                  25                  30

Thr Arg Leu Glu Val His Ser Lys
        35                  40

<210> SEQ ID NO 401
<211> LENGTH: 40
<212> TYPE: PRT
<213> ORGANISM: Artificial Sequence
<220> FEATURE:
<223> OTHER INFORMATION: Synthetic

<400> SEQUENCE: 401

Thr Thr Glu Gln Glu Ala Arg Ser Glu Phe Ala Ala Ala Ile Ala Ala
1               5                   10                  15

Glu Ile Ala Arg Gln Phe Gly Tyr Thr Val Thr Val Gln Lys Ser Gly
            20                  25                  30

Thr Arg Leu Arg Val Arg Val Gly
        35                  40

<210> SEQ ID NO 402
<211> LENGTH: 40
<212> TYPE: PRT
<213> ORGANISM: Artificial Sequence
<220> FEATURE:
<223> OTHER INFORMATION: Synthetic

<400> SEQUENCE: 402

Thr Phe Thr Ser Thr Ala Trp Asn Arg Phe Ser Ala Glu Ile Ala Arg
1               5                   10                  15

Lys Ile Ala Glu Glu Phe Gly Tyr Thr Val Thr Ile Glu Asp Arg Asn
            20                  25                  30

Gly Asp Phe His Val Arg Val Thr
        35                  40

<210> SEQ ID NO 403
<211> LENGTH: 40
<212> TYPE: PRT
<213> ORGANISM: Artificial Sequence
<220> FEATURE:
<223> OTHER INFORMATION: Synthetic

<400> SEQUENCE: 403

Thr Gln Arg Val Arg Ala Ser Ser Arg Phe Ser Ala Met Ile Ala Ala
1               5                   10                  15

Lys Ile Leu Lys Glu Phe Gly Tyr Thr Val His Val Tyr Glu Asp Asn
            20                  25                  30

Gly Arg Phe Glu Ile Glu Ser Arg
        35                  40

<210> SEQ ID NO 404
<211> LENGTH: 40
<212> TYPE: PRT
<213> ORGANISM: Artificial Sequence
<220> FEATURE:
<223> OTHER INFORMATION: Synthetic
```

```
<400> SEQUENCE: 404

Thr Val Thr Thr Val Thr Leu Ser Glu Phe Ala Ala Arg Ile Ala Glu
1               5                   10                  15

Lys Ile Leu Arg Glu Phe Gly Ile Thr Val Glu Val Thr Gln Glu Asn
            20                  25                  30

Gly Thr Trp Lys Val Arg Thr Glu
        35                  40

<210> SEQ ID NO 405
<211> LENGTH: 40
<212> TYPE: PRT
<213> ORGANISM: Artificial Sequence
<220> FEATURE:
<223> OTHER INFORMATION: Synthetic

<400> SEQUENCE: 405

Thr Ile Glu Val Thr Val Arg Ala Glu Phe Ala Ala Arg Ile Ala Tyr
1               5                   10                  15

Lys Ile Met Lys Glu Phe Gly Trp Asp Val Arg Val Arg Gln Glu Asn
            20                  25                  30

Gly Thr Trp Lys Ile Glu Ser Asp
        35                  40

<210> SEQ ID NO 406
<211> LENGTH: 40
<212> TYPE: PRT
<213> ORGANISM: Artificial Sequence
<220> FEATURE:
<223> OTHER INFORMATION: Synthetic

<400> SEQUENCE: 406

Thr Tyr Thr Ile Ile Ala Lys Ser Glu Phe Ala Ala Arg Ile Ala Ala
1               5                   10                  15

Lys Ile Leu Ala Ser Phe Arg Tyr Arg Val Glu Leu Arg Lys His Asn
            20                  25                  30

Gly Thr Val Thr Ile Arg Phe Asp
        35                  40

<210> SEQ ID NO 407
<211> LENGTH: 40
<212> TYPE: PRT
<213> ORGANISM: Artificial Sequence
<220> FEATURE:
<223> OTHER INFORMATION: Synthetic

<400> SEQUENCE: 407

Thr Ser Arg Cys Val Thr Arg Ser Ser Phe Ala Ala Gln Ile Ala Lys
1               5                   10                  15

Asp Ile Leu Ala Glu Phe Gly Tyr Arg Val Glu Val Glu Glu His Asn
            20                  25                  30

Gly Asn Phe Glu Val Arg Tyr Asp
        35                  40

<210> SEQ ID NO 408
<211> LENGTH: 40
<212> TYPE: PRT
<213> ORGANISM: Artificial Sequence
<220> FEATURE:
<223> OTHER INFORMATION: Synthetic

<400> SEQUENCE: 408
```

```
Thr Tyr Thr Thr Val Cys Ser Glu Phe Ala Ala Lys Ile Ala Ala
1               5                   10                  15

Glu Ile Ala Arg Glu Phe Gly Tyr Thr Val Thr Ile Arg Gln Glu Asn
            20                  25                  30

Gly Lys Trp His Val Glu Val Arg
        35                  40
```

<210> SEQ ID NO 409
<211> LENGTH: 43
<212> TYPE: PRT
<213> ORGANISM: Artificial Sequence
<220> FEATURE:
<223> OTHER INFORMATION: Synthetic

<400> SEQUENCE: 409

```
Pro Phe Ala Leu Glu Ile Ala Ala Lys Ile Met Ala Glu Phe Gly Val
1               5                   10                  15

Ser Ser Glu Glu Ile Lys Arg Glu Leu Lys Lys Gln Gly Ala Ser Asp
            20                  25                  30

Asp Thr Ala Glu Glu Leu Ala Arg Arg Ala Gly
        35                  40
```

<210> SEQ ID NO 410
<211> LENGTH: 43
<212> TYPE: PRT
<213> ORGANISM: Artificial Sequence
<220> FEATURE:
<223> OTHER INFORMATION: Synthetic

<400> SEQUENCE: 410

```
Leu Phe Ala Ala Arg Ile Ala Ala Lys Ile Ala Ala Glu Phe Gly Ala
1               5                   10                  15

Ser Pro Asp Glu Ile Lys Glu Ile Leu Lys Arg Ala Gly Val Ser Glu
            20                  25                  30

Asp Glu Ala Glu Gln Ile Val Gln Glu Leu Phe
        35                  40
```

<210> SEQ ID NO 411
<211> LENGTH: 43
<212> TYPE: PRT
<213> ORGANISM: Artificial Sequence
<220> FEATURE:
<223> OTHER INFORMATION: Synthetic

<400> SEQUENCE: 411

```
Arg Phe Ala Cys Ala Ile Ala Phe Lys Ile Leu Trp Glu Phe Gly Tyr
1               5                   10                  15

Ser Pro Glu Glu Ile Arg Glu Ile Leu Lys Arg Ala Gly Cys Ser Pro
            20                  25                  30

Lys Glu Ala Glu Glu Ala Glu Arg Glu Ala Leu
        35                  40
```

<210> SEQ ID NO 412
<211> LENGTH: 40
<212> TYPE: PRT
<213> ORGANISM: Artificial Sequence
<220> FEATURE:
<223> OTHER INFORMATION: Synthetic

<400> SEQUENCE: 412

```
Thr Tyr Thr Ser Ile Val Arg Ala Glu Phe Ala Cys Arg Ile Ala Cys
1               5                   10                  15
```

```
Glu Ile Met Arg Glu Phe Gly Trp Gln Val His Cys Arg Lys His Gly
            20                  25                  30

Thr Thr Cys Lys Val Glu Ser Arg
        35                  40

<210> SEQ ID NO 413
<211> LENGTH: 40
<212> TYPE: PRT
<213> ORGANISM: Artificial Sequence
<220> FEATURE:
<223> OTHER INFORMATION: Synthetic

<400> SEQUENCE: 413

Thr Tyr Thr Val Glu Thr Val Ser Asp Phe Ser Cys Trp Ile Ala Ala
1               5                   10                  15

Glu Ile Ala Arg Glu Phe Gly Tyr Glu Val Glu Leu Arg Lys His Gly
            20                  25                  30

Thr Lys Cys Lys Val Arg Ile Gly
        35                  40

<210> SEQ ID NO 414
<211> LENGTH: 40
<212> TYPE: PRT
<213> ORGANISM: Artificial Sequence
<220> FEATURE:
<223> OTHER INFORMATION: Synthetic

<400> SEQUENCE: 414

Thr Cys Thr Thr Glu Ser Ala Thr Arg Phe Ala Cys Glu Ile Ala Arg
1               5                   10                  15

Glu Ile Ala Arg Glu Phe Gly Tyr Asp Ala Gln Ile Arg Glu Glu Asn
            20                  25                  30

Gly Thr Cys Lys Leu His Val Gly
        35                  40

<210> SEQ ID NO 415
<211> LENGTH: 40
<212> TYPE: PRT
<213> ORGANISM: Artificial Sequence
<220> FEATURE:
<223> OTHER INFORMATION: Synthetic

<400> SEQUENCE: 415

Thr Arg Glu Leu Ile Ala Tyr Ser Asp Phe Ala Cys Arg Ile Ala Glu
1               5                   10                  15

Glu Ile Leu Ala Glu Phe Gly Gln Thr Val Thr Val Lys Arg Asn
            20                  25                  30

Gly Thr Cys His Ile Arg Val Asp
        35                  40

<210> SEQ ID NO 416
<211> LENGTH: 40
<212> TYPE: PRT
<213> ORGANISM: Artificial Sequence
<220> FEATURE:
<223> OTHER INFORMATION: Synthetic

<400> SEQUENCE: 416

Thr Phe Thr Ser His Ala Lys Gln Asp Phe Ala Cys Glu Ile Ala Ala
1               5                   10                  15

Arg Ile Ala Ala Glu Phe Gly Trp Asp Val Gln Val Arg Lys His Gly
            20                  25                  30
```

```
Thr Thr Cys Glu Val Glu Val Arg
        35                  40
```

<210> SEQ ID NO 417
<211> LENGTH: 40
<212> TYPE: PRT
<213> ORGANISM: Artificial Sequence
<220> FEATURE:
<223> OTHER INFORMATION: Synthetic

<400> SEQUENCE: 417

```
Gly Gln Arg Met Val Val Pro Ser Glu Phe Ala Cys Glu Ile Ala Arg
1               5                   10                  15

Gln Ile Leu Glu Glu Phe Gly Gln Thr Val Thr Val Arg Lys Thr Gly
            20                  25                  30

Gly Tyr Cys Glu Ile Glu Ser Asn
        35                  40
```

<210> SEQ ID NO 418
<211> LENGTH: 40
<212> TYPE: PRT
<213> ORGANISM: Artificial Sequence
<220> FEATURE:
<223> OTHER INFORMATION: Synthetic

<400> SEQUENCE: 418

```
Thr Asp Thr Ser Thr Thr Val Ser Pro Phe Ala Lys Ile Ala Cys
1               5                   10                  15

Asp Ile Ile Arg Glu Phe Asn Trp Asp Val Arg Cys Thr Gln Glu Asn
            20                  25                  30

Gly Gln Trp Lys Val Glu Arg Arg
        35                  40
```

<210> SEQ ID NO 419
<211> LENGTH: 40
<212> TYPE: PRT
<213> ORGANISM: Artificial Sequence
<220> FEATURE:
<223> OTHER INFORMATION: Synthetic

<400> SEQUENCE: 419

```
Thr Tyr Thr Ile Ile Ala Tyr Ala Pro Phe Ala Cys Glu Ile Ala Arg
1               5                   10                  15

Gln Ile Leu Glu Glu Phe Asn Tyr Thr Val Thr Arg Thr Thr Asp Gly
            20                  25                  30

Thr Thr Cys Thr Leu Ser Tyr Glu
        35                  40
```

<210> SEQ ID NO 420
<211> LENGTH: 40
<212> TYPE: PRT
<213> ORGANISM: Artificial Sequence
<220> FEATURE:
<223> OTHER INFORMATION: Synthetic

<400> SEQUENCE: 420

```
Thr Gln Arg Val Arg Ala Trp Ser Arg Phe Ala Cys Glu Ile Ala Arg
1               5                   10                  15

Glu Ile Leu Arg Glu Phe Gly Tyr Thr Val His Val Tyr Glu Asp Asn
            20                  25                  30

Gly Arg Cys Glu Ile Glu Ser Arg
        35                  40
```

<210> SEQ ID NO 421
<211> LENGTH: 40
<212> TYPE: PRT
<213> ORGANISM: Artificial Sequence
<220> FEATURE:
<223> OTHER INFORMATION: Synthetic

<400> SEQUENCE: 421

Thr Met Thr Ser Leu Ala Tyr Ser Gln Phe Ala Cys Asp Ile Ala Arg
1               5                   10                  15

Arg Ile Ala Ala Glu Phe Gly Tyr Thr Val Thr Ile Glu Asp Arg Asn
            20                  25                  30

Gly Glu Cys His Leu Thr Val Asp
        35                  40

<210> SEQ ID NO 422
<211> LENGTH: 40
<212> TYPE: PRT
<213> ORGANISM: Artificial Sequence
<220> FEATURE:
<223> OTHER INFORMATION: Synthetic

<400> SEQUENCE: 422

Thr Phe Ile Ser Val Thr Arg Ser Ser Phe Ala Cys Ala Ile Ala Ala
1               5                   10                  15

Gln Ile Leu Gln Glu Phe Asn Ile Pro Tyr Glu Val Glu Thr Arg Gly
            20                  25                  30

Thr Thr Cys Arg Ile Arg Ser Glu
        35                  40

<210> SEQ ID NO 423
<211> LENGTH: 40
<212> TYPE: PRT
<213> ORGANISM: Artificial Sequence
<220> FEATURE:
<223> OTHER INFORMATION: Synthetic

<400> SEQUENCE: 423

Thr Tyr Glu Phe Glu Ala Tyr Ser Pro Phe Ala Cys Thr Ile Ala Glu
1               5                   10                  15

Leu Ile Leu Arg Glu Phe Gly Gln Thr Val Thr Val Glu Glu Arg Asn
            20                  25                  30

Gly Arg Cys Arg Val Arg Ala Asp
        35                  40

<210> SEQ ID NO 424
<211> LENGTH: 40
<212> TYPE: PRT
<213> ORGANISM: Artificial Sequence
<220> FEATURE:
<223> OTHER INFORMATION: Synthetic

<400> SEQUENCE: 424

Thr Met Thr Ser Val Ser Tyr Ser Asp Phe Ala Cys Glu Ile Ala Ala
1               5                   10                  15

Lys Ile Ala Trp Glu Phe Gly Tyr Thr Val Arg Lys Glu Lys Arg Asn
            20                  25                  30

Gly Thr Cys Thr Leu Glu Val His
        35                  40

<210> SEQ ID NO 425
<211> LENGTH: 43

```
<212> TYPE: PRT
<213> ORGANISM: Artificial Sequence
<220> FEATURE:
<223> OTHER INFORMATION: Synthetic

<400> SEQUENCE: 425

Pro Phe Ala Leu Cys Ile Ala Ala Lys Ile Leu Leu Glu Phe Gly Lys
1               5                   10                  15

Asn Pro Asp Glu Ile Arg Glu Phe Leu Arg Asn Ala Gly Tyr Asp Gln
                20                  25                  30

Ser Gln Ala Glu Glu Ala Leu Lys Cys Ala Leu
            35                  40

<210> SEQ ID NO 426
<211> LENGTH: 43
<212> TYPE: PRT
<213> ORGANISM: Artificial Sequence
<220> FEATURE:
<223> OTHER INFORMATION: Synthetic

<400> SEQUENCE: 426

Arg Phe Ala Cys Glu Ile Ala Ala Lys Ile Leu Ser Glu Phe Gly Lys
1               5                   10                  15

Ser Thr Lys Glu Ile Glu Arg Val Leu Arg Glu Cys Gly Val Ser Asp
                20                  25                  30

Asp Glu Ala Glu Glu Ile Leu Arg Arg Tyr Gly
            35                  40

<210> SEQ ID NO 427
<211> LENGTH: 40
<212> TYPE: PRT
<213> ORGANISM: Artificial Sequence
<220> FEATURE:
<223> OTHER INFORMATION: Synthetic

<400> SEQUENCE: 427

Cys Tyr Glu Thr Glu Val His Ser Pro Phe Ala Cys Lys Ile Ala Glu
1               5                   10                  15

Asp Ile Leu Arg Glu Phe Gly Gln Arg Val Glu Arg Gln Asp Asp Gly
                20                  25                  30

Thr Ser Cys Arg Ile Arg Val Cys
            35                  40

<210> SEQ ID NO 428
<211> LENGTH: 40
<212> TYPE: PRT
<213> ORGANISM: Artificial Sequence
<220> FEATURE:
<223> OTHER INFORMATION: Synthetic

<400> SEQUENCE: 428

Cys Glu Thr Arg Thr Tyr Thr Asn Phe Ala Ala Glu Ile Ala Ala Arg
1               5                   10                  15

Ile Glu Ala Tyr Phe Arg Gly Gln Pro Cys Glu Phe Arg Asp Asp Gly
                20                  25                  30

Gly Lys Val Glu Arg Arg Cys Cys
            35                  40

<210> SEQ ID NO 429
<211> LENGTH: 40
<212> TYPE: PRT
<213> ORGANISM: Artificial Sequence
<220> FEATURE:
```

<223> OTHER INFORMATION: Synthetic

<400> SEQUENCE: 429

Cys Trp Glu Thr Thr Val Ser Ser Glu Phe Ala Ala Arg Ile Ala Gln
1               5                   10                  15

Lys Ile Ala Lys Ala Phe Gly Trp Asp Val Gln Phe Gly Asp Asn Gly
            20                  25                  30

Asp Lys Phe Arg Leu Arg Asn Cys
        35                  40

<210> SEQ ID NO 430
<211> LENGTH: 38
<212> TYPE: PRT
<213> ORGANISM: Artificial Sequence
<220> FEATURE:
<223> OTHER INFORMATION: Synthetic

<400> SEQUENCE: 430

Ser Glu Glu Leu Lys Arg Leu Cys Lys Glu Gly Asn Phe Ala Glu Leu
1               5                   10                  15

Ile Arg Phe Ala Ile Glu Ala Glu Phe Asn Arg Asn Pro Glu Glu Ala
            20                  25                  30

Glu Arg Ala Lys Lys Cys
        35

<210> SEQ ID NO 431
<211> LENGTH: 37
<212> TYPE: PRT
<213> ORGANISM: Artificial Sequence
<220> FEATURE:
<223> OTHER INFORMATION: Synthetic

<400> SEQUENCE: 431

Gln Arg Arg Arg Thr Glu Ala Ser Glu Phe Ala Cys Arg Ile Ala Gln
1               5                   10                  15

Glu Ile Leu Arg Glu Phe Gly Trp Gln Trp Thr Gln Asp Gly Arg Thr
            20                  25                  30

Cys Glu Ile His Ala
        35

<210> SEQ ID NO 432
<211> LENGTH: 41
<212> TYPE: PRT
<213> ORGANISM: Artificial Sequence
<220> FEATURE:
<223> OTHER INFORMATION: Synthetic

<400> SEQUENCE: 432

Cys Pro Tyr Cys Glu Trp Ala Lys Glu Ala Ala Lys Asn Gly Asn Phe
1               5                   10                  15

Ala Gln Ala Ile Ala Trp Ala Ile Lys Ala Ser Phe Gln Gly Asp Pro
            20                  25                  30

Ser Cys Ala Gln Cys Ala Leu Asp Val
        35                  40

<210> SEQ ID NO 433
<211> LENGTH: 37
<212> TYPE: PRT
<213> ORGANISM: Artificial Sequence
<220> FEATURE:
<223> OTHER INFORMATION: Synthetic

<400> SEQUENCE: 433

-continued

Ser Cys Thr Thr Cys Asp Cys Asn Asn Phe Ala Cys Lys Ile Ala Ala
1               5                   10                  15

Lys Ile Ala Ala Glu Phe Gly Ala Thr Ser Ser Cys Ser Gly Gly Leu
            20                  25                  30

Leu Thr Phe Cys Phe
        35

<210> SEQ ID NO 434
<211> LENGTH: 37
<212> TYPE: PRT
<213> ORGANISM: Artificial Sequence
<220> FEATURE:
<223> OTHER INFORMATION: Synthetic

<400> SEQUENCE: 434

Thr Arg Tyr Thr Val Cys Trp Gly Ser Phe Ala Cys Lys Ile Ala Tyr
1               5                   10                  15

Glu Ile Ala Arg Glu Phe Gly Cys Gln Cys Gln His Ser Gly Gly Thr
            20                  25                  30

Val Glu Cys Glu Cys
        35

<210> SEQ ID NO 435
<211> LENGTH: 37
<212> TYPE: PRT
<213> ORGANISM: Artificial Sequence
<220> FEATURE:
<223> OTHER INFORMATION: Synthetic

<400> SEQUENCE: 435

Ser Thr Asn Ser Cys Glu Gly Cys Asn Phe Ala Cys Gln Ile Ala Ala
1               5                   10                  15

Glu Ile Ala Arg Asp Phe Gly Cys Asp Val Arg Cys Thr Gly Gly His
            20                  25                  30

Val Glu Ile His Cys
        35

<210> SEQ ID NO 436
<211> LENGTH: 37
<212> TYPE: PRT
<213> ORGANISM: Artificial Sequence
<220> FEATURE:
<223> OTHER INFORMATION: Synthetic

<400> SEQUENCE: 436

Pro Glu Leu Arg Phe Gln Ala Gly Asn Phe Ala Cys Glu Ile Ala Cys
1               5                   10                  15

Arg Ile Ala Lys Glu Phe Gly Cys Thr Cys Thr Arg Glu Gly Asn Thr
            20                  25                  30

Cys Arg Val Ser Cys
        35

<210> SEQ ID NO 437
<211> LENGTH: 37
<212> TYPE: PRT
<213> ORGANISM: Artificial Sequence
<220> FEATURE:
<223> OTHER INFORMATION: Synthetic

<400> SEQUENCE: 437

Thr Cys Glu Cys Cys Asp Asn Pro Ser Phe Ala Glu Lys Ile Ala Cys
1               5                   10                  15

Glu Ile Lys Arg Glu Phe Ala Arg Lys Thr Arg Asp His Gly Asn Lys
            20                  25                  30

Val Cys Asn Cys Phe
            35

<210> SEQ ID NO 438
<211> LENGTH: 37
<212> TYPE: PRT
<213> ORGANISM: Artificial Sequence
<220> FEATURE:
<223> OTHER INFORMATION: Synthetic

<400> SEQUENCE: 438

Glu Thr Arg Glu Val Gln Asn Asp Phe Ala Arg Cys Ile Ala Glu Lys
1               5                   10                  15

Ile Leu Ala Glu Phe Arg Gly Cys Gln Phe Lys Leu Asp Gly Thr Thr
            20                  25                  30

Cys Tyr Val Tyr Cys
            35

<210> SEQ ID NO 439
<211> LENGTH: 37
<212> TYPE: PRT
<213> ORGANISM: Artificial Sequence
<220> FEATURE:
<223> OTHER INFORMATION: Synthetic

<400> SEQUENCE: 439

Thr Thr Glu Cys Val Thr Asp Asp Phe Ala Lys Ile Ile Ala Leu Lys
1               5                   10                  15

Ile Gln Cys Glu Phe Trp Gly Cys Glu Val His Glu Ser Asn Gly Lys
            20                  25                  30

Ile Cys Cys His Cys
            35

<210> SEQ ID NO 440
<211> LENGTH: 42
<212> TYPE: PRT
<213> ORGANISM: Artificial Sequence
<220> FEATURE:
<223> OTHER INFORMATION: Synthetic

<400> SEQUENCE: 440

Thr Thr Cys Gln Glu Phe Ser Asp Gly Thr Phe Ala Glu Ile Ile Arg
1               5                   10                  15

Leu Lys Ile Glu Ala Glu Phe Lys Gly Cys Arg Val Glu Glu Arg Pro
            20                  25                  30

Leu Glu Gly Arg Val Arg Val Cys Cys Gly
            35                  40

<210> SEQ ID NO 441
<211> LENGTH: 38
<212> TYPE: PRT
<213> ORGANISM: Artificial Sequence
<220> FEATURE:
<223> OTHER INFORMATION: Synthetic

<400> SEQUENCE: 441

Thr Cys Glu Glu Val Gln Ala Thr Asn Phe Ala Glu Lys Ile Ala Val
1               5                   10                  15

Glu Ile Lys Ala Gln Phe Lys Gly Cys Pro Tyr Thr Thr Asp Gly Asp
            20                  25                  30

```
Lys Val Thr Ile Cys Cys
        35

<210> SEQ ID NO 442
<211> LENGTH: 41
<212> TYPE: PRT
<213> ORGANISM: Artificial Sequence
<220> FEATURE:
<223> OTHER INFORMATION: Synthetic

<400> SEQUENCE: 442

Thr Gln Cys Phe Gln Asn Cys Ser Ser Pro Phe Ala Cys Arg Ile Ala
1               5                   10                  15

Ala Glu Ile Leu Lys Ala Phe Gly Trp Asp Cys Gln Glu Glu Pro Asp
            20                  25                  30

Asn Asn Arg Ile Cys Cys Gln Glu Gly
        35                  40

<210> SEQ ID NO 443
<211> LENGTH: 40
<212> TYPE: PRT
<213> ORGANISM: Artificial Sequence
<220> FEATURE:
<223> OTHER INFORMATION: Synthetic

<400> SEQUENCE: 443

Cys Asp Gln Met Glu Ala Ser Cys Pro Phe Ala Cys Arg Ile Ala Ala
1               5                   10                  15

Glu Ile Asn Arg Glu Phe Gly Tyr Arg Val Glu Ile His Asp Asp Asn
            20                  25                  30

Gly Arg Cys His Leu Lys Arg Cys
        35                  40

<210> SEQ ID NO 444
<211> LENGTH: 40
<212> TYPE: PRT
<213> ORGANISM: Artificial Sequence
<220> FEATURE:
<223> OTHER INFORMATION: Synthetic

<400> SEQUENCE: 444

Cys Gln Glu Leu Thr Leu Trp Ala Pro Phe Ala Cys Glu Ile Ala Ala
1               5                   10                  15

Arg Ile Met Trp Glu Phe Gly Leu Asp Val Asp Arg Gln Glu Glu Gly
            20                  25                  30

Asn His Cys Arg Leu Arg Ser Cys
        35                  40

<210> SEQ ID NO 445
<211> LENGTH: 38
<212> TYPE: PRT
<213> ORGANISM: Artificial Sequence
<220> FEATURE:
<223> OTHER INFORMATION: Synthetic

<400> SEQUENCE: 445

Pro Gln Arg Thr Trp Thr Thr Ala Pro Phe Ala Cys Ala Ile Ala Glu
1               5                   10                  15

Gln Ile Leu Ala Glu Phe Gly Met Gln Trp Glu Asn Arg Asn Asn Lys
            20                  25                  30

Glu Cys Arg Ala Gln Ala
        35
```

-continued

```
<210> SEQ ID NO 446
<211> LENGTH: 43
<212> TYPE: PRT
<213> ORGANISM: Artificial Sequence
<220> FEATURE:
<223> OTHER INFORMATION: Synthetic

<400> SEQUENCE: 446

Pro Cys Asp Asp Cys Lys Glu Glu Leu Glu Arg Arg Gly Cys Ser Phe
1               5                   10                  15

Ala Val Lys Ile Ala Val Asp Ile Ala Cys Glu Phe Asn Met Ser Ser
            20                  25                  30

Glu Tyr Cys Glu Arg Met Arg Arg Trp Cys Ser
        35                  40

<210> SEQ ID NO 447
<211> LENGTH: 37
<212> TYPE: PRT
<213> ORGANISM: Artificial Sequence
<220> FEATURE:
<223> OTHER INFORMATION: Synthetic

<400> SEQUENCE: 447

Thr Thr Ile Lys Ile Thr Asn Asp Phe Ala Lys Cys Ile Ala Ala Lys
1               5                   10                  15

Ile Leu Ala Glu Phe Trp Gly Cys Lys Phe Glu Glu Asn Gly His Glu
            20                  25                  30

Cys Tyr Val Tyr Cys
        35

<210> SEQ ID NO 448
<211> LENGTH: 42
<212> TYPE: PRT
<213> ORGANISM: Artificial Sequence
<220> FEATURE:
<223> OTHER INFORMATION: Synthetic

<400> SEQUENCE: 448

Thr Glu Cys Tyr Thr Val Thr Asn Phe Ala Glu Glu Ile Ala Val Lys
1               5                   10                  15

Ile Leu Cys Glu Phe Lys Gly Tyr Gln Cys Phe Glu Glu Arg Glu Ser
            20                  25                  30

Gly Thr Thr Arg Thr Val Cys Cys Ser Cys
        35                  40

<210> SEQ ID NO 449
<211> LENGTH: 40
<212> TYPE: PRT
<213> ORGANISM: Artificial Sequence
<220> FEATURE:
<223> OTHER INFORMATION: Synthetic

<400> SEQUENCE: 449

Cys Gln Arg Val Thr Ala Thr Ser Phe Ala Glu Cys Ile Ala Leu Lys
1               5                   10                  15

Ile Leu Ala Glu Phe Trp Gly Cys Pro Ile Thr Glu Gln Pro Gly Lys
            20                  25                  30

Asp Thr Cys Glu Leu Arg Cys Cys
        35                  40

<210> SEQ ID NO 450
```

```
<211> LENGTH: 37
<212> TYPE: PRT
<213> ORGANISM: Artificial Sequence
<220> FEATURE:
<223> OTHER INFORMATION: Synthetic

<400> SEQUENCE: 450

Pro Cys Ala Arg Ile Asp Ser Asn Thr Phe Ala Ala Gln Ile Ala Cys
1               5                   10                  15

Glu Ile Cys Lys Asp Phe Gly Ala Glu Cys Arg Asp Asp Gly Asn Val
            20                  25                  30

Val Glu Cys Cys Leu
        35

<210> SEQ ID NO 451
<211> LENGTH: 39
<212> TYPE: PRT
<213> ORGANISM: Artificial Sequence
<220> FEATURE:
<223> OTHER INFORMATION: Synthetic

<400> SEQUENCE: 451

Arg Thr Glu Thr Tyr Glu His Asp Ala Gln Phe Ala Val Glu Ile Met
1               5                   10                  15

Cys Glu Ile Leu Ala Gln Leu Lys Gly Cys Lys Leu Glu Lys Asp Gly
            20                  25                  30

Lys Arg Cys Arg Leu His Cys
        35

<210> SEQ ID NO 452
<211> LENGTH: 37
<212> TYPE: PRT
<213> ORGANISM: Artificial Sequence
<220> FEATURE:
<223> OTHER INFORMATION: Synthetic

<400> SEQUENCE: 452

Thr Thr Ala Lys Met Ser Ser Ala Gln Phe Ala Cys Lys Ile Ala Ala
1               5                   10                  15

Glu Ile Ala Arg Glu Phe Gly Cys Arg Cys Thr Ile Asp Gly Thr Glu
            20                  25                  30

Cys Tyr Cys Val Cys
        35

<210> SEQ ID NO 453
<211> LENGTH: 37
<212> TYPE: PRT
<213> ORGANISM: Artificial Sequence
<220> FEATURE:
<223> OTHER INFORMATION: Synthetic

<400> SEQUENCE: 453

Glu Thr Arg Arg Cys Lys Gly Phe Ala Glu Cys Ile Arg Cys Glu Ile
1               5                   10                  15

Glu Ala Glu Phe Lys Lys Gly Cys Thr Ser Lys Arg His Gly Glu Tyr
            20                  25                  30

Cys Glu Val Phe Cys
        35

<210> SEQ ID NO 454
<211> LENGTH: 37
<212> TYPE: PRT
<213> ORGANISM: Artificial Sequence
```

<220> FEATURE:
<223> OTHER INFORMATION: Synthetic

<400> SEQUENCE: 454

Pro Cys Thr Gln Val Asp Lys Ser Phe Ala Glu Ala Ile Ala Leu Cys
1               5                   10                  15

Ile Glu Ala Glu Phe Arg Gly Cys Gln Cys Arg Met Asp Gly Leu Val
            20                  25                  30

Val Glu Val Cys Cys
        35

<210> SEQ ID NO 455
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is R or G
<220> FEATURE:
<221> NAME/KEY: MISC_FEATURE
<222> LOCATION: (31)..(31)
<223> OTHER INFORMATION: X is V or K
<220> FEATURE:
<221> NAME/KEY: MISC_FEATURE
<222> LOCATION: (34)..(34)
<223> OTHER INFORMATION: X is Q or E
<220> FEATURE:
<221> NAME/KEY: MISC_FEATURE
<222> LOCATION: (36)..(36)
<223> OTHER INFORMATION: X is R or E
<220> FEATURE:
<221> NAME/KEY: MISC_FEATURE
<222> LOCATION: (38)..(38)
<223> OTHER INFORMATION: X is T or V

<400> SEQUENCE: 455

Thr Ser Xaa Val Arg Ala Thr Ser Lys Phe Ala Ala Leu Ile Ala Ala
1               5                   10                  15

Glu Ile Ala Arg Glu Phe Gly Tyr Thr Val Asp Val Gln Glu Xaa Asn
            20                  25                  30

Gly Xaa Trp Xaa Val Xaa Phe Asp
        35                  40

<210> SEQ ID NO 456
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (5)..(5)
<223> OTHER INFORMATION: X is T or R
<220> FEATURE:
<221> NAME/KEY: MISC_FEATURE
<222> LOCATION: (8)..(8)
<223> OTHER INFORMATION: X is D or N
<220> FEATURE:
<221> NAME/KEY: MISC_FEATURE
<222> LOCATION: (16)..(16)
<223> OTHER INFORMATION: X is A or L
<220> FEATURE:
<221> NAME/KEY: MISC_FEATURE
<222> LOCATION: (25)..(25)

```
<223> OTHER INFORMATION: X is A or D
<220> FEATURE:
<221> NAME/KEY: MISC_FEATURE
<222> LOCATION: (31)..(31)
<223> OTHER INFORMATION: X is N or I

<400> SEQUENCE: 456

Cys Gln Xaa Tyr Xaa Phe Thr Xaa Pro Phe Ala Cys Gln Ile Ala Xaa
1               5                   10                  15

Glu Ile Leu Arg Asp Phe Gly Tyr Xaa Cys Thr Val Gln Thr Xaa Asn
            20                  25                  30

Gly Glu Cys Arg Val Arg Cys Cys
        35                  40

<210> SEQ ID NO 457
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is C, T, pE or G
<220> FEATURE:
<221> NAME/KEY: MISC_FEATURE
<222> LOCATION: (12)..(12)
<223> OTHER INFORMATION: X is C or A
<220> FEATURE:
<221> NAME/KEY: MISC_FEATURE
<222> LOCATION: (30)..(30)
<223> OTHER INFORMATION: X is V or Q
<220> FEATURE:
<221> NAME/KEY: MISC_FEATURE
<222> LOCATION: (35)..(35)
<223> OTHER INFORMATION: X is C or W
<220> FEATURE:
<221> NAME/KEY: MISC_FEATURE
<222> LOCATION: (40)..(40)
<223> OTHER INFORMATION: X is C, T, G or P

<400> SEQUENCE: 457

Xaa Ile Glu Gln Ser Phe Thr Thr Leu Phe Ala Xaa Gln Thr Ala Ala
1               5                   10                  15

Glu Ile Trp Arg Ala Phe Gly Tyr Thr Val Lys Ile Met Xaa Asp Asn
            20                  25                  30

Gly Asn Xaa Arg Leu His Val Xaa
        35                  40

<210> SEQ ID NO 458
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(40)
<220> FEATURE:
<221> NAME/KEY: DISULFID
<222> LOCATION: (12)..(35)

<400> SEQUENCE: 458

Cys Ile Glu Gln Ser Phe Thr Thr Leu Phe Ala Cys Gln Thr Ala Ala
1               5                   10                  15

Glu Ile Trp Arg Ala Phe Gly Tyr Thr Val Lys Ile Met Val Asp Asn
            20                  25                  30

Gly Asn Cys Arg Leu His Val Cys
```

<210> SEQ ID NO 459
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(40)

<400> SEQUENCE: 459

Cys Ile Glu Gln Ser Phe Thr Thr Leu Phe Ala Ala Gln Thr Ala Ala
1               5                   10                  15

Glu Ile Trp Arg Ala Phe Gly Tyr Thr Val Lys Ile Met Gln Asp Asn
            20                  25                  30

Gly Asn Trp Arg Leu His Val Cys
        35                  40

<210> SEQ ID NO 460
<211> LENGTH: 40
<212> TYPE: PRT
<213> ORGANISM: Artificial Sequence
<220> FEATURE:
<223> OTHER INFORMATION: Synthetic

<400> SEQUENCE: 460

Thr Ile Glu Gln Ser Phe Thr Thr Leu Phe Ala Ala Gln Thr Ala Ala
1               5                   10                  15

Glu Ile Trp Arg Ala Phe Gly Tyr Thr Val Lys Ile Met Gln Asp Asn
            20                  25                  30

Gly Asn Trp Arg Leu His Val Thr
        35                  40

<210> SEQ ID NO 461
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is pyroEtamic acid
<220> FEATURE:
<221> NAME/KEY: DISULFID
<222> LOCATION: (12)..(35)
<220> FEATURE:
<221> NAME/KEY: MISC_FEATURE
<222> LOCATION: (40)..(40)
<223> OTHER INFORMATION: X is Gcinamide G-NH2

<400> SEQUENCE: 461

Xaa Ile Glu Gln Ser Phe Thr Thr Leu Phe Ala Cys Gln Thr Ala Ala
1               5                   10                  15

Glu Ile Trp Arg Ala Phe Gly Tyr Thr Val Lys Ile Met Val Asp Asn
            20                  25                  30

Gly Asn Cys Arg Leu His Val Xaa
        35                  40

<210> SEQ ID NO 462
<211> LENGTH: 40
<212> TYPE: PRT
<213> ORGANISM: Artificial Sequence
<220> FEATURE:

```
<223> OTHER INFORMATION: Synthetic
<220> FEATURE:
<221> NAME/KEY: DISULFID
<222> LOCATION: (12)..(35)

<400> SEQUENCE: 462

Gly Ile Glu Gln Ser Phe Thr Thr Leu Phe Ala Cys Gln Thr Ala Ala
1               5                   10                  15

Glu Ile Trp Arg Ala Phe Gly Tyr Thr Val Lys Ile Met Val Asp Asn
            20                  25                  30

Gly Asn Cys Arg Leu His Val Pro
        35                  40
```